United States Patent
Chang et al.

(10) Patent No.: US 11,925,389 B2
(45) Date of Patent: *Mar. 12, 2024

(54) SPINAL DISTRACTION SYSTEM

(71) Applicant: NuVasive Specialized Orthopedics, Inc., San Diego, CA (US)

(72) Inventors: Arvin Chang, West Covina, CA (US); Scott Pool, Laguna Hills, CA (US)

(73) Assignee: NUVASIVE SPECIALIZED ORTHOPEDICS, INC., San Diego, CA (US)

(*) Notice: Subject to any disclaimer, the term of this patent is extended or adjusted under 35 U.S.C. 154(b) by 102 days.

This patent is subject to a terminal disclaimer.

(21) Appl. No.: 17/646,163

(22) Filed: Dec. 28, 2021

(65) Prior Publication Data

US 2022/0192709 A1 Jun. 23, 2022

Related U.S. Application Data

(63) Continuation of application No. 13/730,773, filed on Dec. 28, 2012, now Pat. No. 11,241,257, which is a
(Continued)

(51) Int. Cl.
*A61B 17/70* (2006.01)
*A61B 17/88* (2006.01)
(Continued)

(52) U.S. Cl.
CPC ...... *A61B 17/7002* (2013.01); *A61B 17/7004* (2013.01); *A61B 17/7016* (2013.01);
(Continued)

(58) Field of Classification Search
CPC ............ A61B 17/7002; A61B 17/7004; A61B 17/7011; A61B 17/7052; A61B 17/7055;
(Continued)

(56) References Cited

U.S. PATENT DOCUMENTS 2,702,031 A 2/1955 Wenger
3,111,945 A 11/1963 Von Solbrig
(Continued)

FOREIGN PATENT DOCUMENTS

CN 1697630 A 11/2005
CN 101040807 A 9/2007
(Continued)

OTHER PUBLICATIONS

Buchowski et al., "Temporary Internal Distraction as an Aid to Correction of Severe Scoliosis. Surgical Technique," Journal of Bone and Joint Surgery American Edition. 2007, vol. 89A No. Supp. 2 (Pt. 2). pp. 297-309, Journal of Bone and Joint Surgery, Boston, U.S.A.
(Continued)

*Primary Examiner* — Samuel S Hanna

(57) ABSTRACT

A spinal distraction system, according to one aspect, includes an adjustable spinal distraction rod comprising first and second members, the adjustable spinal distraction rod configured for non-invasive elongation of the first and second members. The system includes an anchor rod configured for mounting to a bone of a subject, the anchor rod having one or more spring-biased tabs disposed at one end thereof, and a connector having first end and a second end, the first end having a receiving cup configured for detachable mounting on the anchor rod, wherein the one or more spring-biased tabs are configured to engage with an inner surface of the receiving cup, the connector having a second end operatively coupled to an end of a first member and wherein the second member is configured for mounting to a second bone of a subject.

20 Claims, 79 Drawing Sheets

Related U.S. Application Data continuation of application No. 12/250,454, filed on Oct. 13, 2008, now abandoned.

(51) Int. Cl.

| | | |
|---|---|---|
| A61B 17/00 | (2006.01) | |
| A61B 17/72 | (2006.01) | |
| A61B 17/80 | (2006.01) | |
| A61B 90/00 | (2016.01) | |
| A61F 2/30 | (2006.01) | |
| A61F 2/44 | (2006.01) | |

(52) U.S. Cl.
CPC ...... *A61B 17/7023* (2013.01); *A61B 17/7025* (2013.01); *A61B 17/705* (2013.01); *A61B 17/7055* (2013.01); *A61B 17/7079* (2013.01); *A61B 17/8858* (2013.01); *A61B 17/8863* (2013.01); *A61B 2017/00199* (2013.01); *A61B 2017/00212* (2013.01); *A61B 2017/00221* (2013.01); *A61B 2017/00411* (2013.01); *A61B 2017/00477* (2013.01); *A61B 17/7011* (2013.01); *A61B 17/7032* (2013.01); *A61B 17/7047* (2013.01); *A61B 17/7052* (2013.01); *A61B 17/7065* (2013.01); *A61B 17/7067* (2013.01); *A61B 17/7216* (2013.01); *A61B 17/8019* (2013.01); *A61B 2090/374* (2016.02); *A61F 2002/30079* (2013.01); *A61F 2002/30616* (2013.01); *A61F 2/442* (2013.01); *A61F 2210/009* (2013.01)

(58) Field of Classification Search
CPC ............ A61B 17/7065; A61B 17/7067; A61B 17/7216; A61B 17/7079; A61B 2017/681; A61F 2002/3055; A61F 2002/30579; A61F 2002/30537; A61F 2002/30601
See application file for complete search history.

(56) References Cited

U.S. PATENT DOCUMENTS

| | | |
|---|---|---|
| 3,372,476 A | 3/1968 | Pfeiffer |
| 3,377,576 A | 4/1968 | Langberg |
| 3,512,901 A | 5/1970 | Law |
| 3,597,781 A | 8/1971 | Eibes |
| 3,810,259 A | 5/1974 | Summers |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,498,262 A | 3/1996 | Bryan |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |

(56) References Cited

U.S. PATENT DOCUMENTS

| | | |
|---|---|---|
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,676,661 B1 | 1/2004 | Martin Benlloch et al. |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,502 B2 | 1/2011 | Pool et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B2 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |

(56) References Cited

U.S. PATENT DOCUMENTS

| | | |
|---|---|---|
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,430,916 B1 | 4/2013 | Winslow et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 11,241,257 B2 | 2/2022 | Chang et al. |
| 2001/0000943 A1 | 5/2001 | Fukuoka et al. |
| 2002/0050112 A1 | 5/2002 | Koch et al. |
| 2002/0072758 A1 | 6/2002 | Reo et al. |
| 2002/0138077 A1 | 9/2002 | Ferree |
| 2002/0164905 A1 | 11/2002 | Bryant |
| 2003/0023240 A1 | 1/2003 | Amrein et al. |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0006342 A1 | 1/2004 | Altarac et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0030395 A1 | 2/2004 | Blunn et al. |
| 2004/0055610 A1 | 3/2004 | Forsell |
| 2004/0133219 A1 | 7/2004 | Forsell |
| 2004/0138663 A1 | 7/2004 | Kosashvili et al. |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0113831 A1 | 5/2005 | Franck et al. |
| 2005/0159637 A9 | 7/2005 | Nelson et al. |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0089642 A1 | 4/2006 | Diaz et al. |
| 2006/0136062 A1 | 6/2006 | DiNello et al. |
| 2006/0142767 A1 | 6/2006 | Green et al. |
| 2006/0149242 A1 | 7/2006 | Kraus et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0123860 A1 | 5/2007 | Francis et al. |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0213751 A1 | 9/2007 | Scirica et al. |
| 2007/0225706 A1 | 9/2007 | Clark et al. |
| 2007/0233098 A1 | 10/2007 | Mastrorio et al. |
| 2007/0239159 A1 | 10/2007 | Altarac et al. |
| 2007/0239161 A1* | 10/2007 | Giger ............... A61B 17/8076 606/86 A |
| 2007/0255088 A1 | 11/2007 | Jacobson et al. |
| 2007/0270803 A1 | 11/2007 | Giger et al. |
| 2007/0276368 A1 | 11/2007 | Trieu et al. |

(56) References Cited

U.S. PATENT DOCUMENTS

| | | |
|---|---|---|
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097441 A1 | 4/2008 | Hayes et al. |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0269742 A1 | 10/2008 | Levy et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112207 A1 | 4/2009 | Walker et al. |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0254088 A1 | 10/2009 | Soubeiran |
| 2009/0275984 A1 | 11/2009 | Kim et al. |
| 2010/0004654 A1 | 1/2010 | Schmitz et al. |
| 2010/0049204 A1 | 2/2010 | Soubeiran |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0121323 A1 | 5/2010 | Pool et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0280551 A1 | 11/2010 | Pool et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060336 A1 | 3/2011 | Pool et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0004494 A1 | 1/2012 | Payne et al. |
| 2012/0019341 A1 | 1/2012 | Gabay et al. |
| 2012/0019342 A1 | 1/2012 | Gabay et al. |
| 2012/0035656 A1 | 2/2012 | Pool et al. |
| 2012/0035661 A1 | 2/2012 | Pool et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0209265 A1 | 8/2012 | Pool |
| 2012/0209269 A1 | 8/2012 | Pool et al. |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | 9808454 | 3/1998 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |

(56) References Cited

FOREIGN PATENT DOCUMENTS

| WO | WO2001045487 A2 | 6/2001 |
|---|---|---|
| WO | WO2001067973 A2 | 9/2001 |
| WO | WO2001078614 A1 | 10/2001 |
| WO | 2006090380 A2 | 8/2006 |
| WO | WO2007013059 A3 | 2/2007 |
| WO | WO2007015239 A3 | 2/2007 |
| WO | 2007144489 A2 | 12/2007 |
| WO | 2008003952 A1 | 1/2008 |
| WO | 2008040880 A2 | 4/2008 |
| WO | 2008040880 A3 | 5/2008 |
| WO | WO2011116158 A3 | 9/2011 |
| WO | WO2013119528 A1 | 8/2013 |
| WO | WO2014040013 A1 | 3/2014 |

OTHER PUBLICATIONS

Abe et al., "Experimental external fixation combined with percutaneous discectomy in the management of scoliosis.", Spine, 1999, pp. 646-653, 24, No. 7.

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", Spine, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

(56) References Cited

OTHER PUBLICATIONS

Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010-2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.

(56) References Cited

OTHER PUBLICATIONS

Thompson et al., "Early onset scoliosis: Future directions", 2007, J Bone Joint Surg Am, pp. 163-166, 89-A, Suppl 1.

Thompson et al., "Growing rod techniques in early-onset scoliosis", Journal of Pediatric Orthopedics, 2007, pp. 354-361, 27, No. 3.

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", Spine, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

\* cited by examiner

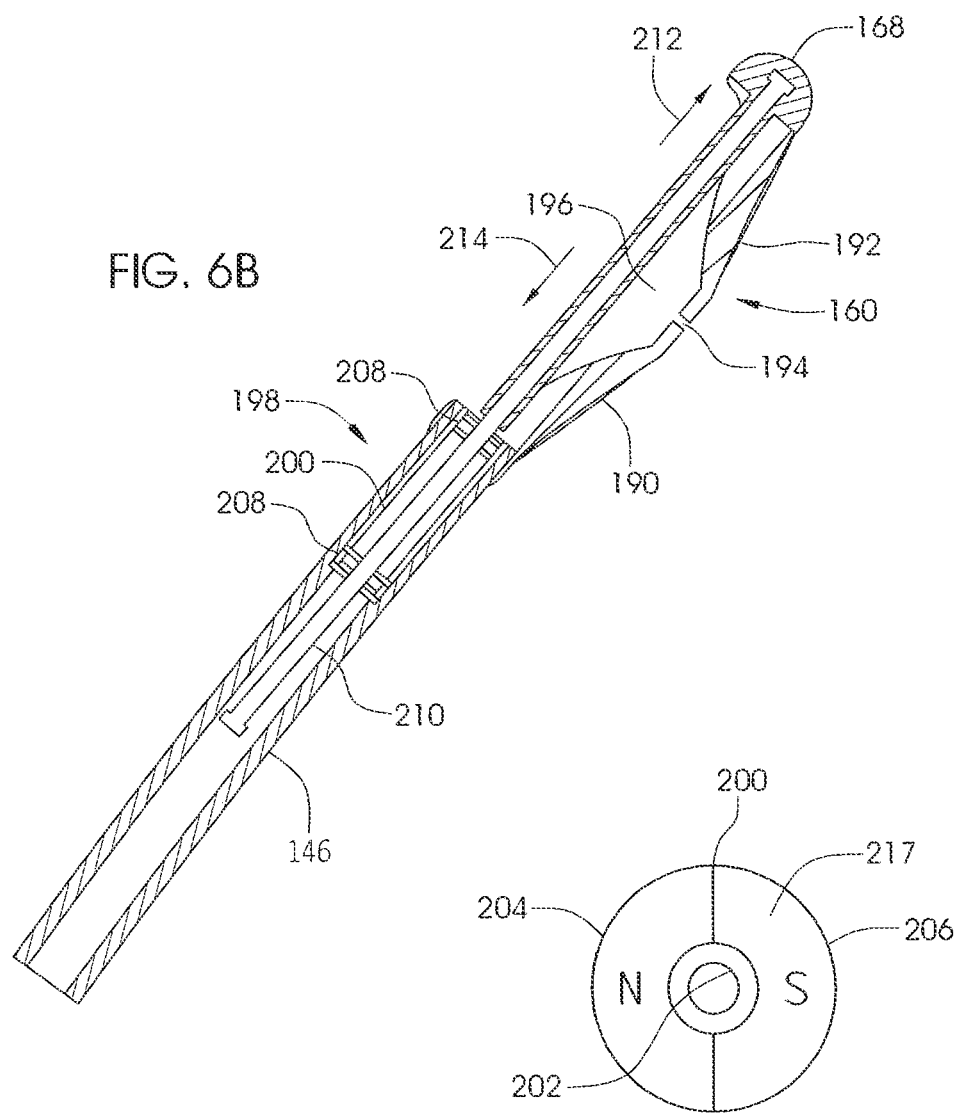

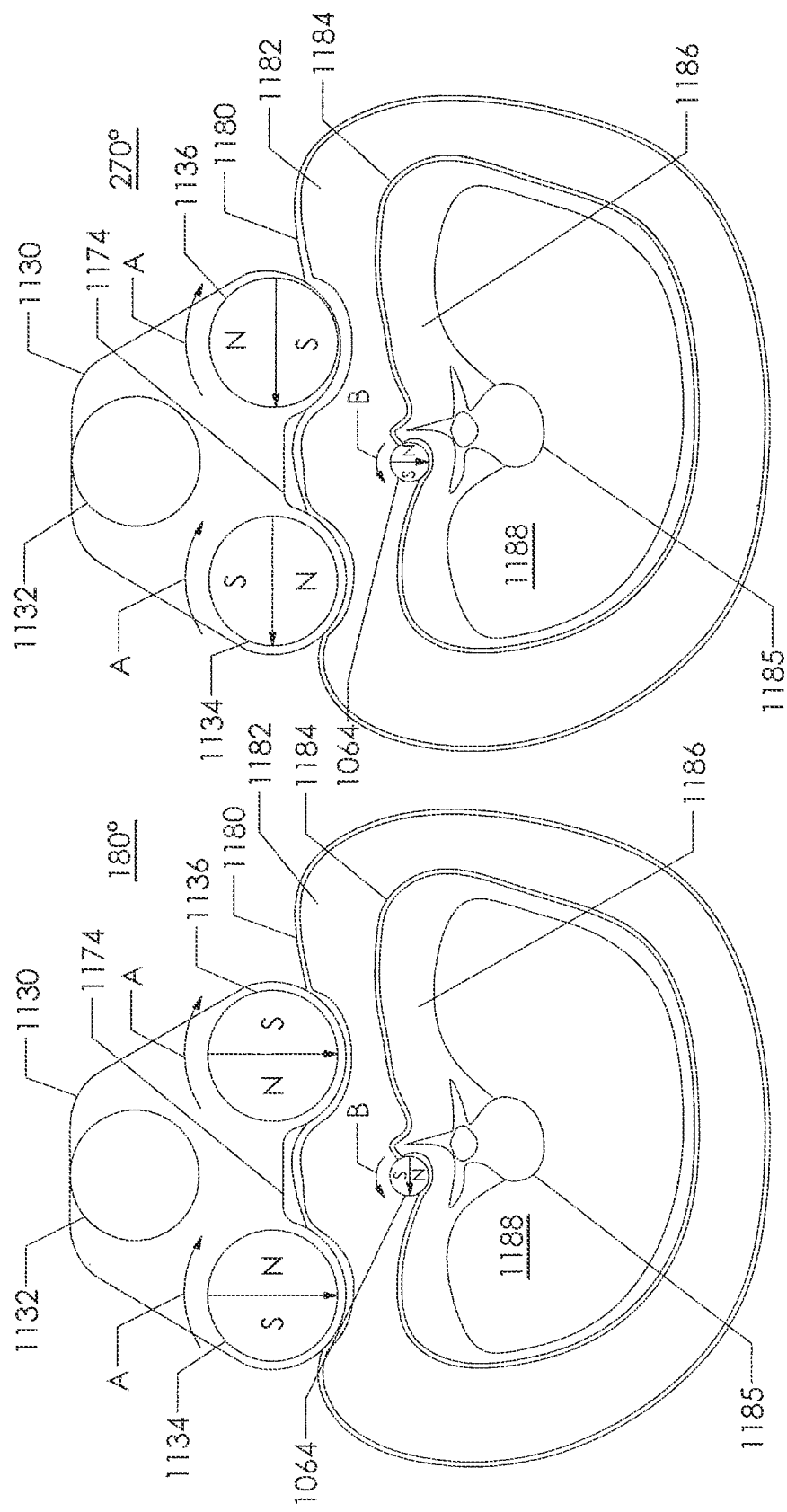

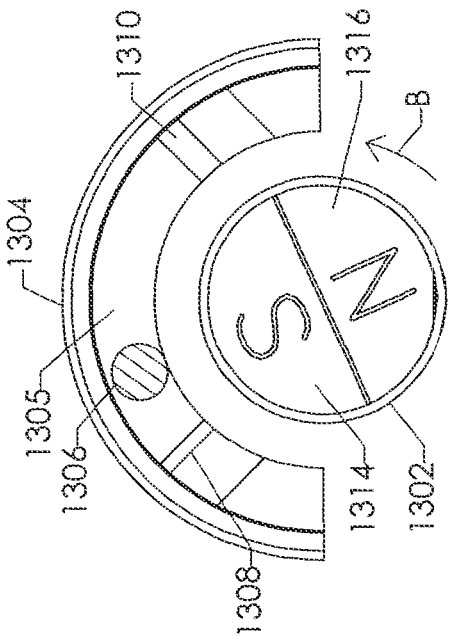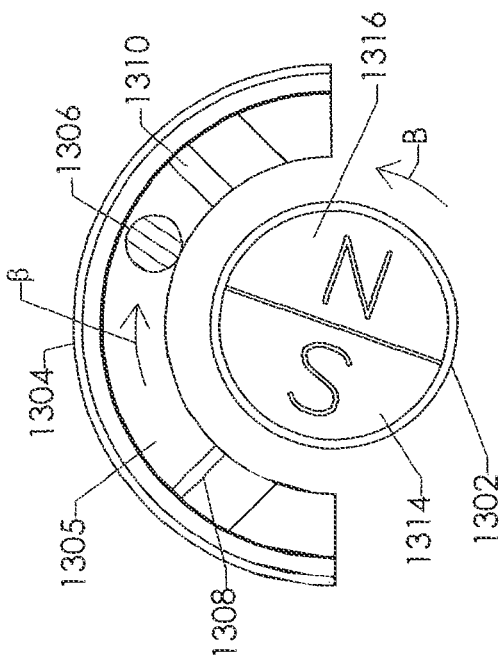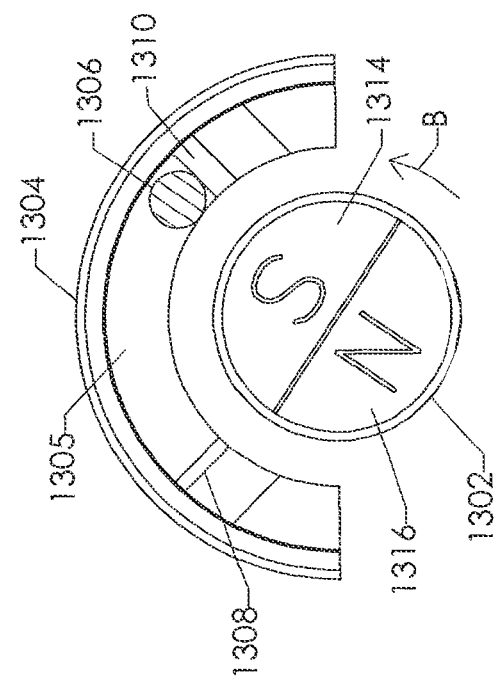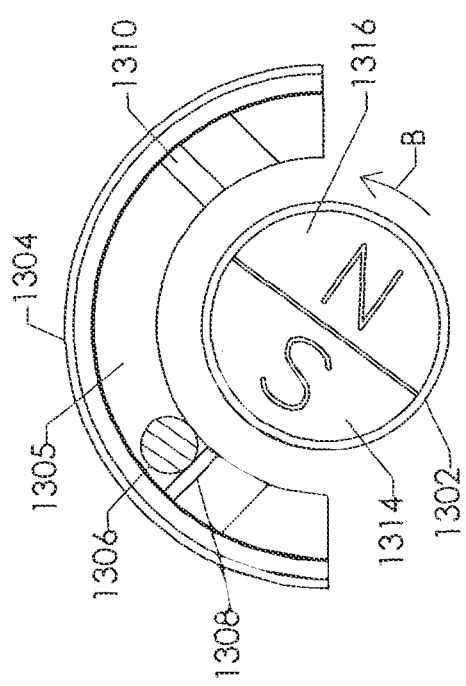
FIG. 23
FIG. 24
FIG. 25
FIG. 26

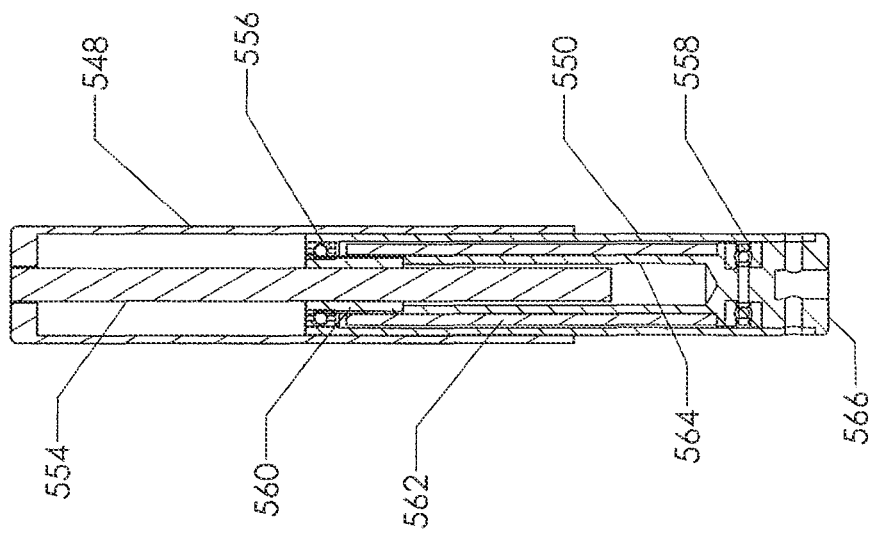
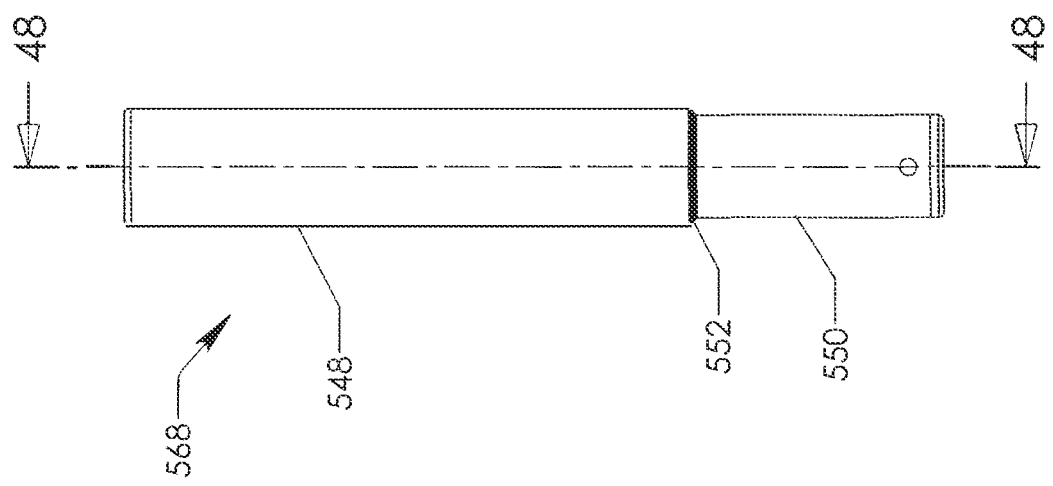

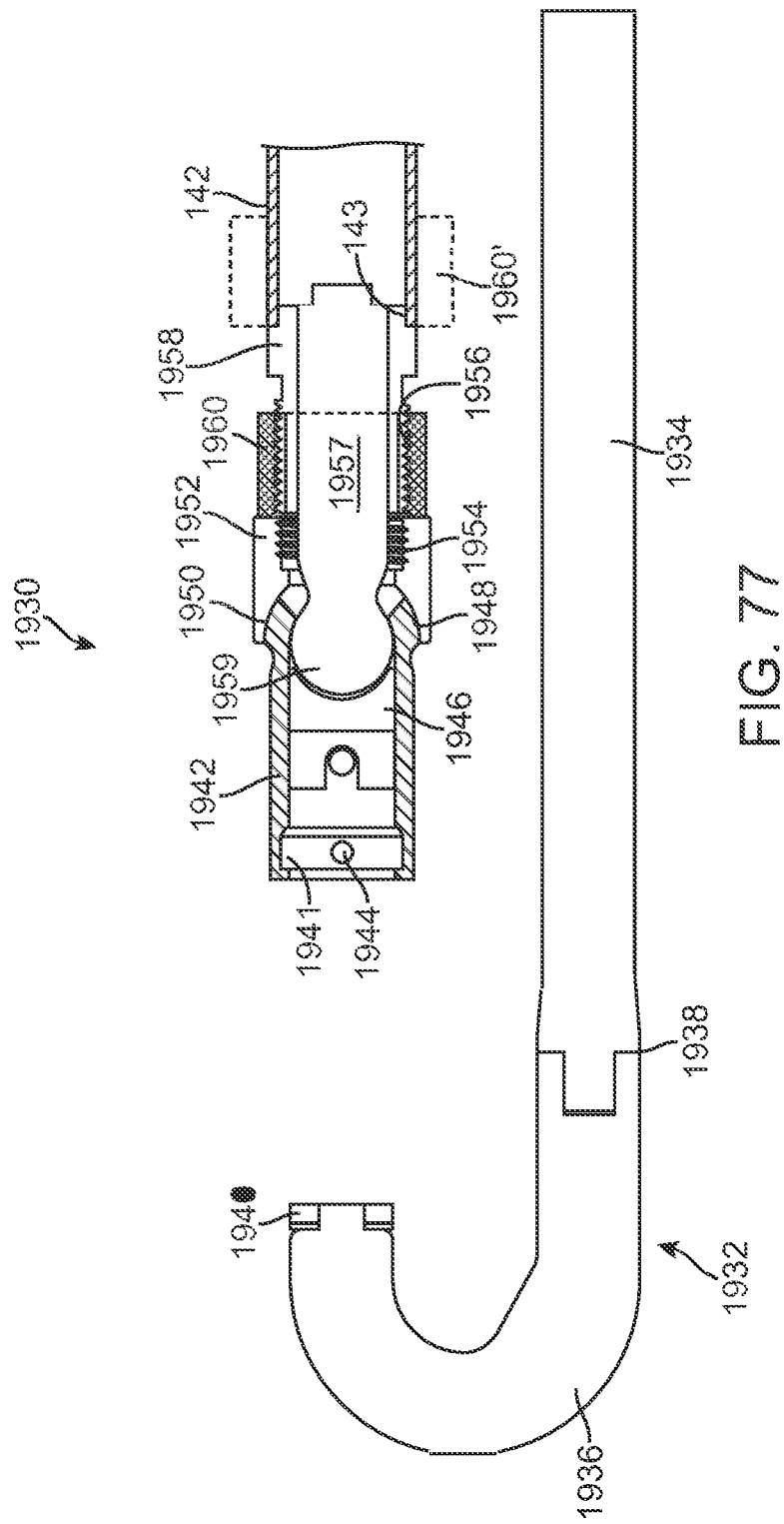

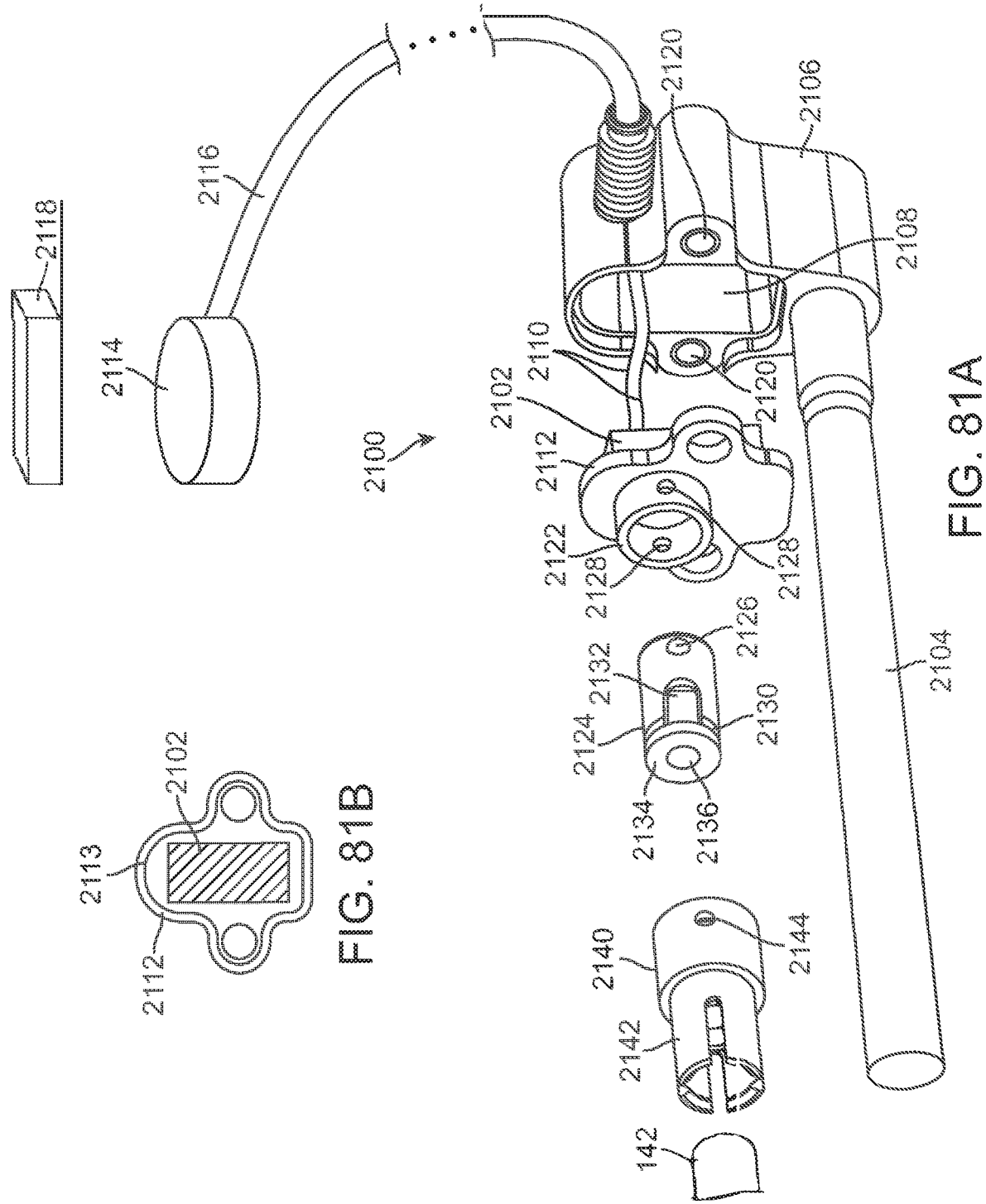

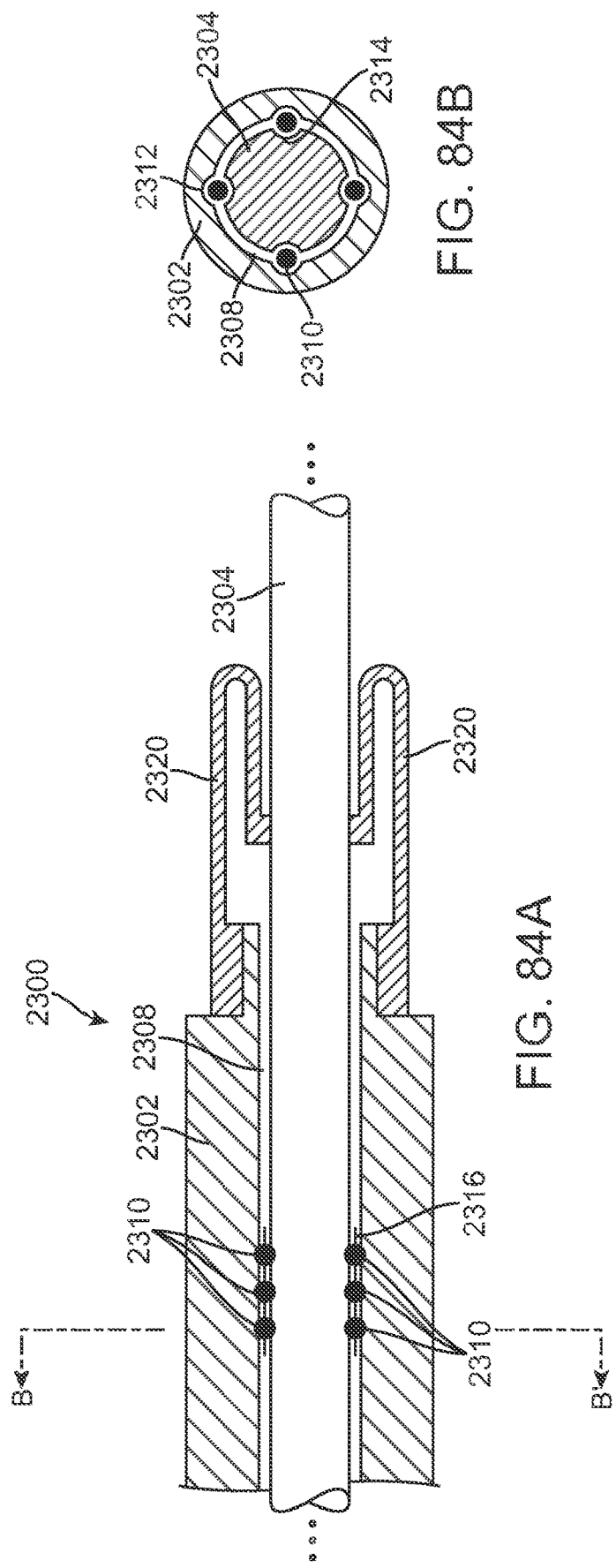

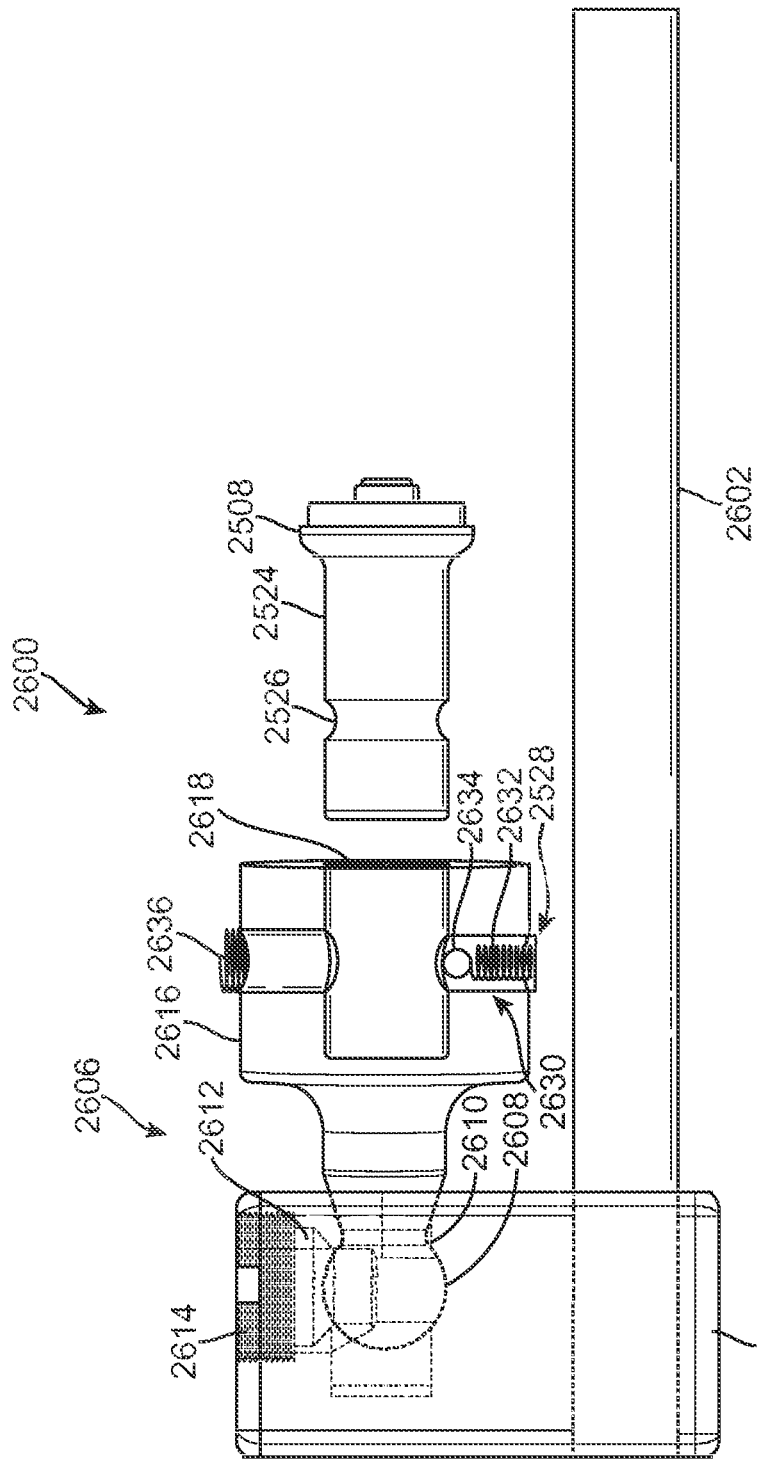

SPINAL DISTRACTION SYSTEM

This application is continuation of U.S. Ser. No. 13/730,773, filed Dec. 28, 2012, now U.S. Pat. No. 11,241,257, issued Feb. 8, 2022; which is a continuation of U.S. Ser. No. 12/250,454 filed Oct. 13, 2008, now abandoned.

FIELD OF THE INVENTION

The field of the invention generally relates to medical devices for treating disorders of the skeletal system.

BACKGROUND OF THE INVENTION

The field of the invention generally relates to medical devices for treating disorders of the skeletal system. Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. There is a large population of grown adults with untreated scoliosis, in extreme cases with a Cobb angle as high as or greater than 90°. Many of these adults, though, do not have pain associated with this deformity, and live relatively normal lives, though oftentimes with restricted mobility and motion. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

Commonly, after surgery, the patient will wear a brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twisting. As these fused patients mature, the fused section can impart large stresses on the adjacent non-fused vertebra, and often, other problems including pain can occur in these areas, sometimes necessitating further surgery. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five, and more often in boys than in girls. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection.

Returning to the AIS patients, the treatment methodology for those with a Cobb angle between 20° and 40° is quite controversial. Many physicians proscribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic, that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spine. Currently a prospective, randomized 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery.

Many physicians feel that the BrAIST trial will show that braces are completely ineffective. If this is the case, the quandary about what to do with AIS patients who have a Cobb angle of between 20° and 40° will only become more pronounced. It should be noted that the "20° to 40°" patient population is as much as ten times larger than the "40° and greater" patient population.

Currently, genetic scientists are at work to find one or more genes that may predispose scoliosis. Once identified, some are still skeptical as to whether gene therapy would be possible to prevent scoliosis, however the existence of a scoliosis gene would no doubt allow for easier and earlier identification of probable surgical patients.

SUMMARY OF THE INVENTION

In a first embodiment, a spinal distraction system includes an adjustable spinal distraction rod comprising first and second members, the adjustable spinal distraction rod configured for non-invasive elongation of the first and second members. The system includes an anchor rod configured for mounting to a bone of a subject, the anchor rod having one or more spring-biased tabs disposed at one end thereof, and a connector having first end and a second end, the first end having a receiving cup configured for detachable mounting on the anchor rod, wherein the one or more spring-biased tabs are configured to engage with an inner surface of the receiving cup, the connector having a second end operatively coupled to an end of a first member and wherein the second member is configured for mounting to a second bone of a subject.

In another embodiment, a spinal distraction system includes an adjustable spinal distraction rod comprising first and second members, the adjustable spinal distraction rod configured for non-invasive elongation of the first and second members. The system further includes an anchor rod configured for mounting to a bone of a subject, the anchor rod having a key at one end thereof. The system includes a rotational joint rotationally mounted on the end of the anchor rod having the key, the rotational joint comprising a receiving cup containing a bushing configured to limit rotation between the joint and the anchor rod, the rotational joint operatively coupled to an end of a first member and wherein the second member is configured for mounting to a second bone of a subject.

In another embodiment, a spinal distraction system includes an adjustable spinal distraction rod comprising first and second members, the adjustable spinal distraction rod configured for non-invasive elongation of the first and second members. The system includes an anchor rod configured for mounting to a bone of a subject, the anchor rod terminating in a ball at one end thereof. The system further includes an articulating joint having a socket portion configured for mounting on the ball of the anchor rod, the articulating joint further comprising a receiving cup portion configured to receive an end of a first member and wherein the second member is configured for mounting to a second bone of a subject.

In still another embodiment, a spinal distraction system includes an adjustable spinal distraction rod comprising first and second members, the adjustable spinal distraction rod configured for non-invasive elongation of the first and second members, the first member having a plurality of spaced apart apertures disposed at one end thereof. The system includes an anchor rod configured for mounting to a bone of a subject. The system further includes a joint operatively coupled to the anchor rod, the joint comprising a socket portion configured to receive the end of a first member containing the plurality of spaced apart apertures, the socket portion having a slot therein, and a pin configured for insertion into the slot and one of the plurality of spaced apart apertures, wherein the first member is configured for telescopic movement within the socket portion and wherein the second member is configured for mounting to a second bone of a subject.

In yet another embodiment, a spinal distraction system includes an adjustable spinal distraction rod comprising first and second members, the adjustable spinal distraction rod configured for non-invasive elongation of the first and second members, the first member having a plurality of spaced apart apertures disposed at one end thereof. The system further includes an anchor rod configured for mounting to a bone of a subject. The system has a joint operatively coupled to the anchor rod, the joint comprising a socket portion configured to receive the end of a first member containing the plurality of spaced apart apertures, the socket portion having a an aperture therein, and a pin configured for insertion into the aperture of the socket portion and one of the plurality of spaced apart apertures, wherein the first member is fixed relative to the socket portion and wherein the second member is configured for mounting to a second bone of a subject.

In another aspect of the invention, a spinal distraction system includes an adjustable spinal distraction rod comprising first and second members, the adjustable spinal distraction rod configured for non-invasive elongation of the first and second members, the first member having a trimable section at one end thereof, the trimable section comprising a threaded bore. The system includes a threaded cap having an aperture, the threaded cap configured to engage with the threaded bore of the trimable section. The system includes an anchor rod configured for mounting to a bone of a subject, and a swivel head operatively coupled to the anchor rod, the swivel head comprising one or more spring-biased tabs configured to pass through the aperture of the threaded cap and provide at least some telescopic movement between the first member and the swivel head, and wherein the second member is configured for mounting to a second bone of a subject.

BRIEF DESCRIPTION OF THE DRAWINGS

FIG. 6B illustrates a detailed view of portion A of FIG. 6A in accordance with an embodiment of the present invention.

FIG. 6E illustrates an end view of a cylindrical magnetic member for actuating a clamp in accordance with an embodiment of the present invention.

FIG. 13A illustrates the permanent magnet of the implantable interface in the 0° position.

FIG. 13B illustrates the permanent magnet of the implantable interface in the 90° position.

FIG. 13C illustrates a cross-sectional representation of the external adjustment device being positioned on a patient's skin. FIG. 13C illustrates the permanent magnet of the implantable interface in the 180° position.

FIG. 13D illustrates a cross-sectional representation of the external adjustment device being positioned on a patient's skin. FIG. 13D illustrates the permanent magnet of the implantable interface in the 270° position.

FIGS. 23-30 illustrate cross-sectional views of the driven magnet along with the acoustic or sonic indicator housing illustrating the rotational orientation of the magnet and the magnetic ball. Various states are illustrated as the magnet rotates in the counter-clockwise direction.

FIG. 47 illustrates an adjustable portion of a distraction device according to one embodiment.

FIG. 48 illustrates a cross-sectional view of the adjustable portion of FIG. 47 taken along the line 48-48 of FIG. 47.

FIG. 77 illustrates another embodiment of a locking joint.

FIG. 81A illustrates a partially exploded view of a coupler configured to house a strain gauge.

FIG. 81B illustrates the back surface of a plate that contains the strain gauge.

FIG. 84A is a cross-sectional view of a low friction seal system.

FIG. 84B is a cross-sectional view taken along the line B-B' of FIG. 84A.

FIG. 92 illustrates a partially exploded view of a j-shaped anchor according to another embodiment.

DETAILED DESCRIPTION OF THE ILLUSTRATED EMBODIMENTS

Figure 1:
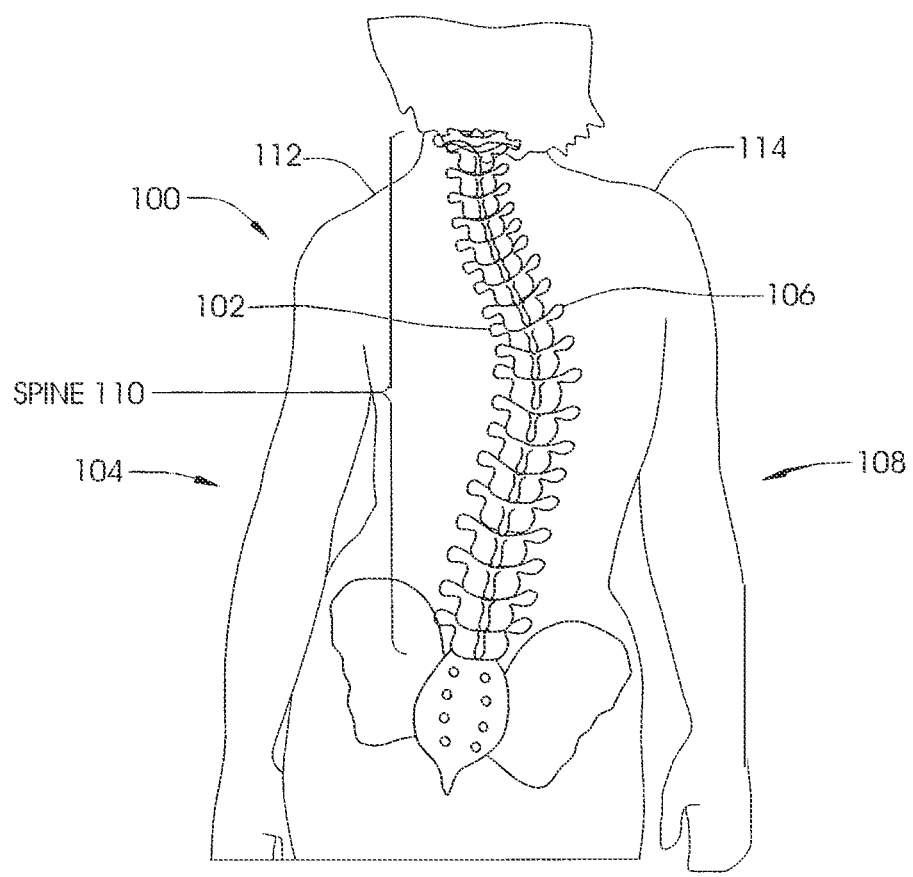
FIG. 1 illustrates the spine of a person with scoliosis.

FIG. 1 illustrates a patient 100 with scoliosis. The concave portion 102 of the spinal curve can be seen on the left side 104 of the patient 100, and the convex portion 106 can be seen on the right side 108 of the patient 100. Of course, in other patients, the concave portion 102 may appear on the right side 108 of the patient 100 while the convex portion 106 may be found on the left side 104 of the patient. In addition, as seen in FIG. 1, some rotation of the spine 110 is present, and unevenness between the left shoulder 112 and right shoulder 114 is seen.

Figure 2:
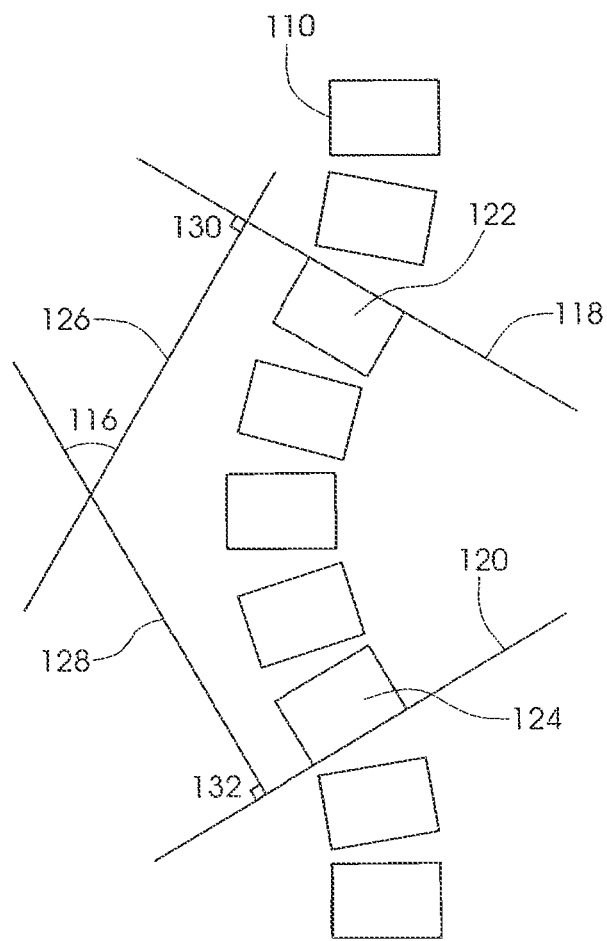
FIG. 2 illustrates the Cobb angle of a scoliotic spine.

FIG. 2 illustrates the Cobb angle 116 of a spine 110 of a patient with scoliosis. To determine the Cobb angle, lines 118 and 120 are drawn from vertebra 122 and 124, respectively. Intersecting perpendicular lines 126 and 128 are drawn by creating 90° angles 130 and 132 from lines 118 and 120. The angle 116 created from the crossing of the perpendicular lines 126 and 128 is defined as the Cobb angle. In a perfectly straight spine, this angle is 0°.

Figure 3:
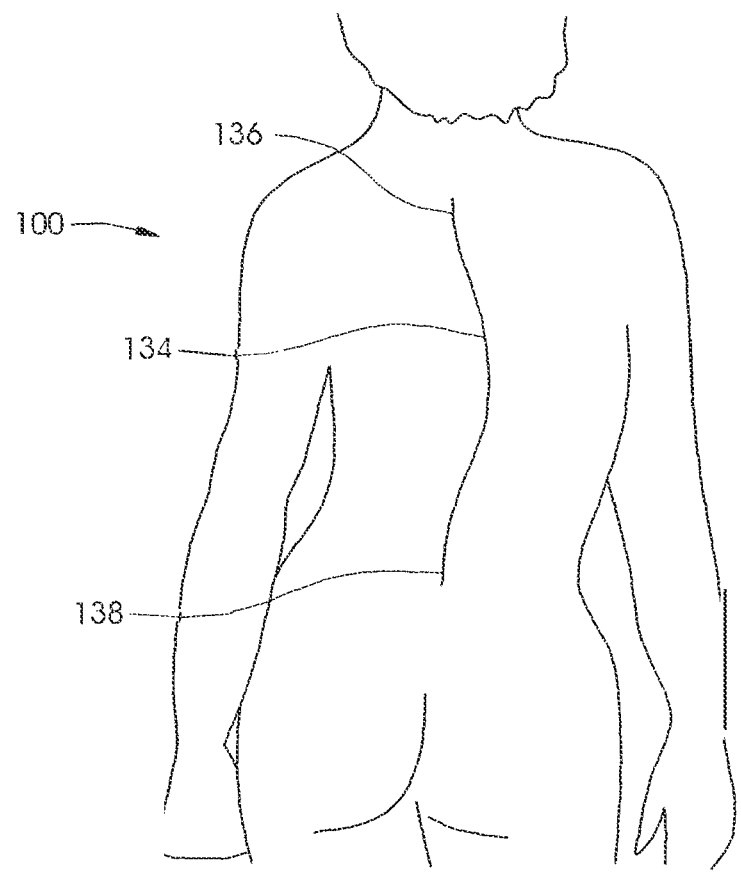
FIG. 3 illustrates the large incision made during prior art scoliosis fusion surgery.

In many Adolescent Idiopathic Scoliosis (AIS) patients with a Cobb angle of 40° or greater, spinal fusion surgery is typically the first option. FIG. 3 illustrates a long incision 134 formed in the patient 100 which is typically made during posterior scoliosis fusion surgery. This type of fusion surgery is known in the prior art. The long incision 134 extends between an upper end 136 and a lower end 138. The length of this incision 134 is longer than the length of the section of the vertebra to be fused. The actual length between the upper end 136 and the lower end 138 varies, depending on the size of the patient, and the extent of the scoliosis, but in AIS patients this length is significantly longer than 15 cm. More typically, it is longer than 25 cm.

Figure 4:
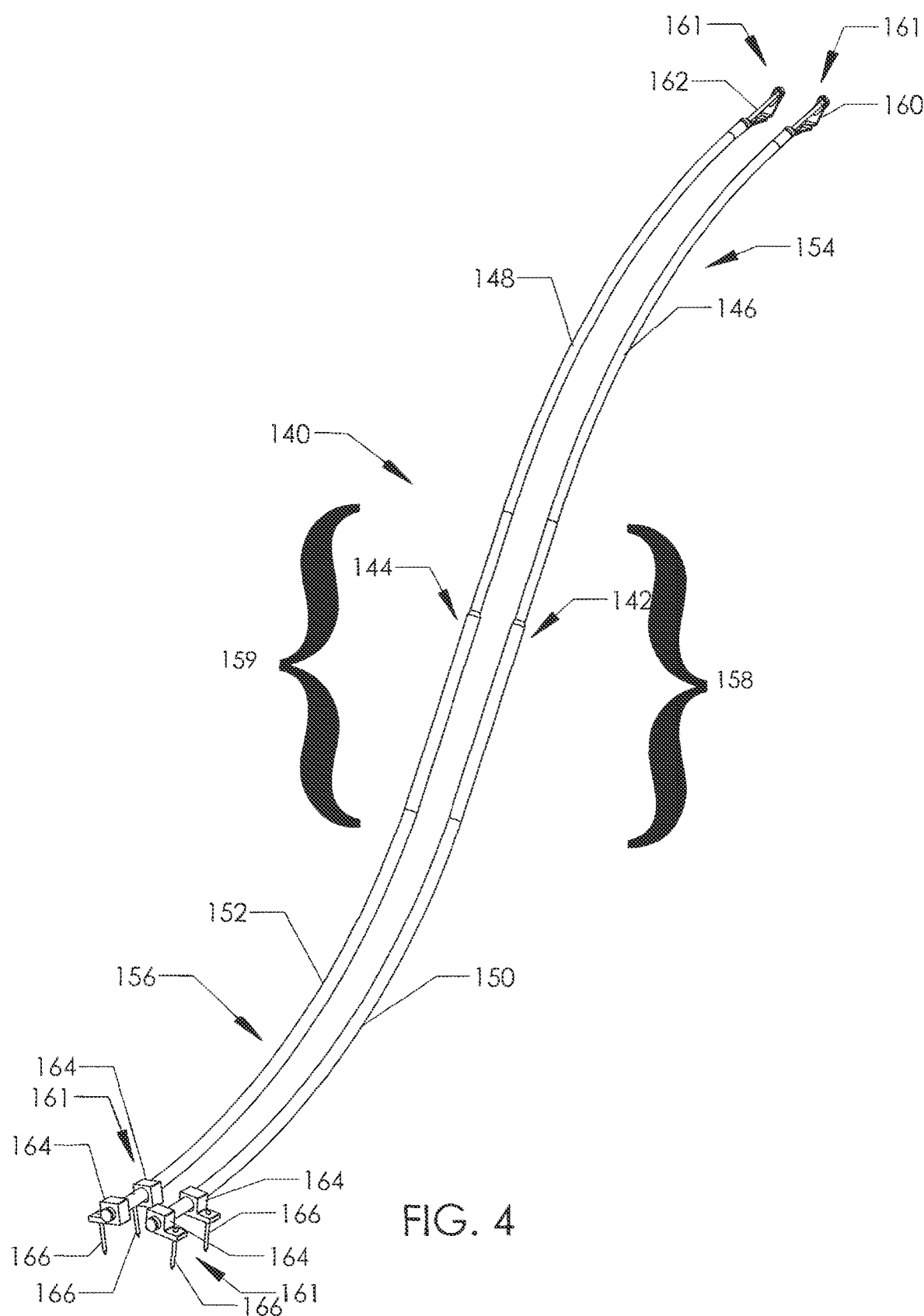
FIG. 4 illustrates a two rod embodiment of the present invention.
Figure 5:
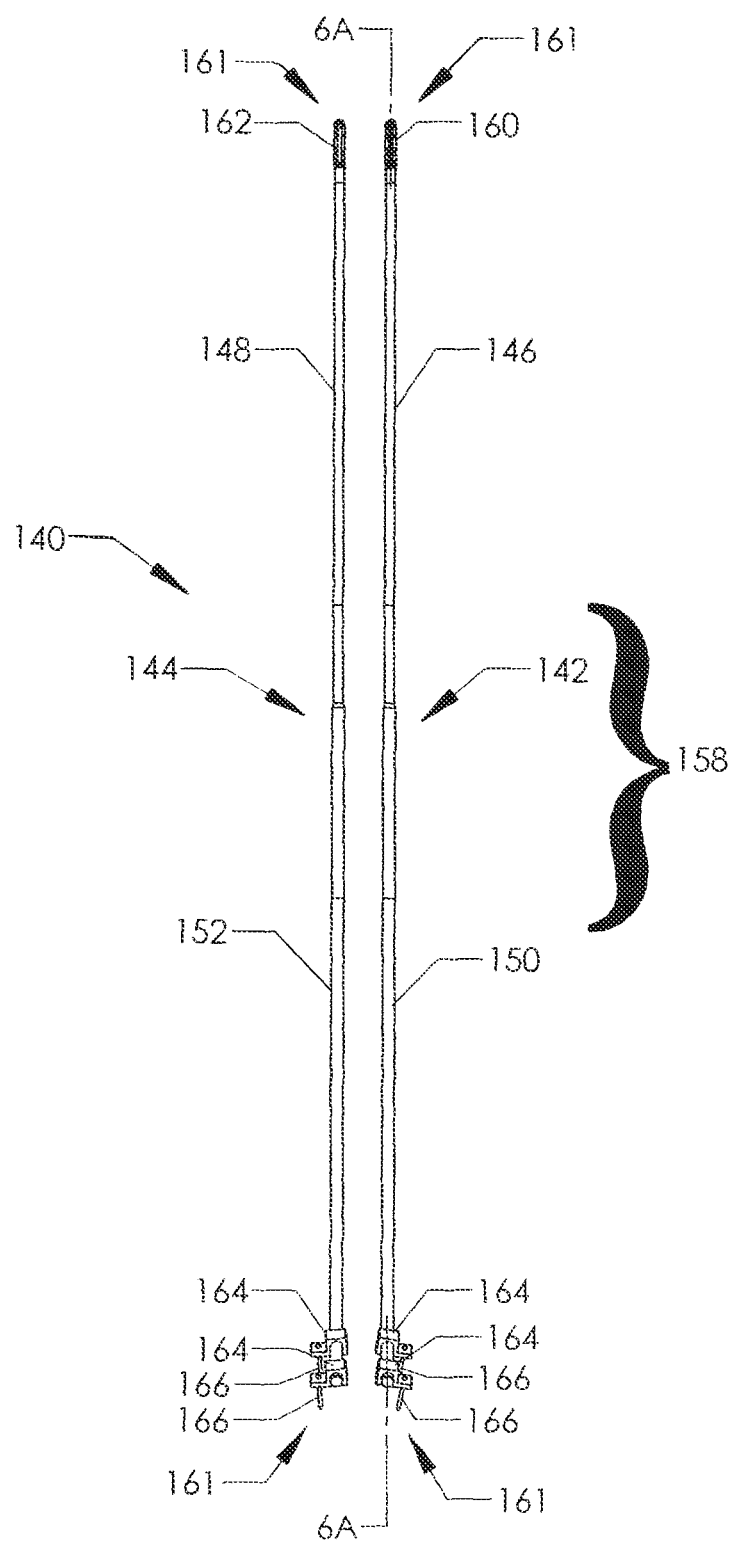
FIG. 5 illustrates a posterior view of the two rod embodiment of the present invention.

FIGS. 4 and 5 illustrate a distraction device 140 for treating scoliosis according to one embodiment of the invention. The distraction device 140, which is an implantable device, includes a first adjustable rod 142 and a second adjustable rod 144. For patient distraction, a first adjustable rod 142 is positioned on one side of the spine 110 while the second adjustable rod 144 is positioned on the opposing side of the spine 110. The spine 110 is omitted from view in FIGS. 4 and 5 for sake of clarity. While the distraction device 140 illustrated in FIGS. 4 and 5 comprises first and second adjustable rods 142, 144, it should be understood that in alternative embodiments, the distraction device 140 may include just a single adjustable rod 142 (the second adjustable rod 144 being omitted entirely) that is implanted within the patient.

Referring back to FIGS. 4 and 5, each adjustable rod 142, 144 includes a first elongate member 146, 148 and a second elongate member 150, 152, that are coupled together by an adjustable portion 158, 159. The adjustable portions 158, 159 include a variable overlapping region between the first elongate members 146, 148 and the second elongate members 150, 152 which allows for the non-invasive adjustment of the length of each adjustable rod 142, 144. In this particular embodiment, the first elongate elements 146, 148 are telescopically contained within hollow receiving portions of the second elongate elements 150, 152, and the adjustable portions 158, 159 are substantially straight. As illustrated, the adjustable rods 142, 144 have an upper curve 154 and a lower curve 156, which allow them to better conform to the natural front-to-back curve of the spine. For example, the upper curve 154 conforms to the normal kyphosis of the upper thoracic region and the lower curve 156 conforms to the normal lordosis of the lumbar region. In one aspect of the invention, the curved portions 154, 156 are bendable in order to better conform with a patient's specific spinal configuration. For the example, the curved portions 154, 156 may be made of a malleable or elastic-type material such that the surgeon can manually alter the particular shape of each adjustable rod 142, 144 to the specific needs of the patient. In a large number of scoliosis patients, especially adolescent idiopathic scoliosis patients, the scoliotic curve does not include the lower lumbar levels of the spine and so the lower curve 156 is not necessary. As explained above, the embodiment illustrated in FIGS. 4 and 5 represents a dual rod configuration. With this configuration, both rods 142, 144 are inserted through the same incision, and can be placed along the spine 110 on two opposite sides of the center line of the spine 110. Alternatively, each may be placed through its own, smaller incision.

Figure 37:
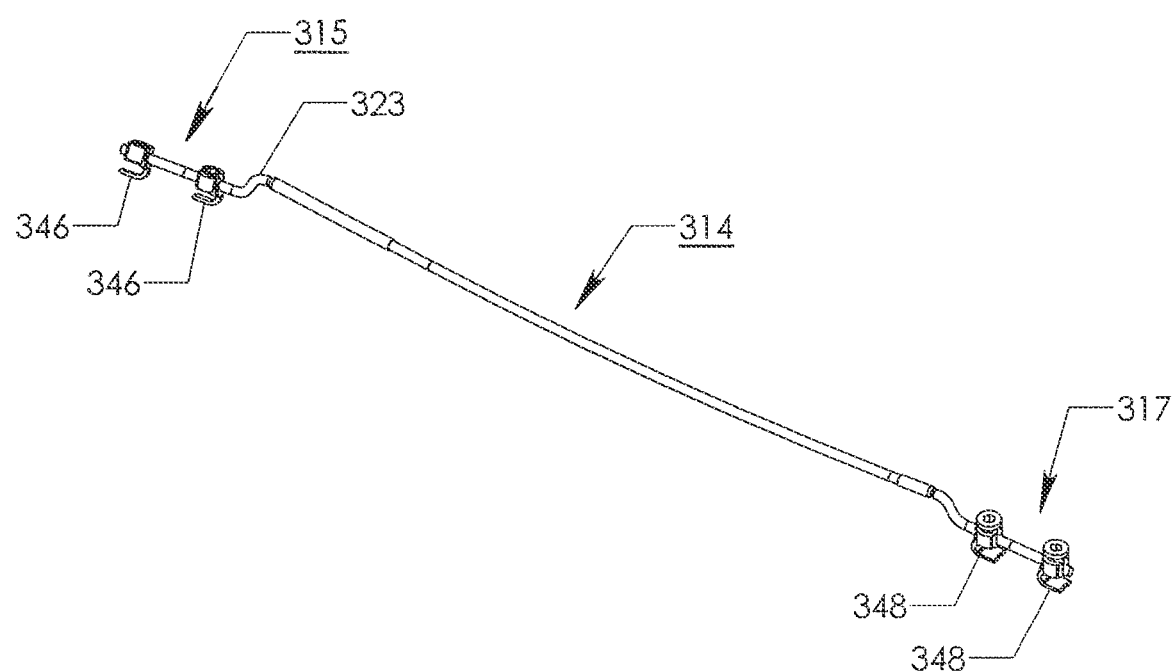
FIG. 37 illustrates a distraction device according to another embodiment. Anchors in the form of hooks are illustrated at opposing ends of the distraction rod.
Figure 38:
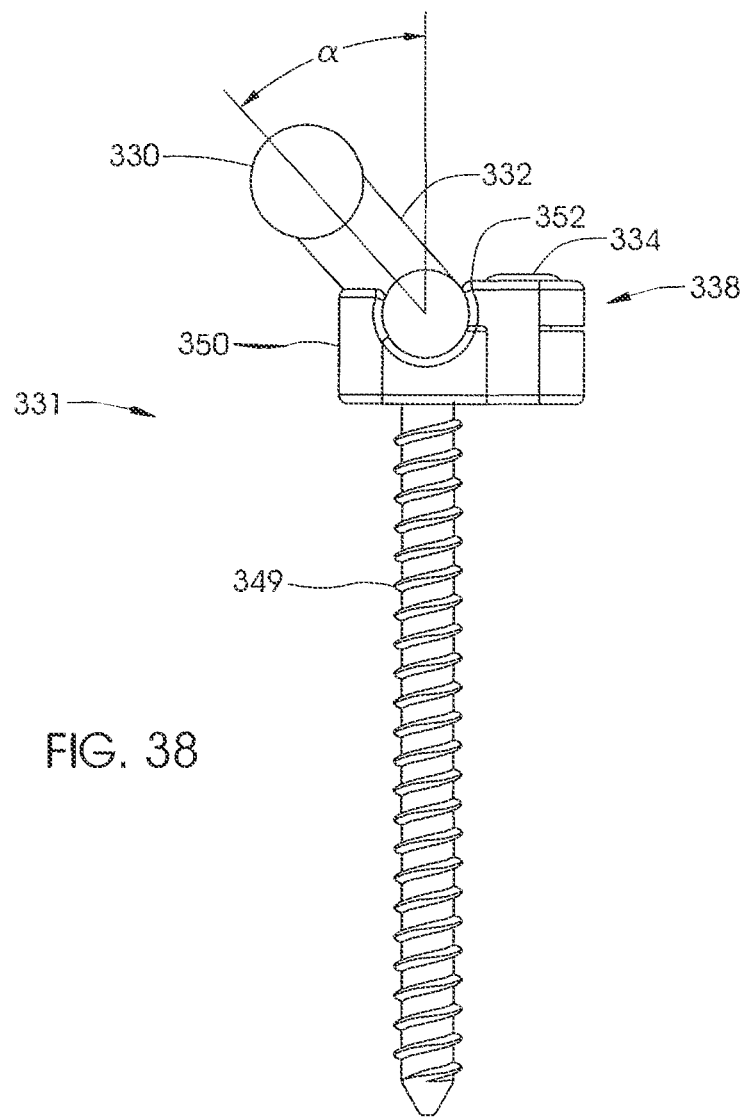
FIG. 38 illustrates a side view of a pedicle screw system used in accordance with the embodiment illustrated in FIG. 36.

Alternatively, a single adjustable rod version 142 can be used, preferably positioned on the concave side of the scoliosis curve. Yet another variation includes a single adjustable rod 142 that does not have either or both of the curves (i.e., curves 154 and 156 omitted). A straight adjustable rod 142 of this nature may be placed further lateral (to the side of the spine 110), and not necessarily have to hug the front-to-back contours of the spine 110 or the muscle covering the spine 110. In still another embodiment, the first elongate member (e.g., 146, 148) and the second elongate member (e.g., 150, 152) do not telescope in relation to one another, but rather are in parallel, at least along the adjustable portion 158, 159. The distraction device 140 is implanted in the patient 100 in order to straighten the scoliotic spine 110. For this reason, each end of the adjustable rods 142, 144 advantageously contains an anchor 161 that allows for securement to a location in the skeletal system. For example, the anchor 161 at either end may include a clamp for clamping to a skeletal structure. Alternatively, either end may comprise a bracket for securing to a section of bone with the use of a bone screw or pedicle screw. The embodiment in FIG. 4 illustrates a clamp 160, 162 at the upper end of the first elongate members 146, 148 and brackets 164 at the end of the second elongate members 150, 152. The brackets 164 can be secured to the second elongate members 150, 152 by a variety of methods, including set screws, welding, soldering, swaging, crimping or mechanical joints. Screws 166 secure the brackets 164 to bony structures, such as the vertebral bodies or the sacrum. The clamp 160, 162 can be used to clamp the distraction device 140 to a rib or the articulation of the rib with the vertebra at the facet. FIGS. 37 and 38, which are described in more detail below, illustrate alternative anchors 161 that may be used to secure the first elongate members 146, 148 or second elongate members 150, 152 to the skeletal structure.

The distraction device 140 is configured such that the adjustable portion(s) 158, 159 change at least one of the distance or force between the anchor or affixation points (e.g., at the spine or other anatomical structure) of the first elongate member(s) 146, 148 and the second elongate member(s) 150, 152. For example, the adjustable portion(s) 158, 159 may increase the length between the anchor or affixation points. Similarly, the adjustable portion(s) 158, 159 may increase the force (e.g., distraction force) between the anchor or affixation points. The adjustable portion(s) 158, 159 may alter both the distance and force at the same time.

Figure 6A:
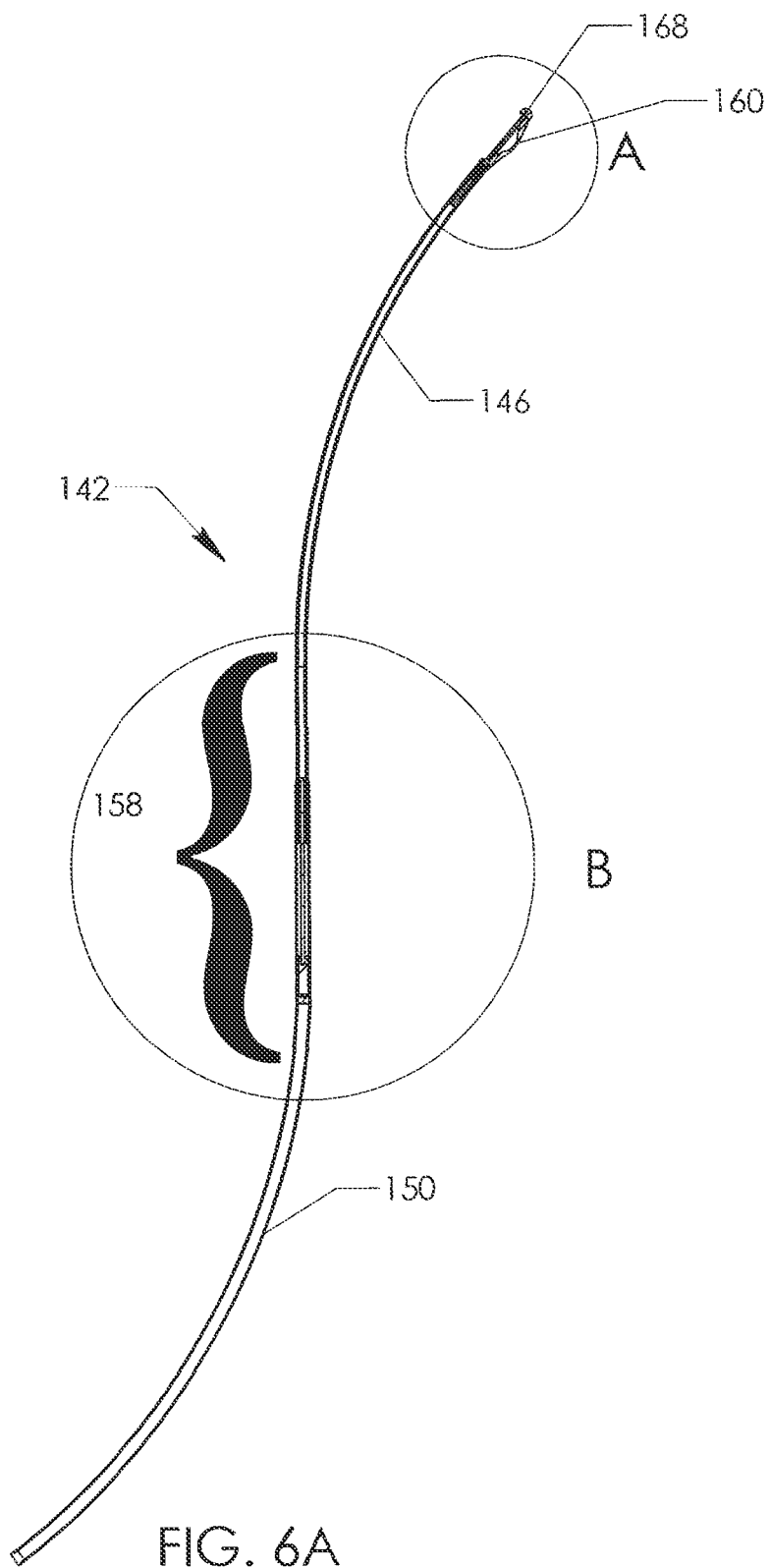
FIG. 6A illustrates a sectional view of a single rod in accordance with an embodiment of the present invention taken through line 6A-6A of FIG. 5.
Figure 7:
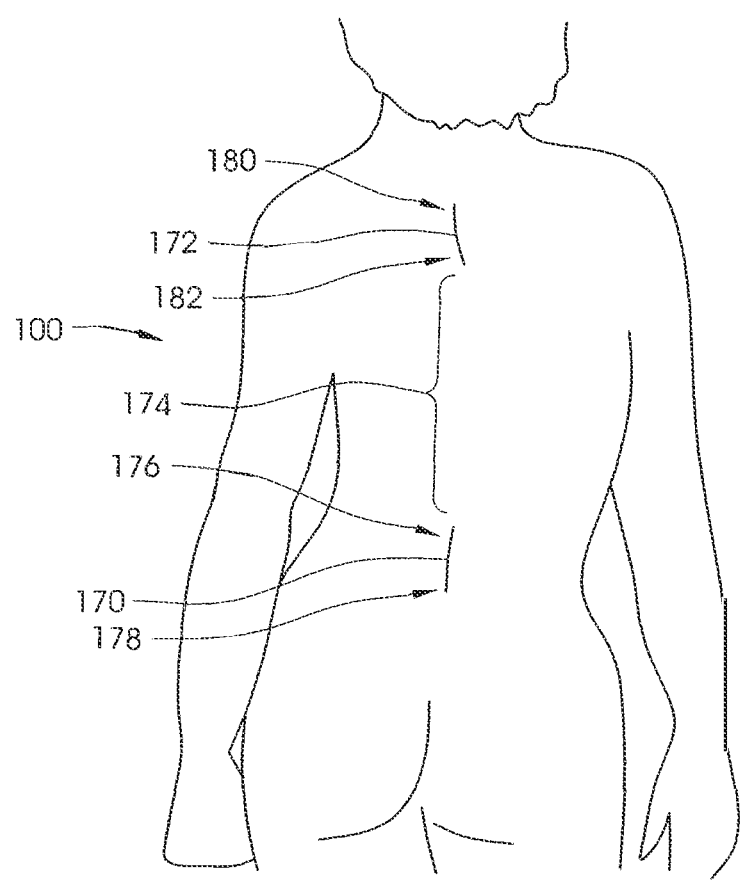
FIG. 7 illustrates the two smaller incisions which are possible using the system of the invention.

FIG. 6A illustrates a sectional view of the first adjustable rod 142 indicating the location of the adjustable portion 158 and the clamp 160. The tip 168 of clamp 160 is shaped to allow for blunt dissection of tissue, so that the adjustable rod 142 may be placed under the skin and pushed for much of the length of the spine 110, so that a large portion of the long incision 134 of FIG. 3 is not necessary. This allows for, for instance, alternative incision geometry, such as that illustrated in FIG. 7. As seen in FIG. 7, a lower incision 170 is made having an upper end 176 and a lower end 178 (for example, by a scalpel) and the first adjustable rod 142 is placed through the lower incision 170 and under the skin. Using a dissection technique, the first adjustable rod 142 is inserted under the skin along an intermediate area 174. The dissection technique may include the use of a scope (laparoscope, arthroscope, endoscope, or the like) and an additional dissecting tool, but usually can be done without these tools. The additional dissecting tool may include, for example, a tapered sheath, which is advanced over the first adjustable rod 142, dissecting the tissue along the way, while being visualized by scope, for example on a monitor. Alternatively, the additional dissecting tool may be a blunt dissecting tool, consisting of two fingers which can be spread apart and brought together, once again, while being visualized by the scope.

Once the clamp 160 of the first adjustable rod 142 (as seen in FIG. 6A) is advanced to the location near the anatomy to be clamped, an upper incision 172 is made having an upper end 180 and a lower end 182 and the location near the anatomy to be clamped is exposed by dissection. The clamp 160 is then actuated to clamp this anatomical structure, and additionally, the opposite end of the first adjustable rod 142 is secured, for example by a bone screw (e.g., pedicle screw) and bracket combination. The adjustment device of the adjustable rod 142 (to be described later) may be adjusted prior to the securement of either end of the first adjustable rod 142, so that the desired length is achieved. After securement of both ends, first adjustable rod 142 may then be adjusted in order to adjust the distraction distance or distraction force between the two locations in the anatomy to a desired amount. In one aspect of the invention, the length of the first adjustable rod 142 may first be adjusted manually by the physician without using the remotely-operated adjustment device as described herein. For example, the initial length of the adjustable rod 142 may be manually set by the physician by pushing or pulling the first and second elongate members 146, 150 relative to one another. Alternatively, the length of the adjustable rod 142 may be adjusted by trimming or removing a portion of the length of the adjustable rod 142.

By having the physician adjust the length of the adjustable rod 142 during initial placement, a distraction force may be applied to the spine 110 without having to use any displacement distance or force that is provided by the remotely-operated adjustment device. For example, there typically is a limited degree of movement that is provided by the remotely-operated adjustment device. When the physician applies a first or initial distraction force upon implantation, the budget of available displacement for the remotely-operated adjustment device is saved for later adjustments.

Still referring to FIG. 7, the two incisions are then closed using standard techniques. As described, the single long incision is now replaced by two, shorter incisions 170, 172, whose combined length when added together is less than the length of the single long incision illustrated in FIG. 3. For example, lower incision 170 and upper incision 172 each has a length of less than 15 cm, and preferably, each has a length of less than 7.5 cm, and more preferably, less than 5 cm.

Figure 8:
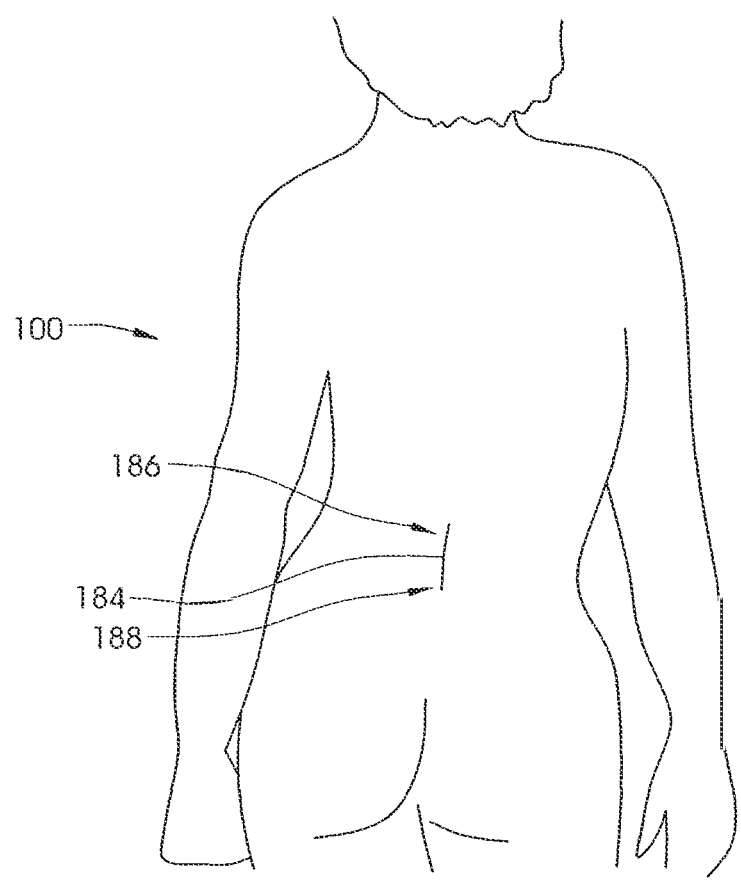
FIG. 8 illustrates a single small incision which is possible using another embodiment of the system of the invention.

An optional magnetic clamping device is illustrated in FIG. 6B, which allows for the entire procedure to be done under a single short incision 184, as seen in FIG. 8. As previously described, a single short incision 184 having an upper end 186 and a lower end 188 is made (for example, by a scalpel) and the first adjustable rod 142 is placed through the single small incision 184 and under the skin. Using a dissection technique, the first adjustable rod 142 is inserted under the skin towards the upper target location. As previously described, this dissection technique may include the use of a scope (laparoscope, arthroscope, endoscope, or the like) and an additional dissecting tool. Once the clamp 160 of the first adjustable rod 142 is advanced to the location near the anatomy to be clamped, one or more dissecting tools and a scope are used to expose the target location, for example a rib or facet articulation. Referring to FIG. 6B, the magnetically-operated clamp 160 includes a first finger 190 and a second finger 192. The first finger 190 is permanently coupled to first elongate element 146 while the second finger 192 is longitudinally adjustable in relation to first finger 190, so that gap 194 may be increased or decreased in response to actuation. A closure device 198 is operated by an external adjustment device such as that illustrated in FIGS. 10-12 in order to increase or decrease gap 194, and therefore open or close clamp 160. As will be described, the clamp 160 is magnetically adjustable, and so the clamping process may be performed non-invasively, therefore making a second incision unnecessary.

The magnetically-operated clamp 160 may be particularly useful if, as expected, the evidence of the ineffectiveness of braces becomes stronger, many physicians will be searching for less invasive procedures to treat scoliosis. Patients will demand that the procedures be as minimally invasive as possible, and one of the big elements in their decision to undergo surgery is the size of the incision, and thus size of the scar, both during and after healing. AIS patient whose Cobb angles are greater than 40° are more likely to be treated with fusion surgery, but patients in the 20° to 40° range may be treatable using fusionless methods which harness the growing power of their spine. Currently, it is known that female AIS patients who have not yet reached menarche (the first menstrual period) are more likely to have a curve that will progress further. Additionally, AIS patients whose age is younger are more likely to have their curves progress. One or more "scoliosis genes" have recently been discovered, and work is being done to create a genetic test that allows identification of a patient whose curve is very likely to progress beyond 40° at a time when her Cobb angle is less than 40°, for example 20°. Because braces are a questionable option, it is expected that a minimally invasive, non-fusion procedure will be the procedure of choice for these patients. Though the incision 184 in FIG. 8 is depicted as a vertical incision, alternatively, it may be made horizontally. For example, the horizontal incision may be made so that it is just below and parallel to the "bikini line", allowing the resulting scar to be more concealed. This could also be done with incision 170 in FIG. 7.

Figure 10:
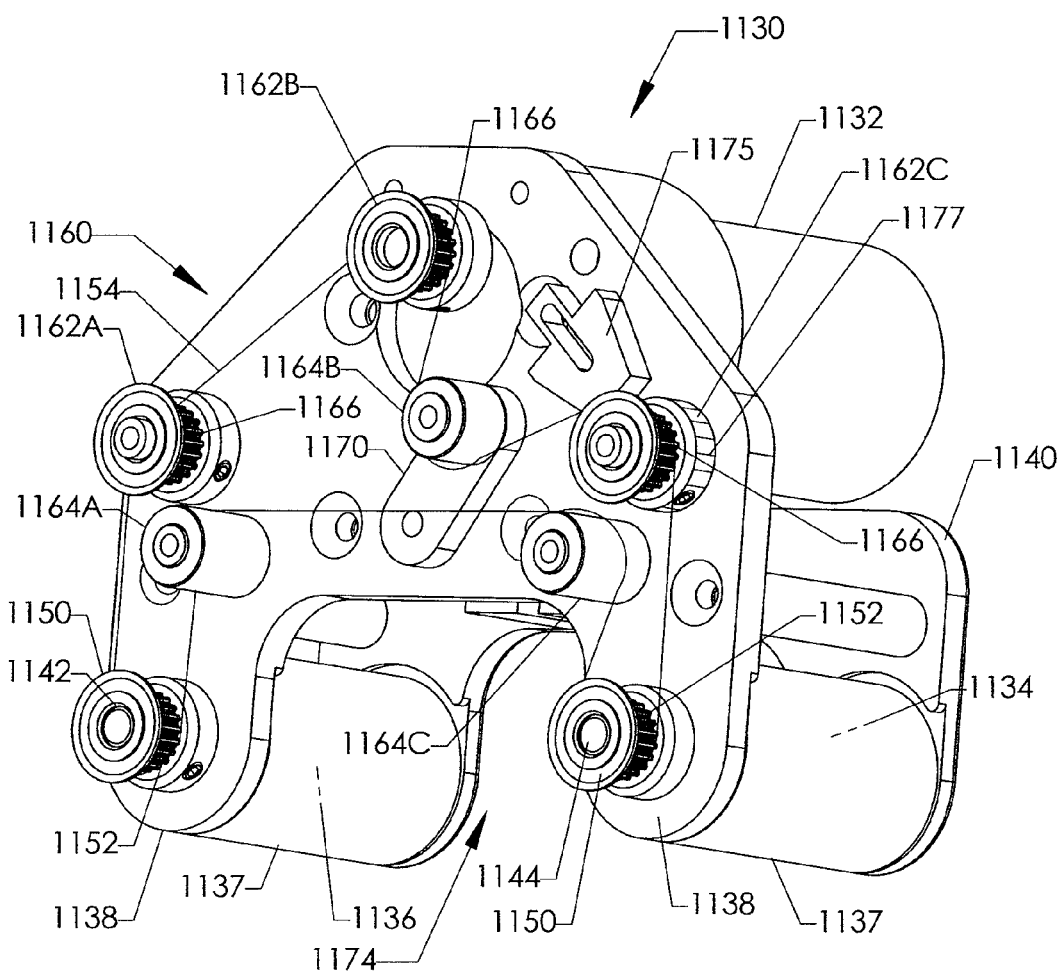
FIG. 10 illustrates a perspective view of an external adjustment device according to one embodiment. The outer housing or cover is removed to illustrate the various aspects of the external adjustment device.
Figure 11:
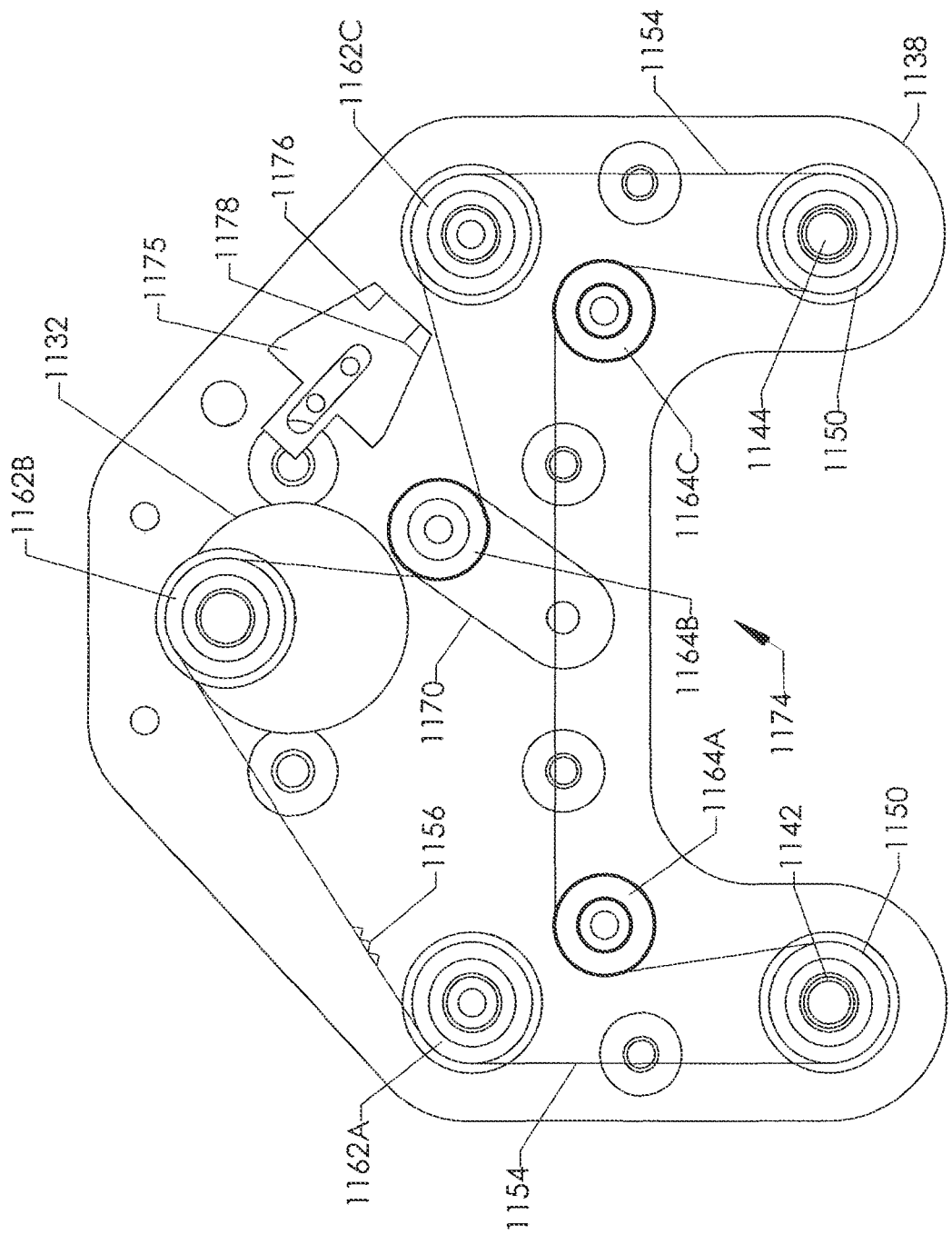
FIG. 11 illustrates a side or end view of the external adjustment device of FIG. 10.
Figure 12:
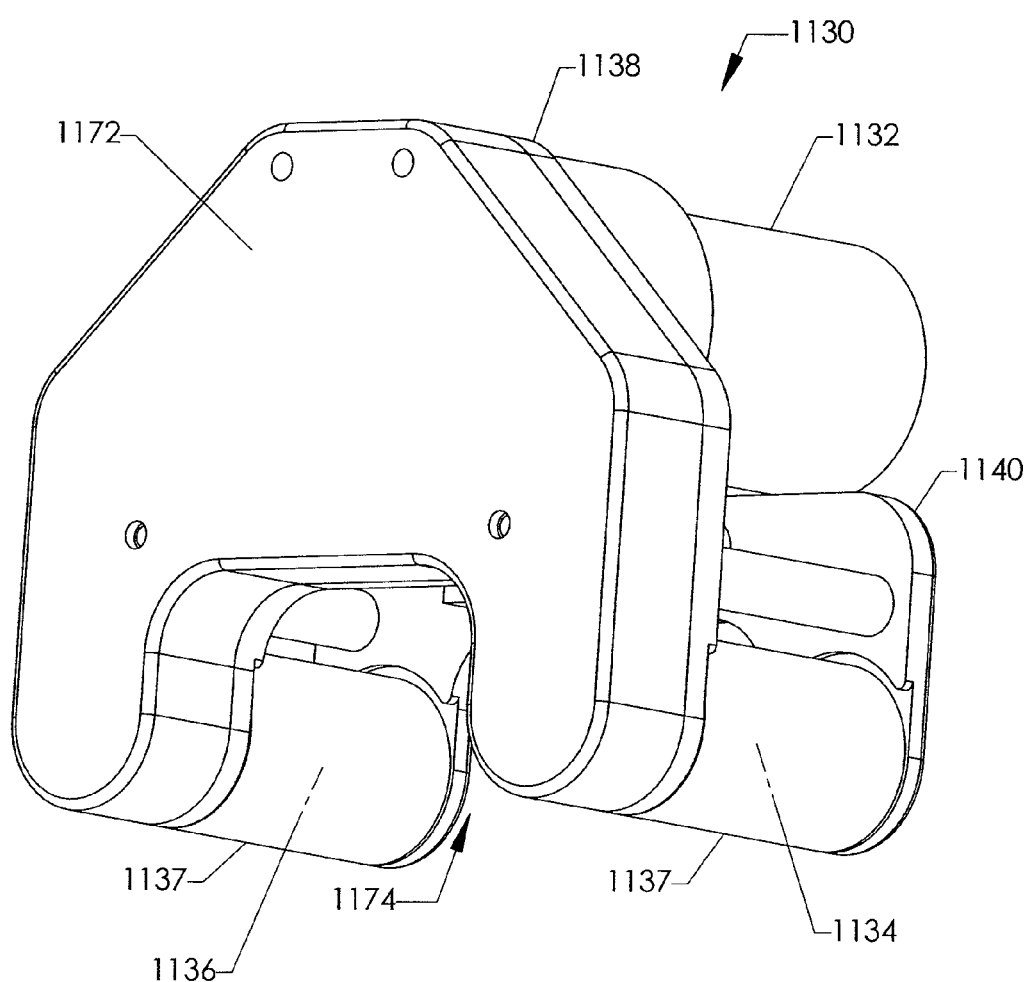
FIG. 12 illustrates a perspective view of an external adjustment device of FIG. 10 with the outer housing or cover in place.

Returning to FIG. 6B, closure device 198 includes a cylindrical magnetic member 200, which can be activated by magnetic coupling with an external adjustment device (such as external adjustment device 1130 illustrated in FIGS. 10-12). Though configurations may vary for this closure device 198, in this particular embodiment, magnetic member 200 is a hollow rare earth magnet, preferably Neodymium-Iron-Boron. As seen from an end view in FIG. 6E, the magnetic member 200 has a threaded insert 202 having a female thread so that when the magnetic member 200 rotates, the threaded insert 202 rotates in unison. Magnetic member 200 is a permanent magnet 217 having a north pole 204 and a south pole 206. Magnetic member 200 is preferably coated with a material, for example Parylene, phenolic resin or Gold, which is non-magnetic, but protective and biocompatible in a body implant application. In certain embodiments, the individual Nd—Fe—B magnets are enclosed within a stainless steel casing/housing or various layers of nickel, gold or copper plating to protect the corrosive Nd—Fe—B material from the environment inside the body. In other embodiments, other magnetic materials may be used, including SmCo (Samarium Cobalt), which is typically available as $SmCo_5$, or $SmCo_{15}$, $Sm_2Co_{17}$, or AlNiCo (Aluminum Nickel Cobalt). In still other embodiments, Iron Platinum (Fe—Pt) may be used. Iron platinum magnets achieve a high level of magnetism without the risk of corrosion, and may possibly preclude the need to encapsulate. In yet other embodiments, the permanent magnets 217 on the implantable interface may be replaced by magnetically responsive materials such as Vanadium Permendur (also known as Hiperco).

It should be noted that magnetic member 200 can also be hermetically sealed within the first elongate element 146. When the external adjustment device 1130 is operated, it applies a moving magnetic field, which causes magnetic member 200 to rotate. Attached to the second finger 192 is a threaded rod 210 which threadedly engages the female thread of the threaded insert 202. When the magnetic member 200 is rotated by the external adjustment device 1130 in a first direction, the threaded rod 210 moves in a first longitudinal direction 212, causing the second finger 192 to move away from the first finger 190, and the gap 194 to open. There may also be a manual adjustment mechanism on the clamp 160 so that the clamp 160 may be opened outside the patient, in preparation for the procedure. When gap 194 is adjusted to be wider than the anatomical structure, for example rib, around which the clamp 160 is to be secured, then through visualization by the scope and manipulation with the dissecting tools, the clamp 160 is placed over the rib, so that rib is contained in cavity 196. At this point the external adjustment device 1130 is operated so that it turns the magnetic member 200 in the opposite direction causing the threaded rod 210 to move longitudinally in a second direction 214, and the two fingers 190, 192 close around the rib. The gap 194 is now smaller than the width of the rib, and thus, the clamp 160 is secure. If the implant is to be removed at a later date, the magnetic clamp mechanism may also be used to remove the implant without having to make an incision adjacent the clamp.

Figure 6C:
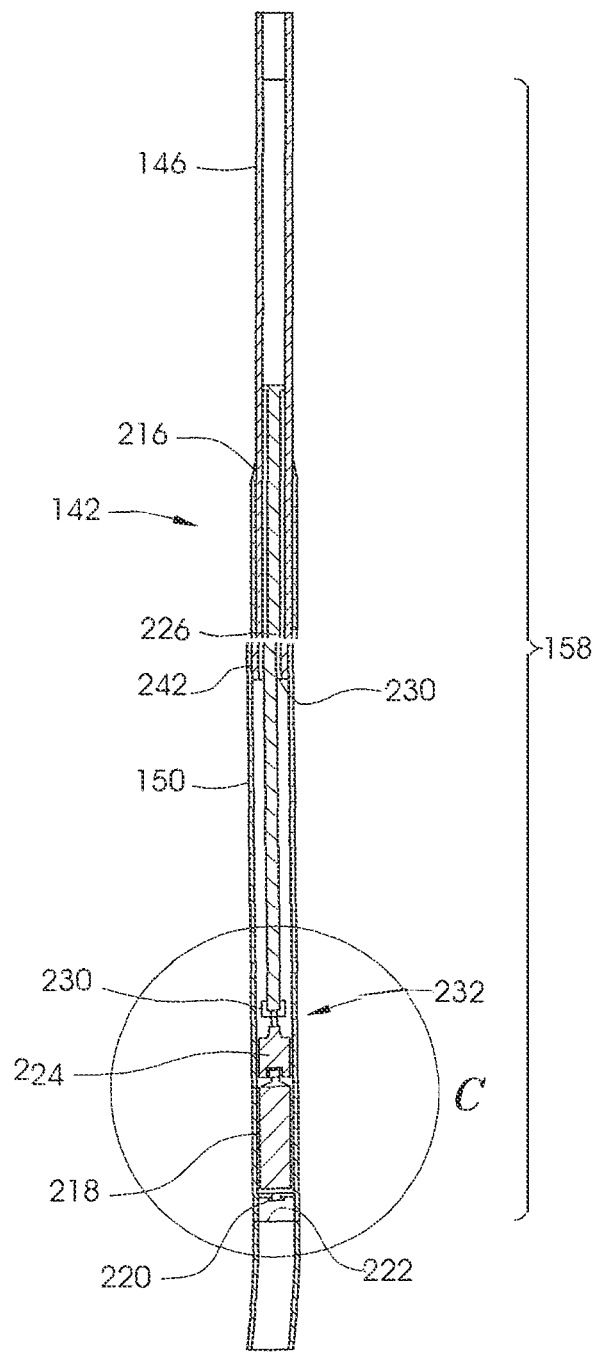
FIG. 6C illustrates a detailed view of portion B of FIG. 6A in accordance with an embodiment of the present invention.
Figure 6F:
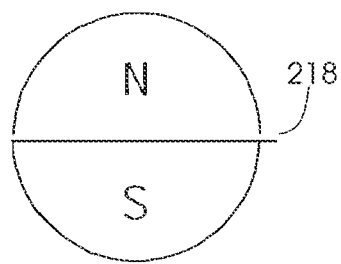
FIG. 6F illustrates an end view of a cylindrical magnetic member for adjusting a distraction device in accordance with an embodiment of the present invention.
Figure 6D:
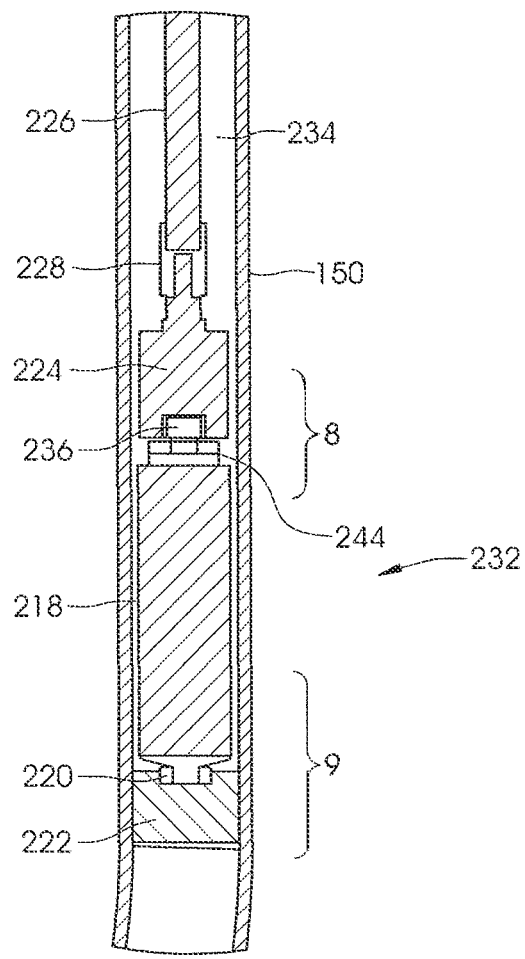
FIG. 6D illustrates a detailed view of portion C of FIG. 6C in accordance with an embodiment of the present invention.

FIG. 6C illustrates a sectional view of the adjustable portion 158 of the first adjustable rod 142. FIG. 6D illustrates a detail of the adjustment device 232. The first elongate element 146 is telescopically contained within the second elongate element 150. The cross-sectional shapes of the first elongate element 146 and the second elongate element 150 may be circular or non-circular, so that they cannot rotate with respect to each other (for example, a keyed configuration). One or both of the elongate elements 146, 150 may contain ribs along the cross section of the adjustable portion 158 in order to minimize contact surface area between the first elongate element 146 and the second elongate element 150 and thus lower frictional resistance. Beveled end piece 216 attached to the second elongate element 150 may serve two purposes. First, it allows for smooth insertion and no catching in tissue when the first adjustable rod 142 is inserted under the skin. Second, it serves as a low friction dynamic seal over the first elongate element 146. Magnetic element 218 comprises a cylindrical permanent magnet which is poled as shown in FIG. 6F. Alternatively, magnetic element 218, may be made from any of the materials described for magnetic member 200 in FIG. 6B. Magnetic element 218 is rotatably secured to an inner cavity 234 of second elongate element 150 by a housing, in this case an acoustic housing 222. A ball bearing 220 is illustrated at one end of the magnetic element 218 in order to reduce rotational friction. A second ball optional bearing (not shown) can be included on the opposite end of the magnetic element 218. Magnetic element 218 is rotated by an external adjustment device 1130 which produces a moving magnetic field.

Figure 6G:
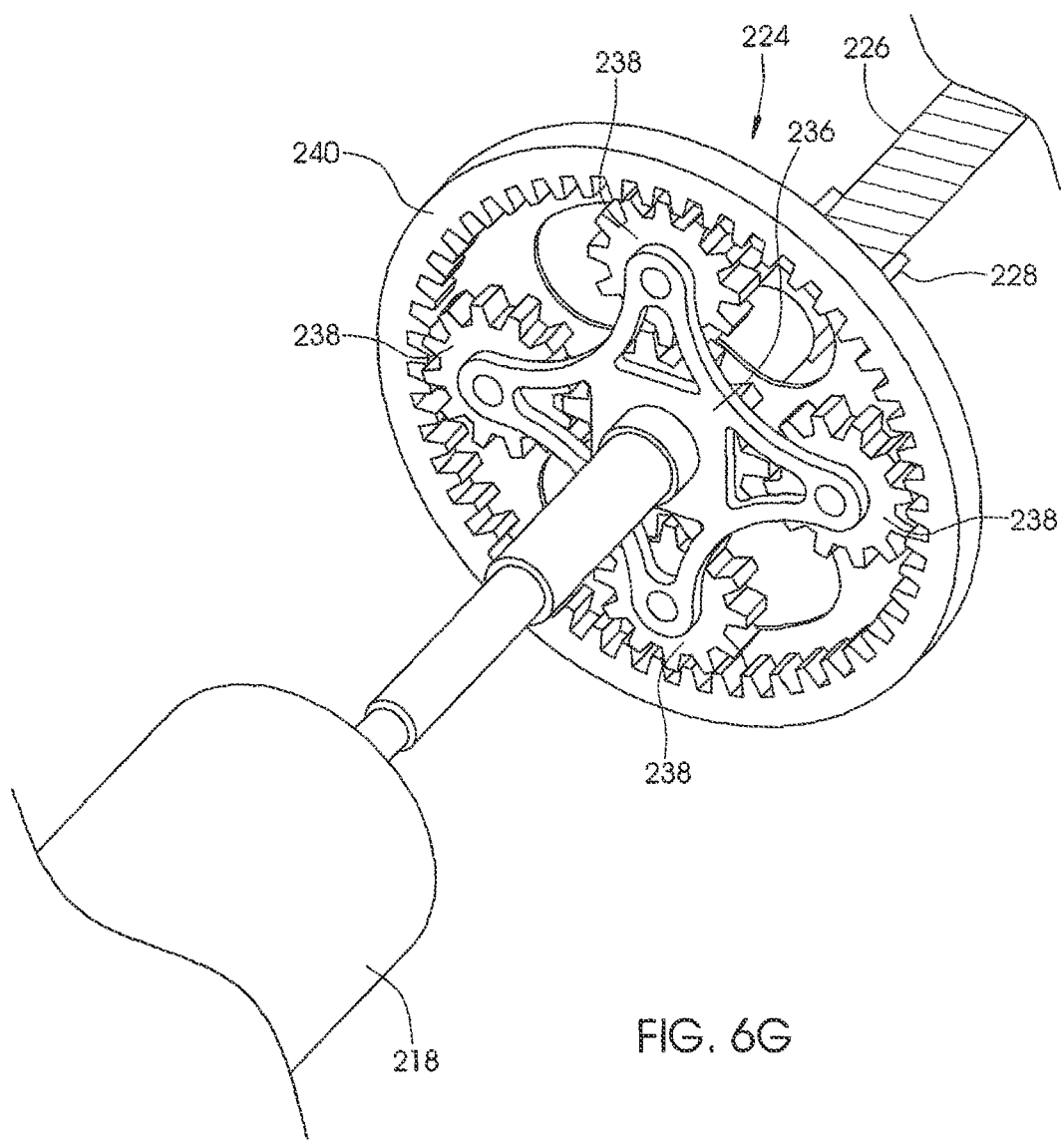
FIG. 6G illustrates the internal planetary gearing of portion of FIG. 7C in accordance with an embodiment of the present invention.

As seen in FIG. 6D, the magnetic element 218 is coupled to a planetary gear set 224, for example, having a 4:1, 16:1 or 64:1 gear reduction, or greater. The purpose of the gear reduction is two-fold. First, it allows the distraction device 140 to be adjusted with a smaller input torque requirement. Second, it adds precision to the adjustment, because a larger number of turns of the magnetic element 218 are required for each adjustment interval. Planetary gear set 224 is shown in detail in FIG. 6G. Sun gear 236 is turned in a one-to-one fashion by the rotation of the magnetic element 218. Sun gear 236 engages a plurality of planetary gears 238 (in this case, four are pictured). Planetary gears 238 engage and turn ring gear 240 which is attached to a lead screw 226 via a coupling 228. The gear ratio is the number of teeth in the ring gear 240 divided by the number of teeth in the sun gear 236. For example if the ring gear 240 has four times as many teeth as the sun gear 236, then the gear ratio is 4:1. In this case, only 25% of the torque is required to drive the lead screw 226 as would have been required to drive it directly, ignoring the variance due to frictional factors. As lead screw 226 turns, it threadedly engages with female thread 230, disposed within end 242 of first elongate element 146. The pitch of lead screw 226 threads is preferably very fine pitch, for example, 40 to 120, or more specifically 80 to 100 threads per inch, in order to minimize friction between the lead screw 226 and the female thread 230, and thus, minimize the required torque. The materials of the lead screw 226, the rods and other components may be made from non-magnetic, implantable materials such as Titanium or Titanium alloys such as Titanium-6% Al-4% V, although they may also be made from other magnetic materials such as stainless steel.

When the magnetic element 218 is rotated by the external adjustment device 1130, the drive train or drive element that is operatively coupled to the rotatable magnetic element 218 drives the lead screw 226 which changes the length of the adjustable portion 158 of the adjustable rod(s) 142, 144. Rotation of the magnetic element 218 in a first direction increases the distance between the anchors 161 located on opposing ends of the adjustable rod(s) 142, 144. Conversely, rotation of the magnetic element 218 in a second (opposing) direction decreases the distance between the anchors 161 located on opposing ends of the adjustable rod(s) 142, 144.

Currently, devices such as the VEPTR, which can be surgically adjusted, are used for early onset scoliosis patients, and their adjustability is used for the purpose of keeping up with the dimensional growth of the patient. It is a purpose of the present invention to create a device which can be non-invasively adjusted in early onset scoliosis patients, but additionally, in adolescent idiopathic scoliosis (AIS) patients and even adult scoliosis patients. The main purpose for the adjustment in AIS patients is to maintain a distraction force, which in a fusionless growing spine serves to steer growth in the desired manner. Currently, in fusionless surgery, non-adjustable distraction devices are actuated at very high distraction forces, because the physicians know that over time, growth and/or changes within the tissue, will cause this distraction force to lessen, possibly becoming less effective with time. Because of these high distraction forces, it is not uncommon to have rods break inside the patient, or for bone screws to become dislodged, due to the high stresses. It has been contemplated that the high forces that have been measured in some distraction devices of well over 100 pounds, are not necessary at any given time to provide correct growth guidance, and that a distraction force of below 45 pounds, and even as low as 20 pounds may be effective in maintaining the desired growth of the spine, especially the unfused spine. That is, as long as this force can be maintained, which is not currently possible in prior art devices without surgical intervention. The present invention allows this lower force to be continually maintained through non-invasive adjustment. The benefit is that lower stresses can be maintained on the bone screws, clamps, and other attachment means as well as the rods themselves, making for a more reliable and durable system. In addition, through the identification of an optimum distraction force, this desired force can be maintained throughout the treatment of the patient post-surgery, by frequent non-invasive adjustments, which can be performed in a doctor's or nurses office, by a physician or non-physician medical personnel, or even by the patient herself at home. In addition, by incorporating an optional force transducer, as part of the distraction device, that is read telemetrically, each adjustment can be done to the precise desired distraction force. Additionally, a slip clutch 244, is in line with the magnetic element 218 can be pre-adjusted by the physician, or during the manufacturing process, so that during each adjustment, the adjustment stops when a critical torque (corresponding to the maximum desired distraction force) is reached. For example, the maximum desired distraction force may be set at 45 pounds. The slip clutch 244 is illustrated in FIG. 6D as being located between the magnetic element 218 and the planetary gear set 224, but it is within the scope of the invention that the slip clutch 244 may be located at any other step along the torque transmission chain.

Figure 9:
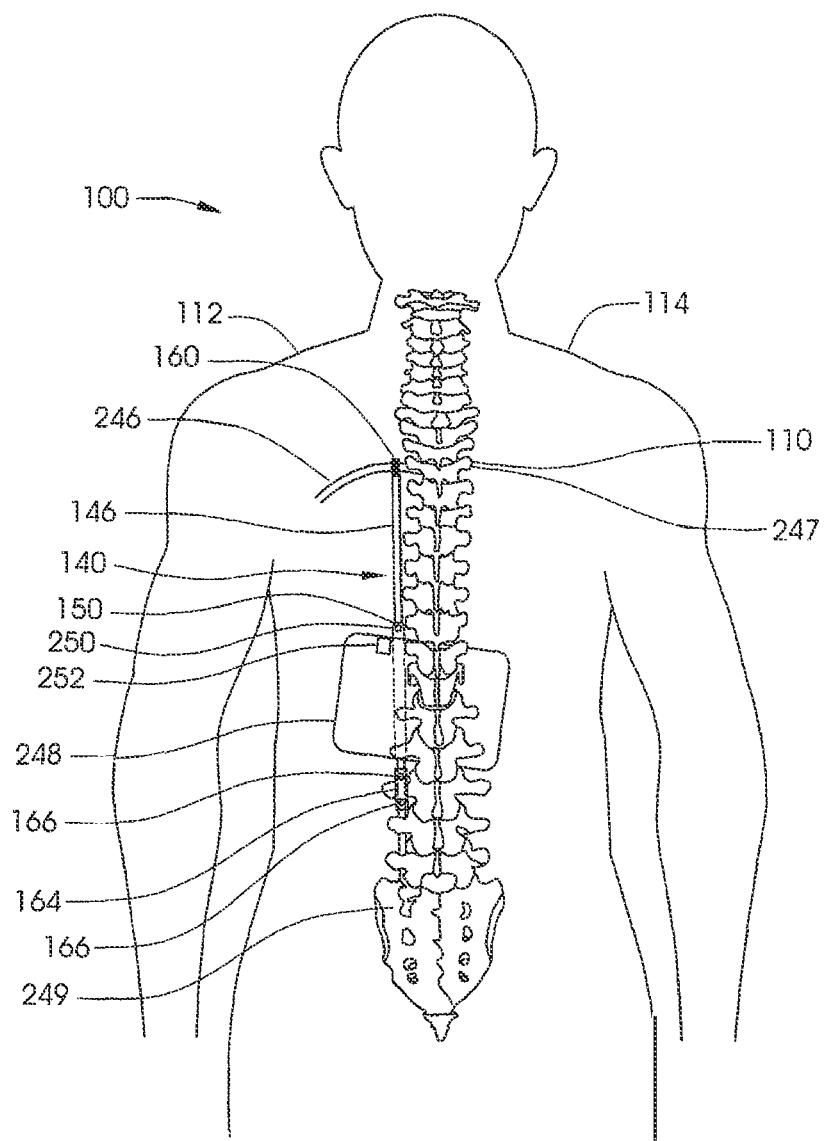
FIG. 9 illustrates a patient with an implanted distraction device during a non-invasive adjustment procedure.

FIG. 9 illustrates a patient 100 with a distraction device 140 implanted on the left side of the spine 110. Though the spine 110 is visible in FIG. 9 for reference, FIG. 9 is actually meant to depict a non-invasive adjustment procedure, and so the patient 100 would typically have all incisions healed and could be wearing clothes. The clamp 160 of the distraction device 140 is secured to a rib 246 at its articulation with a thoracic vertebra 247. A bracket 164 is secured, in this case to a lumbar vertebra with screws 166. Alternatively, the bracket 164 may be secured, for example, to the sacrum 249. A radio frequency identification (RFID) chip 250 is optionally disposed on the second elongate element 150 of the distraction device 140 in accordance with an embodiment of the present invention. An RFID (radio frequency identification) chip 250 may be implanted in a patient during the implantation of the distraction device 140. In certain embodiments, the RFID chip 250 may be implanted subcutaneously in a known location, such as a location near the distraction device 140. In other embodiments, the RFID chip 250 may be located on or within the distraction device 140. An external adjustment device 248 is depicted after being placed against the back of the patient 100. Upon the implantation of the distraction device 140 or after surgical recovery, the external adjustment device 248 stores patient information on the RFID chip 250, including the current size or setting of the distraction device 140, the amount adjusted, the serial number of the distraction device 140, the date of the implantation procedure, patient name, distraction force, adjustment torque, and identification. During subsequent adjustment procedures, the external adjustment device 248 may read the RFID chip 250 to determine information related to the patient, such as the current size or setting of the distraction device 140. At the end of the adjustment procedure, the external adjustment device 248 may store updated patient information, including the size or setting of the distraction device 140, to the RFID chip 250. An RFID antenna 252 in the external adjustment device 248 may be used to power the RFID chip in order facilitate the read and write functions.

Several techniques may be used to determine the adjustment setting (current size, distraction force or condition) of the distraction device 140. For example, the adjustment setting may be determined indirectly by the number of rotations of one of the rotating components of the external adjustment device 248. In certain embodiments, the adjustment setting may be determined by the number of rotations of some dynamic component of the adjustable portion 158 of the distraction device 140, by the number of rotations of any one of the gears or shafts of the distraction device 140, or by the number of rotations of the magnetic element 218. In other embodiments, a feedback mechanism, such as a Hall effect device (two additional magnets that move axially in relation to each other as the lead screw 226 rotates and therefore as the distraction device changes its condition), may be used to determine the current adjustment setting of the distraction device 140. A strain gauge or force transducer disposed on a portion of the distraction device 140 may also be used as an implantable feedback device. For example, the strain gauge may be able to communicate wirelessly the actual distraction force applied to the spine by the distraction device 140. A wireless reader or the like (that also can inductively power the strain gauge) may be used to read the distraction forces. One exemplary strain gauge sensor is the EMBEDSENSE wireless sensor, available from MicroStrain, Inc. of Williston, Vt. 05495. The EMBEDSENSE wireless sensor uses an inductive link to receive power form an external coil and returns digital stain measurements wirelessly.

In still other embodiments, an optical encoder feedback mechanism may be used by placing an optical encoder in line with one of the rotating components of the adjustable portion 158 of the distraction device 140. A through-the-skin optical encoder is even envisioned that shines a light through the skin and fat and counts successive passes of one or more reflective stripes on the specific rotatable component. In other embodiments, the external adjustment device 248 may include an audio sensor to determine the current adjustment setting of the distraction device 140. For example, the sensor may listen to the cycling sound of gearing, thus giving feedback information on the amount of total adjustment. An additional acoustic feedback device is discussed below.

It should be understood that any of the materials of the distraction device 140 can be made from radiopaque materials, so that the position, condition or alignment of the components may be seen during the initial surgical procedure, or during the subsequent adjustment procedures, by use of X-ray. For example, a circumferential notch or alternatively a circumferential bump disposed on the first or second elongate members 148, 146 may be used so that the distance between this notch or bump and some portion of the second elongate members 150, 152 can be measured easily via an X-ray.

It is conceived that the adjustment procedures would preferably take place every three to four weeks in the physicians' clinic. The adjustment may be done by an orthopedic surgeon, but because of the relative ease of the procedure because of the feedback capabilities of the system, the procedure may be done by a nurse practitioner, a physicians' assistant, a technician, or any other non-M.D. personnel. It is even conceived that the patient may have an external adjustment device 1130 at home and be able to adjust themselves at an even more frequent rate. The external adjustment device 1130 can be designed to transmit stored information over the phone to the physician's office. For example, adjustment dates or adjustment parameters such as distraction force or distraction distance.

FIG. 10 illustrates an external adjustment device 1130 which is one embodiment of an external adjustment device 248 according to one aspect of the invention. The external adjustment device 1130 may be used to externally impart rotational motion or "drive" a permanent magnet (e.g., magnetic element 218) located within the distraction device 140. The external adjustment device 1130 includes a motor 1132 that is used to impart rotational movement to two permanent magnets 1134, 1136. The two permanent magnets 1134, 1136 are located in the same driver 1130 and are configured for placement on the same side of the body of the patient or subject. The motor 1132 may include, for example, a DC powered motor or servo that is powered via one or more batteries (not shown) integrally contained within the external adjustment device 1130. Alternatively, the motor 1132 may be powered via a power cord or the like to an external power source. For example, the external power source may include one or more batteries or even an alternating current source that is converted to DC.

Still referring to FIG. 10, the two permanent magnets 1134, 1136 are preferably cylindrically-shaped permanent magnets. The permanent magnets may be made from, for example, a rare earth magnet material such as Neodymium-Iron-Boron (NdFeB) although other rare earth magnets are also possible. For example, each magnet 1134, 1136 may have a length of around 1.5 inches and a diameter of around 1.0 to 3.5 inches. Both magnets 1134, 1136 are diametrically magnetized (poles are perpendicular the long axis of each permanent magnet 1134, 1136). The magnets 1134, 1136 may be contained within a non-magnetic cover or housing 1137. In this regard, the magnets 1134, 1136 are able to rotate within the stationary housing 1137 that separates the magnets 1134, 1136 from the external environment. Preferably, the housing 1137 is rigid and relatively thin walled at least at the portion directly covering the permanent magnets 1134, 1136, in order to minimize the gap between the permanent magnets 1134, 1136 and the internal magnet 1064 (as shown in FIGS. 13A-13D).

As seen in FIG. 10, the permanent magnets 1134, 1136 are rotationally mounted between opposing bases members 1138, 1140. Each magnet 1134, 1136 may include axles or spindles 1142, 1144 mounted on opposing axial faces of each magnet 1134, 1136. The axles 1142, 1144 may be mounted in respective bearings (not shown) that are mounted in the base members 1138, 1140. As seen in FIG. 10, driven pulleys 1150 are mounted on one set of axles 1142 and 1144. The driven pulleys 1150 may optionally include grooves or teeth 1152 that are used to engage with corresponding grooves or teeth 1156 (partially illustrated in FIG. 12) contained within a drive belt (indicated by path 1154).

Still referring to FIG. 10, the external adjustment device 1130 includes a drive transmission 1160 that includes the two driven pulleys 1150 along with a plurality of pulleys 1162A, 1162B, 1162C and rollers 1164A, 1164B, 1164C on which the drive belt 1154 is mounted. The pulleys 1162A, 1162B, 1162C may optionally include grooves or teeth 1166 used for gripping corresponding grooves or teeth 1156 of the drive belt 1154. Pulleys 1162A, 1162B, 1162C and rollers 1164A, 1164B, 1164C may be mounted on respective bearings (not shown). As seen in FIG. 10, pulley 1162B is mechanically coupled to the drive shaft (not shown) of the motor 1132. The pulley 1162B may be mounted directly to the drive shaft or, alternatively, may be coupled through appropriate gearing. One roller 1164B is mounted on a biased arm 1170 and thus provides tension to the belt 1154. The various pulleys 1150, 1162A, 1162B, 1162C and rollers 1164A, 1164B, 1164C along with the drive belt 1154 may be contained within a cover or housing 1172 that is mounted to the base 1138 (as seen in FIG. 12). For safety and convenience, it may be desired for the external adjustment device 1130 to have a removable safety cover that would be placed over the portion containing the permanent magnets 1134, 1136, for example during storage, so that the high magnetic field cannot come closely in contact with anything that would be strongly attracted to it or damaged by it.

Figures 13A, 13B:
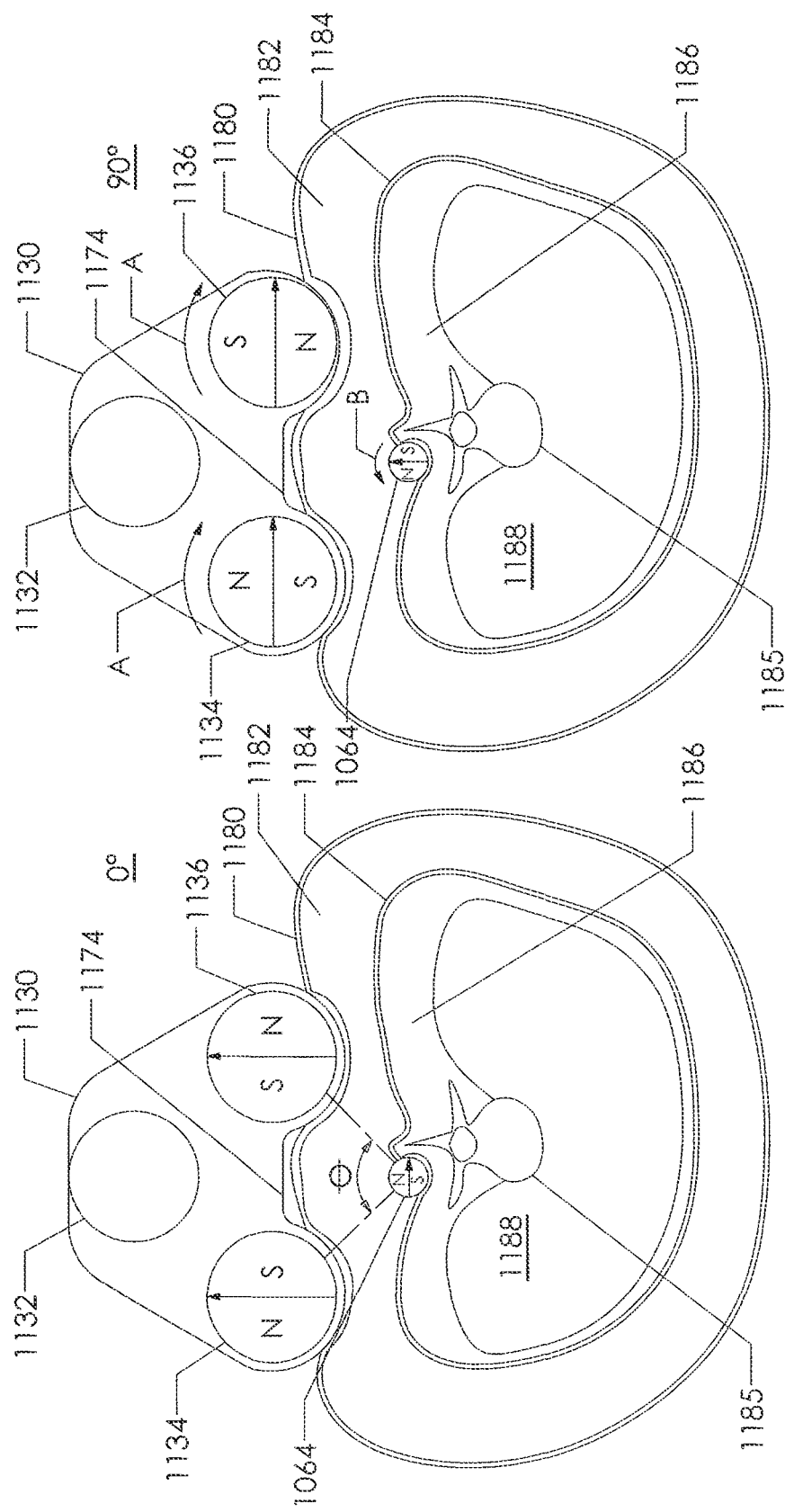
FIG. 13A illustrates a cross-sectional representation of the external adjustment device being positioned on a patient's skin.
FIG. 13B illustrates a cross-sectional representation of the external adjustment device being positioned on a patient's skin.

As seen in FIGS. 10 and 11, rotational movement of the pulley 1162B causes the drive belt 1154 to move around the various pulleys 1150, 1162A, 1162B, 1162C and rollers 1164A, 1164B, 1164C. In this regard, rotational movement of the motor 1132 is translated into rotational movement of the two permanent magnets 1134, 1136 via the drive transmission 1160. In one aspect of the invention, the base members 1138, 1140 are cut so as to form a recess 1174 that is located between the two magnets 1134, 1136. During use, the external adjustment device 1130 is pressed against the skin of a patient, or against the clothing which covers the skin (e.g., the external adjustment device 1130 may be used through clothing so the patient may not need to undress). The recess 1174 allows skin as well as the underlying tissue to gather or compress within the recessed region 1174 as seen in FIGS. 13A and 13B. This advantageously reduces the overall distance between the external drive magnets 1134, 1136 and the magnet 1064 contained within the distraction device 140. By reducing the distance, this means that the externally located magnets 1134, 1136 and/or the internal magnet 1064 may be made smaller. This is especially useful in the case of an obese patient.

In one embodiment, the two permanent magnets 1134, 1136 are configured to rotate at the same angular velocity. In another embodiment, the two permanent magnets 1134, 1136 each have at least one north pole and at least one south pole, and the external adjustment device 1130 is configured to rotate the first magnet 1134 and the second magnet 1136 such that the angular location of the at least one north pole of the first magnet 1134 is substantially equal to the angular location of the at least one south pole of the second magnet 1136 through a full rotation of the first and second magnets 1134, 1136.

FIGS. 13A and 13B illustrate cross-sectional views of the patient having an implanted distraction device 140 containing an internal magnet 1064. For sake of clarity, the first and second elongate members 146, 150 have been removed to illustrate the relationship between the external adjustment device 1130 and the rotationally-driven internal magnet 1064. The internal magnet 1064 is seen disposed on one side of a vertebra 1185. Further, the internal magnet 1064 is seen being outside or external with respect to the fascia 1184 and muscle 1186 of the subject. FIGS. 13A and 13B illustrate an obese patient in which skin and other tissue gather within the recess 1174. It should be understood that obese Adolescent Idiopathic Scoliosis patients are rare, and FIGS. 13A and 13B generally indicate a worst-case situation but as seen in FIGS. 13A and 13B the excess skin and other tissue is easily accommodated within the recess 1174 to enable close positioning between the internal magnet 1064 and the external drive magnets 1134, 1136. For most AIS patients, the air gap or distance between the internal magnet 1064 and the external drive magnets 1134, 1136 is generally one inch or less. In FIGS. 13A through 13D, the internal magnet 1064 is depicted somewhat larger than its size in the preferred embodiment, in order for its poles to be more clearly visible.

Still referring to FIGS. 10 and 11, the external adjustment device 1130 preferably includes an encoder 1175 that is used to accurately and precisely measure the degree of movement (e.g., rotational) of the external magnets 1134, 1136. In one embodiment, an encoder 1175 is mounted on the base member 1138 and includes a light source 1176 and a light receiver 1178. The light source 1176 may include a LED which is pointed or directed toward pulley 1162C. Similarly, the light receiver 1178 may be directed toward the pulley 1162C. The pulley 1162C includes a number of reflective markers 1177 regularly spaced about the periphery of the pulley 1162C. Depending on the rotational orientation of the pulley 1162C, light is either reflected or not reflected back onto the light receiver 1178. The digital on/off signal generated by the light receiver 1178 can then be used to determine the rotational speed and displacement of the external magnets 1134, 1136.

FIGS. 13A, 13B, 13C, and 13D illustrate the progression of the external magnets 1134, 1136 and the internal magnet 1064 that is located within the distraction device 140 during use. Internal magnet 1064 is shown for illustration purposes. Internal magnet 1064 is one possible embodiment of the magnetic element 218 described herein. FIGS. 13A, 13B, 13C, and 13D illustrate the external adjustment device 1130 being disposed against the external surface of the patient's skin 1180 adjacent the spine (not shown for clarity sake).). In the non-invasive adjustment procedure depicted, the patient 100 lies in a prone position, and the external adjustment device 1130 is placed upon the patient's back. However, the adjustment is conceived possible with the patient in supine, standing or positions. The external adjustment device 1130 is placed against the skin 1180 in this manner to remotely rotate the internal magnet 1064. As explained herein, rotation of the internal magnet 1064 is translated into linear motion via the adjustment device 232 to controllably adjust the distraction device 140.

As seen in FIGS. 13A, 13B, 13C, and 13D, the external adjustment device 1130 may be pressed down on the patient's skin 1180 with some degree of force such that skin 1180 and other tissue such as the underlying layer of fat 1182 are pressed or forced into the recess 1174 of the external adjustment device 1130. FIGS. 13A, 13B, 13C, and 13D show the magnetic orientation of the internal magnet 1064 as it undergoes a full rotation in response to movement of the permanent magnets 1134, 1136 of the external adjustment device 1130.

With reference to FIG. 13A, the internal magnet 1064 is shown being oriented with respect to the two permanent magnets 1134, 1136 via an angle θ. This angle θ may depend on a number of factors including, for instance, the separation distance between the two permanent magnets 1134, 1136, the location or depth of where the implantable interface 1104 is located, the degree of force at which the external adjustment device 1130 is pushed against the patient's skin. Generally in applications including some obese patients, the angle θ should be at or around 90° to achieve maximum drivability (e.g., torque). The inventors have calculated that in the AIS application, where there are few obese patients, an angle of about 70° is preferred for the majority of patients when the permanent magnets 1134, 1136 have an outer diameter of about three (3.0) inches.

FIG. 13A illustrates the initial position of the two permanent magnets 1134, 1136 and the internal magnet 1064. This represents the initial or starting location (e.g., 0° position as indicated). Of course, it should be understood that, during actual use, the particular orientation of the two permanent magnets 1134, 1136 and the internal magnet 1064 will vary and not likely will have the starting orientation as illustrated in FIG. 13A. In the starting location illustrated in FIG. 13A, the two permanent magnets 1134, 1136 are oriented with their poles in an N-S/S-N arrangement. The internal magnet 1064 is, however, oriented generally perpendicular to the poles of the two permanent magnets 1134, 1136.

FIG. 13B illustrates the orientation of the two permanent magnets 1134, 1136 and the internal magnet 1064 after the two permanent magnets 1134, 1136 have rotated through 90°. The two permanent magnets 1134, 1136 rotate in the direction of arrow A (e.g., clockwise) while the internal magnet 1064 rotates in the opposite direction (e.g., counter clockwise) represented by arrow B. It should be understood that the two permanent magnets 1134, 1136 may rotate in the counter clockwise direction while the internal magnet 1064 may rotate in the clockwise direction. Rotation of the two permanent magnets 1134, 1136 and the internal magnet 1064 continues as represented by the 180° and 270° orientations as illustrated in FIGS. 13C and 13D. Rotation continues until the starting position (0°) is reached again.

During operation of the external adjustment device 1130, the permanent magnets 1134, 1136 may be driven to rotate the internal magnet 1064 through one or more full rotations in either direction to increase or decrease distraction of the distraction device 140 as needed. Of course, the permanent magnets 1134, 1136 may be driven to rotate the internal magnet 1064 through a partial rotation as well (e.g., ¼, ⅛, 1/16, etc.). The use of two magnets 1134, 1136 is preferred over a single external magnet because the driven magnet 1064 may not be oriented perfectly at the start of rotation, so one external magnet 1134, 1136 may not be able to deliver its maximum torque, which depends on the orientation of the internal driven magnet 1064 to some degree. However, when two (2) external magnets (1134, 1136) are used, one of the two 1134 or 1136 will have an orientation relative to the internal driven magnet 1064 that is better or more optimal than the other. In addition, the torques imparted by each external magnet 1134, 1136 are additive. In prior art magnetically driven devices, the external driving device is at the mercy of the particular orientation of the internal driven magnet. The two-magnet embodiment described herein is able to guarantee a larger driving torque—as much as 75% more than a one-magnet embodiment in the AIS application—and thus the internal driven magnet 1064 can be designed smaller in dimension, and less massive. A smaller internal driven magnet 1064 will have a smaller image artifact when performing MRI (Magnetic Resonance Imaging), especially important when using pulse sequences such as gradient echo, which is commonly used in breast imaging, and leads to the largest artifact from implanted magnets. In certain configurations, it may even be optimal to use three or more external magnets, including one or more magnets each on two different sides of the body (for example front and back).

While the external adjustment device 1130 and adjustment device 232 have generally been described as functioning using rotational movement of driving elements (i.e., magnetic elements) it should be understood that cyclic or non-rotational movement can also be used to drive or adjust the distraction device 140. For instance, cyclic movement of driven magnet 640, magnetic element 218, internal magnet 1064, internally located driven magnet 1402, cylindrical magnet 394, hollow magnet 564, magnet 576, magnet 262, magnets 618, 620, and magnet 1302 may be used to drive or adjust the distraction device 140. Cyclic movement includes partial rotational movement (e.g., rotational movement that is less than a full revolution). Cyclic movement of one or more of the external magnets 624, 626, 1134, 1136 may also be employed.

In still another alternative, linear or sliding motion back-and-forth may also be used to adjust the distraction device 140. In this regard, a single magnet located internal to the patient that slides back-and-forth on a slide or other base can be used to adjust the distraction device 140 using a ratchet-type device. The sliding, internal magnet may be driven via one or more externally-located permanent/electromagnets that slides or moves laterally (or moves the magnetic field) in a similar back-and-forth manner. Rotational movement of the externally-located magnetic element(s) may also be used to drive the internal magnet. The internal magnet may alternatively be able to rotate back-and-forth, thus adjusting the distraction device 140 using a ratchet-type device.

In still another alternative, permanent magnets may be located on a pivoting member that pivots back and forth (like a teeter-totter) about a pivot point. For example, a first permanent magnet having a North pole oriented in a first direction may be located at one end of the pivoting member while a permanent magnet having a South pole oriented in the first direction is located at the other end of the pivoting member. A ratchet-type device may be used to translate the pivoting movement into linear movement that can actuate or adjust the distraction device 140. The first and second internally-located permanent magnets may be driven by one or more externally located magnetic elements (either permanent or electromagnets). External motion of the electric field by linear or even rotational movement may be used to the drive the pivoting member.

Two different models of internal driven magnets were constructed, each from a different Neodymium-Iron-Boron Grade. Both magnets had identical dimensions (0.275" diameter, 0.395" long). One magnet was a grade of approximately N38 and the other was a grade of N50. Both magnets were approximately 2.9 grams in mass. A 1" diameter cylindrical permanent magnet (grade N50 Neodymium-Iron-Boron) was attached to a torque gauge and the peak coupling torque (in inch-ounces) between it and each of the internal drive magnet models was measured for three different angular orientations for the cylindrical permanent magnet, in relation to the internal driven magnet. All magnets were two pole (as in FIGS. 13A-13D). Each of the internal driven magnets was tested individually. The orientation was either 0° (worst case coupling torque), 45° or 90° (best case coupling torque). The data for a one inch air gap (separation between magnets) is listed below in Table 1 below. A one (1) inch air gap is an expected worst case separation in the clinical application of adolescent idiopathic scoliosis. The effect of using two external 1" diameter permanent magnets (as in FIGS. 13A-13D) is shown by addition of the values for the worst case (0°) and best case (90°) orientations.

TABLE 1

| | Peak Coupling Torque (oz-in) at 1" Air Gap | | | |
|---|---|---|---|---|
| Internal driven magnet | 0° orientation of single external magnet | 45° orientation of single external magnet | 90° orientation of single external magnet | Two external magnets (0° orientation + 90° orientation) |
| Grade 38 (approx) | 1.37 | 1.92 | 2.47 | 3.84 |
| Grade 50 | 1.70 | 2.04 | 2.80 | 4.50 |

It can be clearly seen that the additive use of two external permanent magnets, especially if synchronized in the orientation shown in FIGS. 13A-13D, delivers significantly more torque than a single external magnet in any orientation. For the data generated using the 50 grade internal driven magnet, the peak coupling torque using two external permanent magnets was 4.50 ounce-inches, 60.7% greater than a single external permanent magnet oriented at the ideal 90° in relation to the internal driven magnet, and 164.7% greater than a single external permanent magnet oriented at the worst case 0°. This significant increase in torque achieved by using two external permanent magnets, makes it possible to incorporate an especially small internal driven magnet (e.g., less than three grams) into the design of the scoliosis treatment implant, or any implant for manipulating one or more bones or a portion of the skeletal system. For example, the use of two external permanent magnets may impart a coupling torque of at least 3.0 inch-ounces to the internal magnet at a separation distance of around 1.0 inches.

In a gradient echo MRI scan of the breast in a 1.5 Tesla MRI scanner using standard breast imaging coils, a 2.9 gram N50 grade magnet having a 0.275 inch diameter and 0.295" length implanted in the mid-thorax creates an MRI artifact which is small enough to allow full imaging of the breasts. Using the dual 1" diameter external permanent magnets 1134, 1136 as for the external adjustment device 1130, and using the grade 50 for the internal driven magnet 1064 having a mass of 2.9 grams, the 4.50 ounce-inch torque delivered to the magnet will turn an 80 threads per inch lead screw mounted on ball bearing in a sufficient manner to apply a distraction force of approximately 11 pounds. If a 4:1 reduction planetary gear set is incorporated into the design—for example, between the internal driven magnet 1064 and the lead screw 226—then a distraction force of approximately 44 pounds may be delivered. In the system contemplated by this invention, in which several gradual non-invasive adjustments are made, distraction forces on this order (40 to 45 pounds) will be sufficient. In fact, the slip clutch 244 can either be adjusted in the fabrication of the scoliosis implant or can be adjusted by the implanting physician, so that the slip clutch 244 slips at either a maximum threshold torque (to save the materials of the implant from being damaged or pulling out of the bone by too high a distraction force) or at desired threshold torque (at which the desired distraction force is generated).

The maximum threshold torque corresponds to a critical distraction force, and the desired threshold torque corresponds to a desired distraction force. A critical distraction force may correspond to a force at which anchors such as hooks or screws may cause damage to the bone. For example, one critical distraction force is 100 pounds, which in one embodiment of the invention corresponds to a critical threshold slip torque of 41.7 ounce-inches (if no gear reduction, and a 80 threads per inch lead screw is used), 10.4 ounce-inches (if a 4:1 gear reduction and a 80 threads per inch lead screw is used) or 2.6 ounce-inches (if a 16:1 gear reduction and a 80 threads per inch lead screw is used). Similarly, one desired distraction force is 45 pounds, which in one embodiment of the invention corresponds to a desired threshold slip torque of 18.75 ounce-inches (if no gear reduction and an 80 threads per inch lead screw is used) or 4.69 ounce-inches (if a 4:1 gear reduction and an 80 threads per inch lead screw is used). If a desired distraction force is 20 pounds, then in one embodiment of the invention this corresponds to a desired threshold slip torque of 8.33 ounce-inches (if no gear reduction and an 80 threads per inch lead screw is used) or 2.08 ounce-inches (if a 4:1 gear reduction and an 80 threads per inch lead screw is used). In one aspect, the desired threshold distraction is between 2 inch-ounces and 42 inch-ounces. In another aspect, the desired threshold distraction is between 2 inch-ounces and 19 inch-ounces. In still another aspect, the desired threshold distraction is between 2 inch-ounces and 8.5 inch-ounces.

Other distraction devices have been proposed which incorporate a small implantable motor to effect the distraction. The 2.9 gram cylindrical magnet 1064 described as part of the present invention is significantly smaller than the smallest motor which would be feasible in the distraction application, considering torque requirements, etc. In addition, the cost of the magnet 1064 is significantly less than that of a micromotor. The magnet 1064 is also very reliable in relation to a micromotor. The main possible failure would be the loss of the magnetic field, however the inventors have demonstrated that the inventive 2.9 gram magnet 1064 can be placed into the center of a 3.0 Tesla MRI magnet without a significant loss in magnetism. It can also be exposed to temperatures in excess of those used in steam sterilization, for example, without a significant loss of magnetism. Generally, the internal magnet 1064 should be grade N30 or higher, or even grade N48 or higher. While the 2.9 gram cylindrical magnet 1064 has the advantage of being particularly small, in other embodiments, the cylindrical magnet 1064 may have a weight of less than about 10 grams or less than about 6.0 grams. Similarly, the first and second external magnets 1134, 1136 may be a rare earth permanent magnets such as, for instance, Neodymium-Iron-Boron. In addition, the first and second external magnets 1134, 1136 may be grade N30 or higher, or even grade N48 or higher.

Figure 14:
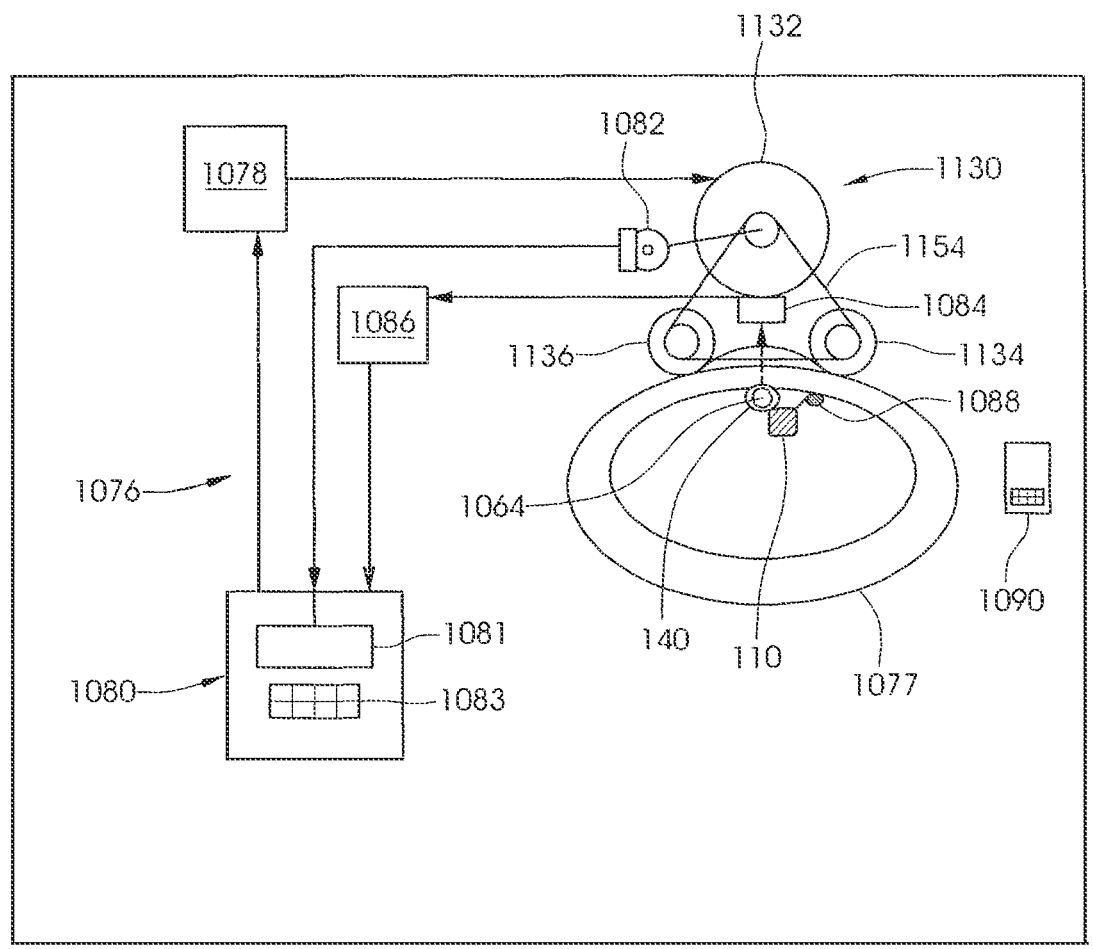
FIG. 14 schematically illustrates a system for driving the external adjustment device according to one embodiment.

FIG. 14 illustrates a system 1076 according to one aspect of the invention for driving the external adjustment device 1130. FIG. 14 illustrates the external adjustment device 1130 pressed against the surface of a patient 1077 (torso face down shown in cross-section). The portion of the distraction device 140 containing the internal driven magnet 1064 is illustrated. The permanent magnet (e.g., the driven magnet 1064) that is located within the distraction device 140 located inside the patient 1077 is magnetically coupled through the patient's skin and other tissue to the two external magnets 1134, 1136 located in the external adjustment device 1130. As explained herein, one rotation of the external magnets 1134, 1136 causes a corresponding single rotation of the driven magnet 1064 located within the distraction device 140. Turning the driven magnet 1064 in one direction causes the distraction device 140 to lengthen, or increase distraction force while turning in the opposite direction causes the distraction device 140 to shorten, or decrease distraction force. Changes to the distraction device 140 are directly related to the number of turns of the driven magnet 1064.

The motor 1132 of the external adjustment device 1130 is controlled via a motor control circuit 1078 operatively connected to a programmable logic controller (PLC) 1080. The PLC 1080 outputs an analog signal to the motor control circuit 1078 that is proportional to the desired speed of the motor 1132. The PLC 1080 may also select the rotational direction of the motor 1132 (i.e., forward or reverse). In one aspect, the PLC 1080 receives an input signal from a shaft encoder 1082 that is used to identify with high precision and accuracy the exact relative position of the external magnets 1134, 1136. For example, the shaft encoder 1082 may be an encoder 1175 as described in FIGS. 10-11. In one embodiment, the signal is a pulsed, two channel quadrature signal that represents the angular position of the external magnets 1134, 1136. The PLC 1080 may include a built in screen or display 1081 that can display messages, warnings, and the like. The PLC 1080 may optionally include a keyboard 1083 or other input device for entering data. The PLC 1080 may be incorporated directly into the external adjustment device 1130 or it may be a separate component that is electrically connected to the main external adjustment device 1130.

In one aspect of the invention, a sensor 1084 is incorporated into the external adjustment device 1130 that is able to sense or determine the rotational or angular position of the driven magnet 1064. The sensor 1084 may acquire positional information using, for example, sound waves, ultrasonic waves, light, radiation, or even changes or perturbations in the magnetic or electromagnetic field between the driven magnet 1064 and the external magnets 1134, 1136. For example, the sensor 1084 may detect photons or light that is reflected from the driven magnet 1064 or a coupled structure (e.g., rotor) that is attached thereto. For example, light may be passed through the patient's skin and other tissue at wavelength(s) conducive for passage through tissue. Portions of the driven magnet 1064 or associated structure may include a reflective surface that reflects light back outside the patient as the driven magnet 1064 moves. The reflected light can then be detected by the sensor 1084 which may include, for example, a photodetector or the like.

In another aspect, the sensor 1084 may operate on the Hall effect, wherein two additional magnets are located within the implantable assembly. The additional magnets move axially in relation to each other as the driven assembly rotates and therefore as the distraction increases or decreases, allowing the determination of the current size of the restriction device.

In the embodiment of FIG. 14, the sensor 1084 is a microphone disposed on the external adjustment device 1130. For instance, the microphone sensor 1084 may be disposed in the recessed portion 1174 of the external adjustment device 1130. The output of the microphone sensor 1084 is directed to a signal processing circuit 1086 that amplifies and filters the detected acoustic signal. In this regard, the acoustic signal may include a "click" or other noise that is periodically generated by rotation of the driven magnet 1064. For example, the driven magnet 1064 may click every time a full rotation is made. The pitch (frequency) of the click may differ depending on the direction of rotation. For example, rotation in one direction (e.g., lengthening) may produce a low pitch while rotation in the other direction (e.g., shortening) may produce a higher pitch signal (or vice versa). The amplified and filtered signal from the signal processing circuit 1086 can then pass to the PLC 1080.

During operation of the system 1076, each patient will have a number or indicia that correspond to the adjustment setting or size of their distraction device 140. This number can be stored on an optional storage device 1088 (as shown in FIG. 14) that is carried by the patient (e.g., memory card, magnetic card, or the like) or is integrally formed with the distraction device 140. For example, a RFID tag 1088 implanted either as part of the system or separately may be disposed inside the patient (e.g., subcutaneously or as part of the device) and can be read and written via an antenna 1090 to update the current size of the distraction device 140. In one aspect, the PLC 1080 has the ability to read the current number corresponding to the size or setting of the distraction device 140 from the storage device 1088. The PLC 1080 may also be able to write the adjusted or more updated current size or setting of the distraction device 140 to the storage device 1088. Of course, the current size may be recorded manually in the patient's medical records (e.g., chart, card or electronic patient record) that is then viewed and altered, as appropriate, each time the patient visits his or her physician.

The patient, therefore, carries their medical record with them, and if, for example, they are in another location, or even country, and need to be adjusted, the RFID tag 1088 has all of the information needed. Additionally, the RFID tag 1088 may be used as a security device. For example, the RFID tag 1088 may be used to allow only physicians to adjust the distraction device 140 and not patients. Alternatively, the RFID tag 1088 may be used to allow only certain models or makes of distraction devices to be adjusted by a specific model or serial number of external adjustment device 1130.

In one aspect, the current size or setting of the distraction device 140 is input into the PLC 1080. This may be done automatically or through manual input via, for instance, the keyboard 1083 that is associated with the PLC 1080. The PLC 1080 thus knows the patient's starting point. If the patient's records are lost, the length of the distraction device may be measured by X-ray and the PLC 1080 may be manually programmed to this known starting point.

The external adjustment device 1130 is commanded to make an adjustment. This may be accomplished via a pre-set command entered into the PLC 1080 (e.g. "increase distraction displacement of distraction device 140 by 0.5 cm" or "increase distraction force of distraction device 140 to 20 pounds"). The PLC 1080 configures the proper direction for the motor 1132 and starts rotation of the motor 1132. As the motor 1132 spins, the encoder 1082 is able to continuously monitor the shaft position of the motor directly, as is shown in FIG. 14, or through another shaft or surface that is mechanically coupled to the motor 1132. For example, the encoder 1082 may read the position of markings 1177 located on the exterior of a pulley 1162C like that disclosed in FIG. 10. Every rotation or partial rotation of the motor 1132 can then be counted and used to calculate the adjusted or new size or setting of the distraction device 140.

The sensor 1084, which may include a microphone sensor 1084, may be monitored continuously. For example, every rotation of the motor 1132 should generate the appropriate number and pitch of clicks generated by rotation of the permanent magnet inside the distraction device 140. If the motor 1132 turns a full revolution but no clicks are sensed, the magnetic coupling may have been lost and an error message may be displayed to the operator on a display 1081 of the PLC 1080. Similarly, an error message may be displayed on the display 1081 if the sensor 1084 acquires the wrong pitch of the auditory signal (e.g., the sensor 1084 detects a shortening pitch but the external adjustment device 1130 was configured to lengthen).

FIGS. 15 through 30 schematically illustrate an acoustic indicator housing 1304 and a driven magnet 1302 as the driven magnet 1302 is rotated in both the clockwise directions (arrow A) and counter-clockwise directions (arrow B). It should be understood that while a description is given with respect to driven magnet 1302, the acoustic sensing features may also apply to magnetic element 218 of FIGS. 6C-6G, the internal magnet 1064 of FIGS. 13A-13D, 14, the internally located driven magnet 1402 of FIG. 35, cylindrical magnet 394 of FIGS. 41, 42, and 44, the hollow magnet 564 of FIG. 48, magnet 576 of FIG. 50, magnet 262 of FIG. 53, and magnets 618, 620 of FIG. 51, magnet 640 of FIG. 52, or even magnetic member 200 of FIG. 6B (these various implementations of driven magnets may be referred to, in some instances, as magnetic elements). The acoustic indicator housing 1304 is illustrated in an annular configuration with respect to the circumference of the driven magnet 1302, but an alternative relationship is contemplated, for example wherein the outer diameter of the acoustic indicator housing 1304 is substantially the same as the outer diameter of the driven magnet 1302, and they are oriented with an end-to-end axial relationship instead of an annular relationship. Acoustic indicator housing 1304 is one possible embodiment of the acoustic housing 222 of FIG. 6C and FIG. 6D. The acoustic indicator housing 1304 is used to create an acoustic signal (e.g., a click) that can be used to count rotational movement of the driven magnet 1302 and also determine its rotational direction. An acoustic signal (i.e., sound) is generated when a magnetic ball 1306 strikes either a first impact surface 1308 or a second impact surface 1310. FIGS. 15-22 illustrate rotation of the driven magnet 1302 in the clockwise direction (arrow A) while FIGS. 23-30 illustrate rotation of the driven magnet 1302 in the counter-clockwise direction (arrow B). When the driven magnet 1302 is rotated in the clockwise direction, the magnetic ball 1306 strikes the first impact surface 1308 two times (2×) per full rotation, with the first impact surface 1308 producing sound with a first amplitude and/or frequency. When the driven magnet 1302 is rotated in the counter-clockwise direction, the magnetic ball 1306 strikes the second impact surface 1310 two times (2×) per full rotation, with the second impact surface 1310 producing sound with a second amplitude and/or frequency.

As illustrated in FIGS. 15-30, the first impact surface 1308 is thinner than the second impact surface 1310, and thus, the first impact surface 1308 is configured to resonate at a higher frequency than the second impact surface 1310. Alternatively, the difference in frequency can be achieved by making the first impact surface 1308 from a different material than the second impact surface 1310. Alternatively, the amplitude of acoustic signal generated by the magnetic ball 1306 hitting the first and second impact surfaces 1308, 1310 may be used to discriminate rotational direction. For example, clockwise rotation may produce a relatively loud click while counter-clockwise rotation may produce a relatively quiet click.

Figure 15:
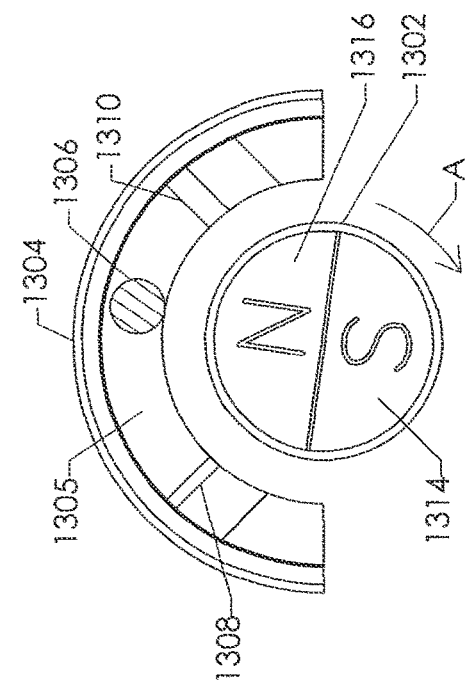
FIGS. 15-22 illustrate cross-sectional views of the driven magnet along with the acoustic or sonic indicator housing illustrating the rotational orientation of the magnet and the magnetic ball. Various states are illustrated as the magnet rotates in the clockwise direction.
Figure 16:
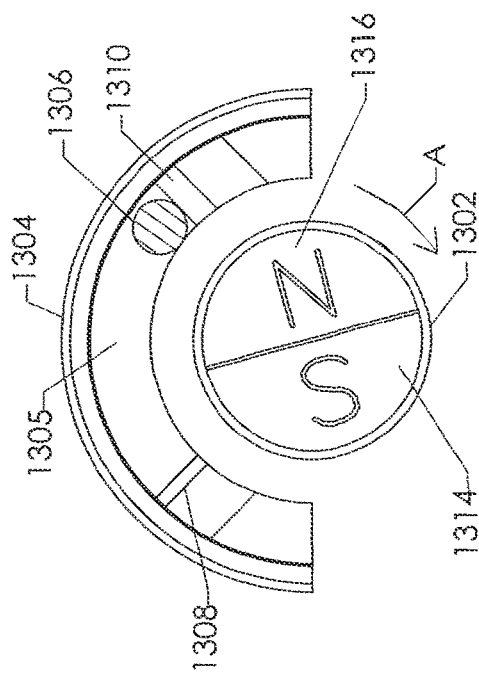
Figure 17:
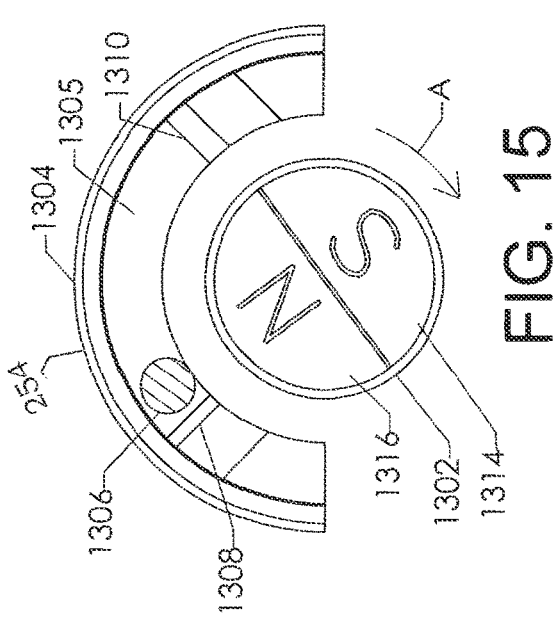
Figure 18:
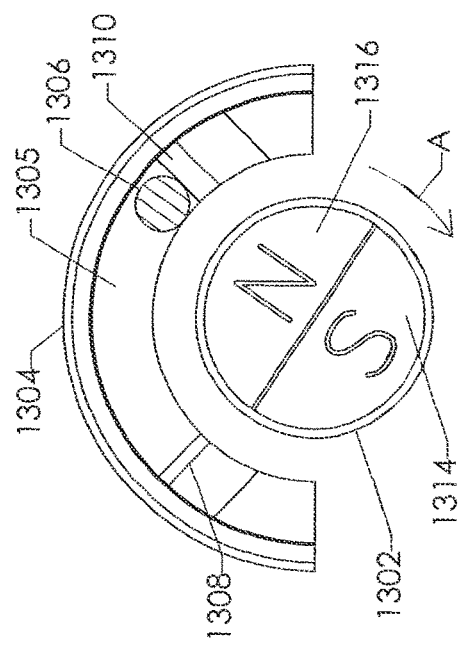
Figure 19:
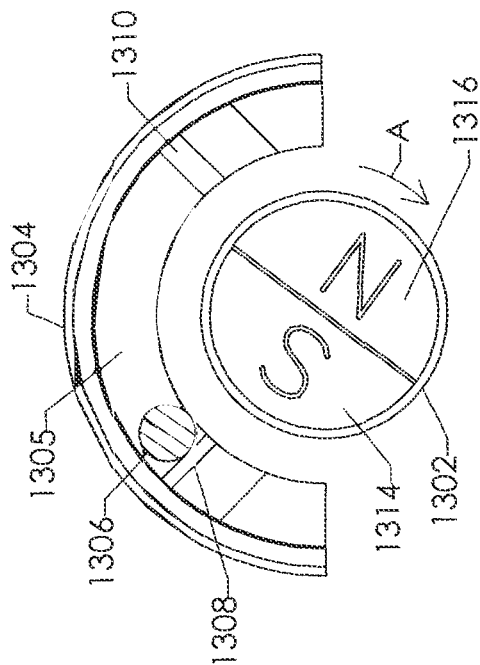
Figure 20:
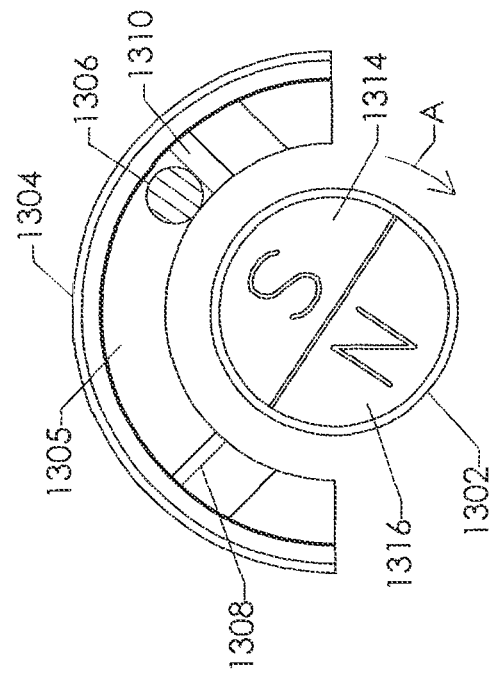
Figure 21:
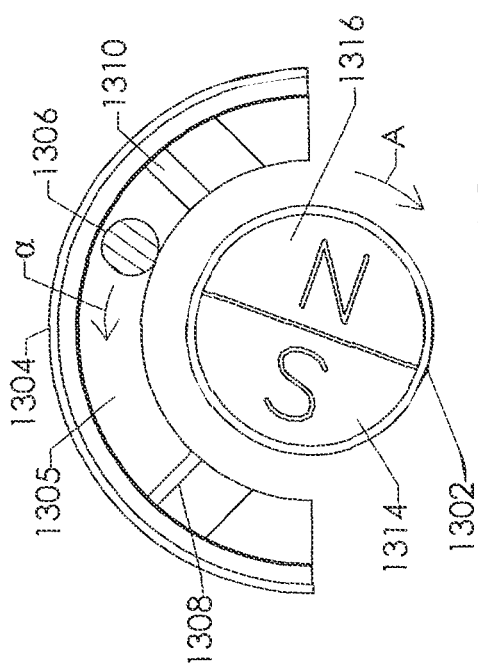
Figure 22:
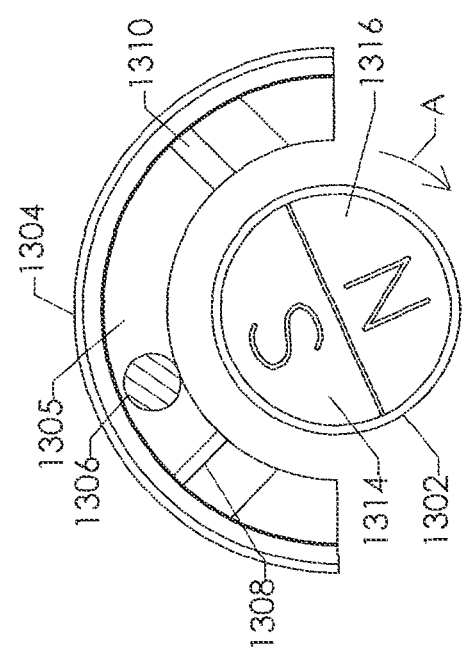

The magnetic ball 1306 is made from a magnetic material, for example 400 series stainless steel. The magnetic ball 1306 is attracted to both a south pole 1314 of the driven magnet 1302 and a north pole 1316 of the driven magnet 1302. As seen in FIG. 15, the driven magnet 1302 begins to rotate in the clockwise direction (arrow A). As pictured, the starting point of the magnetic ball 1306 is adjacent to the north pole 1316 of the magnet 1302. As seen in FIG. 16, as the magnet 1302 rotates, the magnetic ball 1306 follows the north pole 1316. This continues until, as shown in FIG. 17, the magnetic ball 1306 is stopped by the second impact surface 1310. Now, as seen in FIG. 18, the magnetic ball 1306 is trapped against the second impact surface 1310, while the driven magnet 1302 continues to rotate. The magnetic ball 1306 may roll at this point, but it is forced against the second impact surface 1310 by its attraction to the north pole 1316 of the magnet 1302, until the south pole 1314 becomes substantially closer to the magnetic ball 1306 as shown in FIG. 19, at which point the magnetic ball 1306 accelerates towards the first impact surface 1308 in the direction of arrow a, thereby hitting it (as seen in FIG. 20) and creating an acoustic signal or sound having a greater intensity than when the magnetic ball 1306 was stopped by the second impact surface 1310. Now, as the driven magnet 1302 continues to turn, the magnetic ball 1306 follows the south pole 1314 of the driven magnet 1302 as seen in FIG. 21, and continues to follow the south pole 1314 until the magnetic ball 1306 is stopped by the second impact surface 1310 as seen in FIG. 22.

Figure 27:
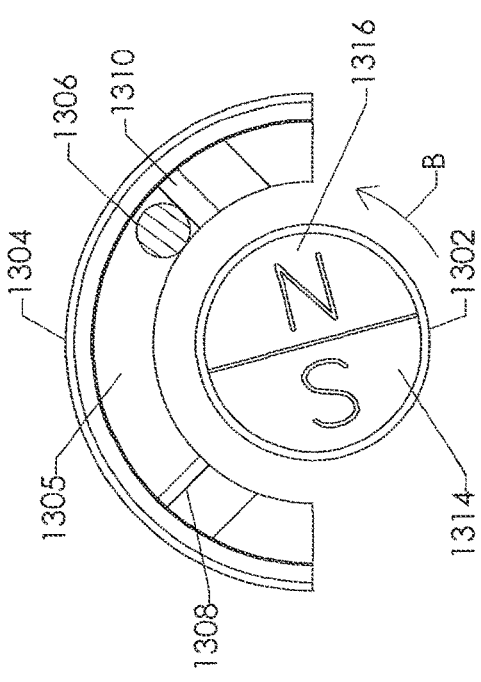
Figure 28:
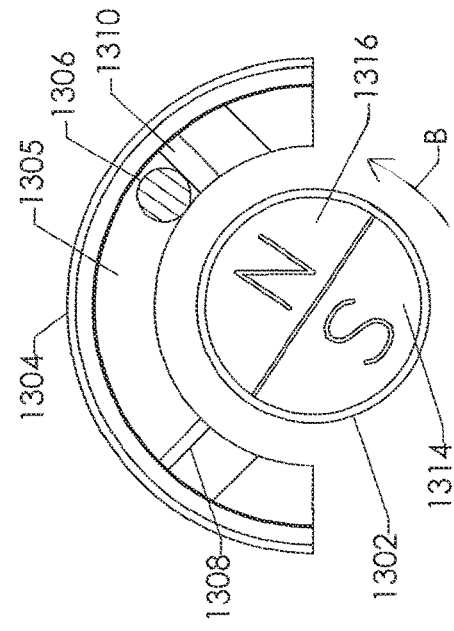
Figure 29:
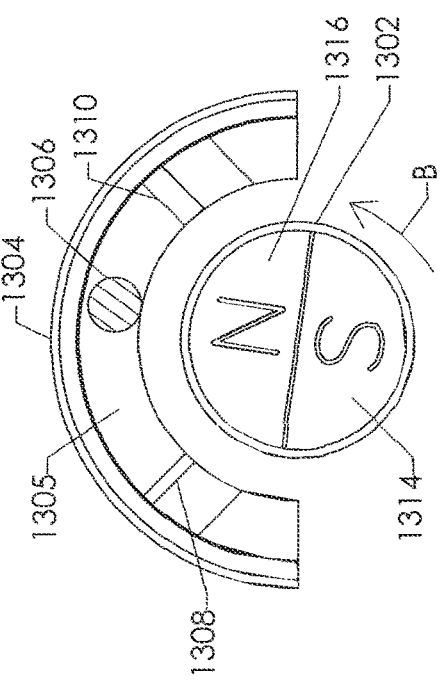
Figure 30:
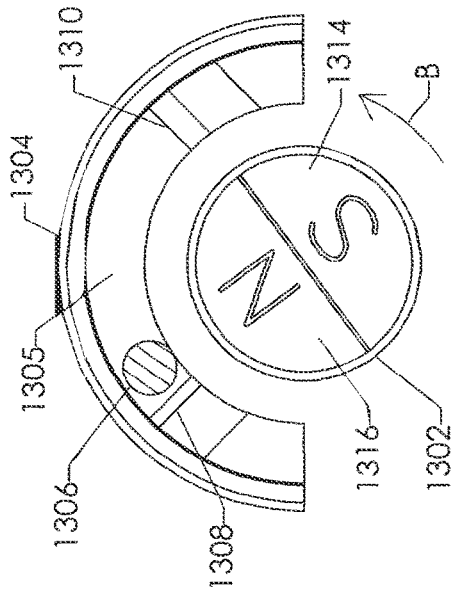

FIGS. 23-30 illustrate the acoustic mechanism being activated by counter-clockwise rotation of the driven magnet 1302. In this process, the first impact surface 1308 serves to stop the magnetic ball 1306, and the magnetic ball 1306 accelerates and impacts the second impact surface 1310, creating a different acoustic signal. For example, the different acoustic signal may include a louder signal or a signal with a different frequency (e.g., pitch). In FIG. 23, the driven magnet 1302 begins to rotate in the counter-clockwise direction (arrow B). As illustrated, the starting point of the magnetic ball 1306 is adjacent the south pole 1314 of the magnet 1302. As seen in FIG. 24, as the magnet 1302 rotates, the magnetic ball 1306 follows the south pole 1314. This continues until, as shown in FIG. 25, the magnetic ball 1306 is stopped by the first impact surface 1308. As seen in FIG. 25, the magnetic ball 1306 is trapped against the first impact surface 1308, while the driven magnet 1302 continues to rotate. The magnetic ball 1306 may roll at this point, but it is forced against the first impact surface 1308 by its attraction to the south pole 1314 of the magnet 1302, until the north pole 1316 becomes closer to the magnetic ball 1306 as shown in FIG. 26, at which point the magnetic ball 1306 accelerates towards the second impact plate 1310 in the direction of arrow 13, thereby hitting it (as seen in FIG. 27) and creating an acoustic signal or sound having a greater intensity than when the magnetic ball 1306 was stopped by the first impact surface 1308. Now as seen in FIG. 28, as the magnet 1302 continues to turn, the magnetic ball 1306 follows the north pole 1316 of the magnet 1302, and continues to follow the north pole 1316 (FIG. 29) until the magnetic ball 1306 is stopped by the first impact surface 1308 as illustrated in FIG. 30.

It can be appreciated that each turn of the magnet 1302 creates two (2) relatively loud strikes, which can be detected by a non-invasive, external device comprising a sonic sensor, for example, a microphone (e.g., sensor 1084 in FIG. 14). If, for example, the magnet 1302 is turning a 0-80 lead screw (e.g., lead screw 226) to adjust the distraction device 140), then each turn represents $\frac{1}{80}$ of an inch in the distraction displacement, and thus each half turn represents $\frac{1}{160}$ of an inch, or 0.00625". If there is gear reduction at the output of the magnet 1302, for example 4:1, then a full turn represents $\frac{1}{320}$ of an inch and each half turn represents $\frac{1}{640}$ of an inch. Therefore, acoustic sensing of this nature allows for very precise control of adjustment of the distraction device 140. If the speed is too high, the sensor can alternatively be programmed to sense only specific turns. Alternatively, a secondary magnet may be disposed on the post gear reduction portion of the torque transmission system, so that the number of turns to sense are fewer in number and less frequent.

It can also be appreciated that the acoustic signal or sound made by the strike due to the acceleration of the magnetic ball 1306 against the first impact surface 1308 during clockwise rotation of the magnet 1302 will contain a different frequency spectrum than the acoustic signal or sound made by the strike due to the acceleration of the magnetic ball 1306 against the second impact surface 1310 during counter-clockwise rotation of the magnet 1302. As one example, the acoustic sensor 1084 illustrated in FIG. 14 may provide a relatively simple, low-cost device in which the direction of the rotation (i.e., increasing distraction vs. decreasing distraction) can be automatically identified. Further, the acoustic sensor 1084 is able to determine the exact number of half rotations in each direction.

The acoustic sensor 1084 may be operatively integrated with a programmable logic controller (PLC) such as the PLC 1080 described herein. In this regard, the exact distraction length of the distraction device 140 can be determined. The PLC 1080 is able to identify the direction of rotation via the frequency of sound, and then change the direction of rotation if this is not the desired direction. The PLC 1080 is also able to count the number of half rotations until amount of restriction is achieved. If there is any slip between the magnets 1134, 1136 of the external device 1130 and the driven magnet 1302, the PLC 1080 will not detect the acoustic signal and thus will not count these as rotations.

There may be cases in which the medical personnel performing the non-invasive adjustment is not aware which direction of rotation of the external device magnets 1134, 1136 will cause increased distraction and which will cause decreased distraction. The PLC 1080, however, will be able to immediately identify the correct direction of rotation by the detected frequency.

Figure 31:
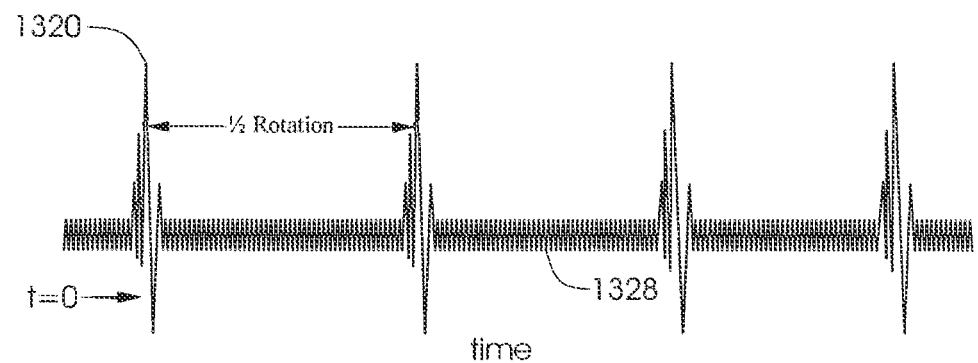
FIG. 31 illustrates the acoustic signal as a function of time of an embodiment of the invention having an acoustic or sonic housing that contains a magnetic ball. Peaks are seen every ½ rotation of the driven magnet in the counter-clockwise direction.
Figure 32:
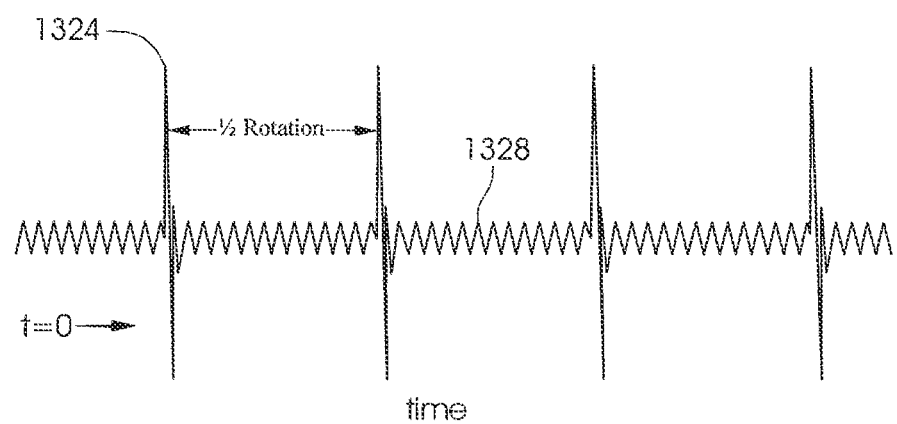
FIG. 32 illustrates the acoustic signal as a function of time of an embodiment of the invention having an acoustic or sonic housing that contains a magnetic ball. Peaks are seen every ½ rotation of the driven magnet in the clockwise direction.
Figure 33:
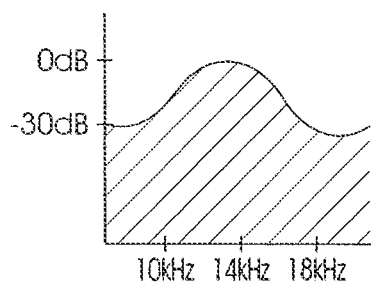
FIG. 33 illustrates the frequency response of the acoustic or sonic housing of the type illustrated in FIGS. 15-30 during counter-clockwise rotation of the driven magnet.
Figure 34:
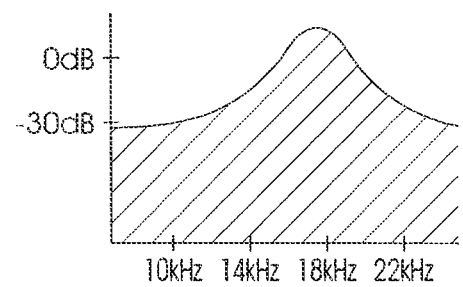
FIG. 34 illustrates the frequency response of the acoustic or sonic housing of the type illustrated in FIGS. 15-30 during clockwise rotation of the driven magnet.

For example, FIG. 31 illustrates the sound 1320 detected from counter-clockwise rotation of the magnet 1302 and FIG. 32 illustrates the sound 1324 detected from clockwise rotation of the magnet 1302. There may be additional background acoustic signals or noise 1328 created by, for example, the sound of the motor 1132 of the external device 1130. In both rotation directions, the acoustic "clicks" 1320 and 1324 look very similar to each other. However, by analyzing the frequency spectrum of the clicks, one is able to discern differences between clockwise and counter-clockwise rotation of the magnet 1302. As seen in FIG. 33, the frequency spectrum for the counter-clockwise rotation is centered at about 14 kHz, while the spectrum for clockwise rotation (FIG. 34) is centered at about 18 kHz. This shift or change in center frequency can be used as a basis for determining the absolute rotational direction of the magnet 1302.

Figure 35:
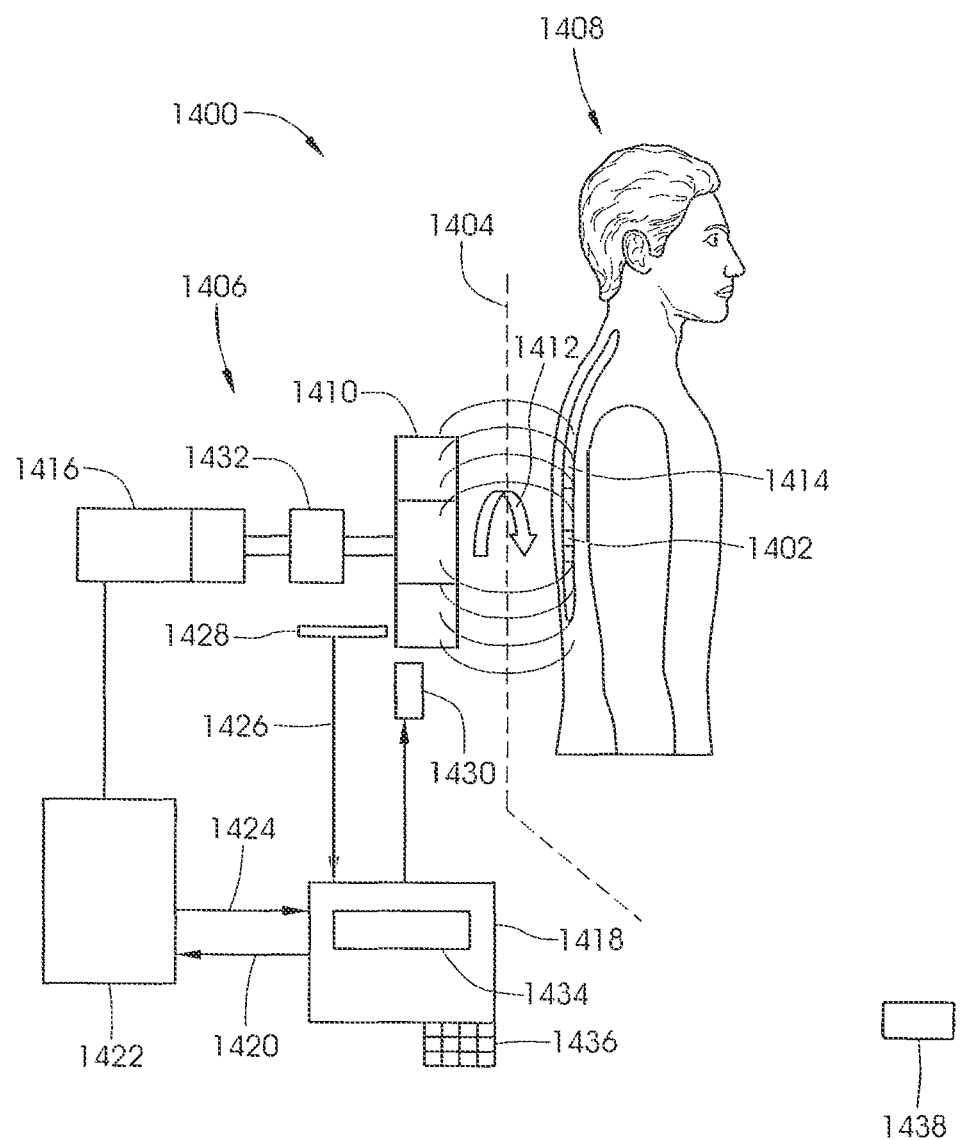
FIG. 35 illustrates a system for driving an internally located driven magnet via an external device using a feedback mechanism.

FIG. 35 illustrates a system 1400 for driving an internally located driven magnet 1402 of a distraction device 140 via an external device 1406 using a feedback device. One or more implanted driven magnets 1402 are coupled magnetically through the skin 1404 of a patient 1408 to one or more external drive magnets 1410. A rotation or movement of the external drive magnets 1410 causes an equal rotation of the driven magnet(s) 1402. Turning the driven magnet(s) 1402 in one direction 1412 causes the distraction device 1414 to increase distraction while turning the driven magnet(s) 1402 in the opposite direction causes the distraction device 1414 to decrease distraction. Changes to the distraction device 1414 distraction distance or distraction force depend upon the number of turns by the one or more drive magnets 1410.

The drive magnets 1410 are rotated by the external device 1406, which has an electric gear motor 1416 which is controlled by a programmable logic controller (PLC) 1418. The PLC 1418 outputs an analog signal 1420 to a motor drive circuit 1422 which is proportional to the motor speed desired. The PLC 1418 receives an analog signal 1424 from the motor drive circuit 1422 that is proportional to the current draw of the motor. The gear motor's 1416 current consumption is proportional to its output torque. An electronic torque sensor may be used for this purpose. The measured current draw may be used to monitor the change in output torque.

The PLC 1418 receives a pulsed input signal 1426 from an encoder 1428 that indicates the angular position of the drive magnets 1410. The PLC 1418 controls a spring loaded braking system 1430 that automatically stops the drive magnet 1410 if there is a loss of electrical power or other emergency.

A slip clutch 1432 is included between the gear motor 1416 and the drive magnet 1410 to prevent the gear motor 1416 from over torqueing the driven magnet 1402 and potentially damaging the distraction device 140, for example, if the distraction device 140 does not have its own slip clutch. The PLC 1418 has a built in screen 1434 to display messages and a keypad 1436 for entering data. External push button switches and indicator lights may be incorporated for user comfort and ease of use.

The motor current (output torque) is monitored continuously whenever the device is turning. If the motor current exceeds the maximum allowable current (based on safety requirements of the device components and/or patient tissue) the gear motor 1416 is stopped and the brake 1430 is applied. This can be done both in software and hardware. The mechanical slip clutch 1432 also prevents over torqueing of the device. An exemplary threshold torque is 5.0 ounce-inches.

In one embodiment, each patient will have a number that corresponds to the distraction displacement of their particular distraction device 1414. A distracted device 1414 will have a number such as 5.0 cm for its distraction displacement and a fully non-distracted device will have a number such as 0.0 cm.

This number can be stored on an electronic memory card 1438 that the patient 1408 carries. The PLC 1418 can read the current number from the memory card 1438 and update the number after adjustment. The patient's number can be recorded manually in the patient's chart and kept at the physician's office or printed on an information card that the patient carries. Alternatively, the information can be stored on and read from an RFID chip implanted in the patient.

The patient's number is first entered into the PLC 1418 so it knows the patient's starting point. If the patient's records are completely lost, the system can always have a new setting manually input based on an X-ray image determination of the distraction displacement of the restriction device 1414.

A physician may adjust the distraction device 1414 several ways. An absolute move to a new distraction displacement (or force) may be entered directly. For example, a patient 1408 currently at 2.00 cm distraction displacement may need to be adjusted to 2.50 cm. The physician simply enters the new distraction displacement and presses a 'GO' button. The physician may prefer a relative (incremental) move from the current distraction displacement. Each press of a button will cause the device to increase or possible decrease a fixed amount, say 0.20 cm of distraction displacement, or 0.02 cm. In another aspect, there may be provided increase and decrease buttons which increase/decrease the distraction of the distraction device 1414 as long as the button is held. It should be noted that the displacement of distraction is a relative term, and that the force gauge disclosed in this invention may be the preferred manner to adjust distraction, instead of a dimensional manner. Further, the PLC 1418 may automatically adjust the external device 1406 to reach the desired final distraction force or length based at least in part on a response generated by a feedback device. The particular feedback device may be any number of devices described herein including strain or force gauge feedback, acoustic feedback, optical feedback, motor current and the like.

Once the external device 1406 is commanded to move, the PLC 1418 slowly ramps up the speed of the gear motor 1416 while monitoring the motor current (torque). A known minimum drive torque must be present for verification that the magnetic coupling to the restriction device is locked and not slipping. This can be monitored with, for example, the acoustic feedback system. The minimum torque value can be a curve that is stored in the PLC 1418 that is based on the amount of distraction, the direction of movement (increasing/decreasing), even the model number or serial number of the distraction device 1414.

Also, if a sudden torque reversal is detected by the PLC 1418, a slip has occurred. As the like magnet poles (North-North & South-South) which are repelling slip past each other, they are attracted to the adjacent opposite poles (North-South & South-North). This causes a momentary reversal of drive torque. This torque reversal can be detected by the PLC 1418. If a slip occurs, the PLC 1418 can subtract the appropriate amount from the move. If too many consecutive slips occur, the PLC 1418 can stop and display a message.

As the drive magnet 1410 rotates, revolutions and fractions of revolutions are counted by the PLC 1418 and converted to changes in the distraction. Once the move is complete, the PLC 1418 stops the gear motor 1416 and applies the brake 1430. It should be understood that the feedback devices mentioned above is applicable to the external device, and to many other types of magnetic drives with the exception of nearby or proximally-located electromagnetic coils which do not have a motor.

Any of the compatible configurations of a distraction device/adjustment mechanism/external adjustment device are contemplated to be combinable as alternative embodiments to those specifically described herein. In addition, the mechanical mechanism of the distraction device can be achieved by any of the designs and methods by using a rotating drive shaft, or by a tension/compression member. In other words, rotation can be done only to proximal assemblies or assemblies within the distraction device, which then, through gearing, cause longitudinal shortening or lengthening of a wire or cable, which pulls tension on a belt or rod to cause the distraction device to increase or decrease distraction (distance or force).

Figure 36:
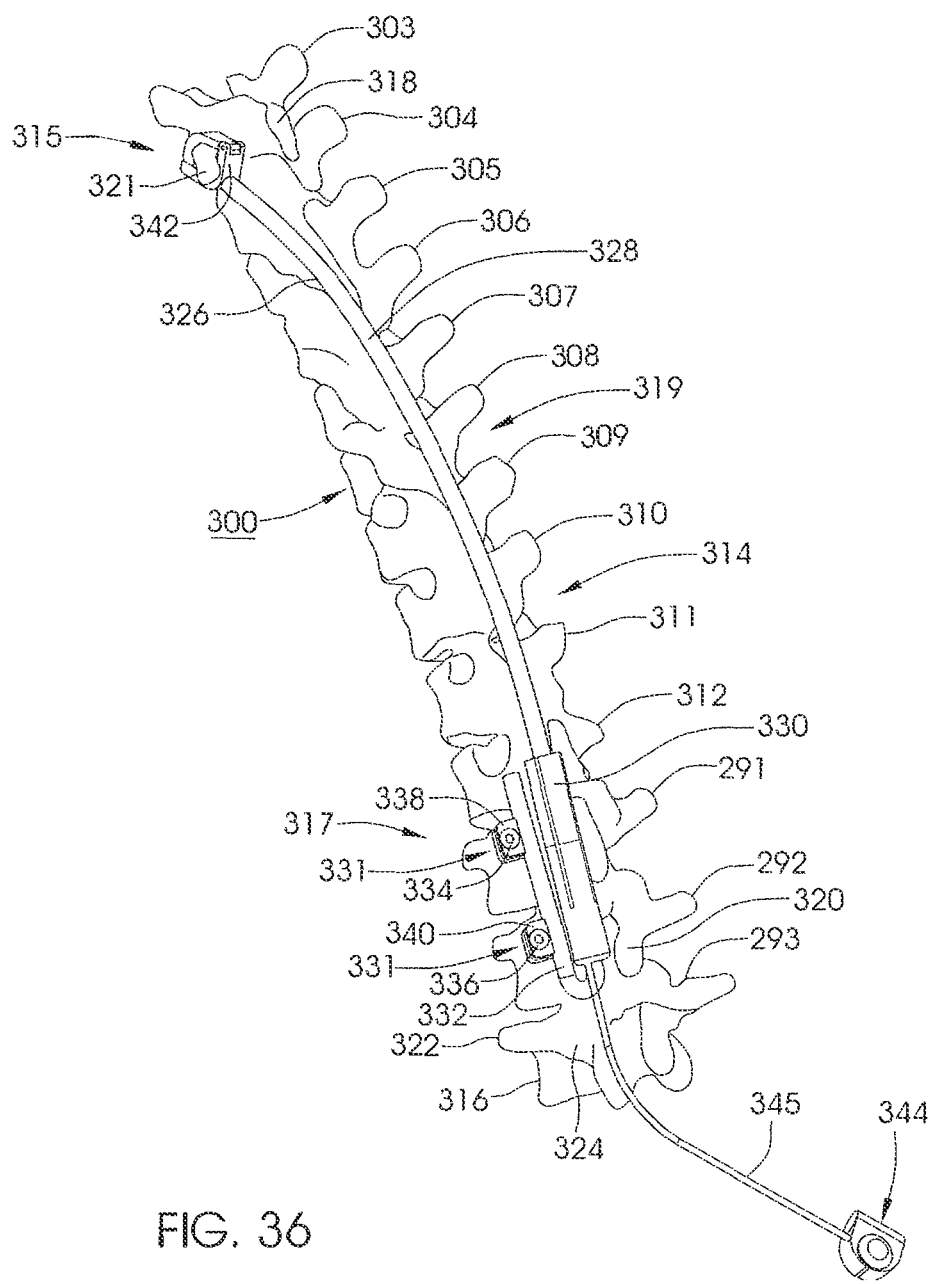
FIG. 36 illustrates a distraction device affixed to a spine of a patient according to one embodiment.

FIG. 36 illustrates an embodiment of a distraction device 314 implanted within a patient and fixated at its upper end 315 and lower end 317 to the patient's spine 300. The illustrated example of the spine 300 includes the particular thoracic and lumbar vertebrae that typically encompass a scoliotic curve, for example the curve of a patient with adolescent idiopathic scoliosis. The T3 through T12 thoracic vertebrae, 303, 304, 305, 306, 307, 308, 309, 310, 311, 312, respectively and the L1 through L3 vertebrae, 291, 292, 293 are depicted in FIG. 36, not in a severe scoliotic condition, but in a very slight residual curve that represents a modest curve that has been partially or completely straightened during the implantation procedure. Each vertebra is different from the other vertebra by its size and shape, with the upper vertebra generally being smaller than the lower vertebra. However, generally, the vertebrae have a similar structure and include a vertebral body 316, a spinous process 318, 320, laminae 326, transverse processes 321, 322 and pedicles 324. In this embodiment, the distraction device 314 includes a distraction rod 328 which is adjustable (lengthwise) via a coupled adjustable portion 330. The distraction device 314 is fixated to the spine 300 via a clamp 342 at the upper end of the distraction rod 328. In FIG. 36, the clamp 342 is secured around the transverse process 321 of the T4 vertebra 304. Alternatively, the clamp 342 may be secured around an adjacent rib (not shown) or rib facet. In still another alternative, the clamp may be replaced by a laminar and pedicle hook system, or pedicle screw system. FIG. 37 illustrates one such alternative embodiment in which a distraction device 314 includes one or more laminar hooks 346 that are used to secure an upper end 315 of the distraction device 314 to the spine (not shown). The lower end 317 of the distraction device is secured to the spine using one or more pedicle hooks 348.

Referring back to FIG. 36, the distraction device 314 is illustrated as being fixated to the spine 300 with a pedicle screw system 331 comprising a connecting rod 332 and two toe clamps 338, 340. This particular embodiment comprises a magnetic adjustment device 344 which is spaced from the adjustable portion 330 via a transmission cable 345.

Turning to FIG. 38, more detail of the pedicle screw system 331 is shown. The pedicle screw 349 passes through a hole in base 350, securing base to the L1 vertebra 291 (FIG. 36) though its pedicle (left pedicle in this case). Locking screw 334 can be loosened to adjust the angle α of the connecting rod 332, and then locking screw 334 can be tightened so that toe clamp 338 securely holds connecting rod 332 in place without further rotation. The second toe clamp 340 is adjusted in the same way, by tightening locking screw 336. Because a scoliotic spine is also rotated (usually the center section is rotated to the right in AIS patients), the non-fusion embodiment presented here allows de-rotation of the spine 300 to happen naturally, because there is no fixation at the middle portion 319 of the distraction device 314.

Figure 39:
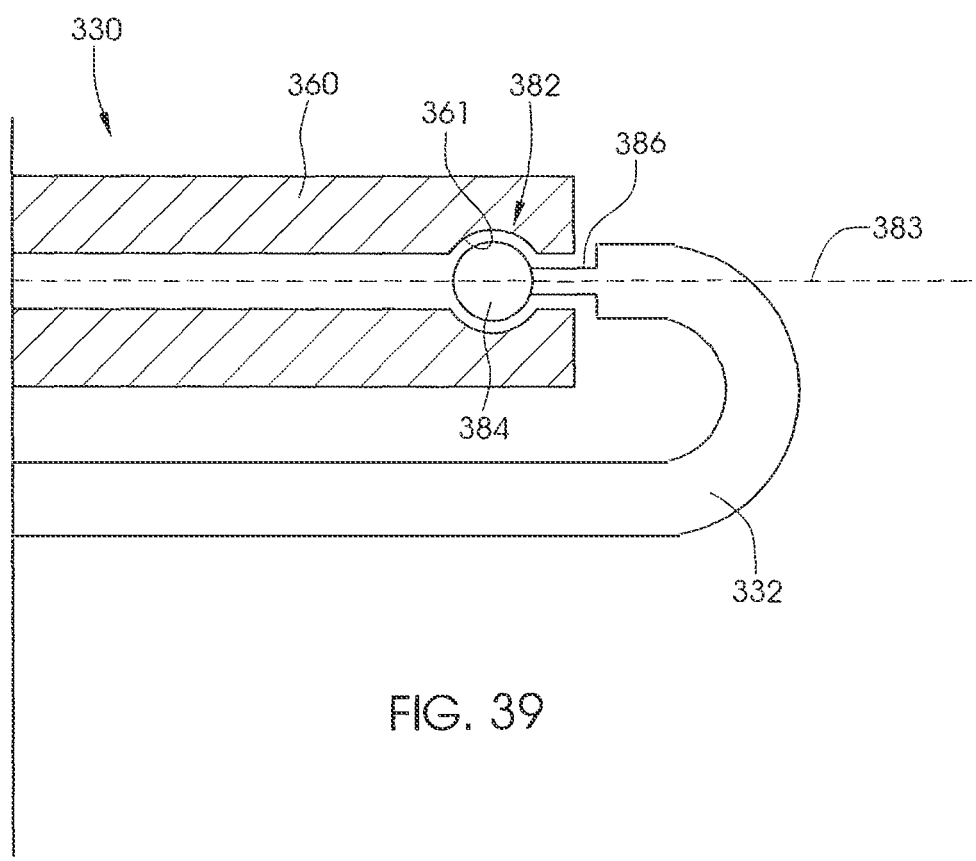
FIG. 39 illustrates the connection between an adjustable portion of the distraction device and a connecting rod that allows for, among other movements, free rotation.

In order to further facilitate this de-rotation, the distraction device 314 allows for free rotation at its ends. For example, turning to FIG. 39, the adjustable portion 330 is attached to the connecting rod 332 via a ball joint 382. The end of the connecting rod 332 has a substantially 180° curve which allows it to meet the adjustable portion 330 along the same axis 383. The extreme end of the connecting rod 332 comprises a stem 386 and a ball 384. A mount 360 is disposed at the end of the adjustable portion 330 and has a partial spherical internal contour 361 to mate with the ball 384, and allow for free rotation. It may also allow for polyaxial motion. It should be noted that distraction rod 328 may be precurved with the typical shape of a normal sagittal spine, but it should also be noted that the curve may be slightly different than standard scoliosis fusion instrumentation, because in the non-fusion embodiment described herein, the distraction device 314 is not flush with the spine but rather is placed either subcutaneous or sub-fascial, and thus is not below the back muscles. The only portions of the distraction device 314 that are designed to be placed below the muscles are the clamp 342 and the portion of the distraction rod 328 immediately adjacent the clamp 342, the pedicle screw system 331 and the connecting rod 332. Thus, FIG. 36 illustrates an embodiment in which the bulk of the hardware associated with the distraction device 314 is placed over the muscle. It should be understood, however, that in alternative configurations, any other part of the entire implantable embodiment may be placed under the muscle (i.e., sub-muscular). It should be appreciated that a much smaller amount of muscle needs to be dissected during the procedure in comparison with current fusion procedures. This will allow for a much shorter procedure, much less blood loss, much quicker recovery, and less time in the hospital/less risk of infection. Further, it may be desirable to produce the "J" curve of the connecting rod 332 or the "S" curve of connecting rod 323 of FIG. 37 with flanges or ribs at their highest stress points in order to increase their durability in demanding implant conditions.

Figures 40, 41:
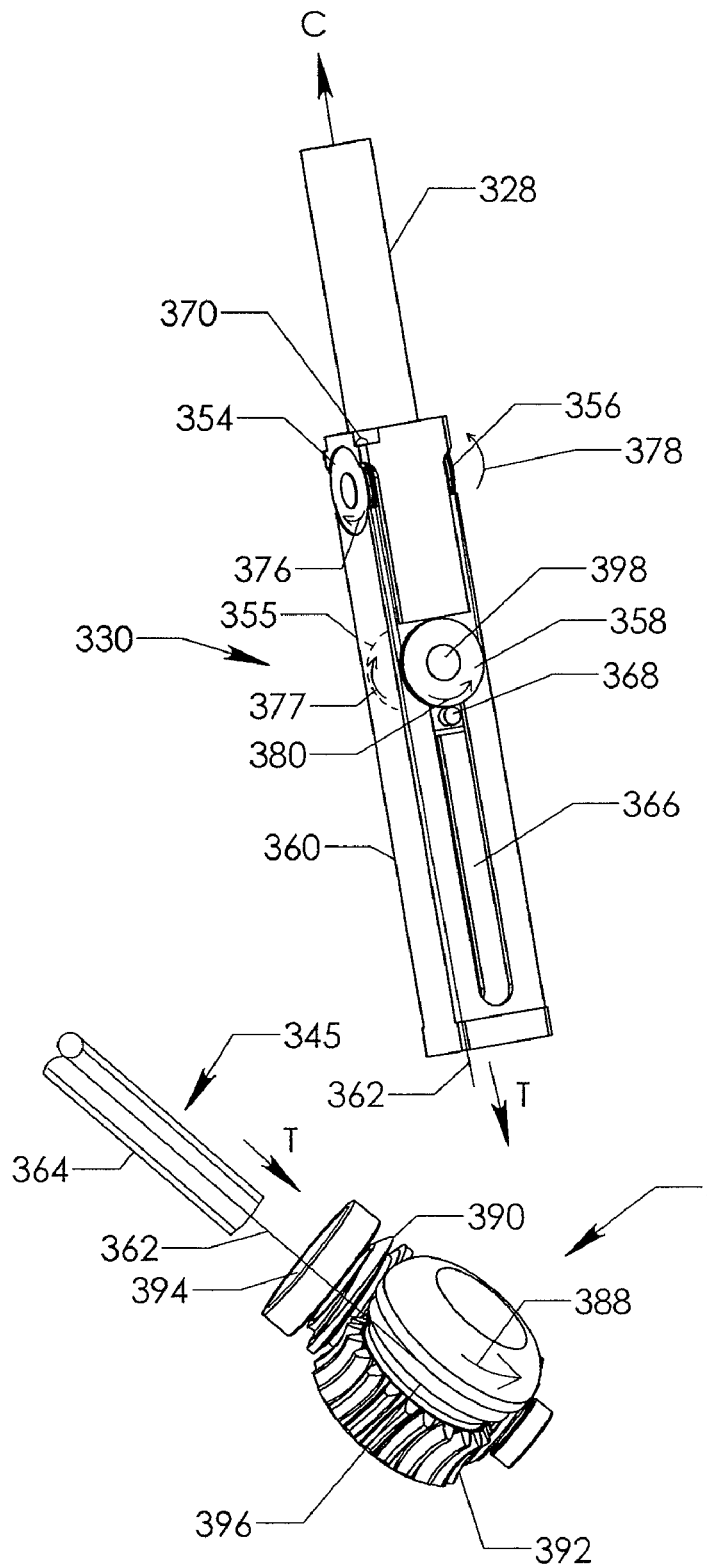
FIG. 40 is a perspective view of an adjustable portion of a distraction device according to another embodiment.
FIG. 41 is a perspective view of a remotely located magnetic adjustment device that is used in connection with the adjustable portion illustrated in FIG. 40.
Figure 42:
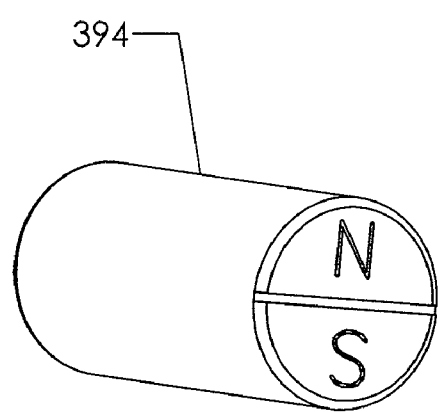
FIG. 42 illustrates a perspective view of a cylindrical magnet that is magnetized in the radial direction according to one embodiment.

FIG. 40 and FIG. 41 illustrate one embodiment of a remotely-located magnetic adjustment device 344 that enables adjustment of the distraction device 314 from a location that is remote from the adjustable portion 330. As explained below, the adjustable portion 330 is operatively coupled to the magnetic adjustment device 344 via a transmission cable 345. For example, the magnetic adjustment device 344 may be placed subcutaneously in the buttocks area or even the abdominal area. Alternatively, the magnetic adjustment device 344 may be located integral to the adjustable portion 330. In its remote configuration, however, the magnetic adjustment device 344 (depicted in FIG. 41 without its protective outer cover) includes a worm 390 and a cylindrical magnet 394 fixedly secured inside the worm 390. The cylindrical magnet 394 is preferably magnetized radially as illustrated in FIG. 42. Activation of an external adjustment device (e.g., external adjustment device 1130) causes the cylindrical magnet 394 and worm 390 to turn. The worm 390 contains threads about its exterior surface and engages with a rotatable gear 392 which, in turn, is operatively coupled to a spool 396. The spool 396 includes a groove or the like about its periphery in which a cable 362 is disposed. During operation of the device, rotational movement of the cylindrical magnet 394 causes rotation of the gear 392 that, in turn, causes rotation of the spool 396. As the gear 392 turns, the spool 396 winds or unwinds a cable 362 that extends through a protective sheath 364 located in the elongated transmission cable 345 that couples the adjustment device 344 to the adjustable portion 330. Depending on the direction of rotation of the gear 392, the cable 362 is either tightened or loosened.

Referring to FIG. 41, as the gear 392 turns in direction 388, tension (T) is increased. The opposite end of cable 362 is secured to frame 360 by stop 370. In one embodiment, the cable 362 is pulled over first pulley 354, which turns in a first rotational direction 376. Cable 362 then wraps around second pulley 355 (shown in phantom) in the back of frame 360 causing second pulley 355 to turn in second rotational direction 377. The cable 362 then wraps around a third pulley 356 causing it to turn in third rotational direction 378. After the third pulley 356, the cable 362 wraps around a fourth pulley 358, causing it to turn in a fourth rotational direction 380. Second pulley 355 and fourth pulley 358 are rotationally attached to the distraction rod 328 via axle 398, and are slidably contained within frame 360 by pin 368 which slides in a groove 366.

The combination of the pulleys 354, 355, 356, 358 act as a block and tackle arrangement that amplifies the force applied to the distraction rod 328 in response to an applied tension (T). For instance, a tension (T) that is placed on cable 362 imparts a compressive force (C) on the distraction rod 328 that is four times as large (i.e., C=4*T). Of course, it should be understood that by driving the cylindrical magnet 394 and worm 390 in the opposite direction, the gear 392 causes the spool 396 to unwind, and thus both T and C are decreased.

Figure 43:
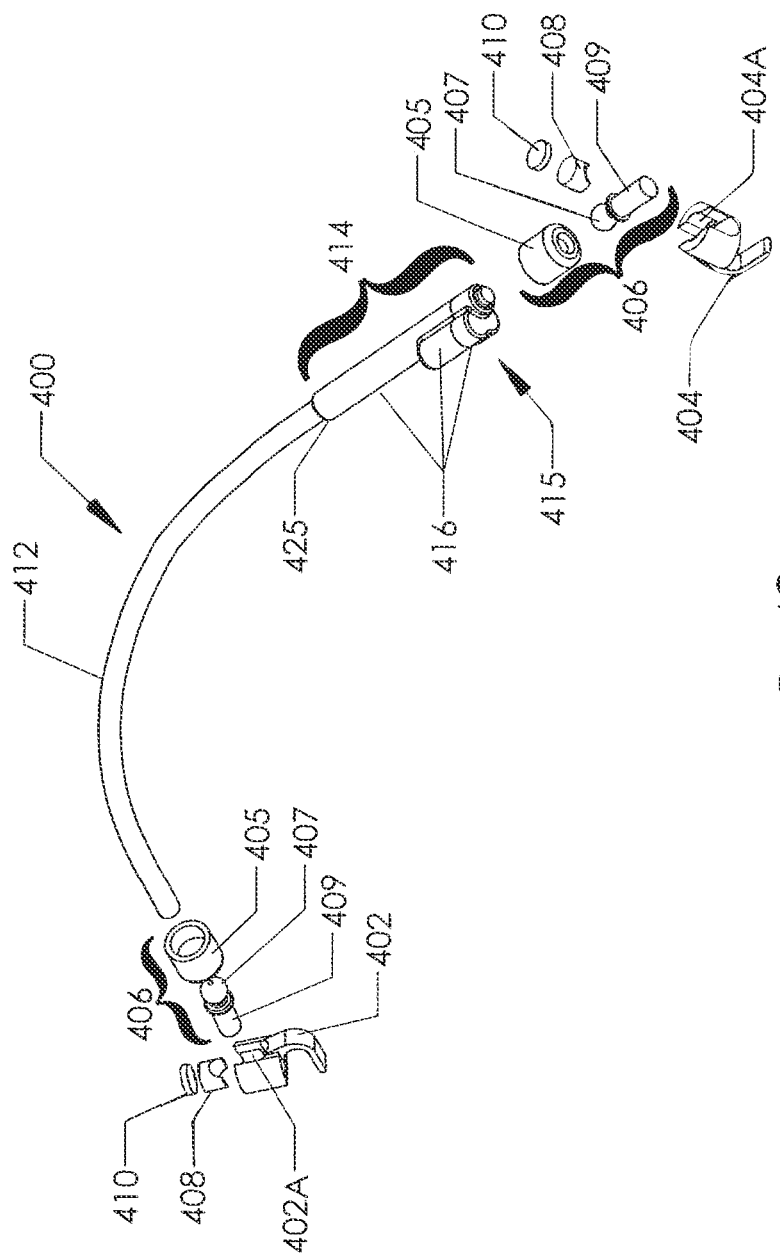
FIG. 43 illustrates a perspective view of a distraction device according to another embodiment.

FIG. 43 illustrates another embodiment of a distraction device 400. In this embodiment, hook fixation systems are used to secure to distraction device 400 to the patient's spine. The hook fixation system is depicted in an exploded configuration in FIG. 43 and includes hooks 402, 404 (for example laminar hooks, facet hooks or rib hooks) located on opposing ends of the distraction device. The hooks 402, 404 are operatively coupled to ball joints 406. Each ball joint 406 includes a coupler 405 that interfaces with a ball 407 or other substantially spherical member disposed at the end of a post 409. The hooks 402, 404 each include a recess 402A, 404A that are dimensioned to receive the post 409 of each ball joint 406. The post 409 is frictionally engaged or locked with respect to its respective hook 402, 404 using a clamping member 408 and overlying cap 410. The coupler 405 includes a receiving portion such as an internal threaded portion (not shown) that interfaces with opposing ends of the distraction rod 412. Of course, the coupler 405 may be secured to distraction rod 412 in other ways such as, for instance, mounting screws, a bond, weld, or even through the use of a cement or other adhesive material. In this regard, once mounted, both hooks 402, 404 are able to articulate about the swivel-action ball joint 406 to accommodate the changing geometry as the spine is subject to distraction forces.

As seen in FIG. 43, the distraction rod 412 is supplied in a pre-curved configuration, and can be cut to the desired length and bent into a custom configuration to fit the patient's specific anatomy. Typically, the portion that is to be cut would be the end of the distraction rod 412 that is located away from the adjustable portion 414. Adjustable portion 414 in this embodiment comprises an offset gearing assembly 415 having a cover 416.

Figure 44:
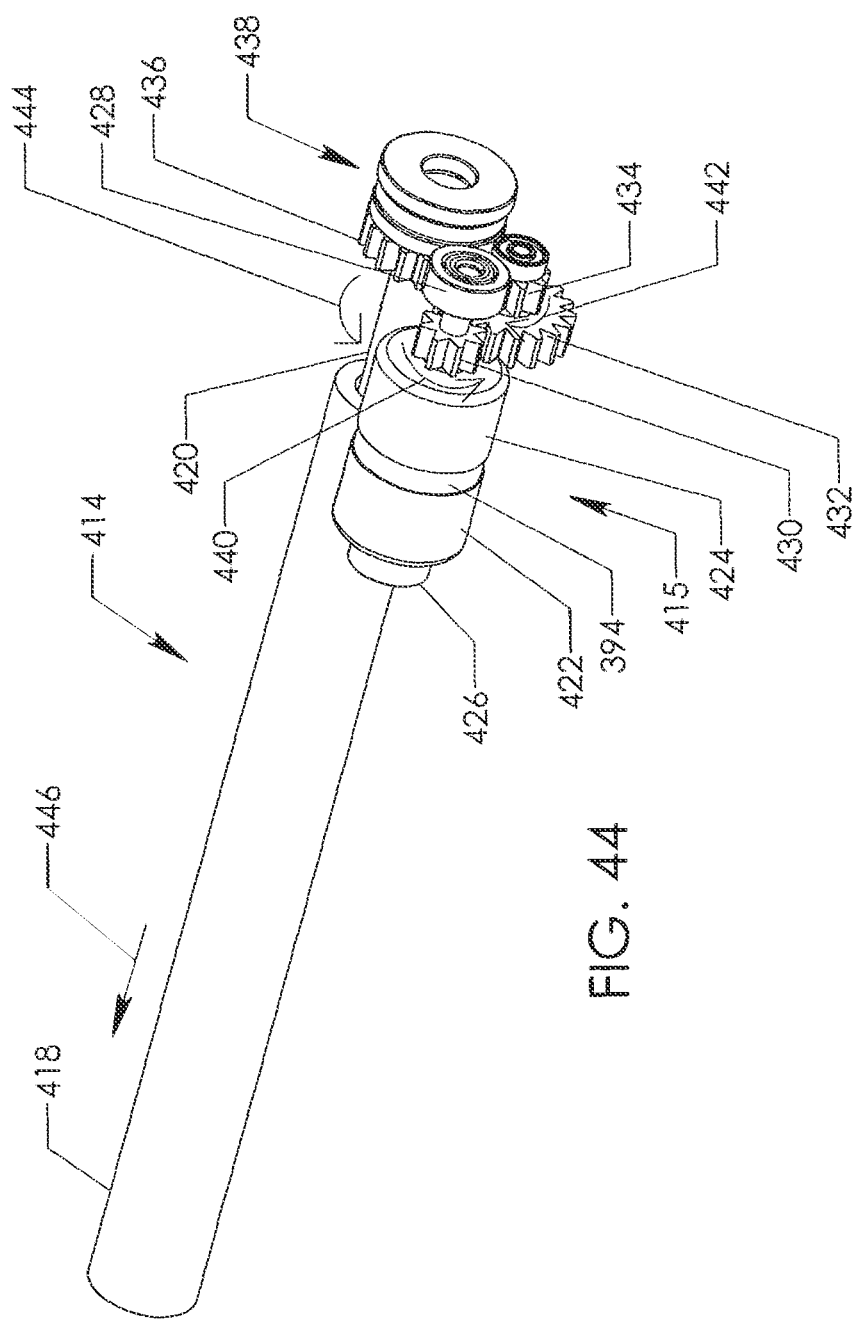
FIG. 44 illustrates the adjustable portion of FIG. 43 without the cover.

FIG. 44 illustrates the offset gearing assembly 415 with the cover 416 removed from the adjustable portion 414 in order to better show the internal components responsible for effecting the distraction forces on the distraction rod 412. As seen in FIG. 44, a cylindrical magnet 394 is rotationally held by cups 422, 424 and the assembly 415 is free to rotate between ball bearings 426, 428 disposed on opposing ends thereof. The cylindrical magnet 394 may include a permanent magnet made out of the materials described herein with respect to the other embodiments. The assembly 415 includes a first gear 430 which rotates as the assembly 415 is rotated about its axis of rotation. An external adjustment device (e.g., 1130) causes cylindrical magnet 394 to turn in a first rotational direction 440 which also causes the first gear 430 to turn in same, first direction 440. The first gear 430 meshes with a second gear 432 causing the same to turn in a second rotational direction 442. A third gear 434 is secured to the second gear 432 and rotates along with second gear 432. The third gear 434 meshes with a fourth gear 436, causing it to turn in a third rotational direction 444. The fourth gear 436 is secured to a lead screw 420 which extends longitudinally inside a sleeve 418 or jacket. A thrust bearing 438 is provided in a face-to-face arrangement with the fourth gear 436 to reduce frictional forces during rotation of the lead screw 420. The inner surface of the sleeve 418 contains a threaded inner bore (not shown) which extends at least a portion of the length of the sleeve 418. Lead screw 420 is allowed to turn because of a thrust bearing 438 located at end of the lead screw 420.

When the lead screw 420 turns in the fourth rotational direction 444 and engages threaded inner bore of sleeve 418, the sleeve 418 begins to move in the distraction direction 446. The sleeve 418 is coupled at one end to the distraction rod 412, and thus, when sleeve 418 and distraction rod 412 are distracted by the offset gearing assembly 415, the distraction device 400, which is coupled to the spine, imparts an increased distraction force. If the cylindrical magnet 394 is turned in the opposite direction, the distraction force is lessened. Because of both the gearing and the lead screw thread, a relatively low torque can be delivered to rotate the cylindrical magnet 394 which, in turn, can impart a very high distraction force on the sleeve 418, and thus the distraction rod 412. In one embodiment, the first gear 430 has eight (8) teeth, second gear 432 has eighteen (18) teeth, third gear 434 has ten (10) teeth, and fourth gear 436 has eighteen (18) teeth. The meshing of the first gear 430 and second gear 432 has a gear ratio of 18:8 and the meshing of the third gear 434 and fourth gear 436 has a gear ratio of 18:10. This creates an overall gear ratio for the offset gearing assembly 415 of 81:10, and thus an output torque to input torque ratio of 4.05. Assuming a typical gear efficiency of 0.90 (due to frictional effects in the each of the two gear meshes), a 6.0 ounce-inch torque applied to the cylindrical magnet 394 can produce an approximate torque of 19.7 ounce-inches on the lead screw. A lead screw 420 having a diameter of approximately 3.5 mm (0.138") and approximately 100 threads per inch has been measured to have an efficiency of approximately 0.084. Thus, a 6.0 ounce-inch torque applied to the cylindrical magnet 394 will produce a distraction force of as high as 65 pounds. This assumes an external adjustment device 1130 having two external magnets 1134, 1136 each having a diameter of approximately two (2) inches.

Returning to FIG. 43, an annular dynamic seal 425 provided at one end of the adjustable portion 414 allows the distraction rod 412 to pass through the end of the adjustable portion 414 without any body fluids or materials being able to enter the adjustable portion 414. The interior of the adjustable portion 414 is thus substantially isolated or sealed off from the surrounding implant environment. While FIG. 43 illustrates a pair of hooks 402, 404 that are used to secure the distraction device 400 to the spine of the patient, it should be understood that other anchors may be used to affix the ends of the distraction device 400 to the spine. For example, screws or other fasteners may be used to secure one or both ends of the distraction device 400 to the patient's spine. Typically, screws are used for the lower portion of the distraction device 400 while hooks or screws are generally preferred for the upper portion of the distraction device 400. Clamps may also be used to secure one or both ends of the distraction device 400 to the patient's spine. Generally, clamping structures are used to secure the upper portion of the distraction device 400 to a rib or transverse process of the subject.

Figure 45:
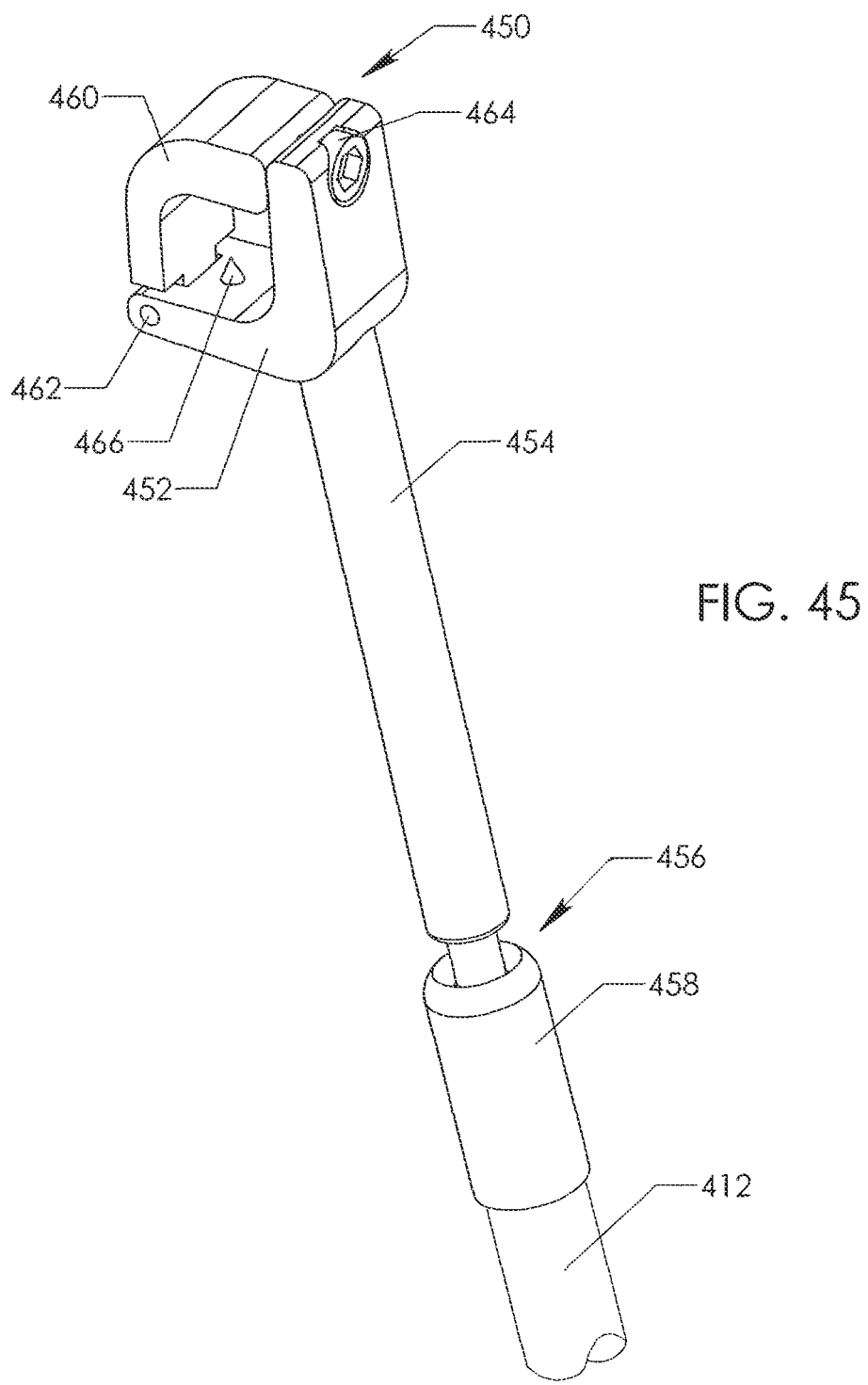
FIG. 45 illustrates a clamp used to affix the distraction device to a patient's anatomical structure according to one embodiment.

For example, FIG. 45 illustrates a clamp 450 that can be used to secure one end of the distraction device 400 to a rib or transverse process. The clamp 450 includes an "L-shaped" bracket 452 that is mounted on a shaft 454. The shaft 454 terminates at a swivel joint 456 that provides swiveling movement between a coupler 458 and the clamp shaft 454. The coupler 458 is configured to receive one end of the distraction rod 412 (e.g., using threads, mounting screw(s), adhesive, cement, laser weld, or the like). The clamp 450 includes a pivoting bracket 460 that pivots about a pin 462 from an open configuration to a closed configuration. The clamp 450 that is illustrated in FIG. 45 pivots from the front of the patient to the back of the patient and is referred to as a "front-to-back" clamp. In alternative configurations, the clamp 450 may be constructed as a "back-to-front" clamp in which the pivoting bracket 460 pivots from the back of the patient to the front. The pivoting bracket 460 can be locked in the closed configuration by the fastener 464 which engages and holds the pivoting bracket 460 to the L-shaped bracket 452. The fastener 464 may be a screw, bolt or the like that can be tightened or loosened by rotation using a tool (e.g., wrench or driver). In one embodiment, the clamp 450 further includes an optional detent 466 or other protuberance on the L-shaped bracket 452 that aids in fixedly securing the clamp 450 to the rib or other anatomical structure.

Figure 46:
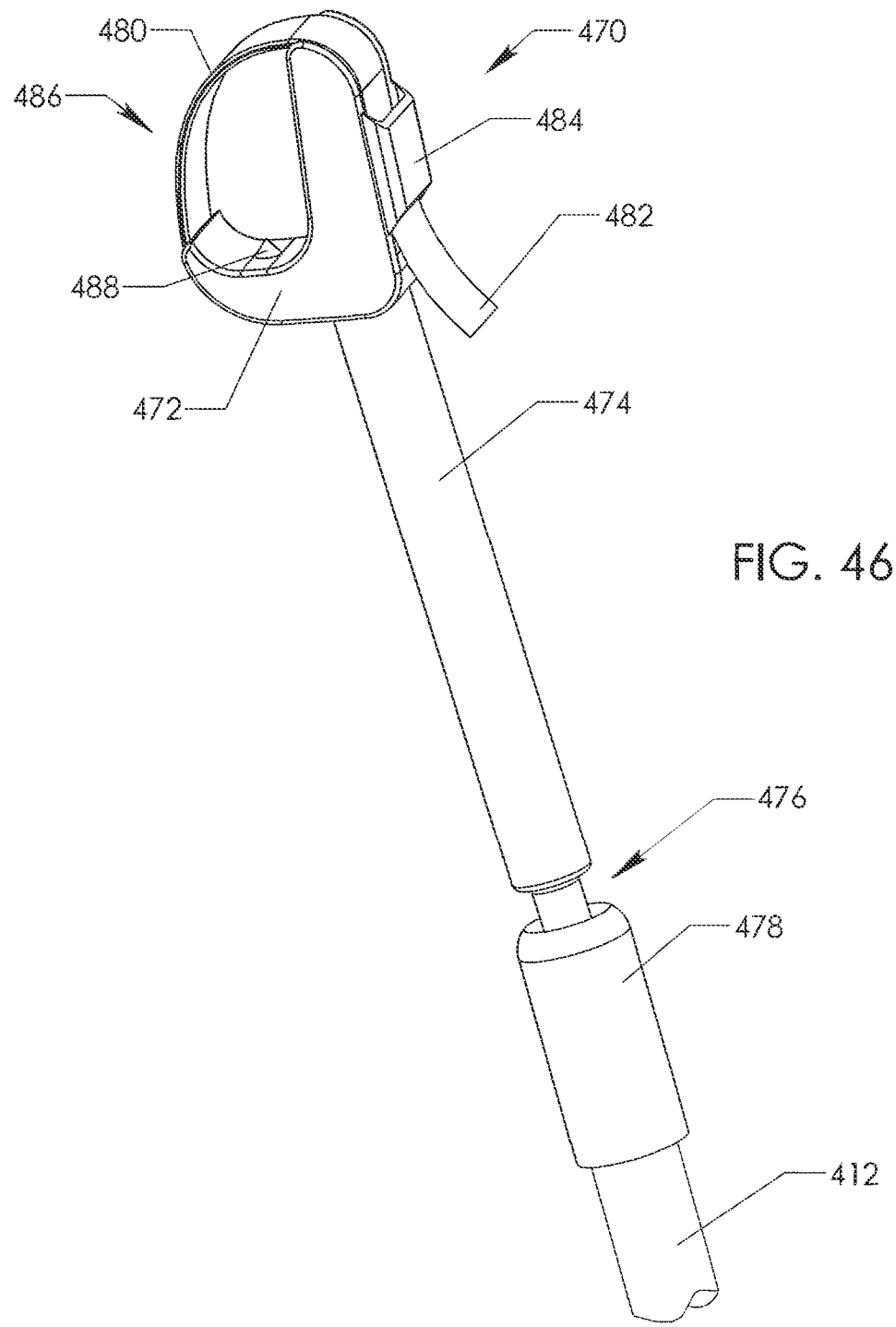
FIG. 46 illustrates a clamp used to affix the distraction device to a patient's anatomical structure according to another embodiment.

FIG. 46 illustrates another embodiment of a clamp 470 that can be used to secure one end of the distraction device 400 to a rib or transverse process. The clamp 470 includes an "J-shaped" bracket 472 that is mounted on a shaft 474. The shaft 474 terminates at a swivel joint 476 that provides swiveling movement between a coupler 478 and the clamp shaft 474. The coupler 478 is configured to receive one end of the distraction rod 412 (e.g., using threads, mounting screw(s), adhesive, cement, laser weld, or the like). The clamp 470 includes a band 480 secured to one end of the J-shaped bracket 472. The band 480 is flexible in nature includes a free end 482 that is insertable into a lock 484 disposed on the J-shaped bracket 472. The band 480 may be made from a polymeric material or even a metallic material. The band 480 preferably has a small thickness that minimizes the amount of material that is exposed to the front side of the patient. Because the patient's lungs are located somewhat near the front portion 486 of the clamp 470, it is preferred to keep the amount of material in this section of the clamp 470 to a minimum. The band 480 provides the ability to ensure that the clamp 470 is secured to the rib or other anatomical structure.

The clamp 470 that is illustrated in FIG. 46 has a band 480 that bends about the clamp 470 from the front of the patient to the back of the patient and is referred to as a "front-to-back" clamp. While the clamp 470 may be constructed as a "back-to-front" clamp in an alternative embodiment, this is not preferred because of the added material thus points toward sensitive organs (e.g., lungs) of the patient. In one embodiment, the clamp 470 further includes an optional detent 488 or other protuberance on the J-shaped bracket 472 that aids in fixedly securing the clamp 470 to the rib or other anatomical structure.

FIGS. 47 and 48 illustrate an alternative embodiment of an adjustable portion 568 that is used in connection with a distraction device 400 utilizing a hollow magnet 562 (FIG. 48). While the description of the adjustable portion 568 is given in the context of the distraction device 400, it should be understood that the alternative embodiment may apply equally to other distraction devices described herein (e.g., distraction devices 140, 314, 1414, etc.). As seen in FIGS. 47 and 48, the adjustable portion 568 is contained within two slidable sections which include an outer tube 548 and an inner tube 550. The outer tube 548 and inner tube 550 are moveable relative to one another as explained below. As best seen in FIG. 48, a hollow magnet 562 is mounted on an inner sleeve 564 and a nut 560 having internal threads thereon. That is to say that the inner sleeve 564 and nut 560 are entirely or at least partially disposed within the hollow portion of the magnet 562. The hollow magnet 562, inner sleeve 564, and nut 560 rotate together in unison, between opposing ball bearings 556, 558. An end cap 566 holds the assembly together. In this embodiment, the hollow magnet 562 permits the lead screw 554 to pass through it, thereby lessening the necessary total length of the adjustable portion 568, and thus the length of a larger diameter portion of the distraction device 400. Rotation of the hollow magnet 562 effectuates rotation of the nut 560 that, depending on the direction of rotation, either pulls inward or pushes outward the lead screw 554 which engages with the internal threads (not shown) of the nut 560. While FIG. 48 illustrates a completely hollow magnet 562, some of the reduced length benefits discussed above may still be gained if only a portion of the magnet 562 were hollow or contained a recess configured to receive the lead screw 554. The magnet 562 is advantageously a permanent magnet and may be formed from the materials described herein with respect to the other embodiments. Still referring to FIG. 48, a dynamic seal 552 is provided at the interface between the outer tube 548 and the inner tube 550 to ensure that no body fluids enter the assembly.

Figure 50:
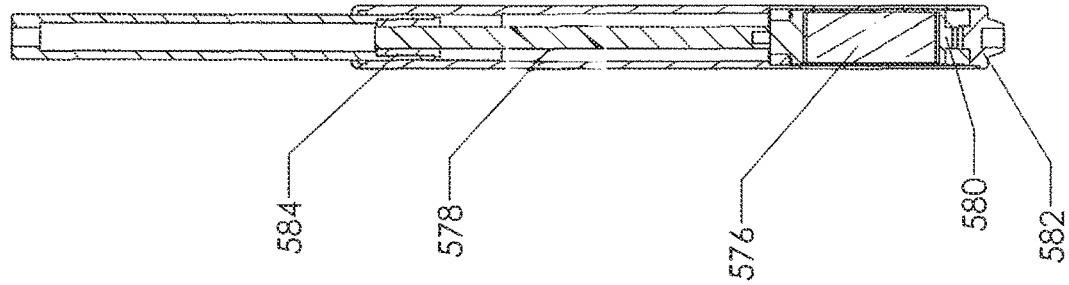
FIG. 50 illustrates a cross-sectional view of the adjustable portion of FIG. 49 taken along the line 50-50 of FIG. 49.
Figure 49:
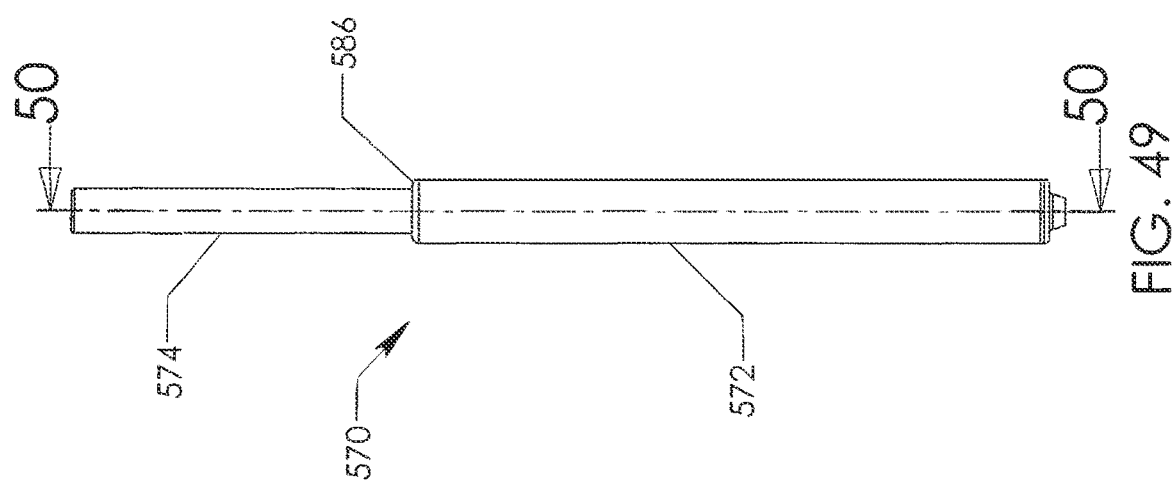
FIG. 49 illustrates an adjustable portion of a distraction device according to one embodiment.

FIGS. 49 and 50 illustrate still another embodiment of an adjustable portion 570. This embodiment is longer but thinner as compared to the adjustable portion 468 illustrated in FIGS. 47 and 48. Again, it should be understood that the alternative embodiment of the adjustable portion 570 may apply to other distraction devices described herein (e.g., distraction devices 140, 314, 1414, etc.). As seen in FIGS. 49 and 50, the adjustable portion 570 is contained within two slidable sections which include an outer tube 572 and an inner tube 574. The outer tube 572 and inner tube 574 are moveable relative to one another as explained below. As best seen in FIG. 50, a rotatable magnet 576 is held within a magnetic cup 580 which rotates on a thrust bearing 582. The magnet 576 is operatively coupled to a lead screw 578 that rotates along with the magnet 576 in response to an externally applied magnetic field as described herein. The adjustable portion 570 does not include an inner sheath such as that illustrated in the prior embodiment (FIGS. 47 and 48) thereby enabling a thinner profile. In this embodiment, the nut 584 is affixed to the inner tube 574. Rotation of the magnet 576 causes rotation of the lead screw 578 which then pulls or pushes the inner tube 574 relative to the outer tube 572. A dynamic seal 586 is provided at the interface between the outer tube 572 and the inner tube 574 to ensure that no body fluids enter the assembly.

In any of the above-described embodiments, the external adjustment device (e.g., external adjustment device 1130) may optionally include a vibrator attached thereto that transmits vibrational motion to the adjustable portion 570 (or other adjustable portions described herein) which lessens frictional effects on the components giving them less resistance. For example, vibration may enhance or better enable axial motion of the outer tubes 448, 572 and inner tubes 450, 574, respectively and enhance freer rotation of the rotational components. The vibrational motion may also be delivered via a separate vibrator device that is separate from the external adjustment device.

Figure 51:
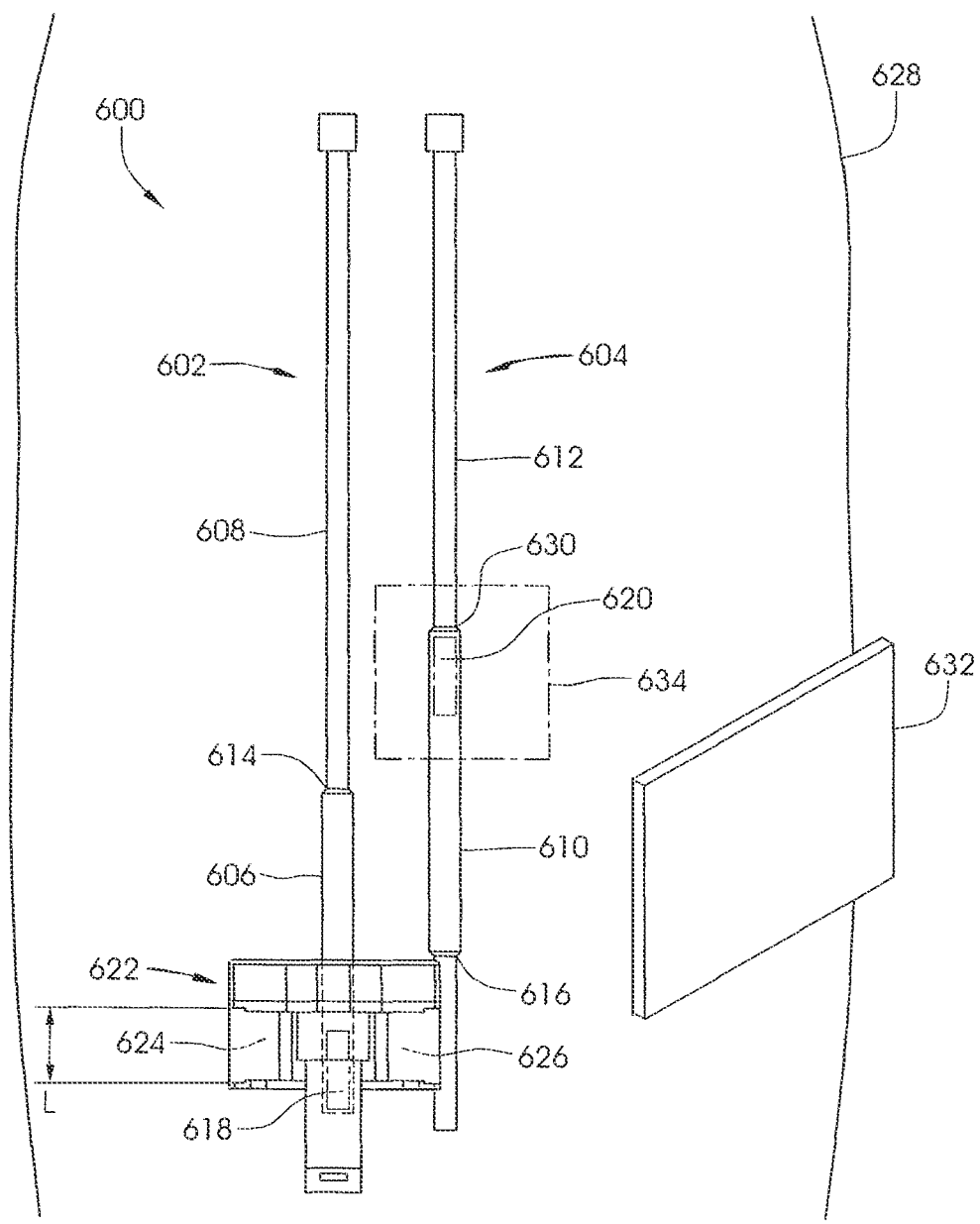
FIG. 51 illustrates an embodiment of a distraction device that includes two (2) adjustable rods, which each rod being independently adjustable.

FIG. 51 illustrates another embodiment of a distraction system 600 undergoing adjustment. In this embodiment, the implanted distraction system 600 includes two distraction devices 602, 604. The first distraction device 602 includes a first adjustable portion 606 and a first rod 608. The first adjustable portion 606 is similar to the adjustable portion 570 of FIGS. 49 and 50, with a first cylindrical permanent magnet 618 located at a far end of the first adjustable portion 606. The distraction system 600 includes a second distraction device 604 having a second adjustable portion 610 and a second rod 612. The second adjustable portion 610 is oriented in an inverted relation with respect to first adjustment portion 606, so that a second cylindrical permanent magnet 620 is not at the same level on the body 628 (e.g., height if the subject is standing up) as the first cylindrical permanent magnet 618. In this regard, the first and second cylindrical permanent magnets 618, 620 are offset from one another relative to their location vis-à-vis the spine. For instance, the second cylindrical permanent magnet 620 is located higher on the body 628 when compared to the first cylindrical permanent magnet 618.

Due to this inversion, the point of telescopic displacement 614 of the first distraction device 602 is also at a different level on the body 628 than the point of telescopic displacement 616 of the second distraction device 604. Due to the oftentimes asymmetric nature of the scoliosis, it may be desired to adjust each of the distraction devices 602, 604 independently from the other. As seen in FIG. 51, an external adjustment device 622 is provided that includes a first permanent magnet 624 and a second permanent magnet 626 that can be selectively placed at the proper level (e.g., height) along the body 628 corresponding to the location of the permanent magnet 618, 620 of the respective distraction device 602, 604 intended for adjustment. The length (L) of each of the permanent magnets 624, 626 of the external adjustment device 622 is preferably longer than the length of the permanent magnet 618, 620 for maximal coupling, yet short enough, for example, one (1) inch long, so that the operation of the external adjustment device 622 allows the permanent magnets 624, 626 to sufficiently couple with the first cylindrical permanent magnet 618, without sufficiently coupling with the second cylindrical permanent magnet 620. It should be noted, that in the inverted version, the second adjustable portion 610 is permanently attached to the second rod 612 at joint 630.

Still referring to the embodiment of FIG. 51, it may be desired to adjust the distraction length (or force) of the first distraction device 602 a certain amount followed by adjustment of the distraction length (or force) of the second distraction device 604. This may be accomplished by first placing the external adjustment device 622 over the first adjustable portion 606 which contains the first permanent magnet 618. The external adjustment device 622 may then be operated to rotate the first permanent magnet 618 with the appropriate number of rotations, or partial rotation as the case may be, to achieve the desired distraction length or force. The external adjustment device 622 may be operatively coupled with a PLC 1080 such as that illustrated in FIG. 14 to automatically adjust the external adjustment device 622. For instance, using the PLC 1080, the external adjustment device 622 may be input to adjust the first distraction device 602 one (1.0) mm. Optionally, external adjustment device 622 and/or PLC 1080 may operate under feedback control. For instance, the acoustic feedback modality described with respect to FIGS. 15-30 may be used to listen for an acoustic signal (e.g., clicks). As another alternative, an optical feedback, force feedback, or magnetic Hall effect feedback control may be used to provide feedback control of the external adjustment device 622.

Once the first adjustable portion 606 has been adjusted as desired, the external adjustment device 622 is moved over the second adjustable portion 610 which contains the second permanent magnet 620, for example directly over the permanent magnet 620. The external adjustment device 622 may then be operated to rotate the second permanent magnet 620 with the appropriate number of rotations, or partial rotation as the case may be, to achieve the desired distraction length or force. For instance, the external adjustment device 622 may be input to adjust the second distraction device 604 one-half (0.5) mm. This may be conducted as described above with respect to the first distraction device 604, including the option use of the PLC 1080 with feedback control.

While the independent adjustment described above pertains to application of a particular distraction distance (e.g., 1 mm or 0.5 mm), it should also be understood that the external adjustment device 622 may be used to adjust the first distraction device 602 to a different distraction force than the second distraction device 604. For instance, the first distraction device 602 may be adjusted to have a force of 40 pounds, while the second distraction device 604 may be adjusted to 30 pounds. Of course, one alternative is leave on the distraction devices 602, 604 at its current or then-current setting with adjustment only being performed on the other distraction device 602, 604.

In still another embodiment, a magnetic shield 632 is used that permits the first and second cylindrical permanent magnets 618, 620 to be closer to one another. For example, if it is desired to adjust the first distraction device 602 and not the second distraction device 604, the magnetic shield 632 is placed at location 634. The external adjustment device 622 is placed with its permanent magnets 624, 626 in proximity to the first cylindrical permanent magnet 618. The magnetic shield 632 diminishes the ability for the permanent magnets 624, 626 to be able to magnetically couple with the second cylindrical permanent magnet 620. The magnetic shield 626 may then be placed at a different location, closer to the first cylindrical permanent magnet 618, in order to independently adjust the second cylindrical permanent magnet 620. The magnetic shield 632 may be made from nickel, iron, steel or a nickel-iron alloy such as Mu-Metal, for example 75% Nickel/15% iron. Other materials with similar magnetic shielding properties may also be used.

Figure 52:
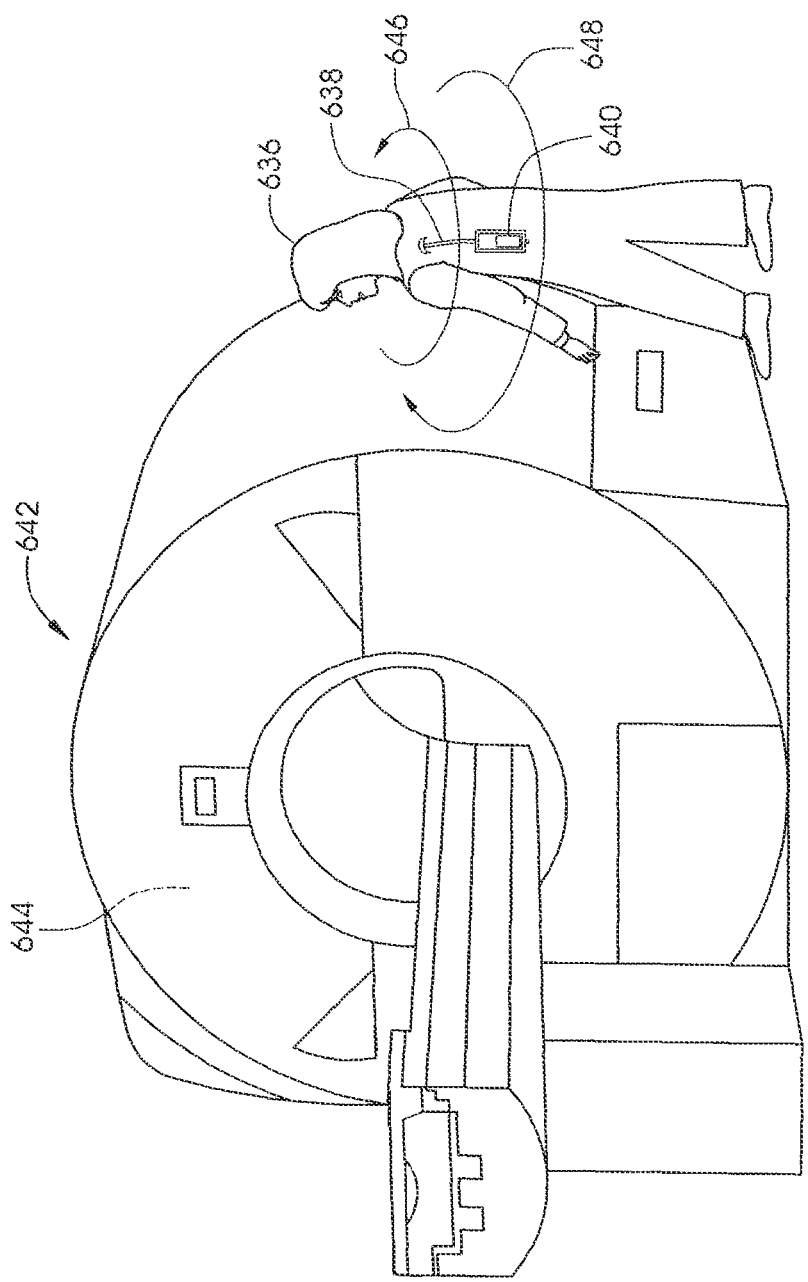
FIG. 52 illustrates a technique of performing an emergency adjustment of a magnetically-actuated distraction device.

FIG. 52 illustrates another embodiment of a technique for the emergency adjustment of a distraction device 638. As seen in FIG. 52, the patient 636 has an implanted distraction device 638 similar to those described herein. In some instances, the patient 636 may be in need of emergency adjustment due to any number of reasons including, for example, incorrect prior adjustment, trauma, bone, joint muscle or connective tissue pain, pregnancy, or growth.

If the patient 636 arrives at a hospital that does not have the external adjustment device 1130, 622 available for use, the implanted distraction device 638 containing the cylindrical permanent magnet 640 may be adjusted by using a magnetic resonance imaging (MRI) scanner 642—a diagnostic instrument that is commonly found in hospitals. Magnetic resonance imaging (MRI) scanners 642 contain a primary magnet 644 comprising a supercooled electromagnetic coil. The primary magnet 644 is designed to be "always on", except in cases of maintenance or malfunction. The primary magnet 644 generates a very large magnetic field (i.e., magnetic flux density). Older MRI scanners had magnetic fields of 0.2 Tesla, for example, but most today have fields of 1.5 Tesla or 3 Tesla while still others are 7 Tesla.

Generally, all of these fields will strongly orient a cylindrical permanent magnet 640, 394 so that it is aligned with the magnetic field of the primary magnet 644 if it is near the MRI scanner 642. It should be understood that while a description is given with respect to driven magnet 640, the acoustic sensing features may also apply to magnetic element 218 of FIGS. 6C-6G, the internal magnet 1064 of FIGS. 13A-13D, 14, the internally located driven magnet 1402 of FIG. 35, cylindrical magnet 394 of FIGS. 41, 42, and 44, the hollow magnet 564 of FIG. 48, magnet 576 of FIG. 50, magnet 262 of FIG. 53, magnets 618, 620 of FIG. 51, and magnet 1302 of FIGS. 15-30.

The torque required to turn the cylindrical permanent magnet 640 into a different orientation than the MRI aligned orientation would be significantly high, and much greater than the rotational resistance of the cylindrical magnet assembly. Therefore, by placing a patient 636 close to the primary magnet 644 of the MRI scanner 642 (for example, at a distance of ten feet or less, or more specifically five feet or less) and by turning the body of the patient in either a first rotational direction 646 or a second rotational direction 648, the implanted distraction device 638 may be adjusted without the need of an external adjustment device 1130, 622. Generally, the patient turns or rotates him or herself about an axis of rotation (which may change slightly during the rotational procedure). For example, the patient may stand on their feet and turn their body. Alternatively, the patient may sit in a swivel chair, for example a chair made of MRI safe materials such as aluminum, and the chair may be spun in the desired direction. If patient turns or is turned in first rotational direction 646, the distraction is reduced. If patient turns or is turned in second rotational direction 648, the distraction is increased. It is desirable that the implanted distraction device 638 is well secured to the patient 636, for example with pedicle screws, hooks or clamps, so that the attraction of the cylindrical permanent magnet 640 to the primary magnet 644 of the MRI device does not cause unsafe displacement of the implanted distraction device 638 at its fixation points. Additionally it is preferable to use mostly non-magnetic materials in the implant, such as Titanium or Titanium alloys such as Ti-6AL-4V, so that the implant itself is not strongly attracted to the primary magnet 644. If the implanted distraction device 638 uses acoustic feedback, such as that described in FIGS. 15 through 34, medical personnel may listen to the patient with an MRI safe stethoscope to confirm that clicks are heard, which would indicate that the magnet 640 is indeed turning. The clicks may also be counted in order to quantify the amount of adjustment precisely.

The above-described use of the primary magnet 644 to adjust the magnet 640 of the distraction device 638 may also be employed in other implantable devices that utilize a rotating or cyclically-movable magnet. For instance, the implantable device may include a restriction device (e.g., gastric band or annuloplasty ring), or a valve, or the other devices. Examples of such devices that may be adjusted in this manner may be found in U.S. Patent Application Publication Nos. 2008-0097487 and 2008-0097496. For this method to work, it should be noted that the magnets don't have to be cylindrical, but the axis of magnetization should not be parallel to the axis of rotation.

As mentioned, one of the benefits of a fully fusionless procedure is the ability to remove the implants after the spine has been able to be manipulated by the initial surgery and the non-invasive adjustments of the distraction device. The embodiments described herein allow for a completely adjustable scoliosis treatment system, which can achieve the goal of a straightened spine and no lifetime implant through a total of two surgical procedures; one procedure to implant the device and one procedure to remove the device. This is a significant improvement to the adjustable scoliosis treatment devices which have been proposed, and require adjustment techniques utilizing surgical incisions. It should be noted that after the initial implant procedure, the physician may desire to have the patient use a brace for a one or a few months, in order to protect the healing process. This protective brace serves a different purpose than the scoliosis braces that attempt to affect the patient's Cobb angle.

It is envisioned that patients may be identified for their genetic susceptibility to scoliosis and treated with a distraction device as described herein. For example, a genetic test may identify that a particular subject that has a current Cobb angle of less than or equal to 30° is predisposed or otherwise at risk for his or her Cobb angle to increase beyond this initial angle (e.g., increase to or beyond 40°). In this regard, a genetic test may be run on the patient's nucleic acid (e.g., DNA or RNA) to identify genes or gene sequences that are associated with this predisposition. If the patient has this genetic susceptibility, a distraction device of the type described herein may be used to preemptively correct or mitigate the anticipated spinal malformation. For example, Gao et al. have been reported that CHD7 gene polymorphisms are associated with susceptibility to idiopathic scoliosis. Gao et al., CHD7 Gene Polymorphisms Are Associated with Susceptibility to Idiopathic Scoliosis, American Journal of Human Genetics, Vol. 80, pp. 957-65 (May 2007). The above-noted Gao et al. publication is incorporated herein as if set forth fully herein. In particular, the CHD7 gene spans 188 kb and contains one non-coding exon and thirty-seven coding exons. The SNP loci associated with idiopathic scoliosis were contained within an ~116 kb region encompassing exons 2-4 of the CHD7 gene. For example, the genetic test may look for the SNP loci discussed above which are associated with IS susceptibility.

Though many of the embodiments described herein have generally been in the area of adolescent idiopathic scoliosis and early onset scoliosis treatment, it is contemplated that the devices and methods described herein also have application in the treatment of adult scoliosis. Adult scoliosis can continue to worsen with time. Though the adult is skeletally mature, the Cobb angle may still continue to increase with time. The relaxation or slight reduction in height that occurs in adults may have some relation with this increase in Cobb angle. Curves above 100° are rare, but they can be life-threatening if the spine twists the body to the point where pressure is put on the heart and lungs. The devices and methods described herein can also be used to treat adult scoliosis, e.g., allowing adult scoliosis to be treated with a minimally invasive and/or fusionless approach. In addition, gradual adjustment of the spine may be desired, especially in the cases of very high Cobb angles. For example, it may be desired to limit the amount of stresses on the bones or on the implant materials, by first adjusting an adult scoliosis patient so that their Cobb angle is reduced 50% or less, then 15% or less each few months, until the spine is straight. As one example, the initial surgical implantation may reduce the Cobb angle by 50% or more by the physician performing manual distraction on the spine. Post-implantation, the Cobb angle can be reduced in a non-invasive manner by application of a constant or periodically changing distraction force. A first non-invasive adjustment may result in a Cobb angle reduction of less than 50%. Additional non-invasive adjustments may be performed which result in even smaller Cobb angle reductions (e.g., less than 15% from original Cobb angle).

In this regard, the Cobb angle may be reduced by a smaller amount over the next few months (e.g., less than around 15% each month post-operation). The non-invasive adjustment of a fusionless implant made possible by the invention allows for a gradual adjustment scheme of this nature. Moreover, the distraction forces used over this period of time are generally low (e.g., distraction force less than 45 pounds) which means, among other things, less patient discomfort, and less chance of failure within the adjustable rods 142, 144. Non-invasive adjustments may be periodically performed when the patient visits his or her physician. This may occur over a span of more than one week (e.g., a several week process). Of course, the number and periodicity of the adjustments is a function of, among other things, the Cobb angle of the patient.

Oftentimes, the adult spine has less dense or even osteoporotic bone, so it may be desirable to combine the sort of gradual adjustment described here with additional methods to strengthen the bone, for example the bone of the vertebral bodies. One method is to strengthen the vertebral body by performing prophylactic vertebroplasty or kyphoplasty, wherein the internal area of the vertebral body is strengthened, for example by injection of bone cement or Polymethyl Methacrylate (PMMA). Additionally, if pedicle screws are used for fixation, the surface of the screws may be treated with a biologic material that promotes bone growth, or a surface characteristic that improves bone adhesion. Any of these methods would further improve the possibilities that the distraction forces would not cause fracture or other damage to the vertebrae of the patient.

Another embodiment includes a bone growing implant, wherein the manipulation of a portion of the skeletal system is limited to a single bone, and the bone growing implant is a distraction device, capable of distracting a first and second locations located on or in the same bone. For example, in many cases of dwarfism, the femur and the humerus bones are short in relation to the other bones. Currently these bones may be grown longer using a device such as the Taylor Spatial Frame, which is an external frame having wires or pins that extend through the skin and attach to the bone. The frame can be continually adjusted by the external adjustment knobs to stimulate bone growth in the desired direction. This device may also be used on patients whose bones stop growing due to, for example, pediatric bone cancer, such as Ewing's sarcoma or osteosarcoma. Another application for this device is in patients who have had broken bones which are healing in an unsatisfactory manner, for example, in the case of one leg that is shorter than the other because of a badly healed femur fracture. One problem that is seen with the Taylor Spatial Frame is the occurrence of pin tract infections, which occur because there is an open channel for bacteria to enter from the outside of the patient to the bone. Another application for bone growth is for selective growth to only one side of the bone, for example in Blount's disease (bowleggedness), in which one side of the bone grows normally while in the other side there is an arrest in the growth plate.

Figure 53:
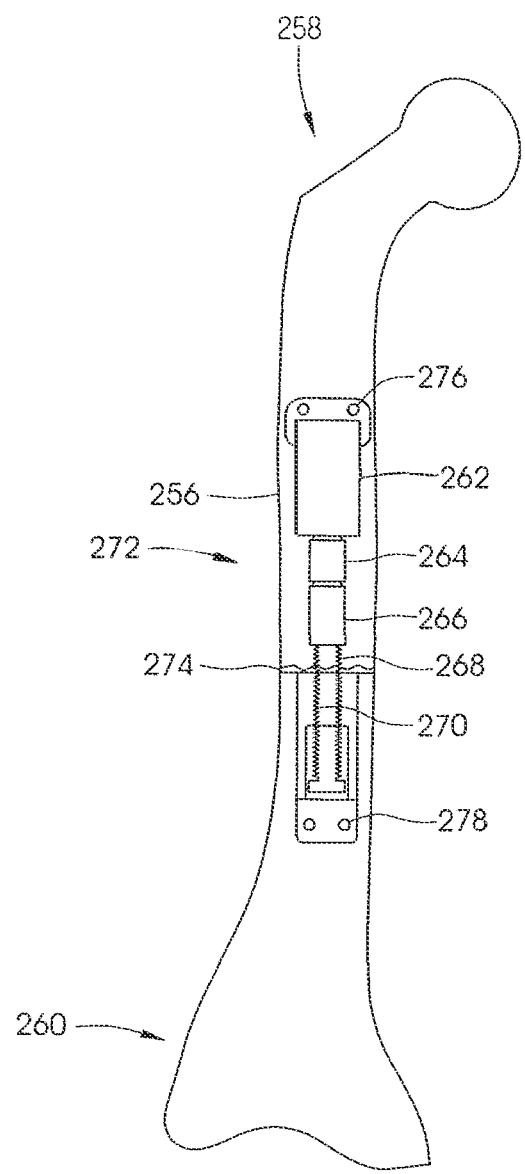
FIG. 53 illustrates an embodiment of a distraction device disposed on a bone.

In all of these bone growth applications, a non-invasively adjustable bone growth distraction device is needed. A device of this nature is presented as an embodiment of this invention in FIG. 53. A bone growth distraction device 272 is attached to bone 256 having a proximal portion 258 and a distal portion 260 by a proximal securement member 276 and a distal securement member 278. The securement members 276, 278 may operate using any number of securement devices or methods known to attach a device to bone, including screws, clamps or even adhesive materials. In cases of a bone fracture, a fracture site 274 is illustrated, though it should be noted that this fracture is not always present in some of the applications previously mentioned. As seen in FIG. 53, the bone growth distraction device 272 includes a cylindrical magnet 262 that is configured to rotate on its axis in response to an externally applied magnetic field (as described above in the context of other embodiments). Rotation of the cylindrical magnet 262 effectuates rotation of a planetary gear set 266. An optional slip clutch 264 is illustrated as being disposed between the cylindrical magnet 262 and the planetary gear set 266, though slip clutch 264 may be disposed at any other location along the drive transmission. Rotation of the planetary gear set 266 in a first direction (e.g., either clockwise or counter-clockwise depending on configuration) causes lead screw 268 to turn within internal thread 270 causing distraction (e.g., elongation) of the bone 256. Bone growth distraction device 272 may be implanted in a single operation. Subsequent adjustments are performed non-invasively, and if desired can be performed frequently in order to precisely control bone growth. An adjustment device such as external adjustment device 1130 described herein may be used to rotate the cylindrical magnet 262. The cylindrical magnet 263 may be dimensioned and made of the same materials as described herein with respect to the other embodiments.

Figure 54:
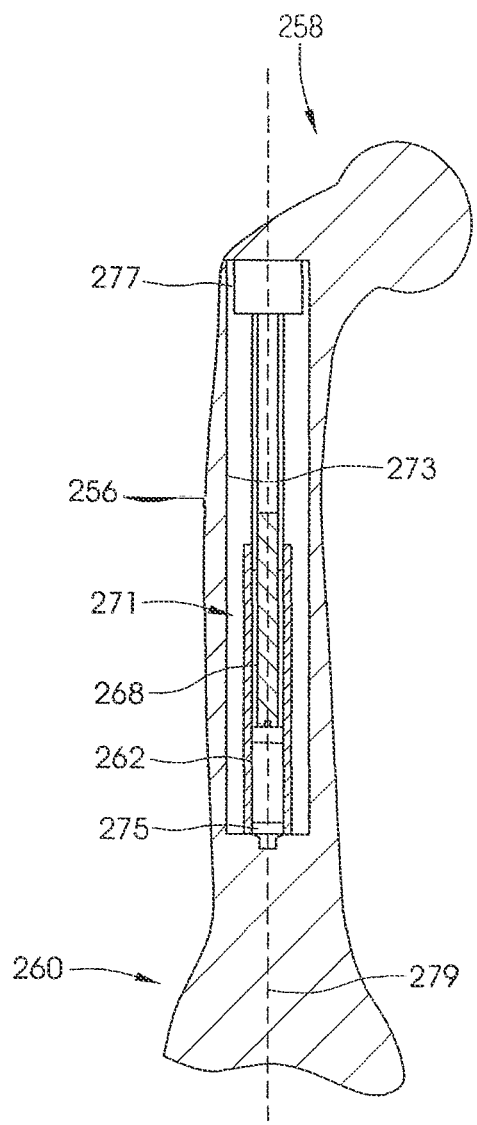
FIG. 54 illustrates an embodiment of a distraction device disposed within the intramedullary canal of a bone.

While FIG. 53 may be especially effective in treating Blount's disease, or any other condition that requires selective growth (for example on one side of the bone), FIG. 54 illustrates an alternative embodiment of the invention incorporating an intramedullary magnetic elongation device. Bone distraction device 271 is placed within the intramedullary canal 273 and secured at first attachment point 275 and second attachment point 277. By being centered within the intramedullary canal 273, the bone distraction device 271 is capable of lengthening the bone 256 substantially parallel to its longitudinal axis 279. It should be understood that the embodiments described herein may be applicable to bones and/or skeletal structures other than those specifically described or illustrated in the drawings. For instance, the embodiments may be utilized in the tibia, mandible, jawbone, and the like.

Figure 55:
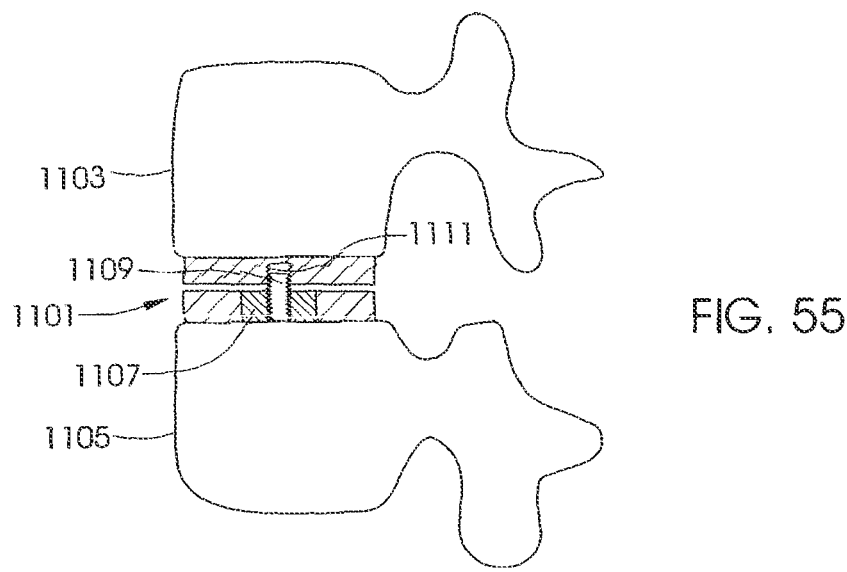
FIG. 55 illustrates an embodiment of a distraction device for intervertebral placement.

Other orthopedic distraction devices are conceived using the present invention. FIG. 55 illustrates a distraction device 1101 configured for replacement of an intervertebral disk, and for distraction between a first vertebral body 1103 and a second vertebral body 1105. Intervertebral disks can degenerate, bulge, herniate or thin, and cause accompanying back pain. Degenerative disk disease (DDD) has caused a large increase in the use of intervertebral disk replacement devices. Current intervertebral disk replacement devices have had incomplete success, due to a large rate of patients whose pain returns with time. The inventive art describes an intervertebral disk replacement device that allows for additional adjustment after disk replacement surgery and after the healing period. If a patient has recurring pain, the device may be adjusted non-invasively to increase or decrease distraction in order to eliminate recurrent pain.

Using the external adjustment device 1130 in the same non-invasive manner as the other embodiments an internal magnet 1107 is non-rotated. Internal magnet 1107 is coupled to lead screw 1109 so that rotation motion changes the displacement between lead screw 1109 and the female thread 1111 inside a portion of the distraction device 1101.

This technique may also be used to treat other spinal problems, such as spondylolisthesis. In certain situations, the entire vertebral body may be removed, for example due to a crushed, fractured or diseased vertebral body. The embodiment of FIG. 55 may be supplied in a number of sizes, for example thicknesses, in order to fill the desired dimension between the other vertebral bodies.

Figure 56:
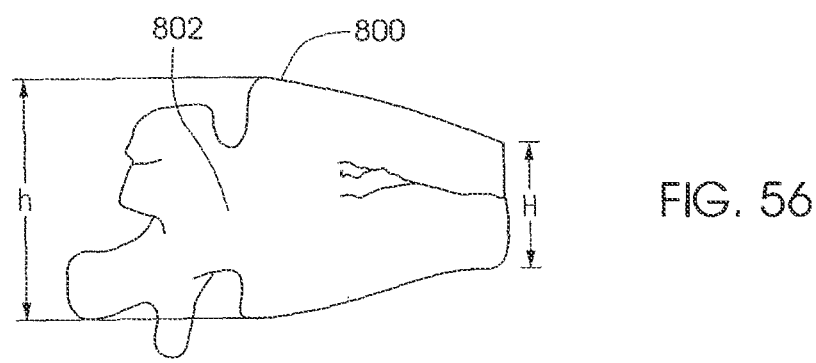
FIG. 56 illustrates a fractured vertebral body.
Figure 57:
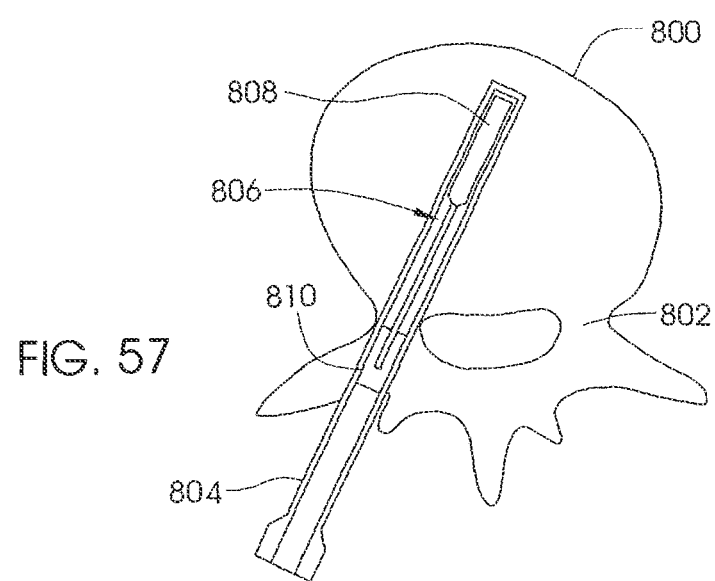
FIG. 57 illustrates a distraction device being placed into the vertebral body of FIG. 56.
Figure 58:
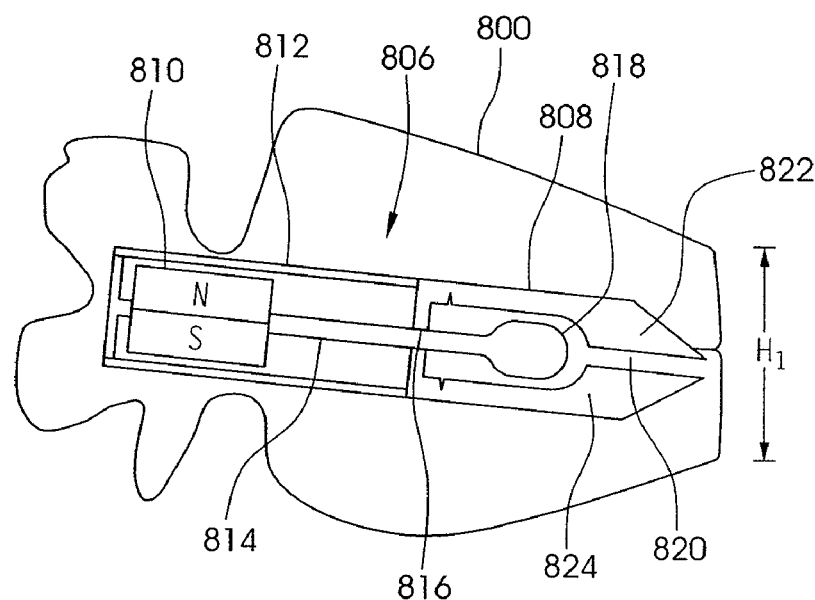
FIG. 58 illustrates a distraction device within a vertebral body.
Figure 59:
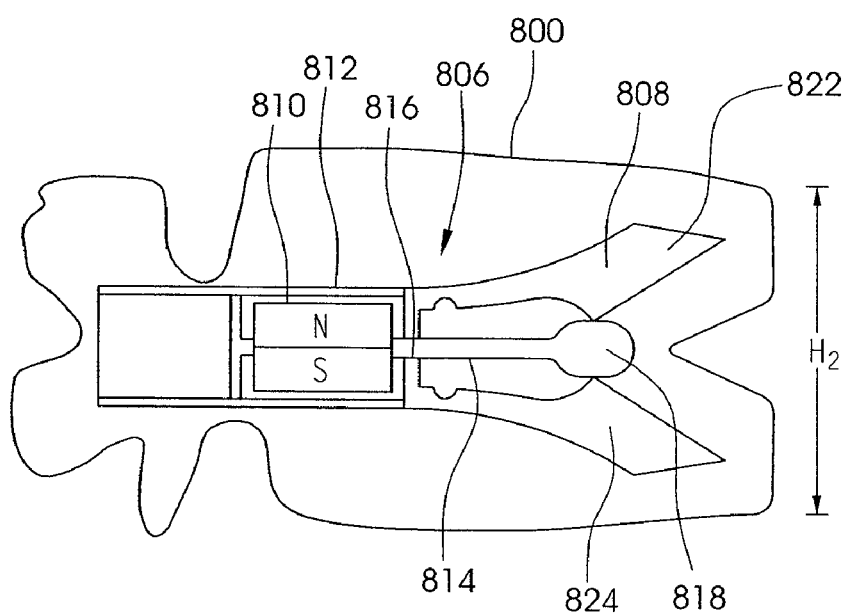
FIG. 59 illustrates a distraction device manipulated to add height to a vertebral body.

FIGS. 56 through 60 illustrate a device for modification of a fractured vertebra is illustrated. Vertebrae can become weak with osteoporosis, and may fracture easily, causing an increased kyphosis and increasing the risk of fracture of subsequent vertebrae. Fractured vertebral body 800 is illustrated in FIG. 56. The fracture shown is a wedge fracture, which is very common in this type of patient. Anterior height H has been significantly reduced in comparison to original height h. Currently, fractured vertebrae can be treated by a vertebroplasty procedure, in which cement, for example polymethyl methacrylate (PMMA) is injected into the inside of the vertebral body. Vertebroplasty does very little in terms or restoring height. An alternative method known as kyphoplasty is sometimes performed during which a balloon is inflated inside the vertebral body to crush in inner bone material prior to filling with the cement. Kyphoplasty has shown to increase height slightly, but the height gain is still considered unsatisfactory by many surgeons. In an alternative embodiment of the invention illustrated in FIG. 57 a hole is drilled through one of the pedicles 802 which lead to the vertebral body 800. Cannula 804 is placed through the hole and distraction device 806 is placed through the cannula 804. If desired, a kyphoplasty balloon may be placed through the cannula first in order to pre-dilate. Cannula 804 may be partially or completely removed at this point. Distraction device 806 comprises a protective sheath 812, a distraction head 808 and a cylindrical magnet 810. Protective sheath 812 is configured to be secured inside of pedicle 802 and/or inside vertebral body 800. Cylindrical magnet 810 is free to rotate within protective sheath 812 and is coupled to externally threaded shaft 814. As cylindrical magnet 810 is rotated by an external rotating magnetic field (for example that from external adjustment device 1130) threaded shaft 814 rotates within internal thread 816 causing threaded shaft 814 to extend axially. As threaded shaft 814 extends, dilating tip 818 is forced through separation 820, forcing apart first distractor 822 and second distractor 824 and increasing the height of the fractured vertebral body from $H_1$ to $H_2$. It can be appreciated that the external adjustment device 1130 can apply a significant torque to the cylindrical magnet 810 and thus allow a high separation force applied to the two distractors 822, 824 of the distraction head 808. Several options are now possible at this point.

In the first option, the cylindrical magnet 810 may be removed from the assembly and cement may be applied through the protective sheath 812 to fully set the vertebral body in its distracted configuration, leaving the protective sheath 812 and the distraction head 808 permanently implanted.

Figure 60:
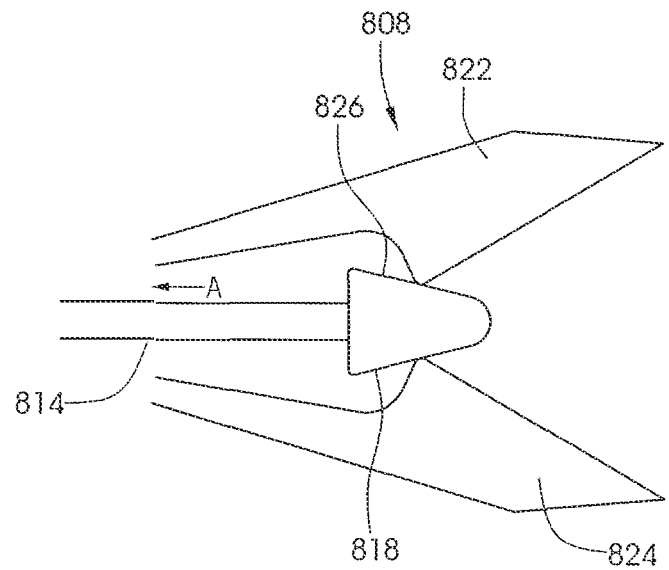
FIG. 60 illustrates an alternative configuration of a distraction device for use in a vertebral body.

In the second option, no cement is applied and the patient is recovered with the entire distraction device 806 intact. After reviving from anesthesia, and most likely also following recovery from the normal pain that accompanies post-surgery, the patient returns for a non-invasive adjustment, wherein the distraction device is adjusted to the specific distraction height that most reduces pain. For example, FIG. 60 shows the dilating tip 818 having a tapered outer diameter 826. By adjusting the distraction device 806 in either direction, the extent of the spread of the two distractors 822, 824 can be controlled. Though the distraction head 808 may be made from numerous metallic or polymeric materials, it may be preferably made of a highly elastic metal, such as nickel-titanium, so that the two distractors 822, 824 will return towards their original unexpanded configuration as the dilating tip 818 moves in direction A. This entire non-invasive adjustment process has not been possible with prior devices which could only be manipulated during surgery, when patient is unconscious. Once the patient is at a desired adjustment level with little or no pain, an additional procedure may be performed to remove the magnet and/or inject cement.

In the third option, the cement is injected at the end of the initial implantation operation, but the distraction device 806 is left intact. It is common for cement to remodel or even recede, for example after 18 months. With the present invention, this is less likely, because the distraction head 808 in its expanded configuration serves as additional reinforcement. In addition, if the cement were to remodel or recede, an additional adjustment procedure can be performed during which the two distractors 822, 824 are further spread and more cement is injected.

Figure 61:
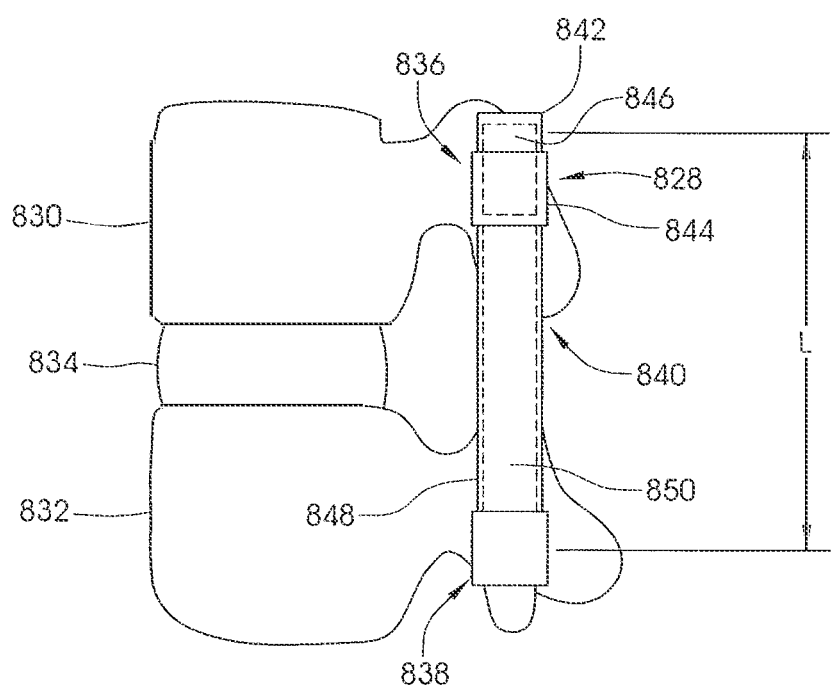
FIG. 61 illustrates a non-invasively adjustable dynamic stabilization device.

FIG. 61 illustrates the present invention incorporated into a motion preservation (or dynamic stabilization) device 828. The motion preservation device 828 is attached to a first vertebra 830 and a second vertebra 832 with pedicle screws. First and second vertebrae 830, 832 are separated by intervertebral disk 834. Second head 838 is static and is attached to second vertebra 832. First head 836 is adjustable and comprises first portion 842, which is attached to first vertebra 830 and second portion 844 which can be adjusted by using external adjustment device 1130 to rotate internal magnet 846. Intermediate portion 840 comprises an outer spacer 848 and an inner cord 850. Outer spacer 848 and inner cord 850 are preferably made from polymeric materials that allow for some deformation and therefore limited movement between first vertebra 830 and second vertebra 832. By non-invasively adjusting first head 836 with the external adjustment device 1130, the length L can be manipulated so that the desired condition is reached wherein the range of motion allowed by the implant is tailored so that it is within the range of motion where no pain is encountered, and the range of motion for which pain is present is eliminated. Current dynamic stabilization devices do not have this non-invasive adjustability. Therefore, a surgeon is never sure whether the patient's device will maintain a range of motion for which patient feels no pain. The embodiment of this invention allows the ability to adjust the device while the patient is not under anesthesia and after the patient has recovered from any post-surgery pain, so that the real pain that is intended to be cured can actually be assessed.

With respect to distraction devices (e.g., distraction devices 140, 314, 602, 604, 638, 1414) that are utilized in treating spinal deformities such as scoliosis, there is a need have a variety of securement schemes of affixing the ends of the distraction device to their respective anchor points. In particular, certain applications like non-fusion applications may require one or more degrees of freedom between the anchor points and the adjustable rod (e.g., adjustable rod 142). For example, a growing or extending adjustable rod may require a certain degree of movement or articulation between the end of the rod and the anchor points to compensate for the altered geometry and forces induced upon the subject's skeletal structure during the distraction process. Still other applications for the distraction devices may require a fixed or non-articulating joint between the adjustable rod and their respective anchor points. For example, fusion applications may require one or more fixed joints between the distraction device and the subject's skeletal structure. Further, different types of scoliosis may demand different attachment schemes. For instance, AIS and non-AIS scoliotic conditions may require different attachment schemes for the distraction device.

Along these same lines, both ends of the adjustable rod may require different attachment schemes. For example, one end of the adjustable rod may be more suitable for a fixed or relatively fixed anchor to the skeletal system while the opposing end of the adjustable rod may require a degree of articulation or movement. The adjustable rod may also be used for partial fusion applications where, for example, fusion is only done between the vertebrae on the ends where the pedicle screws or hooks are attached. Further, some applications may require an attachment point that can adjust between a fixed configuration and an articulating configuration. Still other contemplated attachment schemes may be adjustable between different degrees of freedom. Typically, these adjustments are made manually by the physician at the time the distraction device is implanted. However, they may also be done minimally invasively or even non-invasively, for example, by a magnetically activated switch.

It would be advantageous for devices that can be convertible between a rigid state and a non-rigid date (i.e., have one or more degrees of freedom of motion) because the same system could be employed for both fusion cases and non-fusion cases. Because of the convertible nature of the hardware, a single system may be adaptable to the different clinical constructions that may be desired. In addition, surgeons may have differing preferences as to the system needed to treat a particular patient's condition. For example, in non-fusion cases, some physicians would like to have the system be more rigid which, in their opinion, would allow better correction of the coronal deformity (e.g., scoliosis). Other physicians would prefer to have the system exhibit rotational freedom so that a sagittal curve (e.g., kyphosis or lordosis) that is desired for the future is already pre-bent. While the patient is still lordotic, the curve of the rod can generally lie down on the side so that there is not too large of a bulge in the patient's back. When the coronal curve is corrected, the curve in the rod for the desired kyphosis is in the sagittal plane. Also, a system having freedom of motion helps greatly to reduce the stresses (e.g., bending, torsional forces) in the rod, and thus increase implant longevity.

The ability of the distraction device to have a certain degree of axial play or movement benefits patient safety, for example in case where the patient bends way too much forward, e.g. violently. The attachment screws or hooks will not, for example damage the vertebra or the spinal cord. Also, in the situation where the patient grows over many months and does not have any lengthening procedures, this axially directed sliding motion protects the patient from having too much stress on the vertebra and the fixation points. This slidability also can act as a sort of shock absorber, lowering the sudden stress increases in the whole system.

Figure 62A:
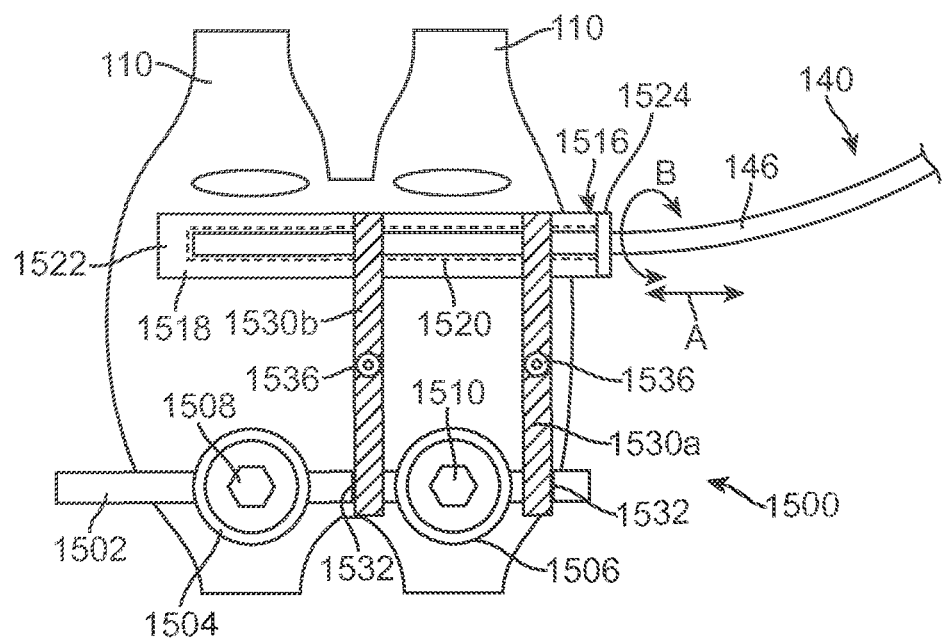
FIG. 62A illustrates a fixation device according to one embodiment.
Figure 62B:
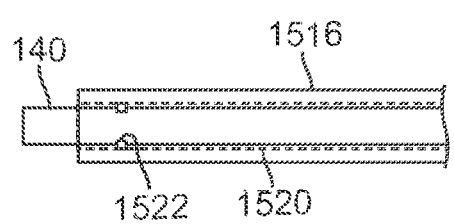
FIG. 62B illustrates a socket of the fixation device having an adjustable rod disposed therein.
Figure 62D:
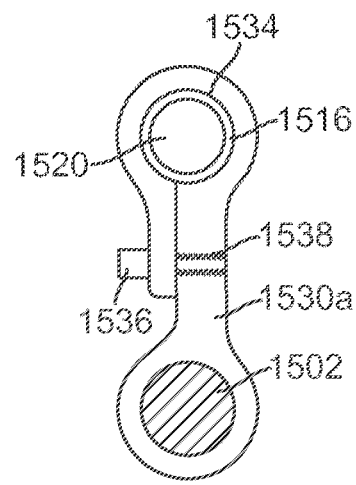
FIG. 62D illustrates a side view of a clamping member.
Figure 62C:
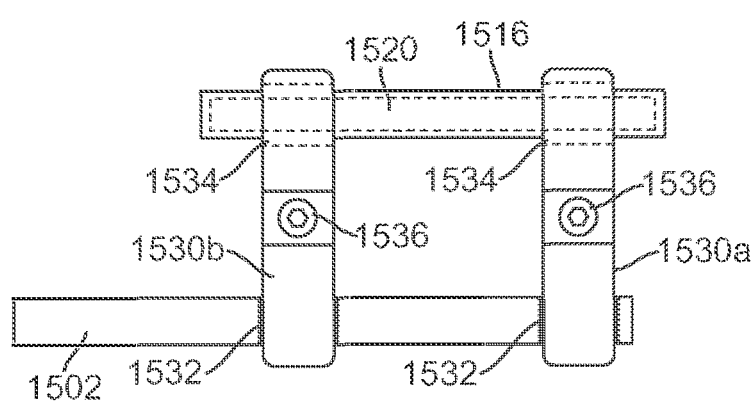
FIG. 62C illustrates a plurality of clamping members securing the socket to an anchor rod.
Figure 62E:
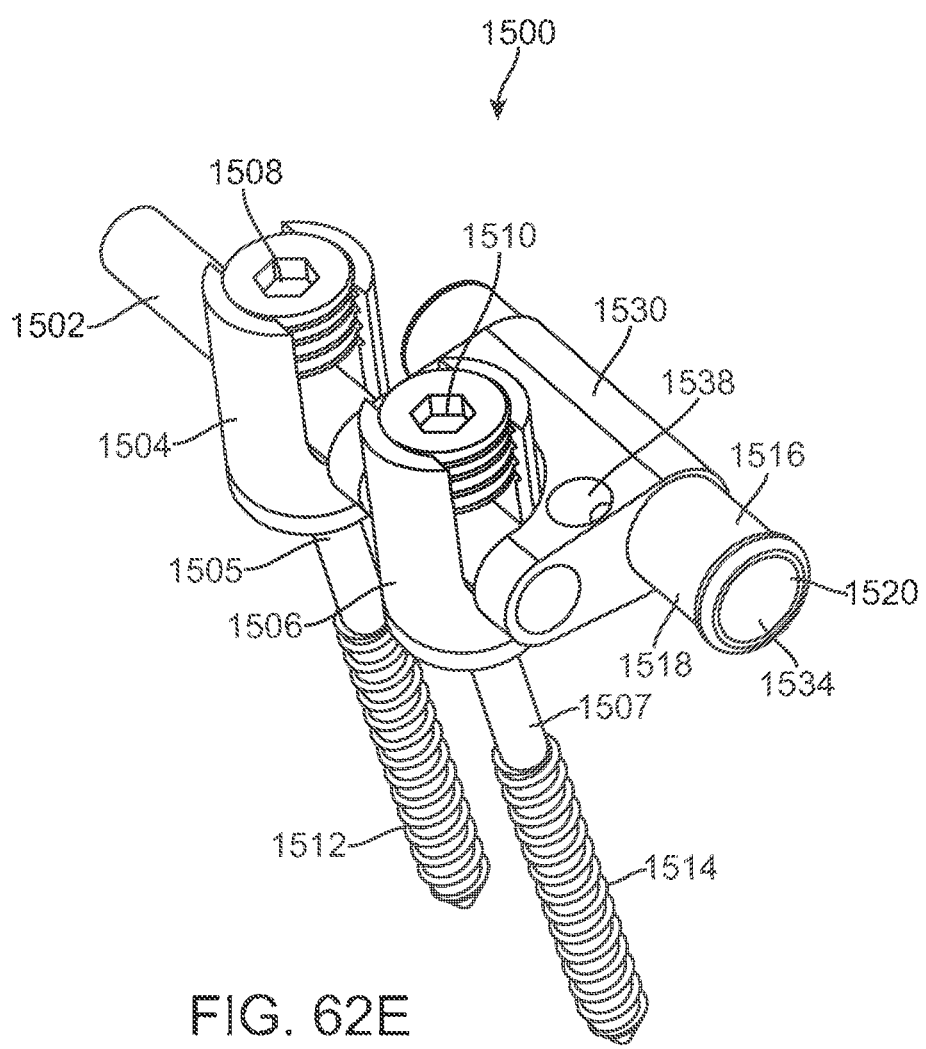
FIG. 62E illustrates a perspective view of a fixation device.

FIGS. 62A-62E illustrates a fixation device 1500 according to one embodiment. The fixation device 1500 includes an anchor rod 1502 and is configured for being fixedly secured to a subject's spine 110 (illustrated in FIG. 62A). The anchor rod 1502 is secured to the spine 110 by one or more fasteners 1504, 1506. The one or more fasteners 1504, 1506 may comprise screws 1505, 1507 typically used in spinal applications such as, for instance, pedicle screws. The fasteners 1504, 1506 have respective apertures 1508, 1510 for receiving a tool such as an Allen wrench or other wrench (not shown) for tightening or loosening the fasteners 1504, 1506. As best seen in FIG. 62E, the fasteners include threaded portions 1512, 1514 that engage with the spinal bone tissue to secure the anchor rod 1502. The anchor rod 1502 may be formed from a stiff or semiflexible biocompatible metal. The length of the anchor rod 1502 may vary depending on the application but it generally may be several centimeters long.

Still referring to FIG. 62A, the fixation device 1500 includes a socket 1516 that is configured to receive one end of the distraction device 140 and in particular a terminating end of an elongate member (e.g., elongate member 146) that forms the adjustable rod 142. While reference is made to distraction device 140 it should be understood that the fixation device 1500 may be used in connection with other distraction devices described herein that are used in spinal applications such as distraction devices 140, 314, 602, 604, 638, 1414. Reference will be made herein to distraction device 140 (and adjustable rod 142) for ease of reference but it should be understood that fixation device 1500 along with other embodiments described herein may be used with a variety of different distraction devices.

The socket 1516 may include a tubular-shaped socket 1516 that has an outer wall 1518 and a lumen 1520 extending there through. The lumen 1520 of the socket 1516 has in inner diameter (ID) that is configured to permit the elongate member (e.g., elongate member 146) of the adjustable rod 142 to telescope axially in and out in the direction of arrow A (FIG. 62A). The lumen 1520 is also configured to allow free rotation in the direction of arrow B (FIG. 62A). The degree of clearance between the inner surface of the outer wall 1518 and the adjustable rod 142 diameter will allow for some degree of angular movement, though it will still prevent kinking or "jack-knifing." While some axial movement of the adjustable rod 142 within the socket 1516 is permitted, the socket 1516 is configured to provide a distal stop 1522 so that the adjustable rod 142 can apply a distraction force to the subject's spine 110. The distal stop 1522 may include a blind tube which prevents further advancement of the adjustable rod 142 or it may include a rim or detent within the socket lumen 1520 to prevent further distal advancement of the adjustable rod 142 within the socket 1516. FIG. 62B illustrates an embodiment of the socket 1516 in which the adjustable rod 142 extends partially from the distal end thereof. A stop 1522 located within the lumen 1520 may be used to prevent further distal advancement of the adjustable rod 142. The socket 1516 may include an optional thrust collar 1524 that allows for bottoming out, so that the socket 1516 can't be pushed out when fasteners 1536 (described below) are loosened.

Referring to FIGS. 62A and 62C, the fixation device 1500 includes one or more clamping members 1530 a, 1530 b that are configured to secure the socket 1516 relative to the anchor rod 1502. The clamping members 1530 a, 1530 b are advantageously configured to allow a degree of lateral offset between the socket 1516 and the anchor rod 1502. In one aspect, the clamping members 1530 a, 1530 b are fixedly secured to the anchor rod 1502 via welds 1532. Of course, the clamping members 1530 a, 1530 b may be secured to the anchor rod 1502 via other techniques such as through the use of an adhesive or even a frictional engagement. The clamping members 1530 a, 1530 b terminate in an aperture 1534 (best seen in FIGS. 62C and 62D) dimensioned to receive the outer diameter of the socket 1516. The clamping members 1530 a, 1530 b may comprise multiple pieces as illustrated in FIGS. 62A and 62C or, alternatively, a single unitary piece 1530 as illustrated in FIG. 62E may be used. Regardless, the single clamping member 1530 or the multiple clamping elements 1530 a, 1530 b have fasteners 1536 for tightening or loosening the aperture 1534 on the outer surface of the socket 1516. In this regard, a friction fit is formed between the aperture 1534 and the socket 1516. The fasteners 1536 may include screws that pass through threaded apertures 1538 (best seen in FIGS. 62D and 62E).

To implant the fixation device 1500 the fasteners 1504, 1506 are first placed on the subject's spine at the appropriate locations. The fixation device 1500 described herein is particularly suitable for use on the upper end of the adjustable rod 142 (e.g., first elongate member 146 as illustrated in FIG. 4). After placement of the fasteners 1504, 1506, the adjustable rod 142 is bent and/or manipulated as needed. The adjustable rod 142 (e.g., first elongate member 146) may be cut or trimmed to the appropriate length to fit the patient. The socket 1516 is then slipped over the cut end of the adjustable rod 142. The anchor rod 1502 is then secured to the fasteners 1504, 1506. An adjustment is then made to push the socket 1516 axially until the cut end of the adjustable rod 142 is firmly rested against the distal stop 1522. Once this configuration is reached, the fasteners 1536 are tightened to secure the socket 1516 relative to the anchor rod 1502. Of course, the physician may need to loosen/tighten the various fasteners 1504, 1506 and 1536 to reach the final desired location of the fixation device 1500 and adjustable rod 142.

It should be understood that the fixation device 1500 may be implanted by the physician using a different ordering of the operations described above. For example, some physicians may want to first attach the anchor rod 1502 using the fasteners 1504, 1506 (e.g., pedicle screws). The adjustable rod 142, which is cut or trimmed to the appropriate length, is inserted into the socket 1516. The socket 1516 may be positioned relative to the anchor rod 1502 using the single clamping member 1530 or the multiple clamping elements 1530 a, 1530 b. The fasteners 1536 may be tightened once the proper orientation is reached. Still other sequences can be used to affix the fixation device 1500 to the patient.

Figure 63:
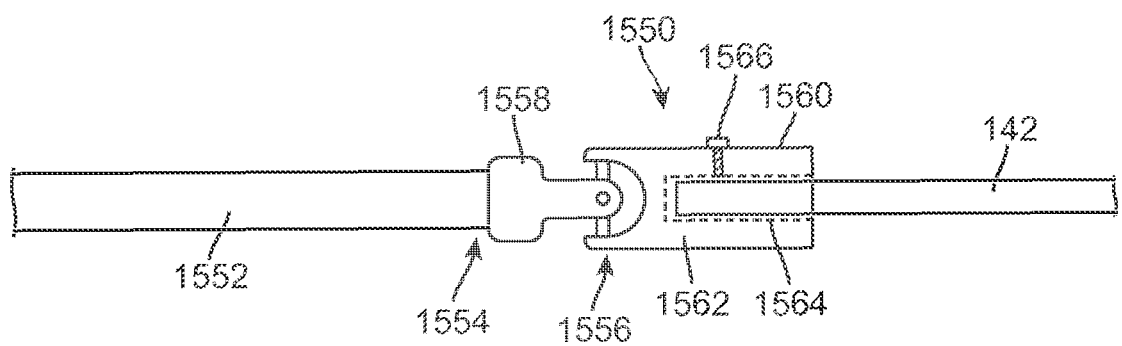
FIG. 63 illustrates one embodiment of an articulating joint.

FIG. 63 illustrates an articulating joint 1550 that is used to join an adjustable rod 142 to an anchor rod 1552. In this embodiment, the anchor rod 1552 is fixedly secured to the subject's spine 110 at one end using, for example, a fastener such as a pedicle mounting screw (not shown). The free end 1554 of the anchor rod 1552 is joined to the end of the adjustable rod 142 (e.g., first elongate member 146) with a universal joint 1556. The universal joint 1556 is formed from two articulating hinges 1558, 1560 that are roughly offset 90° from one another. One hinge 1560 of the universal joint 1556 includes a socket portion 1562 that is configured to receive the free end of the adjustable rod 142. Typically, this end of the adjustable rod 142 is cut or trimmed by the physician upon implantation of the distraction device. The depth of the recess 1564 in the socket portion 1562 is constructed to permit some telescopic or axial movement between the adjustable rod 142 and the socket portion 1562. Of course, the allowable motion is not enough such that the adjustable rod 142 would become disconnected from the socket portion 1562. A socket 1562/adjustable rod 142 engagement length of around 5 cm is exemplary. The adjustable rod 142 may also freely rotate within the recess 1564. In an alternative arrangement, the adjustable rod 142 is locked in the recess 1564 of the socket portion 1562 using a lock 1566. The lock 1566 may comprise a set screw or the like that engages with the adjustable rod 142 to prevent both radial and axial motion of the adjustable rod 142 relative to the socket portion 1562. An advantage of the above-noted articulating joint 1550 is that it allows pivoting of the adjustable rod 142 but no rotation.

Figure 64:
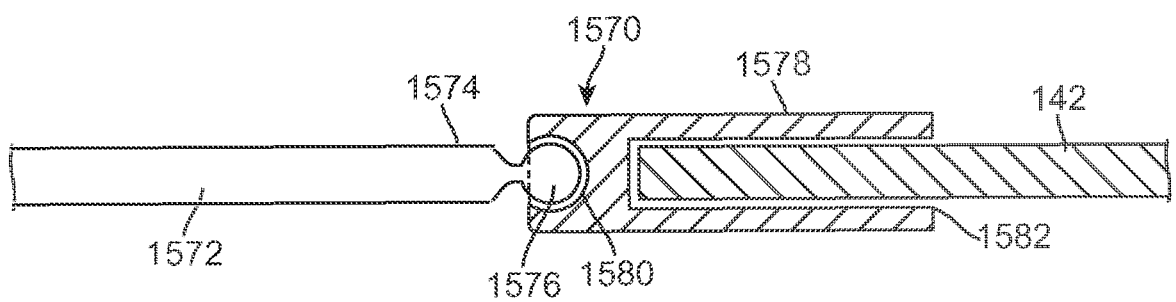
FIG. 64 illustrates another embodiment of an articulating joint.

FIG. 64 illustrates another embodiment of an articulating joint 1570 that is used to join an adjustable rod 142 to an anchor rod 1572. The anchor rod 1572 is fixedly secured to the subject's spine 110 at one end using, for example, a fastener such as a pedicle mounting screw (not shown). The free end 1574 of the anchor rod 1572 terminates in a ball or spherical end 1576. An elongated cup 1578 having a spherical recess 1580 at one end is mounted on the ball 1576. In this regard, the ball 1576 and the spherical recess 1580 form a ball swivel joint. The elongated cup 1578 has a recess 1582 that is dimensioned to receive an end of the adjustable rod 142. The depth or length of the recess 1582 is such that adjustable rod 142 may move axially within the recess 1582 without fully disengaging from the elongated cup 1578. This configuration is advantageous because it eliminates any tension load on the interface.

Figure 65:
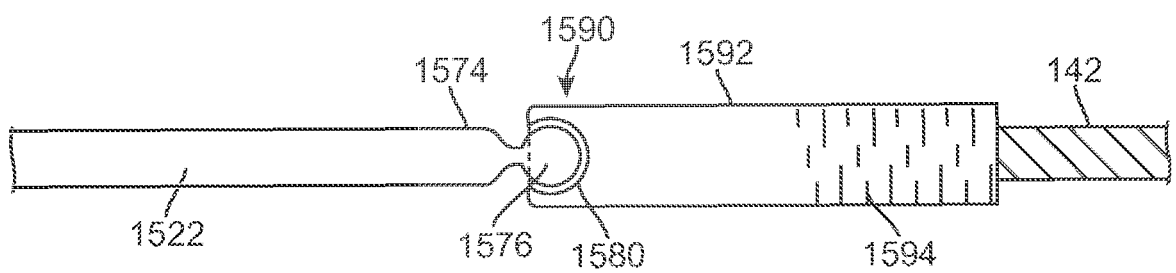
FIG. 65 illustrates another embodiment of an articulating joint.

FIG. 65 illustrates another embodiment of an articulating joint 1590 that is similar to that illustrated in FIG. 64 with similar features denoted by the same reference numerals. In this embodiment, the elongated cup 1592 has a plurality of slits 1594 formed at one end. The plurality of slits 1594 imparts a degree of flexibility onto the elongated cup 1592. The plurality of slits 1594 may be formed using conventional laser cutting techniques known to those skilled in the art. As an alternative, the embodiment of FIG. 65 may comprise a rigid rod having slits 1594 formed via a laser. In this embodiment, the ball or spherical end 1576 is omitted.

Figure 66:
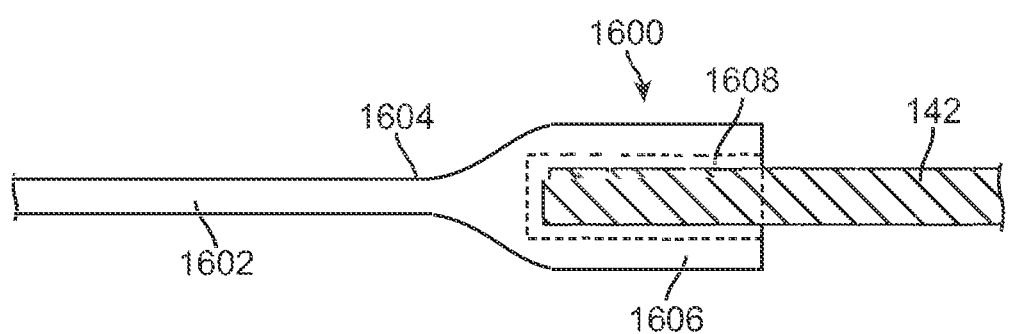
FIG. 66 illustrates another embodiment of an articulating joint.

FIG. 66 illustrates another embodiment of an articulating joint 1600. In this embodiment, the joint 1600 includes an anchor rod 1602 that is fixedly secured to the subject's spine 110 at one end using, for example, a fastener such as a pedicle mounting screw (not shown). The free end 1604 of the anchor rod 1602 terminates in a receiving cup 1606 that includes a recess 1608 dimensioned to receive an end of the adjustable rod 142. The anchor rod 1602 may be somewhat malleable or bendable by the physician to that same may be configured into the desired orientation. The length of the recess 1608 of the receiving cup 1606 is such that telescopic or axial motion is permitted between the adjustable rod 142 and the receiving cup 1606. The length is, however, long enough to prevent the adjustable rod 142 from slipping out of the receiving cup 1606. It should be understood that the embodiments of FIGS. 65 and 66 may, as an alternative arrangement, utilize a set screw much like the lock 1566 (e.g., set screw) of FIG. 63.

Figure 67:
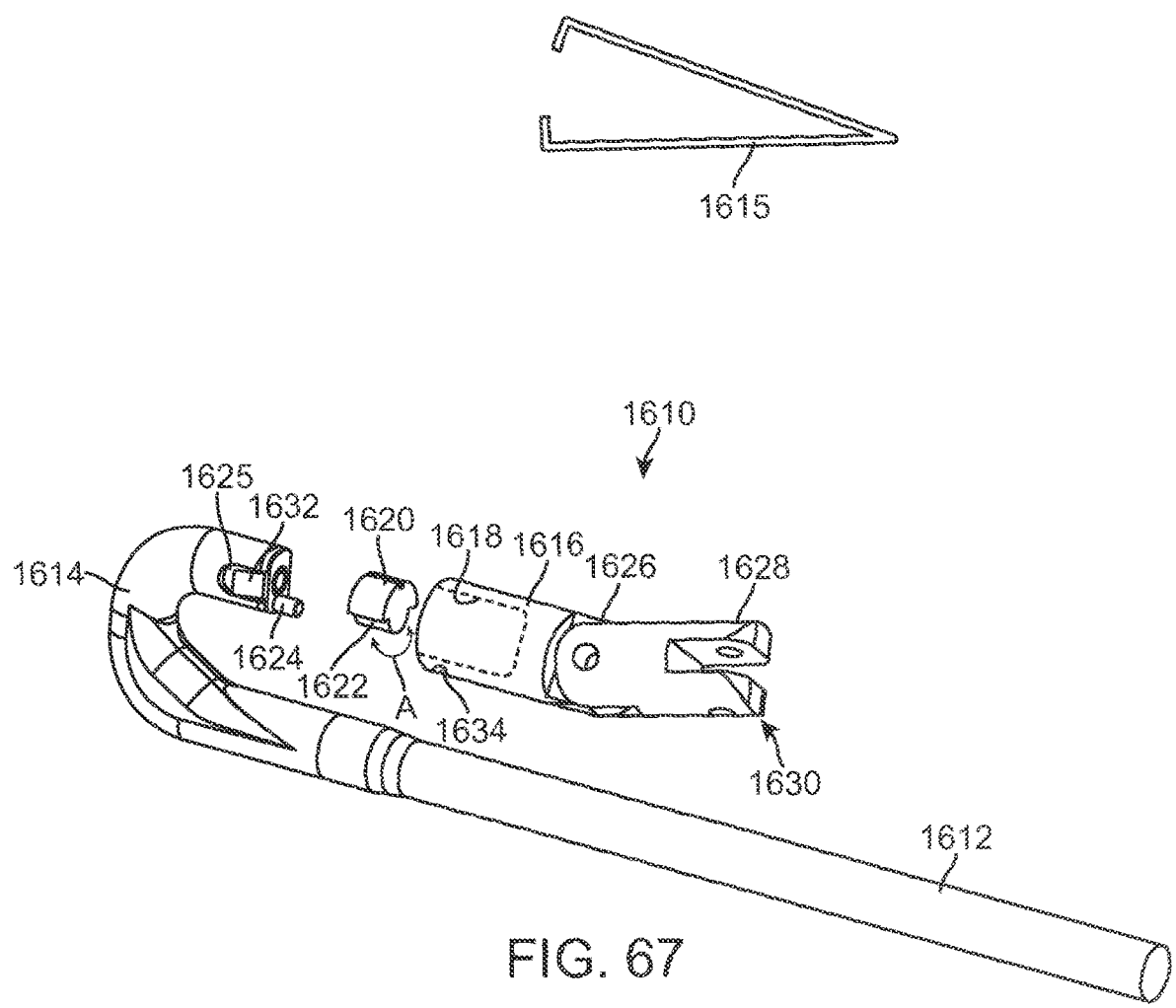
FIG. 67 illustrates another embodiment of an articulating joint.

FIG. 67 illustrates another embodiment of an articulating joint 1610 that is used to join an adjustable rod (not shown) to an anchor rod 1612. The anchor rod 1612 is fixedly secured to the subject's spine 110 at one end using, for example, a fastener such as a pedicle mounting screw (not shown). While FIG. 67 illustrates the anchor rod 1612 having a j-shaped bend 1614 the anchor rod 1612 may also have a straight configuration such as illustrated in FIGS. 63-65. The articulating joint 1610 includes a receiving cup 1616 having a recess 1618 formed thereon that is configured to receive the end of the j-shaped bend 1614. As seen in FIG. 67, a bushing 1620 is interposed between the end of the j-shaped bend 1614 and the receiving cup 1616. The bushing 1620 may be configured as a limiter disc that fits within recess 1618 of the receiving cup 1616. The bushing 1620 includes a slotted portion 1622 that engages with a pin or "key" 1624 that projects from the end of the j-shaped bend 1614. The key (or pin) may have any number of geometries. As illustrated, the pin 1624 may be affixed directly to the end of the j-shaped bend 1614 or, alternatively, the pin 1624 may be affixed to a separate bushing 1625 that is inserted into an end of the j-shaped bend 1614.

When the bushing 1620 is located within the receiving cup 1616, the bushing allows the receiving cup 1616 to rotate in the direction of arrow A through an angle θ. In particular the angle of the slotted portion 1622 determines the extent to which the receiving cup 1616 can rotate in the direction of arrow A. In one aspect of the invention, the physician may be provided with a variety of bushings 1620 with each having different angled slotted portions 1622 (i.e., different θs). The physician can then choose the bushing 1620 that is most suited to the particular patient or application. For example, in a fusion application, it can be limited to 5° in each direction whereas in a non-fusion application, it can be limited to 45° in each direction, Still referring to FIG. 67, the receiving cup 1616 terminates at a joint 1626 that includes a hinge 1628 that forms one part of a universal joint 1630. The remaining half (not illustrated) of the universal joint 1630 is then coupled to the adjustable rod 142. For example, the remaining half of the universal joint 1630 may include a socket portion that is configured to receive the free end of the adjustable rod 142 or the actuator.

Still referring to FIG. 67, spring-biased tabs 1632 are located on the end of the j-shaped bend 1614 and are configured to lock the receiving cup 1616 to the anchor rod 1612. The spring-biased tabs 1632 may engage with corresponding recesses, a lip, or rim within the recess 1618 of the receiving cup 1616 to lock the same into place. The receiving cup 1616 may be removed from the end of the j-shaped bend 1614 by inserting a tool 1615 into the aperture 1634 to depress the respective spring-biased tab(s) 1632 radially inward so the receiving cup 1616 can be pulled off the anchor rod 1612.

Figure 68A:
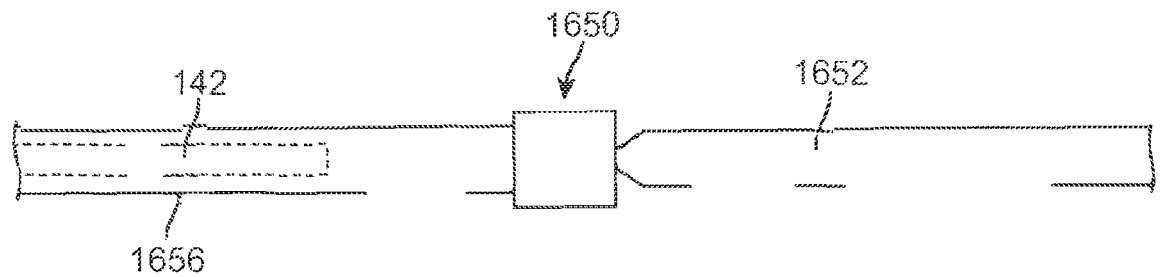
FIG. 68A illustrates another embodiment of an articulating joint.
Figure 68B:
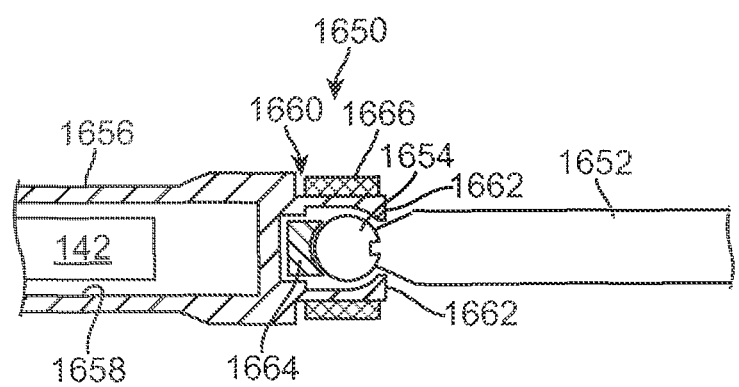
FIG. 68B illustrates a cross-sectional view of an articulating joint similar to that illustrated in FIG. 68A.
Figure 68C:
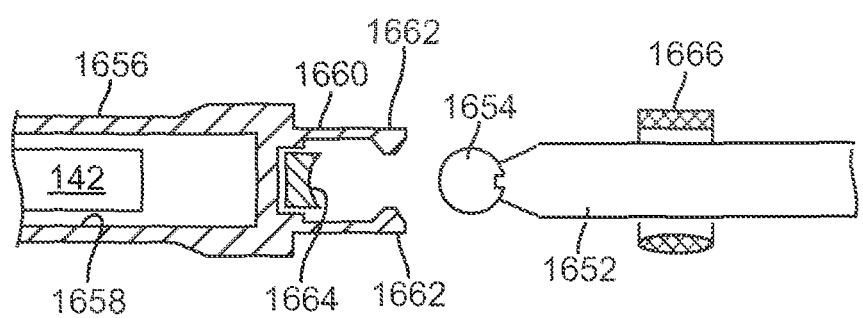
FIG. 68C illustrates a cross-sectional view of the articulating joint of FIG. 68B with the anchor rod removed from the socket.

FIGS. 68A-C illustrate another embodiment of an articulating joint 1650 that is used to join an adjustable rod 142 to an anchor rod 1652. In this embodiment, the anchor rod 1652 terminates at a ball 1654 (seen in FIGS. 68B and 68C). The ball 1654 may be a separate structure that is welded or otherwise bonded to the anchor rod 1652 or it may be integrally formed with the anchor rod 1652. The articulating joint 1650 includes an elongated cup 1656 that includes a recess 1658 therein that is configured to receive an end of the adjustable rod 142. The depth or length of the recess 1658 is such that adjustable rod 142 may move axially within the recess 1658 without fully disengaging from the elongated cup 1656. The elongated cup 1656 includes a socket 1660 into which the ball 1654 is mounted. The socket 1660 includes a plurality of flexible fingers 1662 configured to retain the ball 1654 within the socket 1660. The socket 1660 also includes a bearing 1664 in the base of the socket 1660 that provides an articulating surface for the ball 1654. The bearing 1664 may be made from a low friction material such as an Ultra High Molecular Weight Polyethylene (UHMWPE) material. The articulating joint 1650 further includes a sleeve 1666 that is slidably mounted about the periphery of the anchor rod 1652 that can be axially slid over the flexible fingers 1662 to aid in locking the ball 1654 within the socket 1660.

Figure 69A:
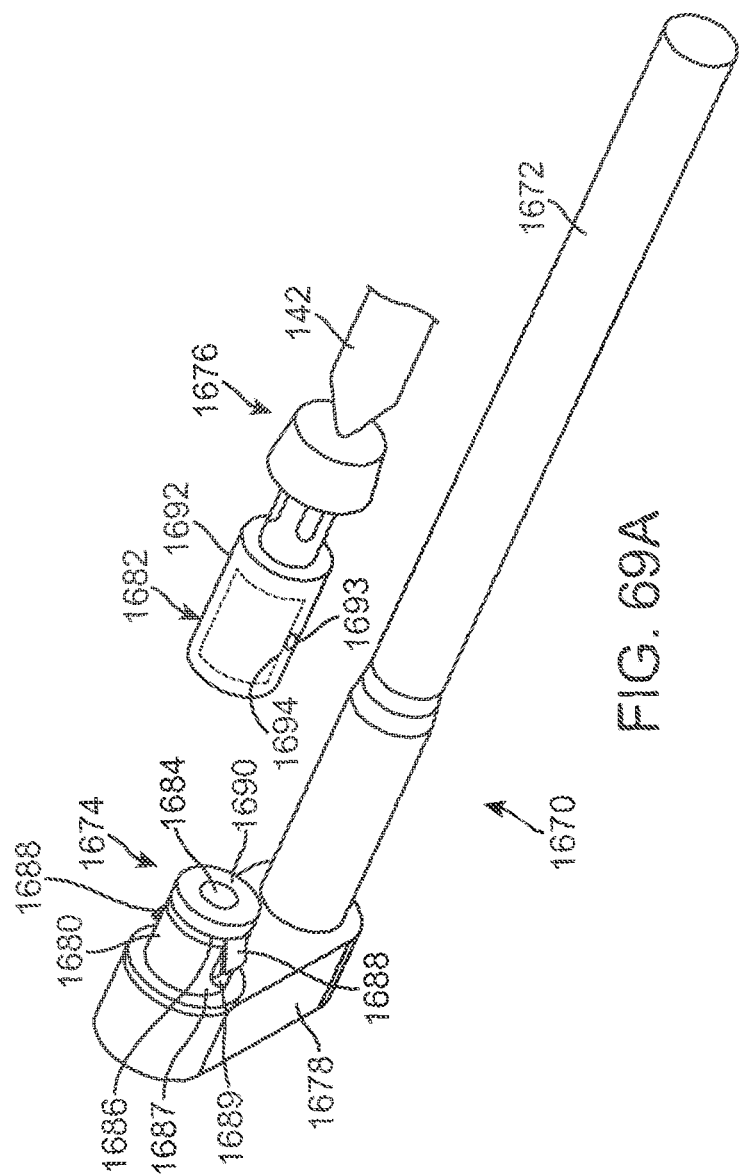
FIG. 69A illustrates a perspective view of another embodiment of an articulating joint.
Figure 69B:
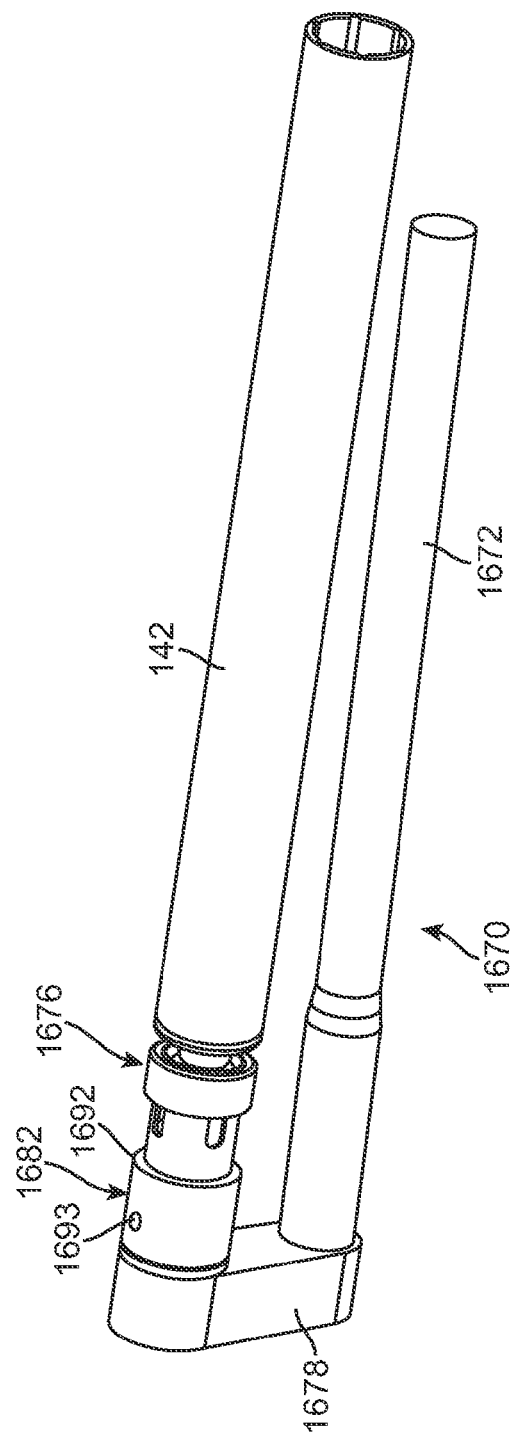
FIG. 69B illustrates a perspective view of the articulating joint with the adjustable rod coupled to the articulating joint.

FIGS. 69A-69B illustrate still another embodiment of an articulating joint 1670 that is used to join an adjustable rod 142 to an anchor rod 1672. In this embodiment, a snap-fit connector 1674 is used to join an articulating joint 1676 to the anchor rod 1672. As illustrated in FIGS. 69A and 69B, the anchor rod 1672 includes an elbow portion 1678 such that the snap-fit connector 1674 is laterally offset and reverses direction. It should be understood, however, that the snap-fit connector 1674 may be utilized without the elbow portion 1678 in the anchor rod 1672. The snap-fit connector 1674 includes a male end 1680 and a female end 1682. The male end 1680 includes a post 1684 having a leaf spring 1686 mounted thereon that includes one or more spring-biased tabs 1688 that project outwardly from the post 1684. A washer 1690 is affixed to the post 1684 via a weld or other connection and serves as a back support plate to the leaf spring 1686. The female end 1682 comprises an elongated cup portion 1692 having a recess 1694 formed therein so that the cup portion 1692 can be pushed over the male end 1680. The recess 1694 has one or more recesses, grooves, or slots that are configured to receive the spring-biased tabs 1688. To "lock" the snap-fit connector 1674, the physician advances the elongated cup portion 1692 over the male end 1680 (or vice versa) until the spring-biased tabs 1688 click and lock into place. The snap-fit connector 1674 may be undone by radial inward pressure on the spring-biased tabs 1688 to release the male end 1680 from the elongated cup portion 1692. An aperture 1693 provided in the elongated cup portion 1692 may provide an access passageway for insertion of a tool or the like to depress the spring-biased tabs 1688. As seen in FIG. 69A, the elongated cup portion 1692 is connected to an articulating joint 1676 that engages with the adjustable rod 142.

The leaf spring 1686 may be made from titanium sheet metal stock in which one or more edges are bent outwardly to form the individual spring-biased tabs 1688. The leaf spring 1686 may be mounted on a mount bushing 1687 forms part of the male end 1680. The mount bushing 1687 may also include recesses 1689 formed therein to receive the corresponding spring-biased tabs 1688 when a radially-inward force is applied thereto.

Figure 70A:
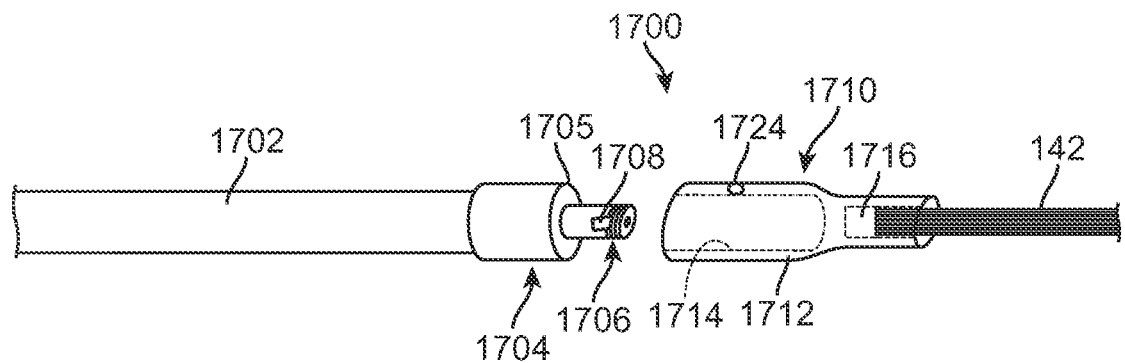
FIG. 70A illustrates another embodiment of an articulating joint.
Figure 70B:
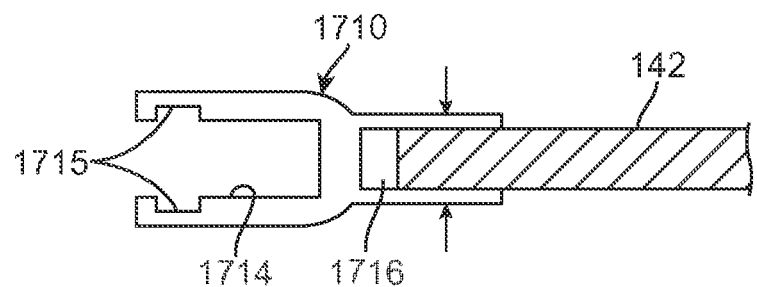
FIG. 70B is a cross-sectional view of a portion of the articulating joint of FIG. 70A.
Figure 70D:
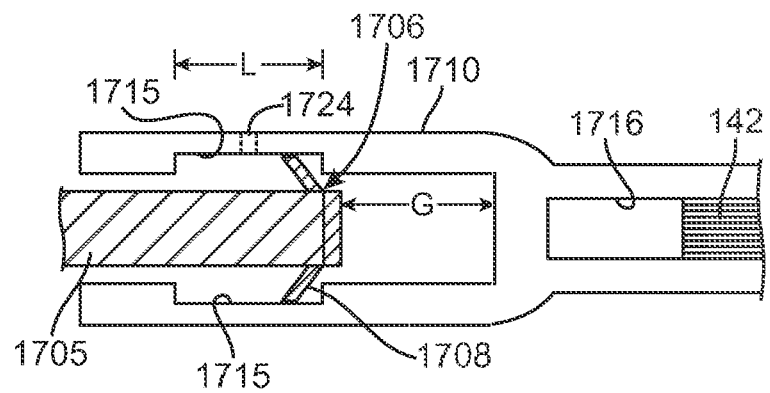
FIG. 70D is an enlarged, cross-sectional view of a portion of the articulating joint of FIGS. 70A and 70B illustrating insertion of the male end of the connector.
Figure 70C:
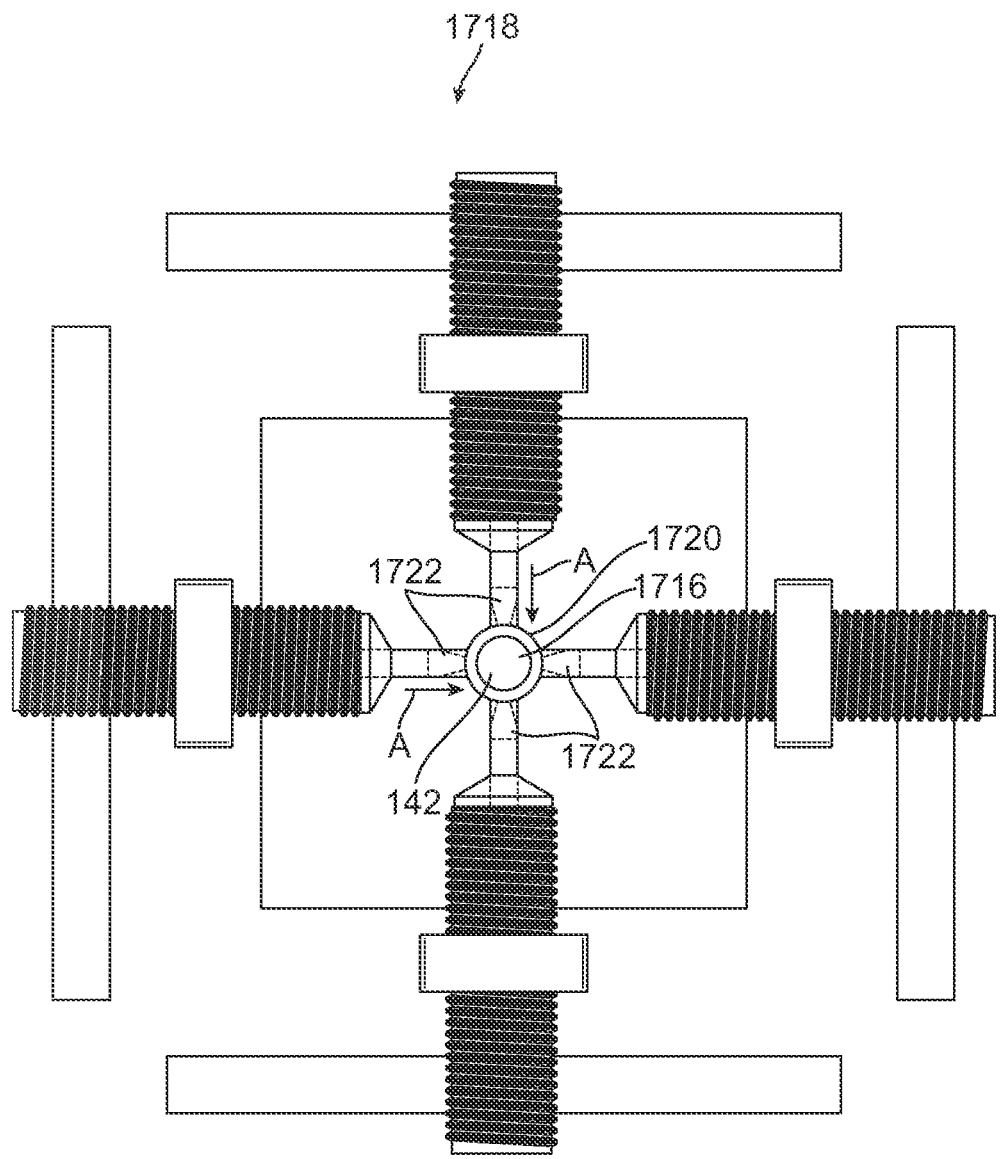
FIG. 70C is a plan view of a crimping tool.

FIGS. 70A-70D illustrate another embodiment of an articulating joint 1700 that is used to join an adjustable rod 142 to an anchor rod 1702. In this embodiment, the snap-fit connector 1704 includes a male end 1705 having a leaf spring 1706 with one or more spring-biased tabs 1708. The snap-fit connector 1704 also includes a female end 1710 that includes an elongated cup 1712 that includes a recess 1714 configured to receive the male end 1705. The recess 1714 has one or more recesses, grooves, or slots 1715 (as illustrated in FIG. 70B) that are configured to receive the spring-biased tabs 1708. To "lock" the snap-fit connector 1704, the physician advances the elongated cup portion 1712 over the male end 1705 until the spring-biased tabs 1708 click and lock into place. The snap-fit connector 1704 may be undone by radial inward pressure on the spring-biased tabs 1708 to release the male end 1705 from the elongated cup portion 1712. In this embodiment, the elongated cup 1712 is secured to the adjustable rod 142 via a crimp fit. Alternatively, the adjustable rod 142 may be secured using a set screw, compression ring, friction fit, or other techniques. In particular, the elongated cup portion 1712 includes a socket 1716 that is dimensioned to receive an end of the adjustable rod 142. To secure the adjustable rod 142 to the socket 1716, a crimping tool 1718 such as that illustrated in FIG. 70C is utilized. The crimping tool 1718 includes an aperture 1720 dimensioned to receive the socket 1716. With the adjustable rod 142 disposed inside the socket 1716, the crimping elements 1722 are rotated to apply a crimping force between the socket 1716 and the adjustable rod 142. FIG. 70C illustrates the crimping force (arrows A) being applied to the socket 1716 to secure the adjustable rod 142 to the female end 1710. The crimping tool 1718 may be downsized for in situ attachment. This embodiment provides the advantage that the adjustable rod 142 may be cut or otherwise trimmed to the appropriate length but the cut or trimmed end may still be secured to the joint 1700.

The snap-fit connector 1704 may be disconnected by applying a radially inward force to the spring-biased tabs 1708. One or more apertures 1724 located in the elongated cup portion 1712 may provide access for insertion of a tool (not shown) to release the male end 1705 from the female end 1710. As best seen in FIG. 70B, the length of the slots 1715 which retain the spring-biased tabs 1708 may be lengthened or shortened to adjust the amount of axial, telescopic, or even rotational movement between the adjustable rod 142 and the anchor rod 1702. For example, FIG. 70D illustrates the length (L) of the slots which can be used to adjust the amount of telescopic movement permitted between the anchor rod 1702 and the adjustable rod 142. In addition, the gap (G) formed between the end of the male end 1705 and the end of the elongated cup 1712 can be visualized under x-ray to determine if the distraction device is under tension. In particular, if a gap is present then this means that there is tension along the adjustable rod 142. The width of the slot 1715 about the elongated cup portion 1712 may modulate the degree of rotational movement.

Figure 71A:
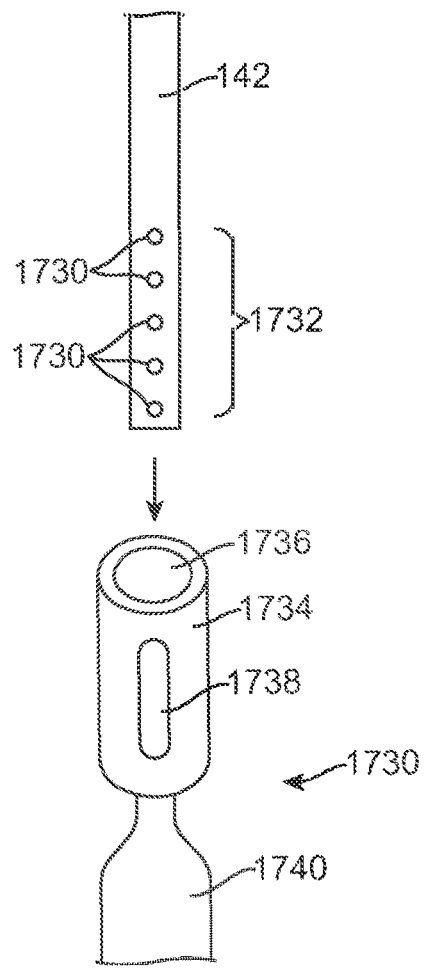
FIG. 71A illustrates a perspective view of another embodiment of an articulating joint.

FIGS. 71A-71D illustrate another embodiment of articulating joint 1730 that is used to join an adjustable rod 142 to an anchor rod (not shown). FIG. 71A illustrates an end of the adjustable rod 142 that contains a number of apertures 1730 that are uniform with respect to pitch. The apertures 1730 are located in a trimable section 1732 of the adjustable rod 142. In particular, the physician is able to cut or trim the adjustable rod 142 to the appropriate length for the patient. FIG. 71A also illustrates a socket 1734 includes a recess 1736 that is sized to receive the cut or trimmed adjustable rod 142. The socket 1734 includes a slot 1738 along a length of the socket 1734. In some embodiments, multiple slots 1738 may be oriented along the length of the socket 1734. The socket 1734 is connected to a polyaxial swivel 1740 which articulates in one or more degrees of freedom. The polyaxial swivel 1740 mates with an anchor rod or an intermediate coupler (not shown). Alternatively, the polyaxial swivel 1740 may be omitted in which case the anchor rod or other coupler is secured to the socket 1734.

Figure 71B:
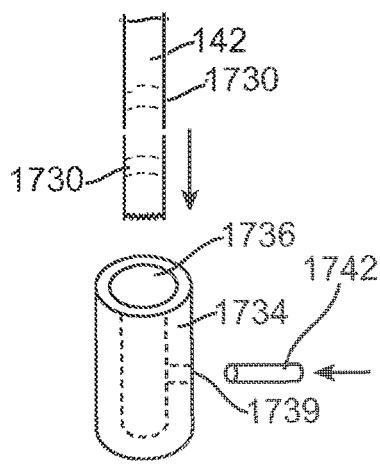
FIG. 71B illustrates a perspective view of another embodiment of an articulating joint.
Figure 71C:
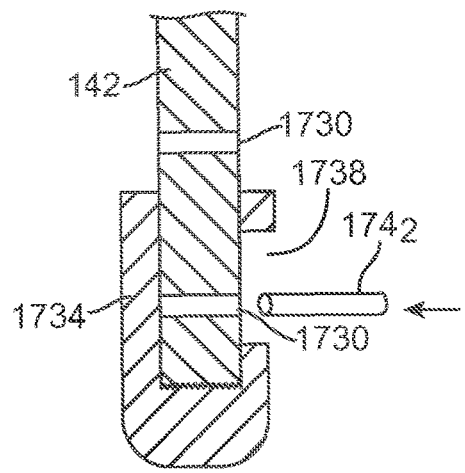
FIG. 71C illustrates a side view of an articulating joint.

Turning now to FIGS. 71B and 71C, the cut end of the adjustable rod 142 is inserted into the recess 1736 of the socket 1734. The apertures 1730 are aligned as needed with the one or more slots 1738 disposed in the socket 1734 as illustrated in FIG. 71A. Alternatively, instead of a slot 1738, the socket 1734 may contain an aperture 1739. A pin 1742 is then press fit into one of the apertures 1730 via a slot 1738 (or aperture 1739). A portion of the pin 1742 extends beyond the outer perimeter of the adjustable rod 142 and extends through the slot 1738 thereby permitting axial or telescoping movement between the adjustable rod 142 and the socket 1734. While telescoping movement is allowed, the pin 1742 prevents radial movement between the two parts. In the embodiment of FIG. 71B, neither telescopic nor radial motion would be permitted. The length of the slot(s) 1738 may be formed to alter the degree of telescopic movement. In addition, while a single pin 1742 is disclosed in the drawings, multiple pins 1742 in different apertures 1730 may be used.

Figure 71D:
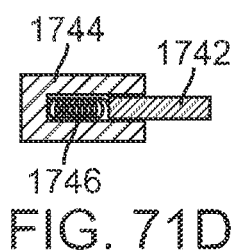
FIG. 71D illustrates a side view of a spring-biased pin contained in a housing.

In one embodiment, additional force may push the pin 1742 completely into the aperture 1730 thereby enabling the adjustable rod 142 and the socket 1734 to be separated from one another. FIG. 71D illustrates another embodiment in which the pin 1742 is contained within a housing 1744 that contains a spring 1746 which tends to push the pin 1742 in the radially outward direction. In this embodiment, the spring 1746 and pin 1742 are located in the aperture 1730 and the pin 1742 extends outwardly because of the bias of the spring 1746.

FIGS. 72A-72D illustrate another embodiment of an articulating joint 1750 that is used to join an adjustable rod 142 to an anchor rod (not shown). In this embodiment, the adjustable rod 142 terminates at one end in a trimable section 1752. The trimable section 1752 includes a longitudinal bore 1754 that extends down a length of the adjustable rod 142. The bore 1754 may contain threads 1756 as explained in more detail herein. The physician may cut or otherwise break the trimable section 1752 along a portion thereof to adjust the length of the adjustable rod 142 during the implantation procedure. An end cap 1758 is provided that is configured for insertion into the end of the trimable section 1752. The end cap 1758 includes corresponding threads 1760 that engage with the threads 1756 within the bore 1754. Alternatively, the end cap 1758 may not include threads but may instead be press-fit into the bore 1754 and attached with an adhesive or other bonding technique. The end cap 1758 further includes an aperture 1762 that provides access for locking means described below.

Figure 72A:
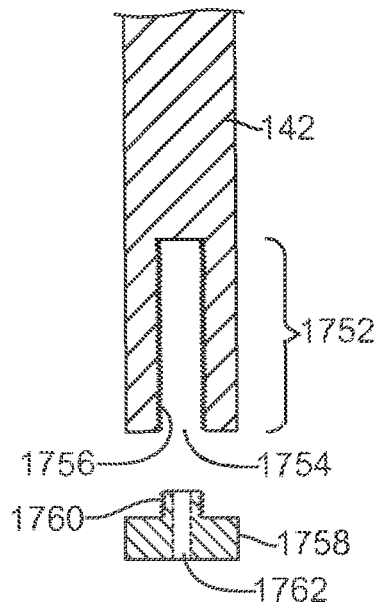
FIG. 72A illustrates another embodiment of an articulating joint including a trimable section of an adjustable rod and an end cap.
Figure 72B:
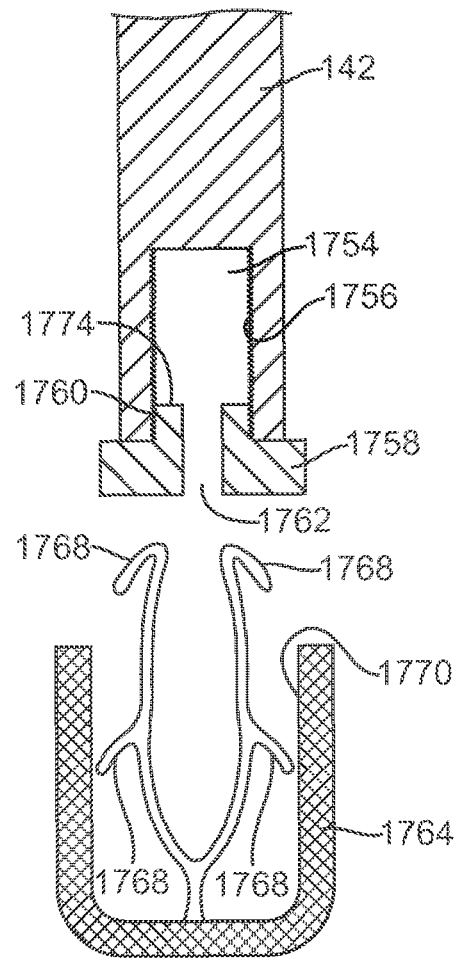
FIG. 72B illustrates a polyaxial swivel head adjacent to the adjustable rod containing the end cap.

FIG. 72B illustrates a polyaxial swivel head 1764 that is configured to engage with the adjustable rod 142 and the end cap 1758. The polyaxial swivel head 1764 is either directly or indirectly (via a coupler or the like) connected to an anchor rod of the type described herein. The polyaxial swivel head 1764 provides one or more degrees of freedom of movement with respect to the anchor rod that is connected thereto (not shown). The polyaxial swivel head 1764 includes spring-biased tabs 1768 that extend along a length of an inner recess 1770 formed in the polyaxial swivel head 1764. The spring-biased tabs 1768 are configured such that when the polyaxial swivel head 1764 is advanced over the trimable section 1752 of the adjustable rod 142, the spring-biased tabs 1768 pass through the aperture 1762 in the end cap 1758. The spring-biased tabs 1768 thus form a locking arrangement between the polyaxial swivel head 1764 and the adjustable rod 142 because the spring-biased tabs 1768 are prevented from withdrawing proximally out of the aperture 1762 given the step or rim 1774 formed on the end cap 1758.

Figure 72C:
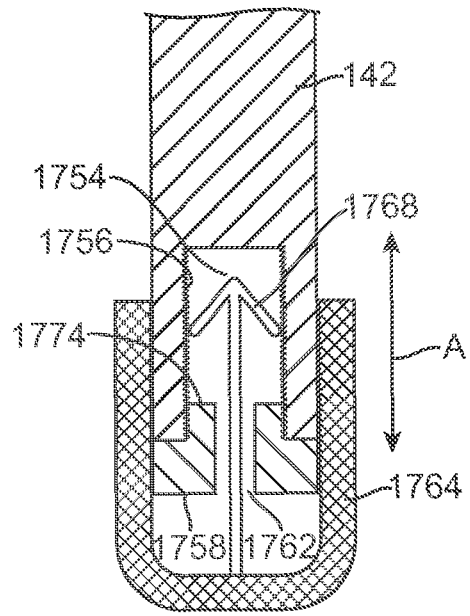
FIG. 72C illustrates an embodiment of an articulating joint with the polyaxial swivel head coupled to the adjustable rod.
Figure 72D:
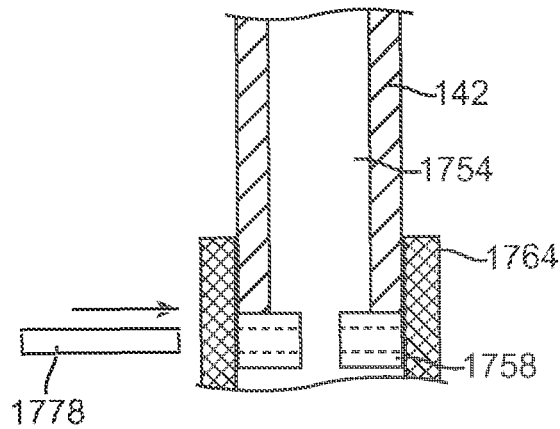
FIG. 72D illustrates an embodiment of an articulating joint with the polyaxial swivel head according to another embodiment.

As seen in FIG. 72C, once the polyaxial swivel head 1764 is engaged with the adjustable rod 142, there is a degree of telescopic or axial movement (illustrated by arrow A) permitted between the polyaxial swivel head 1764 and the adjustable rod 142. The degree of this movement may be adjusted, for example, by adjusting the degree to which the spring-biased tabs 1768 extend within the bore 1754. While the FIGS. 72B and 72C illustrate a step or rim 1774 formed in the end cap 1758, in an alternative construction, the step or rim 1774 may be omitted and replaced with a stop member 1778 that may be inserted through the end cap 1758 as illustrated in FIG. 72D. The stop member 1778 may include a rod or pin that extends through the end cap 1758. The stop member 1778 may be removable so that the polyaxial swivel head 1764 can be disengaged from the adjustable rod 142.

Figure 73A:
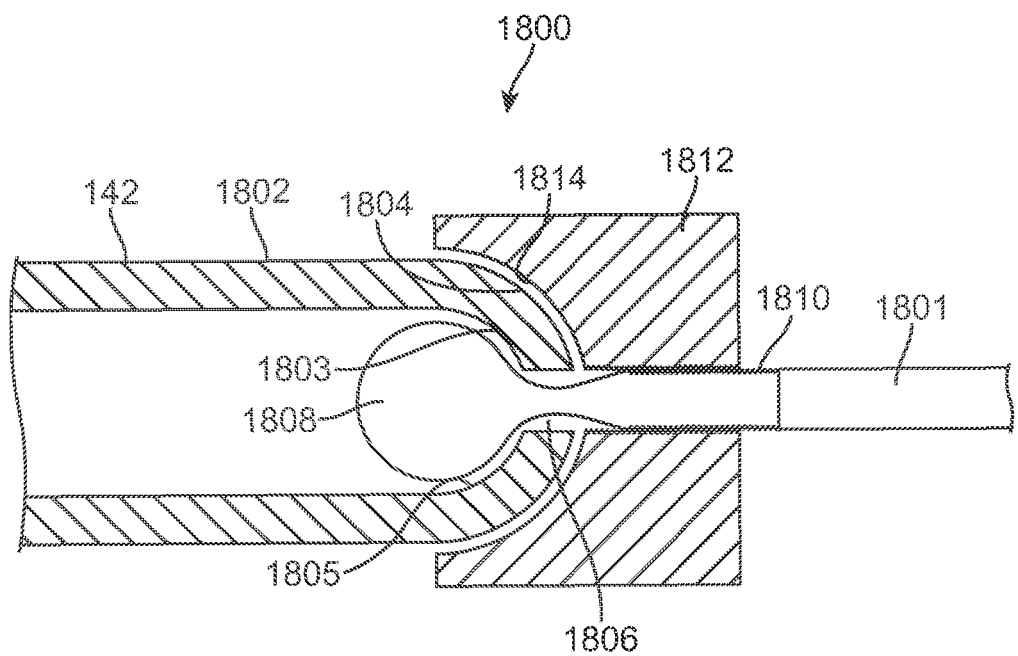
FIG. 73A illustrates one embodiment of a locking swivel joint.
Figure 73B:
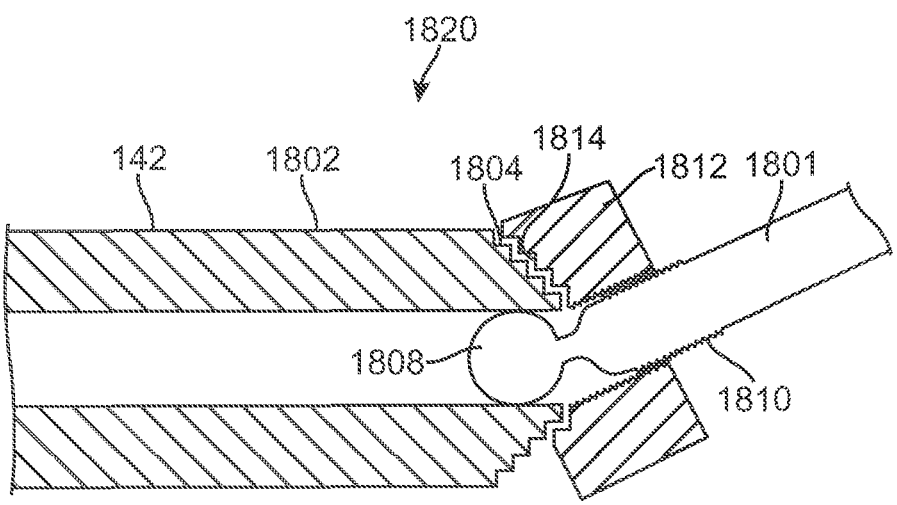
FIG. 73B illustrates another embodiment of a locking swivel joint.
Figure 73C:
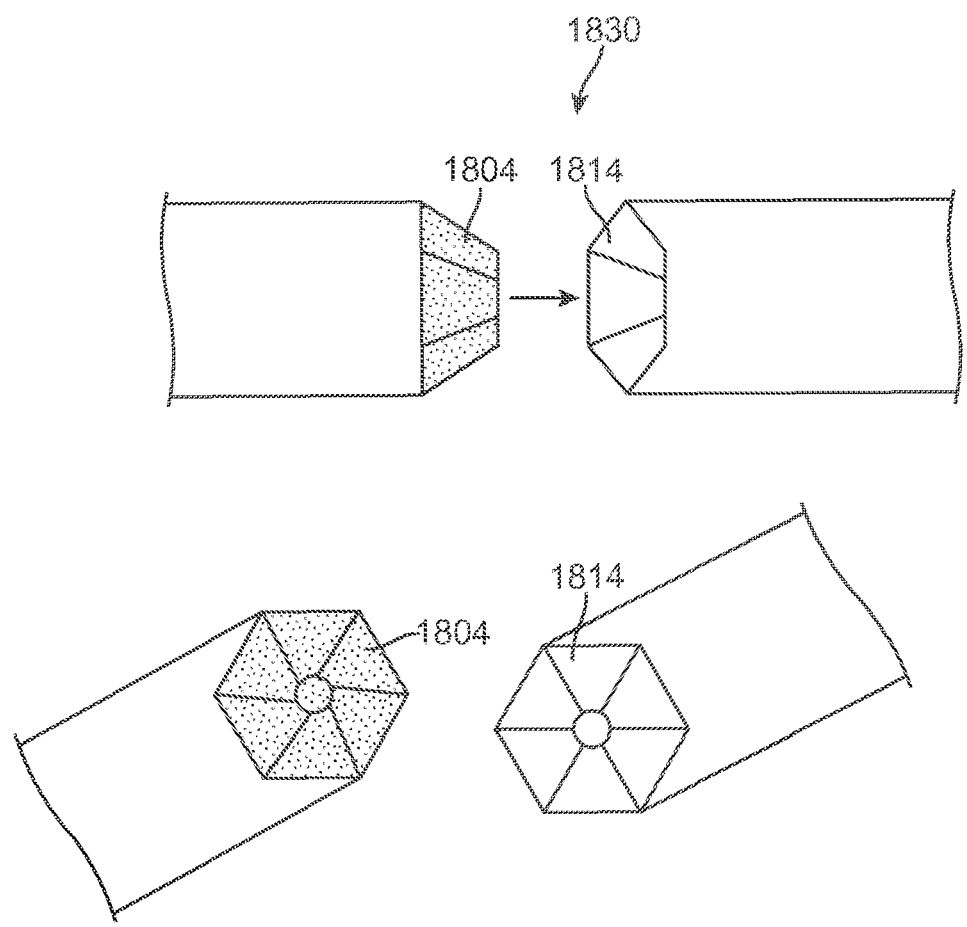
FIG. 73C illustrates another embodiment of a locking swivel joint.

FIGS. 73A-73C illustrate various embodiments of a locking swivel joint 1800. The locking swivel joint 1800 permits the swivel joint 1800 to articulate in one or more degrees of freedom or, alternatively, be locked down to prevent movement in all or one or more degrees of freedom. The locking swivel joint 1800 is particularly useful for joining an adjustable rod 142 and a fixed anchor rod 1801. For example, non-fusion applications for the adjustable rod 142 may require a certain degree of articulation in the swivel joint

1800. Fusion applications, on the other hand, may require a rigid structure in which the swivel joint 1800 is locked to prevent or limit articulation. FIG. 73A illustrates a locking swivel joint 1800 that includes a cup portion 1802 that includes a contact surface 1804 at one end thereof. The contact surface 1804 may be an arcuate or rounded surface. Alternatively, the contact surface 1804 may have a series of bumps or a rough texture on it. An aperture 1806 is formed in the end of the cup portion 1802 that is configured to receive a ball 1808 that is secured to an end of the anchor rod 1801. The ball 1808 may be welded or otherwise bonded to the end of the anchor rod 1801 or it may be formed integrally therewith. The anchor rod 1801 further includes a threaded portion 1810 located adjacent to the ball 1808.

A nut 1812 is disposed about the anchor rod 1801 and includes threads therein for engaging with the threaded portion 1810 of the anchor rod 1801. The nut 1812 further includes a contact surface 1814 configured to engage with the contact surface 1804 of the cup portion 1802. To lock the swivel joint 1800 the nut 1812 is tightened about the threaded portion 1810. Advancement of the nut 1812 causes the respective contact surfaces 1804, 1814 to engage with one another. The two contact surfaces 1804, 1814 will bind, creating an equal and opposite binding force on the ball 1808 and the inner edge of the cup portion 1802. This creates two friction surfaces thereby locking the swivel joint 1800 from any swiveling action. While FIG. 73A illustrates the ball 1808 on the end of the anchor rod 1801, it should be understood that the ball 1808 may be located on the adjustable rod 142 (not shown) with the anchor rod 1801 connected to or including the cup portion 1802. Also, as the ball 1808 is being pulled back, there is contact between surfaces 1803, 1805 on the ball.

FIG. 73B illustrates another embodiment of a locking swivel joint 1820. The locking swivel joint 1820 is similar to that illustrated in FIG. 73A with the difference that the contact surface 1804 of the cup portion 1802 is tiered or scalloped. In addition, the contact surface 1814 of the nut 1812 is also tiered or scalloped such that when the two contact surfaces 1804, 1814 touch one another, this aids in locking the anchor rod 1801 relative to the cup portion 1802. While both surfaces 1804, 1814 may be textured or scalloped, it should be understood that only one of the surfaces 1804, 1814 needs to be textured or scalloped, because the surface can itself create high stress points that lead to increased friction.

FIG. 73C illustrates another locking swivel joint 1830 that includes contact surfaces 1804, 1814 that are polygonal in nature. In particular, the contact surfaces 1804, 1814 illustrated in FIG. 73C comprise a hexagonal, faceted surface. One contact surface 1804 is convex while the other contact surface 1814 is concave. When the mating contact surfaces 1804, 1814 of the locking swivel joint 1830 are brought into contact with one another using a locking nut (not shown) such as that described above, the two contact surfaces 1804, 1814 are prevented from rotating relative to one another.

Figure 74:
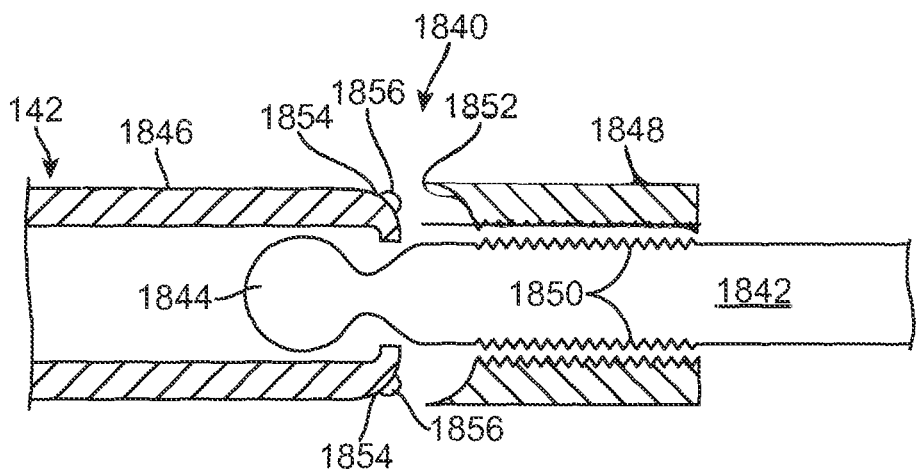
FIG. 74 illustrates yet another embodiment of a locking swivel joint.

FIG. 74 illustrates still another locking swivel joint 1840. In this embodiment, anchor rod 1842 terminates at a ball 1844 that is configured for placement within a cup 1846. The cup 1846 may be disposed on the end of the adjustable rod 142. A threaded nut 1848 disposed about the periphery of the anchor rod 1842 engages with corresponding threads 1850 located on the anchor rod 1842. The nut 1848 includes a contact surface 1852 that is configured to engage a contact surface 1854 disposed at the end of the cup 1846. The contact surface 1854 of the cup 1846 includes an abutment or raised portion 1856 about all or a portion thereof. The abutment 1856 may include ring made from deformable material that is disposed about all or a portion of the contact surface 1854. The abutment 1856 may also comprise a raised surface area that is formed in the contact surface 1854. When the nut 1848 is tightened over the anchor rod 1842, the contact surface 1852 formed thereon will come into contact with the abutment 1856. Additional tightening will cause deformation of the contact surfaces 1852, 1854 and create a mechanical lock between the cup 1846 and the anchor rod 1842 which prevents any rotational movement. For example, the abutment 1856 may be formed from a harder material as compared to the contact surfaces 1852, 1854 such that tightening of the nut 1848 causes contact surfaces 1852, 1854 to deform. Alternatively, the abutment 1856 may be formed from a softer material as compared to the contact surfaces 1852, 1854 such that tightening of the nut 1848 causes the abutment 1856 (e.g. ring) to deform and increases the frictional contact forces.

Figure 75A:
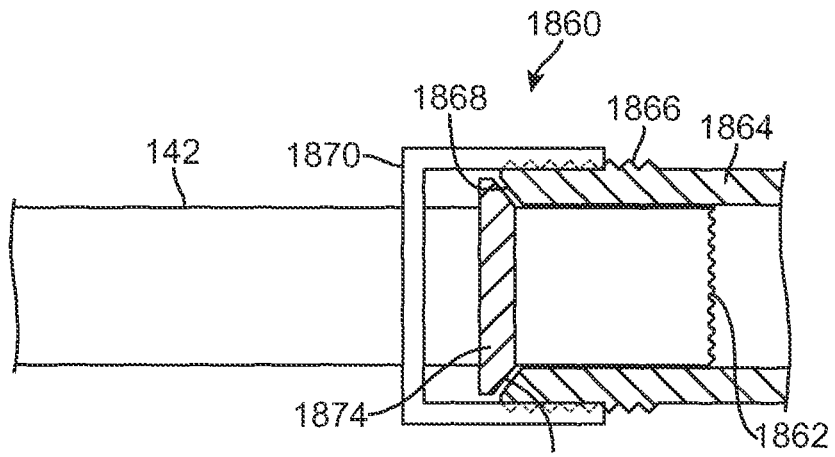
FIG. 75A illustrates still another locking swivel joint. The swivel joint is in the unlocked state.
Figure 75B:
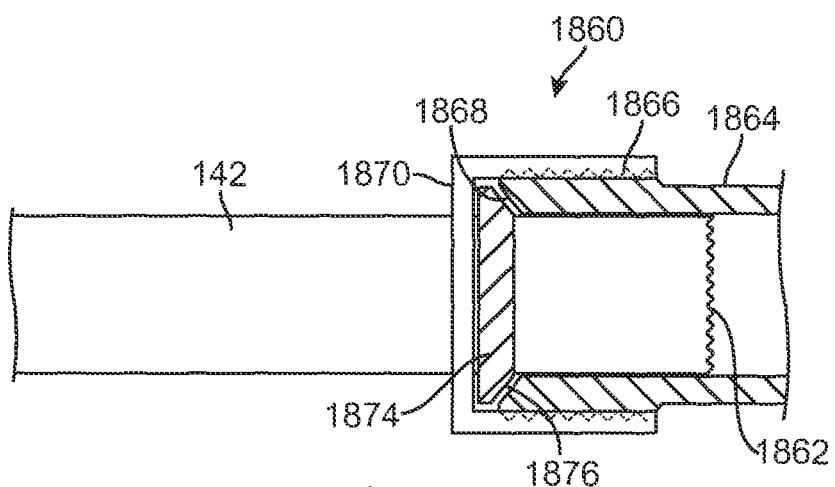
FIG. 75B illustrates still another locking swivel joint. The swivel joint is in the locked state.

FIGS. 75A and 75B illustrate a locking joint 1860 that is configured to lock the trimmed end 1862 of an adjustable rod 142 to a locking tube 1864. The locking tube 1864 may be connected directly or indirectly to, for example, an anchor rod. The locking tube 1864 includes a threaded portion 1866 at a free end thereof. The locking tube 1864 includes a chamfered surface 1868 at the end thereof. A locknut 1870 having an aperture sized to permit passage of the trimmed end 1862 of the adjustable rod 142 is mounted on the locking tube 1864. The locknut 1870 has corresponding threads (not shown) that engage with the threaded portion 1866. The locking joint 1860 includes a compression ring 1874 that is interposed between the locknut 1870 and the chamfered surface 1868 of the locking tube 1864. The compression ring 1874 may include a full ring or an incomplete ring (e.g., a ring with a slit or slot in the ring for relief purposes). The compression ring 1874 includes a contact surface 1876 that is configured to contact the chamfered surface 1868 when the locknut 1870 is tightened.

FIG. 75A illustrates the locking joint 1860 in an unlocked state. In this state, the compression ring 1874 can slide freely over the trimmed end 1862 of the adjustable rod 142. In addition to sliding motion, the compression ring 1874 can also rotate freely over the trimmed end 1862 of the adjustable rod 142. FIG. 75B illustrates the locking joint 1860 in a locked state after the locknut 1870 has been tightened over the locking tube 1864. The locknut 1870 compresses the compression ring 1874 up against the chamfered surface 1868. This causes the compression ring 1874 to deform and physically grip the trimmed end 1862 of the adjustable rod 142. This locks the adjustable rod 142, thereby preventing rotation and telescopic or axial movement of the adjustable rod 142 relative to the locking joint 1860.

Figure 76A:
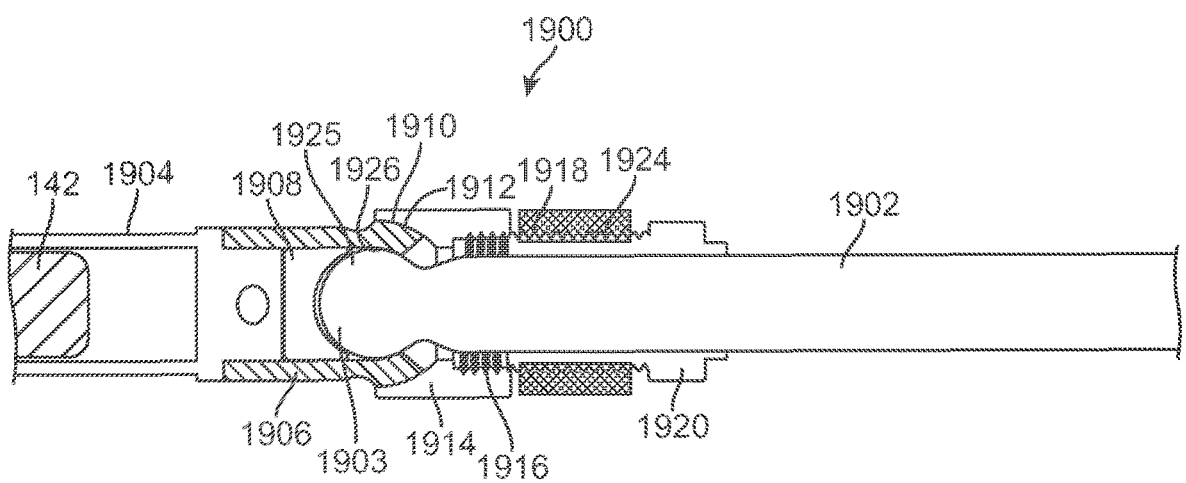
FIG. 76A illustrates yet another embodiment of a locking swivel joint.
Figure 76B:
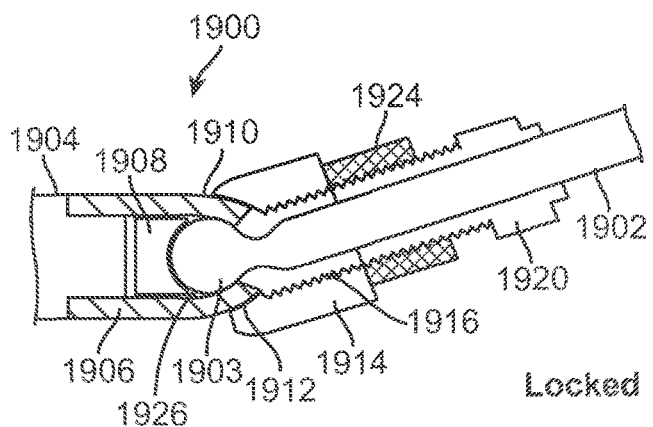
FIG. 76B illustrates the swivel joint in the locked state.
Figure 76C:
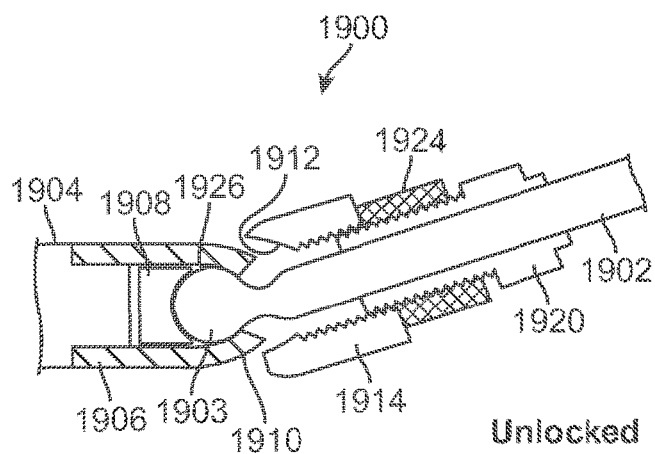
FIG. 76C illustrates the swivel joint in the unlocked state.

FIGS. 76A-76C illustrate yet another embodiment of a locking joint 1900. The locking joint 1900 may be used to permit selective articulation or non-articulation between an anchor rod 1902 and an adjustable rod 142. The locking joint 1900 includes an elongate socket 1904 dimensioned to receive a free end (e.g., a trimmed end) of the adjustable rod 142. The elongate socket 1904 is coupled to a housing 1906 that contains a bearing 1908 made from a low friction material such as an Ultra High Molecular Weight Polyethylene (UHMWPE) material. The housing 1906 includes a contact surface 1910 which may include an angled or arcuate shaped portion that is configured to mate with a contact surface 1912 of a friction nut 1914. The friction nut 1914 includes internal threads 1916 that mate with threads 1918 of a bushing 1920 mounted about the periphery of the anchor rod 1902. A locking nut 1924 having internal threads is mounted about the bushing 1920 and interfaces with the outer threads 1918 of the bushing 1920.

As seen in FIGS. 76A-76C, the anchor rod 1902 terminates in a ball 1903 that is contained in the housing 1906. FIG. 76B illustrates the "locked" configuration whereby the locking nut 1924 is turned and thus rotates down the bushing 1920 to force the contact surface 1912 of the friction nut 1914 into the contact surface 1910 of the housing 1906. This friction causes the surfaces 1910, 1912 to bind to one another thus prevents any type of swiveling motion between the adjustable rod 142 relative to the anchor rod 1902. Also, the surface 1925 of the ball 1903 also binds with the inner surface 1926 of the housing 1906. FIG. 76C illustrates the "unlocked" configuration whereby the locking nut 1924 is rotated in the opposite direction on the bushing 1920 thereby releasing the contact surface 1912 of the friction nut 1914 from the contact surface 1910 of the housing 1906. In the unlocked configuration, the anchor rod 1902 is able to freely articulate within the housing 1906. Frictional forces (wedged together) between the friction nut 1914 and the locking nut 1924 keep the friction nut 1914 fixed in the unlocked configuration thereby enabling unimpeded articulation of the locking joint 1900.

FIG. 77 illustrates another embodiment of locking joint 1930 that is similar to the locking joint 1900 in FIGS. 76A-76C. In this embodiment, the locking joint 1930 is releasably secured to the end of a j-shaped anchor rod 1932. The j-shaped anchor rod 1932 includes a straight segment 1934 that is connected to an elbow 1936 at a joint 1938. The joint 1938 may comprise a weld or the like. It should be understood that the j-shaped anchor rod 1932 may be formed from a single piece and may be other shapes (e.g., straight or the like). The end of the elbow 1936 includes a spring-biased locking ring 1940. The locking ring 1940 releasably engages with a recess 1941 located within a housing 1942 of the locking joint 1930. In this regard, a snap lock is formed between the housing 1942 and the end of the elbow 1936. The snap lock may be released by insertion of a tool or the like (not shown) into the aperture 1944 to apply a radially-directed inward force on the locking ring 1940.

Much like the embodiment of FIGS. 76A-76C, the housing 1942 contains a bearing 1946 made from a low friction material such as an Ultra High Molecular Weight Polyethylene (UHMWPE) material. The housing 1942 includes a contact surface 1948 which may include an angled or arcuate shaped portion that is configured to mate with a contact surface 1950 of a friction nut 1952. The friction nut 1952 includes internal threads 1954 that mate with threads 1956 of a bushing 1958 mounted about the periphery of a rod 1957 terminating at a ball 1959 contained within the housing 1942. The rod 1957 may include a free end of an adjustable rod 142. Alternatively, the locking joint 1930 may be affixed, bonded, or secured to the trimmed end of an adjustable rod 142 as is illustrated in FIG. 77. For example, the free end 143 of the adjustable rod 142 is illustrated as secured to a proximal end of the bushing 1958. A locking nut 1960 having internal threads is mounted about the bushing 1958 and interfaces with the outer threads 1956 of the bushing 1958. FIG. 77 illustrates a locked configuration of the locking joint 1930 whereby the locking nut 1960 creates a frictional bind between contact surfaces 1948, 1950 to prevent articulating movement at the locking joint 1930. The joint 1930 may be unlocked by loosening the locking nut 1960 which retracts the friction nut 1952 away from the housing 1942. In an alternative construction, the locking nut 1960' may be moved proximally and located about the exterior of the adjustable rod 142 which is illustrated in phantom in FIG. 77. This last modification makes the construct shorter but it has a larger outer diameter.

Figure 78A:
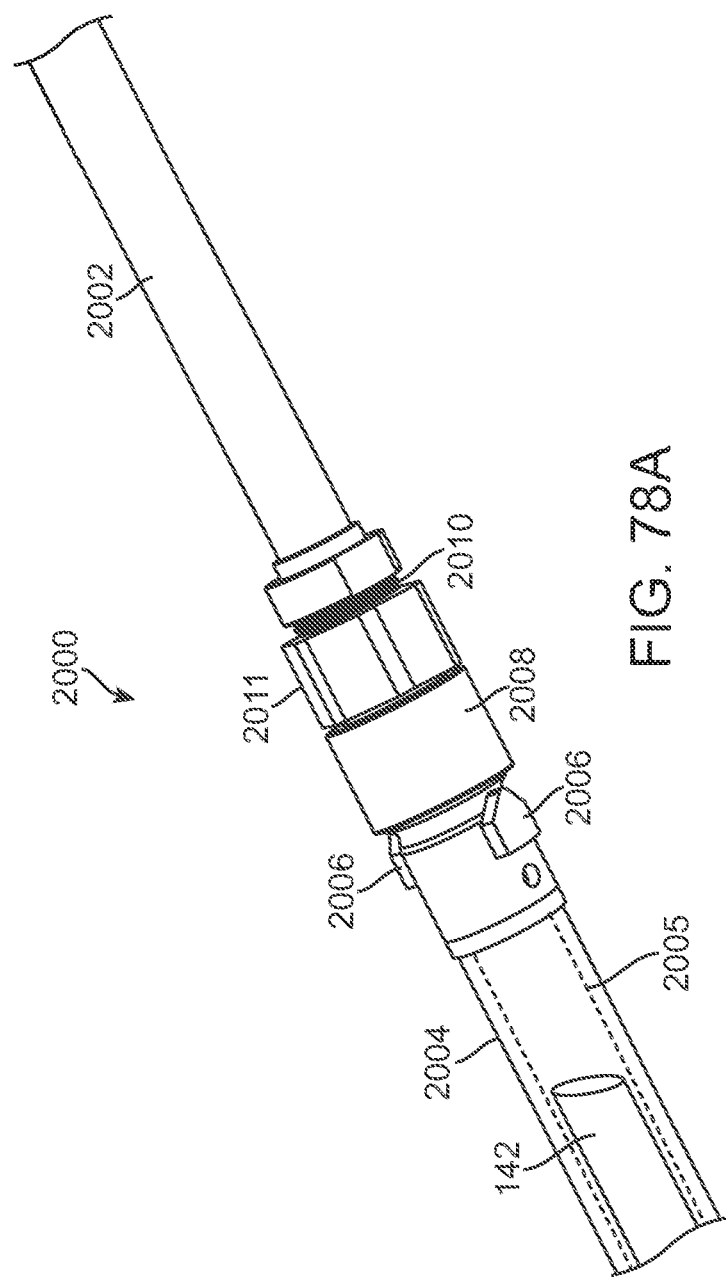
FIG. 78A illustrates an embodiment of a swivel joint using one or more cam limiters.
Figure 78B:
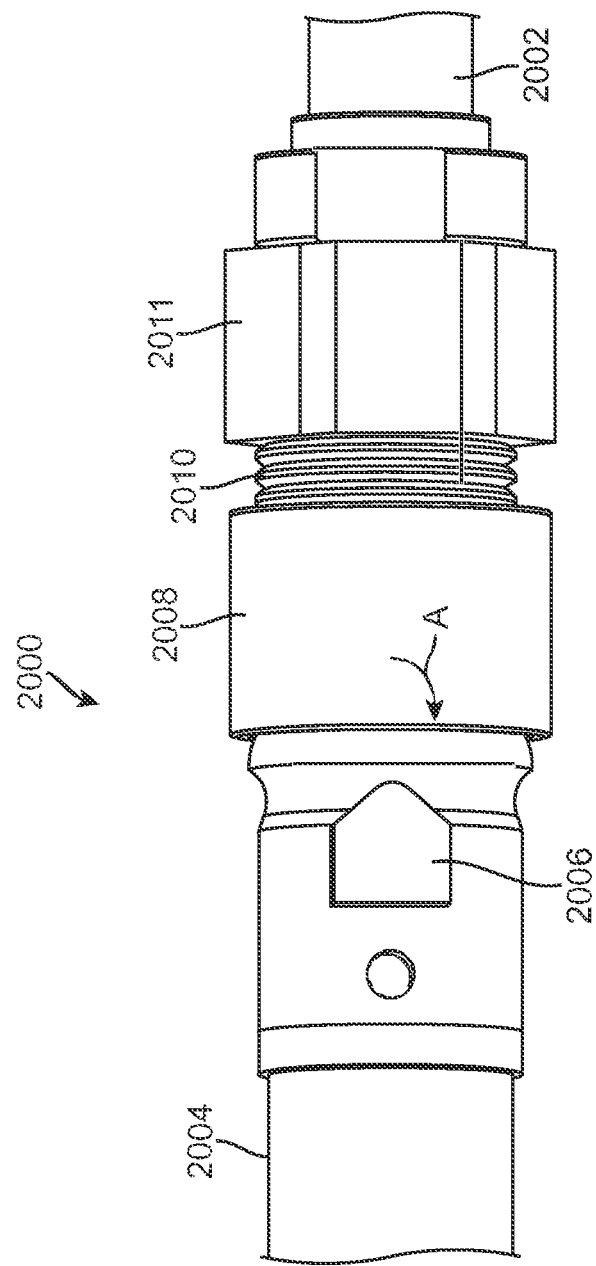
FIG. 78B illustrates a close-up, side view of the swivel joint of FIG. 78A. The friction nut is located close to the cam limiter.
Figure 78C:
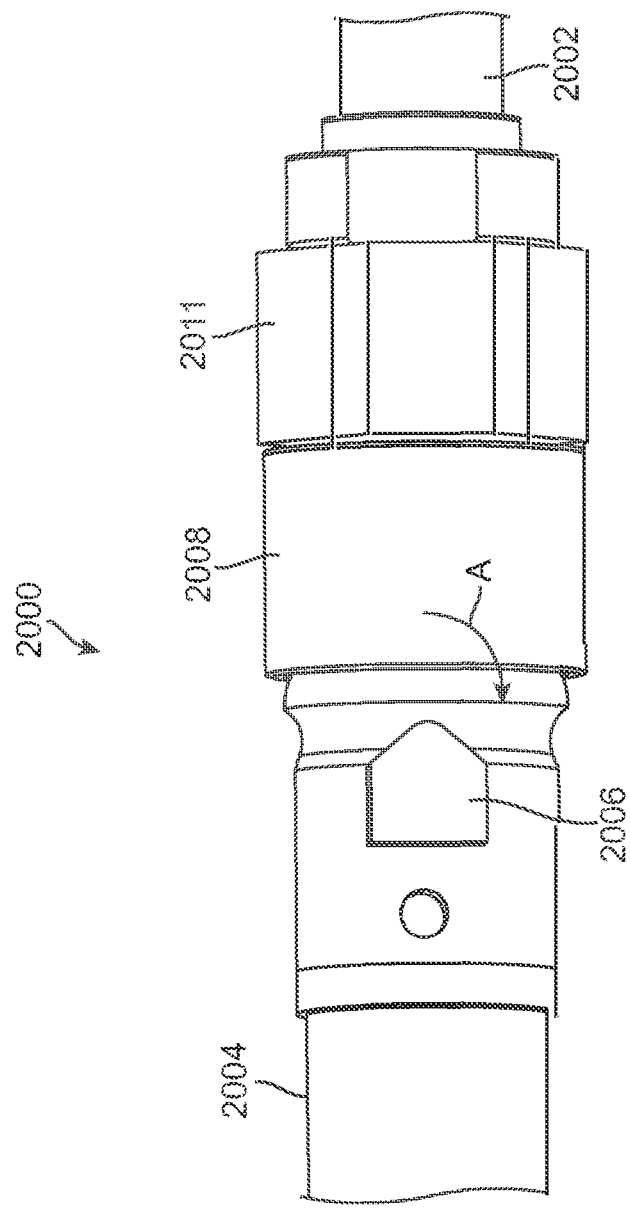
FIG. 78C illustrates a close-up, side view of the swivel joint of FIG. 78A. The friction nut is located away from the cam limiter.

FIGS. 78A-78C illustrates a swivel joint 2000 according to one aspect of the invention. The swivel joint 2000 provides an articulating connector between an anchor rod 2002 and the adjustable rod 142. As seen in FIGS. 78A-78C, the swivel joint 2000 includes a socket 2004 that includes a recess 2005 therein for receiving the end of the adjustable rod 142 (e.g., trimable end). The socket 2004 may comprise a tubular construct as is described elsewhere herein with respect to other embodiments. One or more cam limiters 2006 are disposed about the periphery of the socket 2004. The cam limiters 2006 are configured to restrict or even stop articulation in one or more degrees of freedom. In this regard, the cam limiters 2006 may provide a swiveling or articulation envelope which can define the boundary of movement between the anchor rod 2002 and the adjustable rod 142 at the swivel joint 2000. While two such cam limiters 2006 are illustrated in FIGS. 78A-78C, it is possible that only a single cam limiter 2006 is used. For example, the cam limiter 2006 may include a ring which could limit movement in multiple planes. Such a ring may have bumps or other features along the edges. Similarly, a plurality of cam limiters 2006 disposed in a pattern about the periphery of the socket 2004 may be used. Alternatively, multiple rings may be used. The ring(s) may also be located on the opposing side of the swivel joint 2000 in order to limit rotation and/or swivel.

Still referring to FIGS. 78A-78C, the degree of articulation of the socket 2004 (and thus the adjustable rod 142) relative to the anchor rod 2002 is limited by contact between the one or more cam limiters 2006 and a friction nut 2008. The friction nut 2008 includes internal threads (not shown) that engage with corresponding threads 2010 disposed on a periphery of the swivel joint 2000. The friction nut 2008 can thus be advanced toward or retracted away from the one or more cam limiters 2006 by rotation of the friction nut 2008 in either the clockwise or counter-clockwise directions. A locking nut 2011 may be used to fix the position of the friction nut 2008 along the threads 2010. FIG. 78B illustrates the swivel joint 2000 when the friction nut 2008 is positioned close or adjacent to the cam limiters 2006. In this configuration, articulation or swiveling action is restricted or prevented in the direction of arrow A. At the same time, the swivel joint 2000 allows articulating motion in other directions. FIG. 78C illustrates the swivel joint 2000 when the friction nut 2008 is positioned far away from the cam limiters 2006. Here, the added gap between the cam limiters 2006 and the friction nut 2008 will allow a greater degree of pivoting in the direction of arrow A. Thus, by adjusting the position of the friction nut 2008, the allowable pivot angle of the swivel joint 2000 may be adjusted.

Figure 79:
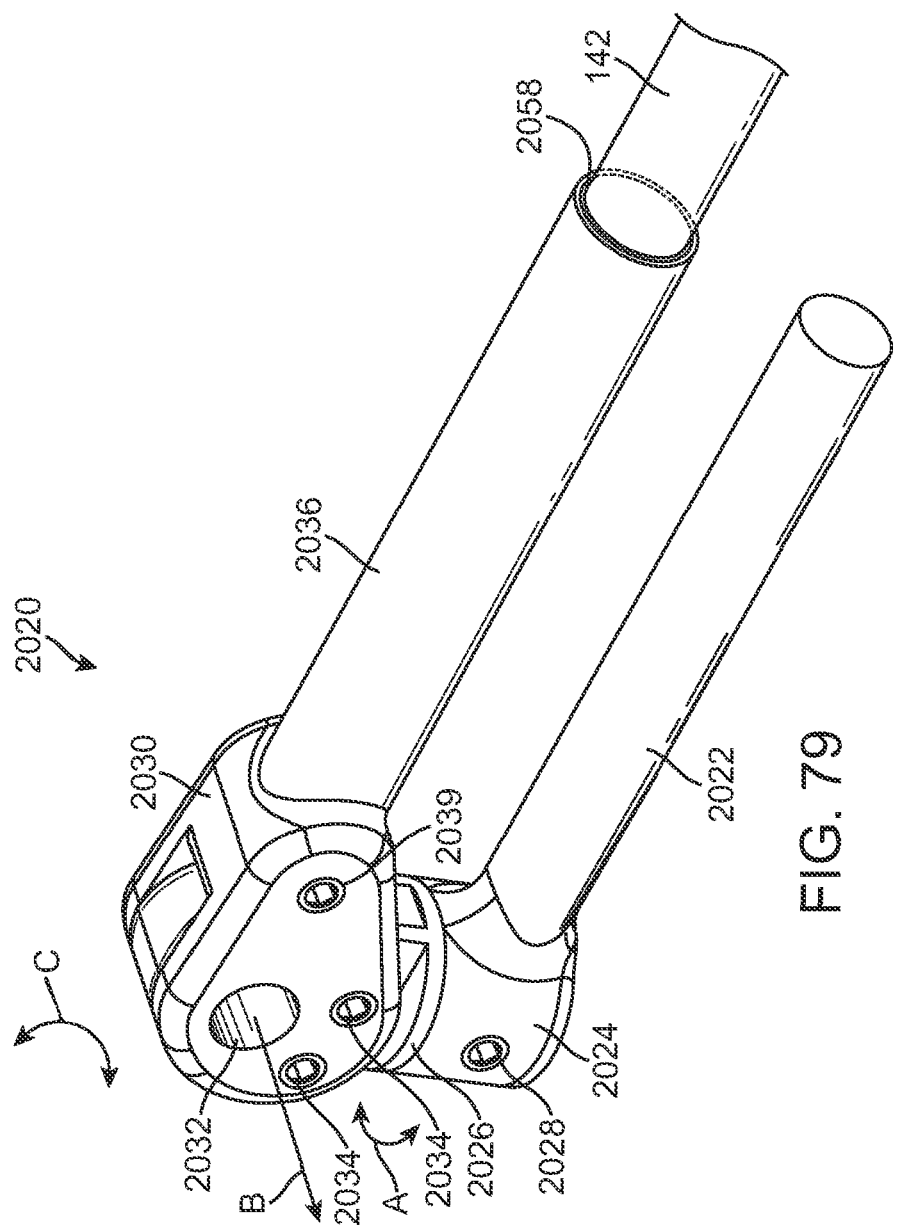
FIG. 79 illustrates an articulating joint according to one embodiment.

FIG. 79 illustrates an articulating joint 2020 according to another embodiment. In this embodiment, the articulating joint 2020 connects an anchor rod 2022 to an adjustable rod 142. The anchor rod 2022 terminates at one end thereof in a base 2024. A turret 2026 is mounted on the base 2024 and is able to pivot on the base 2024 in the direction of arrow A (e.g., side to side pivoting). A fastener 2028 such as a screw is located in the base 2024 and is able to limit pivoting of the turret 2026 relative to the base 2024. For example, the physician can adjust the pivot of the turret 2026 to the appropriate location and then tighten fastener 2028 to lock the turret 2026 with respect to the base 2024. A socket portion 2030 is pivotably mounted on the turret 2026. The socket portion 2030 pivots about rod 2032. The center of axis of the rod 2032 is illustrated by arrow B in FIG. 79. The socket portion 2030 is thus able to pivot in the direction of arrow C (e.g., up and down pivoting). This pivoting movement is generally orthogonal to the pivoting movement of the turret 2026 with respect to the base 2024. A pair of fasteners 2034 such as screws is located in the socket portion 2030 and can be tightened to prevent pivoting motion in the direction of arrow C. Again, the physician can adjust the pivot of the socket portion 2030 to the appropriate location and then tighten fasteners 2034 to lock the socket portion 2030 with respect to the turret 2026. The socket portion 2030 includes an elongate tubular section 2036 that includes a lumen 2088 therein that is dimensioned for passage of the end of an adjustable rod 142. Another fastener 2039 located in the socket portion 2030 may be tightened to secure the adjustable rod 142 within the elongate tubular section 2036. Alternatively, the adjustable rod 142 may be able to freely move within the elongate tubular section 2036 (e.g., telescopic or axial movement and/or rotational movement).

Figure 80:
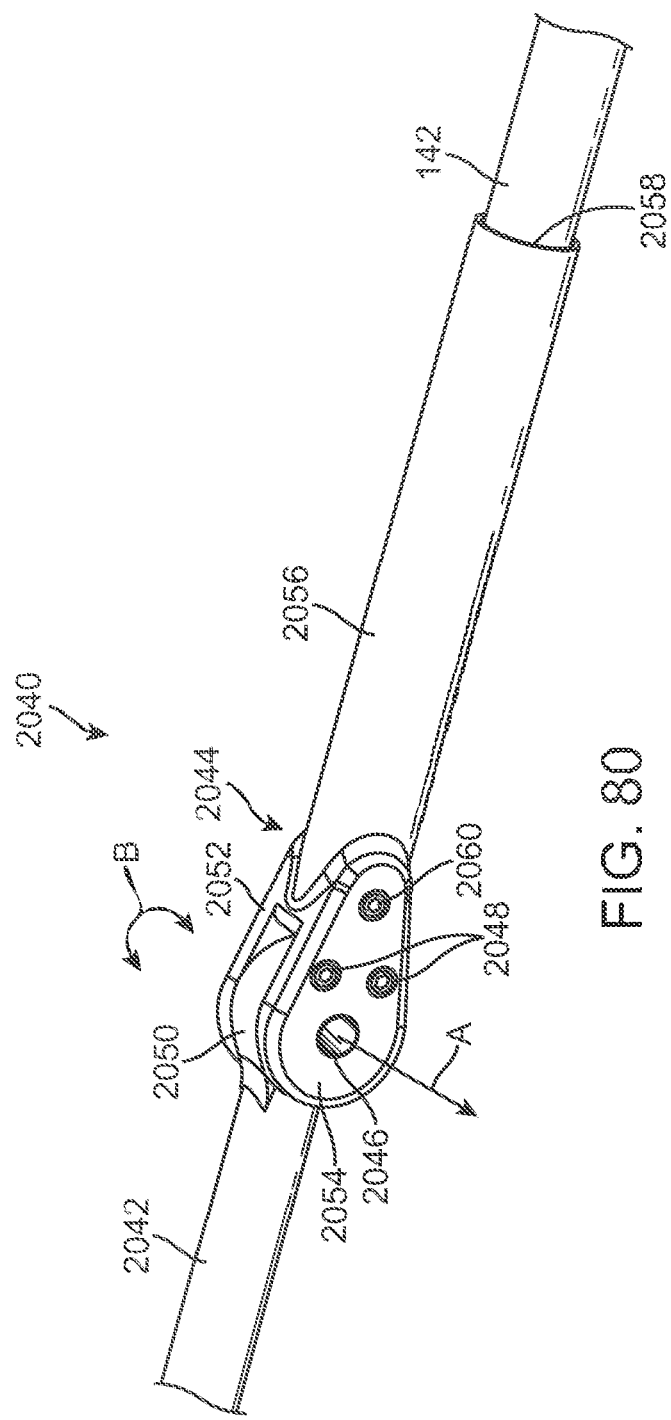
FIG. 80 illustrates an articulating joint according to another embodiment.

FIG. 80 illustrates another embodiment of an articulating joint 2040 according to anther embodiment. In this embodiment, the articulating joint 2040 connects an anchor rod 2042 to an adjustable rod 142. The articulating joint 2040 includes a socket portion 2044 that pivots about rod 2046. The center of axis of the rod 2046 is illustrated by arrow A in FIG. 80. The socket portion 2044 is thus able to pivot in the direction of arrow B. A pair of fasteners 2048 such as screws is located in the socket portion 2044 and can be tightened to prevent pivoting motion in the direction of arrow B. The physician can adjust the pivot of the socket portion 2044 to the appropriate location and then tighten fasteners 2048 to lock the socket portion 2044 with respect to the anchor rod 2042. The anchor rod 2042 terminates at a head 2050 that is held within two arms 2052, 2054 of the socket portion 2044. The socket portion 2044 includes an elongate tubular section 2056 that includes a lumen 2058 therein that is dimensioned for passage of the end of an adjustable rod 142. Another fastener 2060 located in the socket portion 2044 may be tightened to secure the adjustable rod 142 within the elongate tubular section 2056. Alternatively, the adjustable rod 142 may be able to freely move within the elongate tubular section 2056 (e.g., telescopic or axial movement and/or rotational movement).

FIGS. 81A and 81B illustrates an embodiment of a coupler 2100 that houses a strain gauge 2102 that is configured to connect an anchor rod 2104 and an adjustable rod 142. The coupler 2100 includes a housing 2106 that includes a cavity 2108 sized to contain the strain gauge 2102 along with any associated electronics and wiring 2110. As seen in FIGS. 81A and 81B, the strain gauge 2102 is mounted on the backside of a plate 2112. The strain gauge 2102 may be bonded to the backside of the plate 2112 using an adhesive or other bond known to those skilled in the art. Application of a load against the plate 2112 will cause the same to deform. This deformation is then picked up by the strain gauge 2102 where the forces are converted into one or more electrical signals which are communicated to a remotely located telemetric unit 2114. Electrical wiring 2110 may be protected via a wire harness 2116 that couples the housing 2106 and the telemetric unit 2114. The telemetric unit 2114 can transmit signals to a remotely located receiver 2118 that is disposed external to the subject which can then display or otherwise communicate strain readings to the physician or other health care worker, and can display them, for example, as force using internal computation. The telemetric unit 2114 is typically placed somewhere under the skin of the patient and away from the subject's spine 110.

The plate 2112 may be secured to the face of the housing 2106 using screws or the like (not shown) that are inserted into threaded holes 2120. When the plate 2112 is secured to the housing 2106 a substantially sealed environment is created within the cavity 2018. In this regard, the strain gauge 2102 and any associated electronics are kept potted in a dry space substantially free of bodily fluids which would interfere with the longevity and operation of the strain gauge 2102. One or more seals 2113 may be provided on the back side of the plate 2112 to aid in creating the sealed condition. As best seen in FIG. 81A, the front face of the plate 2112 includes a cup 2122 that is dimensioned to receive a male fitting 2124. The male fitting 2124 may be secured within the cup 2122 using spring-biased clips or bearings 2126 that fit within recesses 2128. Alternatively, a pin may be used to secure the male fitting 2124 to the cup 2122. In yet another alternative, the male fitting 2124 may be permanent secured to the cup 2122 using a weld or other bonding technique.

The male fitting 2124 includes a spring-biased clip 2130 at one end thereof. The spring-biased clip 2130 includes a pair of tabs 2132 that extend laterally outward from the male fitting 2124. The spring-biased clip 2130 may be secured to the male fitting 2124 using a washer 2134 that is welded or bonded to a pin 2136 on the male fitting 2124 to form a sandwich-type of arrangement. The male fitting 2124 can be inserted into and retained by the cup 2122. Still referring to FIG. 81A, a female coupler 2140 is provided that slidable over the male fitting 2124. The female coupler 2140 includes a recess therein (not shown in FIG. 81A) that receives and locks with the pair of tabs 2132 of the spring-biased clip 2130. The female coupler 2140 further includes a socket portion 2142 configured to receive the end of an adjustable rod 142 (e.g., trimable section of adjustable rod 142). The female coupler 2140 may be removed from the male fitting 2124 by inserting a tool or the like (not shown) into the aperture 2144 to provide a radially-inward force to depress the pair of tabs 2132.

Figure 82A:
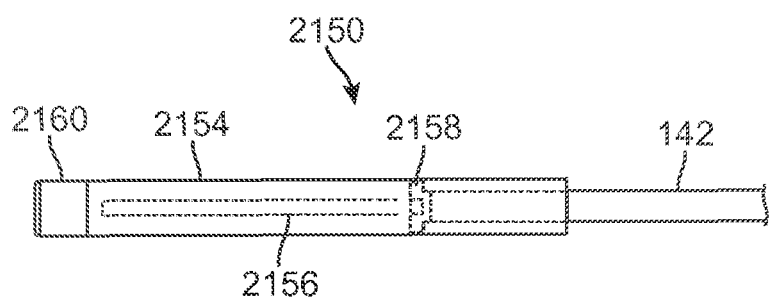
FIG. 82A illustrates a coupler configured to prevent rotational motion according to one embodiment.
Figure 82C:
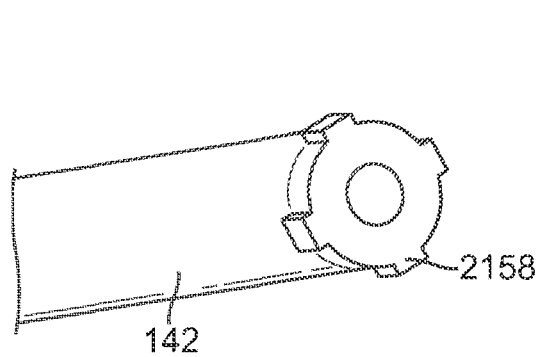
FIG. 82C illustrates a rod having a splined end that is configured for insertion into the tubular portion.
Figure 82B:
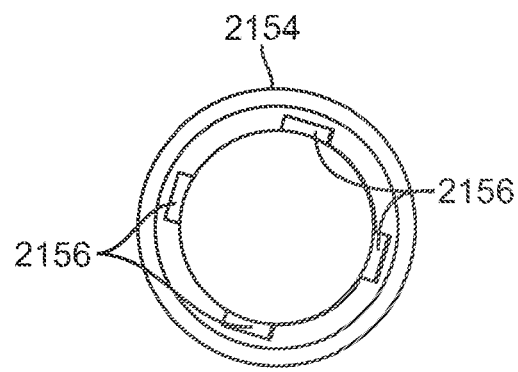
FIG. 82B illustrates an end view of the tubular portion of the coupler.

FIGS. 82A-82C illustrate a coupler 2150 that is designed to prevent rotational movement between an adjustable rod 142 and an anchor point such as, for instance, an anchor rod. As seen in FIGS. 82A and 82B, the coupler 2150 includes a tubular portion 2154 that includes one or more longitudinal channels 2156 formed in the interior surface. Referring now to FIGS. 82A and 82C, an adjustable rod 142 includes a splined tip 2158 that is configured to fit within the longitudinal channels 2156. In this regard, the adjustable rod 142 may move axially or telescopically within the tubular portion 2154 without any rotational movement of the adjustable rod 142. The end of the tubular portion 2154 terminates in a head 2160. The head 2160 may be adapted or configured for mounting to a portion of the patient's spine 110 or other skeletal structure. The head 2160 may also be coupled to some intermediate structure that is affixed to the patient's spine 100 or other location on the skeletal system. While an adjustable rod 142 is shown extending into the tubular portion 2154, the coupler 2150 may also have the anchor rod extending into the tubular portion 2154. In this case, the splined tip 2158 may be disposed on the end of an anchor rod as opposed to the adjustable rod 142. By preventing rotation, this keeps the adjustable rod 142 from losing distraction distance in case there is ever a low distraction force (e.g., from growth, lack of lengthening, tissue relaxation). In the case of a low or zero distraction force, the torsional resistance on the rotation of the drive magnet may be higher than the lead screw 578 to nut 584 torsional resistance (e.g., FIG.

50). Also, this feature of limiting rotation can be used in fusion applications where fusion won't occur if there is too much rotation.

Figure 83A:
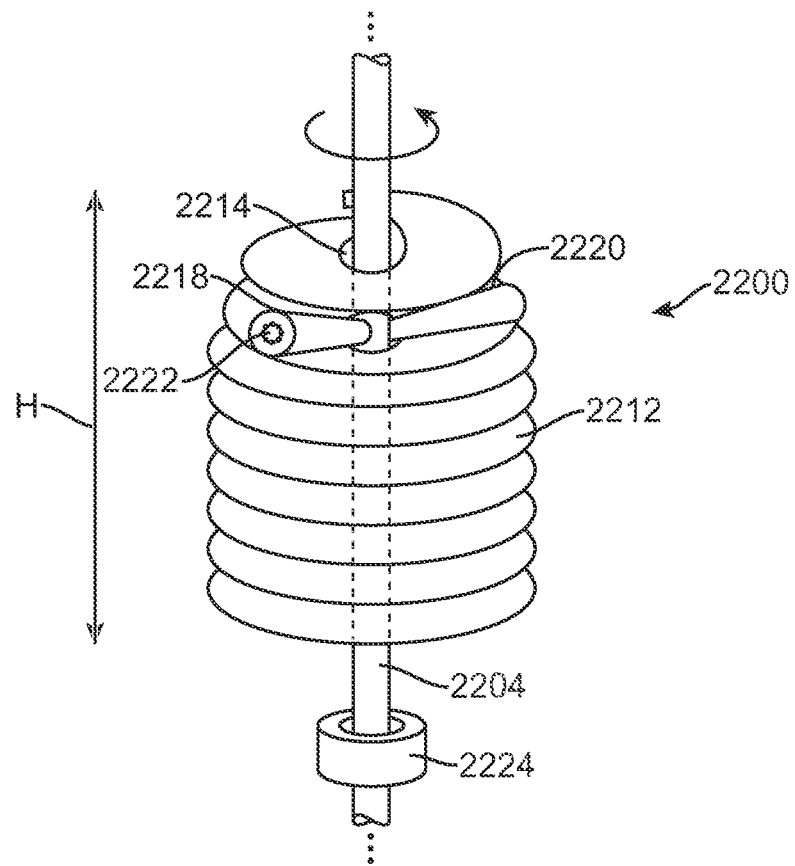
FIG. 83A illustrates a perspective view of a high efficiency lead screw according to one embodiment.
Figure 83B:
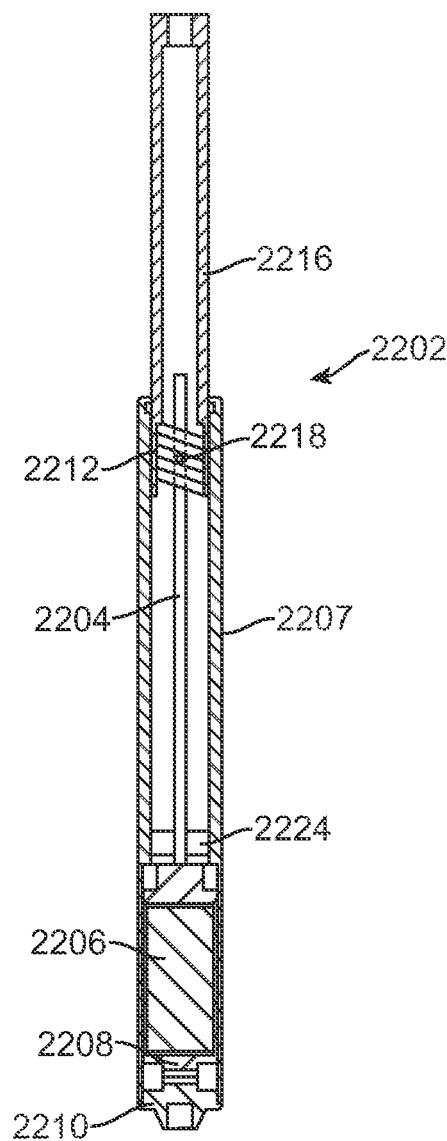
FIG. 83B is a cross-sectional view of an adjustable portion of an adjustable rod having the high efficiency lead screw of FIG. 83A.

FIGS. 83A and 83B illustrates an embodiment of a high efficiency lead screw system 2200 that is used to alter the length of an adjustable portion 2202 of an adjustable rod 142. The lead screw system 2200 includes a shaft 2204 that is operatively coupled to a permanent magnet 2206 rotationally mounted within a housing or cup 2208 which rotates on a thrust bearing 2210. The magnet 2206 is contained within the adjustable portion 2202. For instance, the magnet 2206 is contained in an outer tube 2207 as illustrated in FIG. 83B. The magnet 2206 rotates in response to an externally applied magnetic field as described in detail herein. Rotation of the magnet 2206 causes rotation of the shaft 2204. The lead shaft 2204 passes through a spiral-shaped shim 2212 that includes a central aperture 2214. The spiral-shaped shim 2212 is a helical ramp that is made from a thin, hard material. While not limiting, the spiral-shaped shim 2212 may be made of a material having a thickness of several thousandths of an inch (e.g., 0.002 inches). The material may include, for example, a metal or alloy. The spiral-shaped shim 2212 has a thin cross section that makes the same flexible along the length of the axis of the spiral-shaped shim 2212. The spiral-shaped shim 2212 is secured to one part of the adjustable portion 2202 forming the adjustable rod 142.

As seen in FIG. 83B, the spiral-shaped shim 2212 is secured to an inner surface of an inner tube 2216. The spiral-shaped shim 2212 should be able move slightly in the fashion of an accordion. For instance, the outer periphery of the spiral-shaped shim 2212 may be welded or otherwise bonded to an inner surface of the inner tube 2216. The shaft 2204 includes a pair of rollers 2218, 2220 affixed to the shaft 2204. The rollers 2218, 2220 may be rotationally mounted on a bearing such as roller bearings 2222. The rollers 2218, 2220 may also be tapered along their length (e.g., 2×, 3×, 4×) to provide a better contact surface with the underlying spiral-shaped shim 2212. The rollers 2218, 2220 are able to roll along the surface of the spiral-shaped shim 2212 in response to rotational movement of the shaft 2204. The height of the spiral-shaped shim 2212 (H) illustrated in FIG. 83A provides a displacement length of the inner tube 2216 relative to the outer tube 2207. Rotation of the shaft 2204 will cause the rollers 2218, 2220 to travel down the spiral-shaped shim 2212 which causes corresponding extension of the inner tube 2216 relative to the outer tube 2207. Of course, were the rollers 2218, 2220 to move up the spiral-shaped shim 2212, this would cause retraction of the inner tube 2216 relative to the outer tube 2207. As seen in FIG. 83A, an optional bearing 2224 may be provided about the shaft 2204 to aid in the rotational mounting of the shaft 2204. The high efficiency lead screw system 2200 described herein is very efficient due to the rolling contact surfaces which leads to very low frictional losses. This results in a very efficient driving system.

FIGS. 84A and 84B illustrates a low friction seal system 2300 formed between an outer housing 2302 and an inner rod 2304. The low friction seal system 2300 may be used between a junction of one end of an adjustable rod 142 as the inner rod 2304 and a coupler or joint that is secured to an anchor rod, for example. The outer housing 2302 includes a lumen or recess 2308 therein that is dimensioned to receive the rod 2304. The housing 2302 may take the form of a tube or the like. A set of circumferentially located ball bearings 2310 are located in grooves 2312, 2314 formed in the housing 2302 and rod 2304, respectively. The ball bearings 2310 may be secured in position using a cage 2316 (as seen in FIG. 84A). By having the ball bearings 2310 disposed in grooves 2312, 2314, telescopic or axial motion of the rod 2304 is permitted within the housing 2302. In contrast, rotational motion of the rod 2304 within the housing 2306 is prevented. As seen in FIG. 84A, an invertable/evertable sealing diaphragm 2320 is affixed at one end to a portion of the outer housing 2302 and at the other end to the rod 2304. The sealing diaphragm 2320 may be engaged to the housing 2302 and the rod 2304 using an adhesive, weld, or even a mechanical fitting. The sealing diaphragm 2320 advantageously prevents bodily fluids or other contaminants from entering the recess 2308 of the housing 2302.

Figure 85:
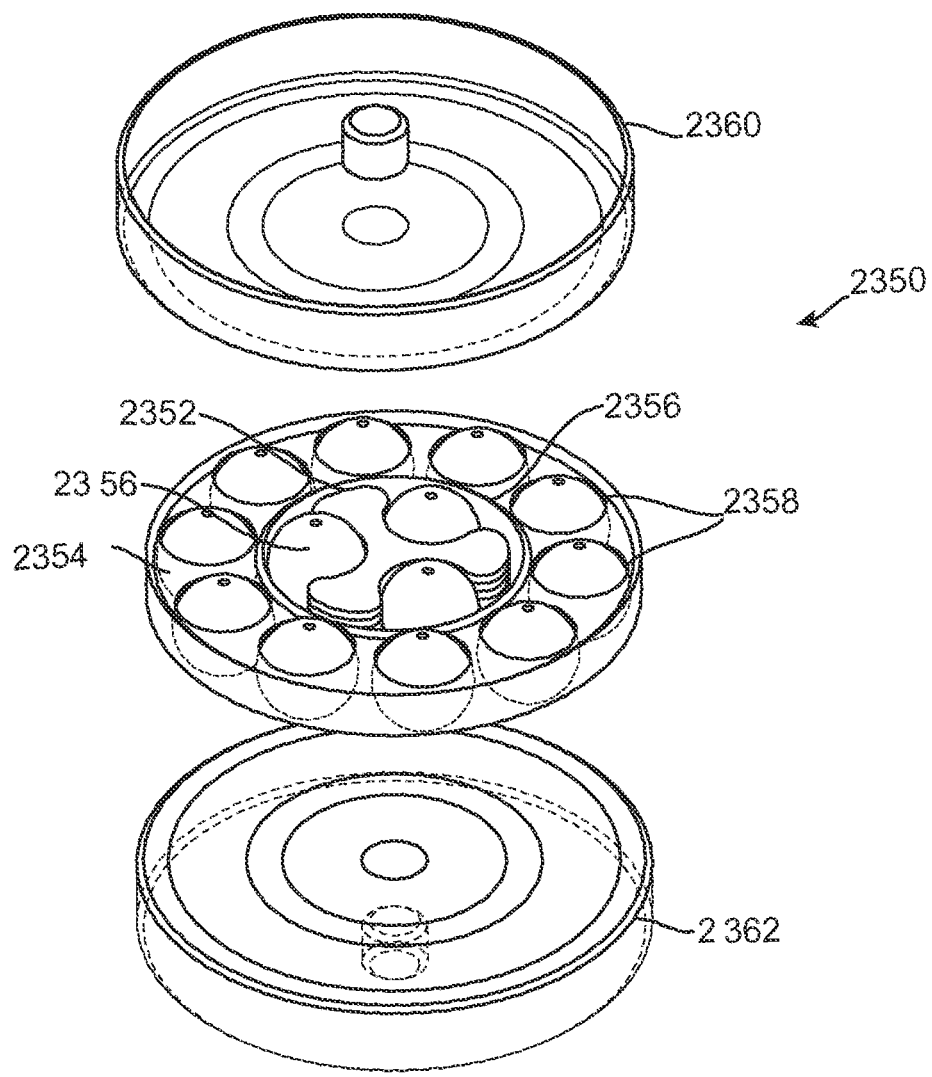
FIG. 85 is a perspective view of a dual race thrust bearing.

FIG. 85 illustrates a thrust bearing 2350 according to one embodiment. The thrust bearing 2350 is a dual-race thrust bearing 2350 that includes both an inner race 2352 and an outer race 2354. A first plurality of ball bearings 2356 is located in the inner race 2352 while a second plurality of ball bearings 2358 is located in the outer race 2354. Two end caps 2360, 2362 encapsulate the ball bearings 2356, 2358 into a single thrust bearing 2350. The thrust bearing 2350 illustrated in FIG. 85 may be used in the thrust bearings 438, 582, 2210 described herein. The thrust bearing 2350 decreases the stress on each ball 2356, 2358 while maintaining a small overall diameter. Therefore, larger distraction forces may be achieved without the thrust bearing 2350 being the limiting factor.

Figure 86:
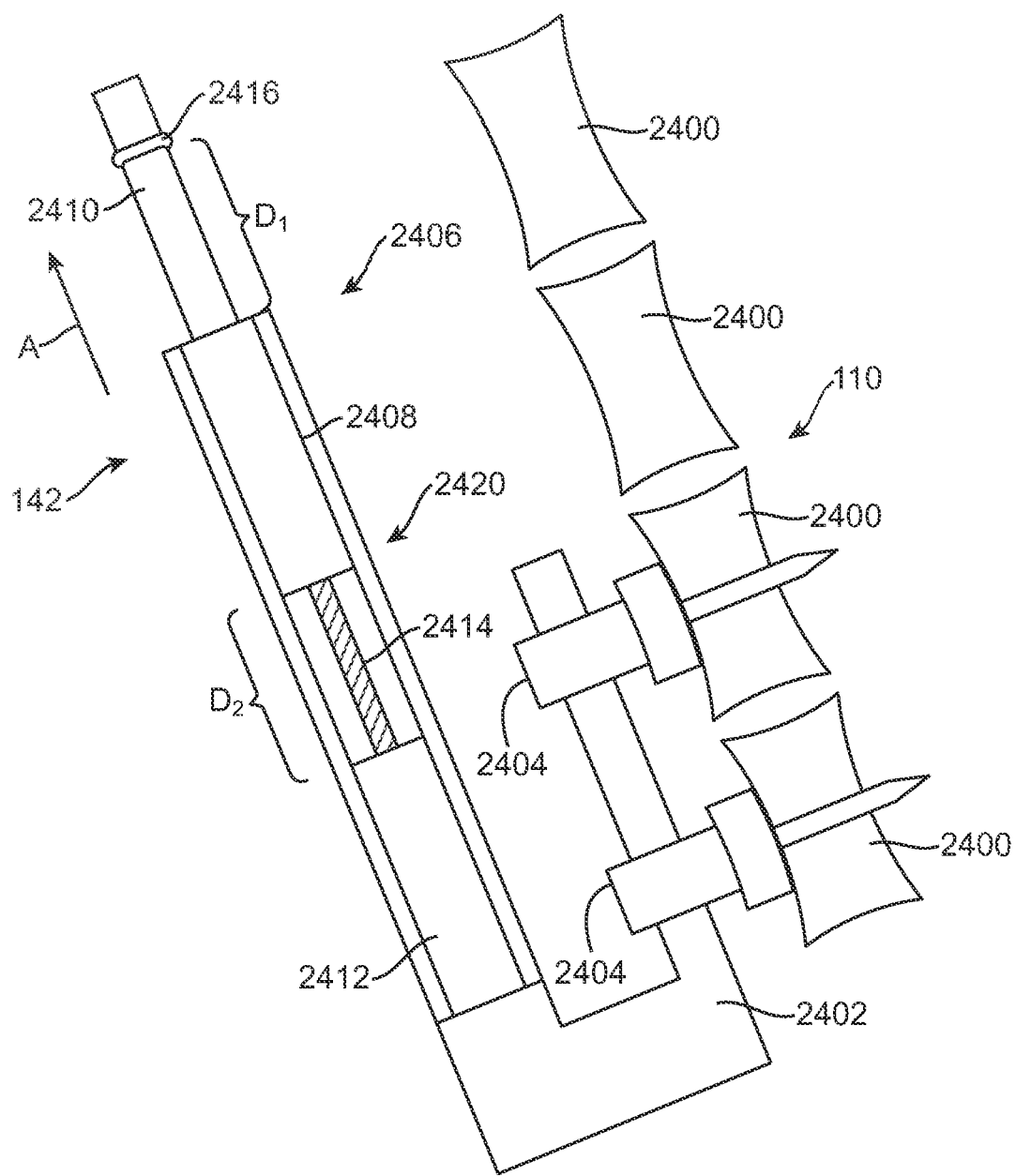
FIG. 86 is a representation of a radiographic image taken of an adjustable rod secured to the spine of a subject.

FIG. 86 is a representation of a radiographic image of an adjustable rod 142 that is mounted to a subject's spine 110. The individual vertebral bodies 2400 are illustrated along with the anchor rod 2402 and pedicle screws 2404. The anchor rod 2402 is coupled to an adjustable portion 2406 of the adjustable rod 142. The adjustable portion 2406 includes the outer tube 2408 and telescoping inner rod 2410. The magnet 2412 is coupled to a lead screw 2414 that rotates in response to rotational motion of the magnet 2412 which is induced by an external drive. Rotation of the lead screw 2414 results in axial movement of the inner rod 2410 in the direction of arrow A. The degree of distraction may be monitored by examination of the radiographic image. For example, in one embodiment, a radiopaque band or marker 2416 is located on the rod 2410. The radiopaque band or marker 2416 may include a radiopaque material that is applied the rod 2410. Alternatively, the radiopaque band or marker 2416 can be a material that is more or less dense than surrounding structures or it can be discernable from its geometry or position (e.g., a bump or protrusion). The distance ($D_1$) between this marker 2416 and the end of the outer tube 2408 may be used to quantify the degree of distraction. In another embodiment, the degree of distraction is determined by measuring the distance ($D_2$) between the edge of the magnet 2412 on the radiographic image and the trailing edge 2420 of the telescoping rod 2410 in the radiographic image. This distance can be used because $D_1=D_2$. In this regard, there may be no need for marker 2416.

Figure 87:
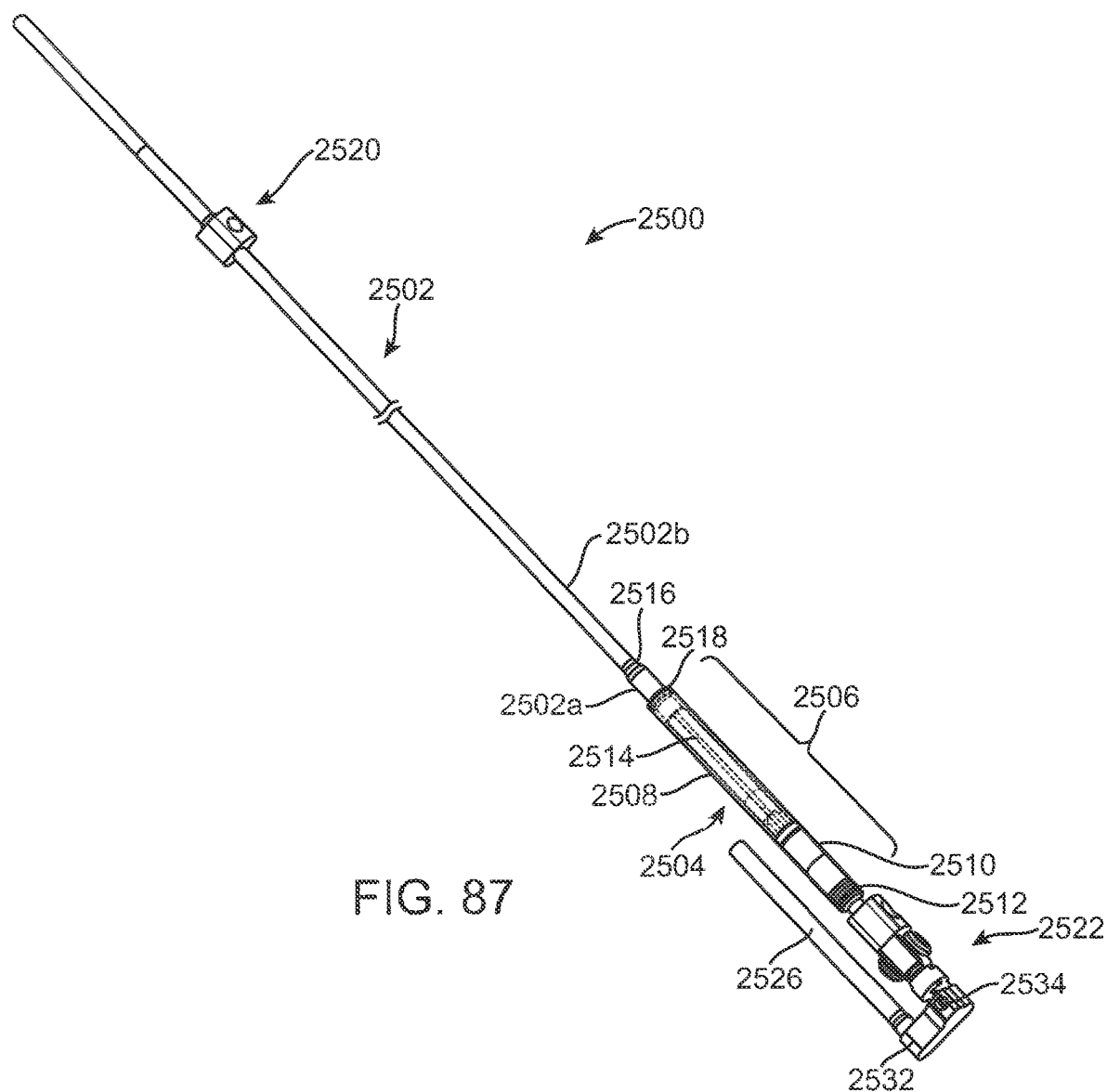
FIG. 87 illustrates another embodiment of a distraction device.

FIG. 87 illustrates one embodiment of a distraction device 2500. The distraction device 2500 generally comprises first and second elongate members 2502, 2504 that are configured for at least partial telescopic movement with respect to one another. One of the elongate members, e.g., second elongate member 2504 includes an adjustable portion 2506 that effectuates telescopic movement between the elongate members 2502, 2504. For example, the second elongate member 2504 comprises a housing 2508 that holds a permanent magnet 2510 (housing 2508 is partially removed to illustrate interior components). The permanent magnet 2510 is configured for rotation within the housing 2508 in response to an externally applied magnetic field. The permanent magnet 2510 may be operatively coupled to a thrust bearing 2512 such as thrust bearing 2350 illustrated in FIG. 85. The permanent magnet 2510 is also operatively coupled to a lead screw 2514. The lead screw 2514 engages with a nut (not shown in FIG. 87) disposed in the first elongate member 2502. The arrangement of the nut and lead screw 2514 may be similar to that illustrated in FIG. 50. The first elongate member 2502 may comprise a single rod that has different diameter portions 2502 a, 2502 b along its length. For example, a first portion 2502 a which interfaces with the adjustable portion 2506 may have a larger diameter while the second portion 2502 b (e.g., remainder of the first elongate member 2502) may have a narrower or smaller diameter. A dynamic seal 2518 is formed at the interface between the housing 2508 and the first portion 2502 a of the first elongate member 2502.

The distraction device 2500 illustrated in FIG. 87 is configured for smaller patients, for example patients that are less than ten (10) years old. The reduced diameter portion 2502 b is relatively small in size which is advantageous for the relatively smaller implantation site in younger patients yet it still provides the proper distraction force. As seen in FIG. 87, the first portion 2502 a transitions to the narrower, second portion 2502 b via a taper 2516. In one aspect, the diameter of the first portion 2502 a of the first elongate member 2502 may be between about 5.0 mm and about 8.0 mm while the diameter of the second portion 2502 b of the first elongate member 2502 may be between about 3.0 mm and about 6.0 mm. The preferred diameter for the first portion 2502 a of the first elongate member 2502 may be 6.35 mm and the preferred diameter of the second portion 2502 b of the first elongate member 2502 is 4.5 mm or 5.5 mm.

As illustrated in FIG. 87, the distraction device 2500 is coupled to the patient via an I-shaped anchor 2520 and a J-shaped anchor 2522. In particular, the second elongate member 2504 which includes the adjustable portion 2506 is operatively coupled to a bone or bony structure of the subject using the J-shaped anchor 2522. The first elongate member 2502 is operatively coupled to a bone or bony structure of the subject using the I-shaped anchor 2520.

Figure 88:
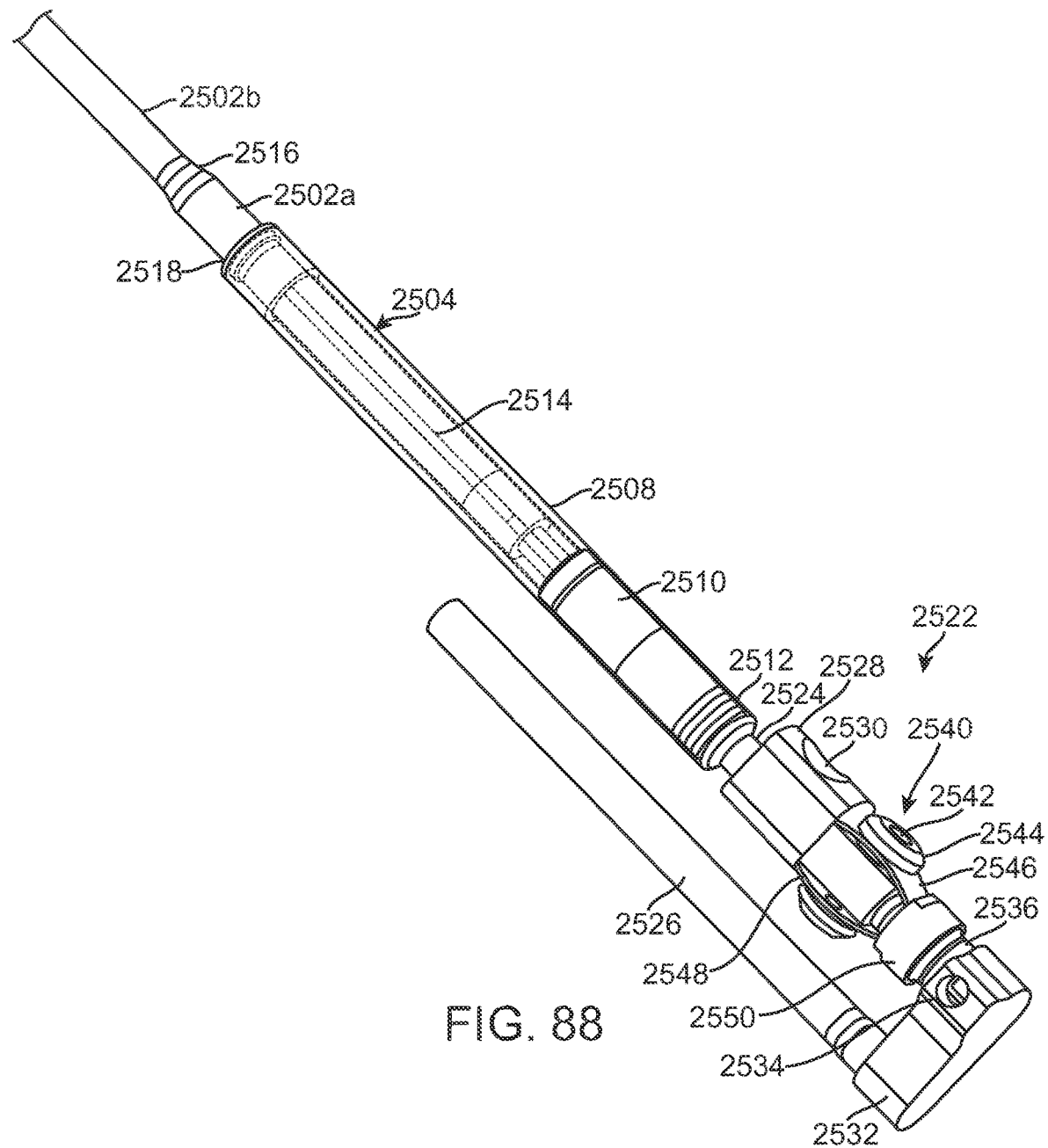
FIG. 88 illustrates a magnified view of one end of the distraction device illustrated in FIG. 87.
Figure 89:
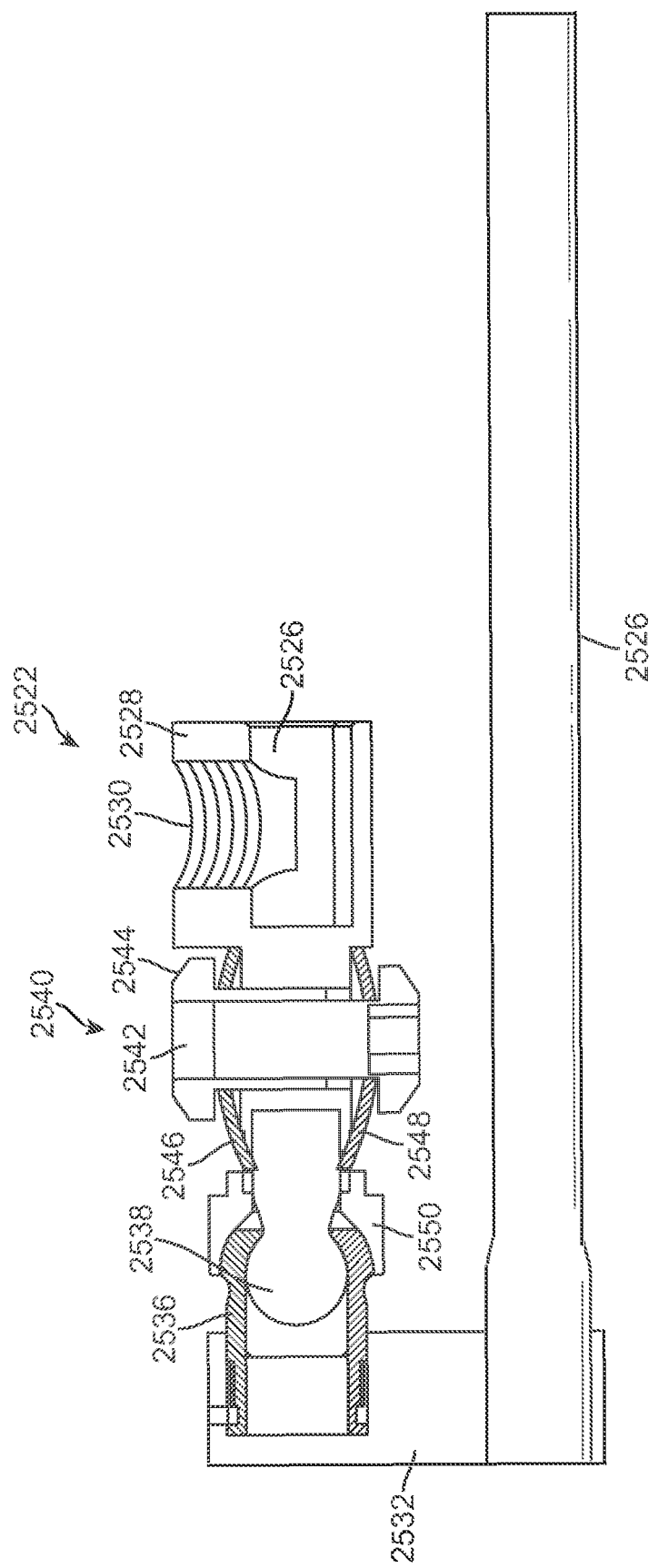
FIG. 89 illustrates a cross-sectional view of the j-shaped anchor illustrated in FIGS. 87 and 88.

FIGS. 88 and 89 illustrate the J-shaped anchor 2522. The housing 2508 that includes the permanent magnet 2510 has a projection 2524 which inserts into a cavity 2526 (FIG. 89) located at one end of a connector 2528 that forms part of the of J-shaped anchor 2522. By tightening a set screw (not shown) which engages with threaded hole 2530 of the connector 2528, the projection 2524 may be secured to the connector 2528, and thus to the J-shaped anchor 2522. Similarly, anchor rod 2526 is operatively coupled to a base 2532 having a threaded aperture 2534 into which a set screw (not shown) can be tightened, allowing base 2532 to be secured to swivel cup 2536. The swivel cup 2536 is configured to receive a ball 2538 (seen in FIG. 89) that is operatively coupled to the connector 2528. The ball 2538 can thus swivel inside swivel cup 2536. A locking device 2540 allows ball 2538 to be locked in place within the swivel cup 2536, if desired. For example, an Allen type wrench (not illustrated) may be placed into a hole 2542 of a tightening screw 2544 and tightened, compressing spring plates 2546, 2548. The naturally curved spring plates 2546, 2548 are then flattened and create an axial force on a friction cup 2550 which frictionally locks ball 2538, swivel cup 2536 and friction cup 2550 together. While a pair of spring plates 2546, 2548 are illustrated, it should be understood that only a single plate (e.g., 2546, 2548) may be used in an alternative embodiment.

During a surgical procedure, for example, during a non-fusion surgery, in which the surgeon desires to have a dynamic swivel, the locking device 2540 will not be tightened. In a surgery, for example, a fusion surgery or a non-fusion surgery in which a surgeon desires a more static system, the locking device 2540 will be tightened. Alternatively, the locking device 2540 may be tightened completely, but the set screw connecting the connector 2528 and the projection 2524 may be left un-tightened, thus allowing rotational freedom of the device.

Figure 90:
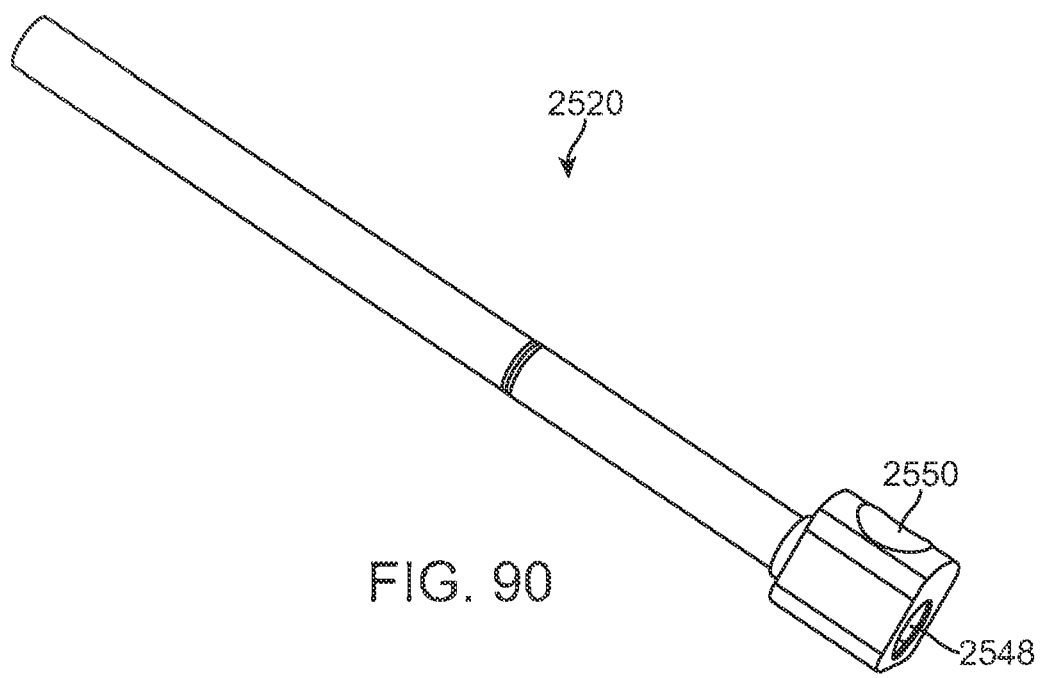
FIG. 90 illustrates a perspective view of the I-shaped anchor illustrated in FIG. 87.
Figure 91:
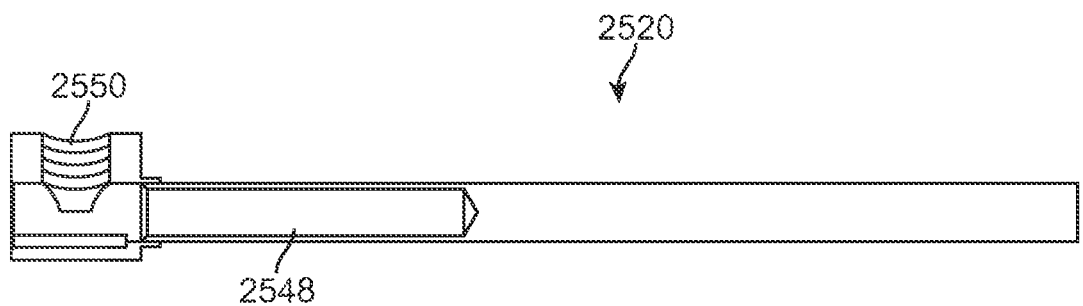
FIG. 91 illustrates a cross-sectional view of the I-shaped anchor of FIG. 90.

The I-shaped anchor 2520 is illustrated in FIGS. 90 and 91. The adjustable rod (e.g., first elongate member 2502) is cut to its desired length and inserted into a cavity 2548 of I-shaped anchor 2520. The first elongate member 2502 can be left free to telescope within cavity 2548. Alternatively, a set screw (not shown) may be tightened within aperture 2550 to secure the first elongate member 2502 to the I-shaped anchor 2520, and thus not allow rotational motion. In the cases wherein it is desired that the first elongate member 2502 is free to telescope within cavity 2548, it may be further desired that the diameter of the first elongate member 2502 be somewhat smaller than the inner diameter of the cavity 2548, so that there is enough play to allow for a small, controlled amount of angular movement (e.g., around 0° to around 5°).

FIG. 92 illustrates an embodiment of a J-shaped anchor 2600. As seen in FIG. 92, an anchor rod 2602 is attached to a base 2604. A swivel joint 2606 is provided at one end of the base 2604. The swivel joint 2606 includes a ball 2608, a recess 2610 located within the base 2604 that is configured to receive the ball 2608. The recess 2610 may include an aperture 2612 (e.g., threaded aperture) that is configured to receive a set screw 2614. The ball 2608 is formed as part of a connector 2616 having cavity 2618. The cavity 2618 is configured to receive a projection from the housing, e.g., housing 2508 and projection 2524 (also illustrated in FIGS. 88 and 89). The projection 2524 may include a groove 2526 that, as explained below, is configured to interface with a locking member 2528. For example, in one aspect, the locking member 2528 may include a spring and ball plunger 2630 that is formed by a spring 2632 and a plunger ball 2634 that engage with the groove 2526 at end of the projection 2524. This configuration allows for free rotation. Alternatively, a set screw (not shown) may be tightened in a hole 2636 to lock connector 2616 and housing 2508 together (via projection 2524) and thus inhibit rotation.

While embodiments of the present invention have been shown and described, various modifications may be made without departing from the scope of the present invention. The invention, therefore, should not be limited, except to the following claims, and their equivalents.

What is claimed:

1. An adjustable implant comprising:
   an adjustable spinal distraction rod comprising:
   an inner rod configured to be coupled to a first bone portion, wherein the inner rod includes at least one longitudinally extending channel formed within an interior surface of the inner rod and including an internal threads, and an externally splined tip at an end of the inner rod,
   an outer rod configured to be coupled to a second bone portion, wherein the outer rod includes: a housing containing a lead screw configured to engage with the internal threads and a magnet coupled to the lead screw, wherein the magnet is positioned proximate a first end of the housing and configured to rotate the lead screw within the housing, and at least one longitudinally extending channel formed in an interior surface of the housing, wherein the splined tip configured to mate with the at least one longitudinally extending channel, wherein the outer rod is configured to telescopically move relative to the inner rod, and wherein the magnet and the lead screw are configured to rotate about an axis of rotation that is substantially coaxial with a longitudinal axis of telescopic movement of the outer rod relative to the inner rod, an anchor rod configured to be fixedly secured to a third bone portion; and a locking swivel joint releasably secured to the anchor rod at a first end and releasably secured to the adjustable spinal distraction rod at a second end, the locking swivel joint having:

a housing coupled with an end of one of the anchor rod and the adjustable spinal distraction rod;

a bushing positioned about a periphery of the other one of the anchor rod and the adjustable spinal distraction rod, wherein the other one of the anchor rod and the adjustable spinal distraction rod, about which the bushing is positioned, terminates in a ball disposed within the housing of the locking swivel joint; and a locking nut mounted about the bushing and being moveable about the bushing between a locked configuration and an unlocked configuration, wherein the locking swivel joint is configured to pivot the adjustable spinal distraction rod relative to the anchor rod in the unlocked configuration, and configured to mechanically lock a position of the adjustable spinal distraction rod relative to the anchor rod in the locked configuration; and wherein movement of the inner rod with respect to the outer tube is configured to treat a spinal deformity.

2. The adjustable implant of claim 1, wherein the splined tip restricts rotation of the inner rod with respect to the outer rod.

3. The adjustable implant of claim 1, where the outer rod includes an adjustable rod that is configured to telescopically move relative to the inner rod.

4. The adjustable implant of claim 1, wherein the at least one longitudinally extending channel includes at least two longitudinally extending channels and the splined tip includes at least two splines, wherein each spline of the at least two splines the splined tip is disposed in a respective one of the at least two longitudinally extending channels.

5. The adjustable implant of claim 1, wherein the at least one longitudinally extending channel includes a plurality of circumferentially spaced and longitudinally extending channels, and the splined tip includes a corresponding plurality of circumferentially spaced splines, wherein each spline of the plurality of splines on the splined tip is disposed in a respective one of the corresponding equally spaced longitudinally extending channels.

6. The adjustable implant of claim 5, wherein the plurality of circumferentially spaced and longitudinally extending channels further comprises four such channels, and the corresponding plurality of circumferentially spaced splines further comprises four such splines.

7. The adjustable implant of claim 5, wherein the plurality of longitudinally extending channels are equally spaced about the interior surface of the outer rod, and the corresponding plurality of splines are equally spaced about an outer diameter of the splined tip of the inner rod.

8. The adjustable implant of claim 1, wherein the inner rod further includes a head configured to be coupled to the first bone portion.

9. The adjustable implant of claim 8, wherein the first bone portion includes a spine of a patient.

10. The adjustable implant of claim 1, wherein the inner rod includes a head configured to be coupled to an intermediate structure, and wherein the intermediate structure is configured to be coupled to the first bone portion.

11. An adjustable implant comprising:

an adjustable spinal distraction rod comprising:

an inner rod configured to be coupled to a first bone portion;

an outer rod configured to be coupled to a second bone portion and configured to telescopically move relative to the inner rod, wherein one of the inner rod or outer rod includes at least one longitudinally extending channel formed within an interior surface thereof and including an internal threads, and an externally splined tip at an end of the inner rod, wherein the other one of the inner rod or outer rod includes: a housing containing a lead screw configured to engage with the internal threads and a magnet coupled to the lead screw, wherein the magnet is positioned proximate a first end of the housing and configured to rotate the lead screw within the housing, and at least one longitudinally extending channel formed in an interior surface of the housing, wherein the splined tip configured to mate with the at least one longitudinally extending channel, and wherein the magnet and the lead screw are configured to rotate about an axis of rotation that is substantially coaxial with a longitudinal axis of telescopic movement of the outer rod relative to the inner rod, an anchor rod configured to be fixedly secured to a third bone portion; and a locking swivel joint releasably secured to the anchor rod at a first end and releasably secured to the adjustable spinal distraction rod at a second end, the locking swivel joint having:

a housing coupled with an end of one of the anchor rod and the adjustable spinal distraction rod;

a bushing positioned about a periphery of the other one of the anchor rod and the adjustable spinal distraction rod, wherein the other one of the anchor rod and the adjustable spinal distraction rod, about which the bushing is positioned, terminates in a ball disposed within the housing of the locking swivel joint; and a locking nut mounted about the bushing and being moveable about the bushing between a locked configuration and an unlocked configuration, wherein the locking swivel joint is configured to pivot the adjustable spinal distraction rod relative to the anchor rod in the unlocked configuration, and configured to mechanically lock a position of the adjustable spinal distraction rod relative to the anchor rod in the locked configuration; and wherein movement of the inner rod with respect to the outer tube is configured to treat a spinal deformity.

12. The adjustable implant of claim 11, wherein the splined tip restricts rotation of the inner rod with respect to the outer rod.

13. The adjustable implant of claim 11, where the outer rod includes an adjustable rod that is configured to telescopically move relative to the inner rod.

14. The adjustable implant of claim 11, wherein the at least one longitudinally extending channel includes at least two longitudinally extending channels and the splined tip includes at least two splines, wherein each spline of the at least two splines on the splined tip is disposed in a respective one of the at least two longitudinally extending channels.

15. The adjustable implant of claim 14, wherein the at least one longitudinally extending channel includes four longitudinally extending channels, and the splined tip includes four splines, wherein each spline of the four splines on the splined tip is configured to be disposed in a respective one of the four longitudinally extending channels.

16. The adjustable implant of claim 15, wherein the four splines are equally spaced about an outer circumference of the splined tip, and the four longitudinally extending channels are correspondingly circumferentially equally spaced about the interior surface of the outer rod.

17. The adjustable implant of claim 11, wherein the inner rod further includes a head configured to be coupled to the first bone portion.

18. The adjustable implant of claim 17, wherein the first bone portion includes a spine of a patient.

19. The adjustable implant of claim 11, wherein the inner rod includes a head configured to be coupled to an intermediate structure.

20. The adjustable implant of claim 19, wherein the intermediate structure is configured to be coupled to the first bone portion.

* * * * *